United States Patent
Naik et al.

(10) Patent No.: US 11,155,517 B2
(45) Date of Patent: Oct. 26, 2021

(54) 4-SUBSTITUTED PHENYLAMINE DERIVATIVES AND THEIR USE TO PROTECT CROPS BY FIGHTING UNDESIRED PHYTOPATHOGENIC MICOORGANISMS

(71) Applicant: PI INDUSTRIES LTD., Gurgaon (IN)

(72) Inventors: Maruti N. Naik, Karnataka (IN); Vishal Ashok Mahajan, Pune (IN); Mahesh Prakash More, Maharashtra (IN); Avinash Desai, Telangana (IN); Manoj Ganpat Kale, Maharashtra (IN); Sulur G. Manjunatha, Bangalore (IN); Hagalavadi M. Venkatesha, Bengaluru (IN); Santosh Shridhar Autkar, Maharashtra (IN); Ruchi Garg, Uttar Pradesh (IN); Jatin Samanta, West Bengal (IN); Alexander G. M. Klausener, Pulheim (DE); Konstantin Poscharny, Dusseldorf (DE)

(73) Assignee: PI INDUSTRIES LTD., Gurgaon (IN)

( * ) Notice: Subject to any disclaimer, the term of this patent is extended or adjusted under 35 U.S.C. 154(b) by 264 days.

(21) Appl. No.: 16/341,459

(22) PCT Filed: Oct. 11, 2017

(86) PCT No.: PCT/IB2017/056276
§ 371 (c)(1),
(2) Date: Apr. 12, 2019

(87) PCT Pub. No.: WO2018/069841
PCT Pub. Date: Apr. 19, 2018

(65) Prior Publication Data
US 2019/0382338 A1    Dec. 19, 2019

(30) Foreign Application Priority Data
Oct. 14, 2016   (IN) .............................. 201611035245

(51) Int. Cl.
| | | |
|---|---|---|
| *C07C 257/12* | (2006.01) | |
| *C07C 317/32* | (2006.01) | |
| *C07C 323/41* | (2006.01) | |
| *C07D 211/12* | (2006.01) | |
| *C07D 265/30* | (2006.01) | |
| *C07D 295/13* | (2006.01) | |
| *A01N 37/52* | (2006.01) | |
| *A01N 43/40* | (2006.01) | |
| *A01N 43/84* | (2006.01) | |

(52) U.S. Cl.
CPC .......... *C07C 257/12* (2013.01); *C07C 317/32* (2013.01); *C07C 323/41* (2013.01); *C07D 211/12* (2013.01); *C07D 265/30* (2013.01); *C07D 295/13* (2013.01); *A01N 37/52* (2013.01); *A01N 43/40* (2013.01); *A01N 43/84* (2013.01)

(58) Field of Classification Search
None
See application file for complete search history.

(56) References Cited

U.S. PATENT DOCUMENTS

| | | | |
|---|---|---|---|
| 4,173,637 A | 11/1979 | Nishiyama et al. | |
| 8,080,688 B2 | 12/2011 | Kunz et al. | |
| 8,299,301 B2* | 10/2012 | Kunz | C07C 257/12 |
| | | | 564/225 |

(Continued)

FOREIGN PATENT DOCUMENTS

| | | |
|---|---|---|
| CN | 101337940 A | 1/2009 |
| CN | 102057925 A | 5/2011 |
| CN | 102060818 A | 5/2011 |

(Continued)

OTHER PUBLICATIONS

Rodriguez et al., "Guanidine and 2-Aminoimidazoline Aromatic Derivatives as α2-Adrenoceptor Antagonists, 1: Toward New Antidepressant with Heteroatomic Linkers", Journal of Medical Chemistry, vol. 50, pp. 4516-4527 (2007).
Ross et al., "Friedel-Crafts acylation reactions using metal triflates in ionic liquid", Green Chemistry, 2002, vol. 4, Issue 2, pp. 129-133.
Kulp et al., "Oxidative Decyanation of Benzyl and Benzhydryl Cyanides. A Simplified Procedure", J. Org. Chem., 1983, 48, pp. 4097-4098.
Effenberger et al., "Perfluoroalkanesulfonic Acid Catalyzed Acylations of Alkylbenzenes: Synthesis of Alkylanthraquinones", Synthesis 2000, No. 10, pp. 1427-1430.
Sarvari et al., "Simple and Improved Procedure for the Regioselective Acylation of Aromatic Ethers with Carboxylic Acids on the Surface of Graphite in the Presence of Methanesulfonic Acid", SYNTHESIS 2004, No. 13, pp. 2165-2168.

(Continued)

*Primary Examiner* — Alton N Pryor
(74) *Attorney, Agent, or Firm* — Fay Sharpe LLP

(57) ABSTRACT

This invention related to 4-substituted phenylamine derivatives of the general formula (I), wherein $R^1$ to $R^9$ and A have the meanings as defined in description. The invention further relates to methods for their preparation and use of said compounds to fight undesired phytopathogenic microorganisms, and agents for said purpose, comprising said phenylamine derivatives, all according to the invention. This invention further relates to a method for fighting undesired phytopathogenic microorganisms by application of said 4-substituted phenylamine derivatives of general formula (I) to such undesired microorganisms and/or to their habitat, according to the invention.

(I)

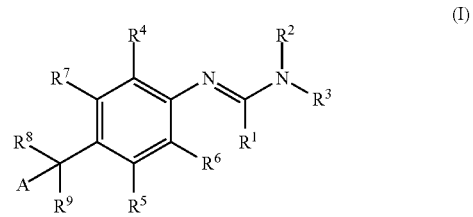

18 Claims, No Drawings

(56) References Cited

U.S. PATENT DOCUMENTS

| | | | |
|---|---|---|---|
| 2011/0082036 A1* | 4/2011 | Desbordes | A01N 43/56 504/100 |
| 2011/0130282 A1 | 6/2011 | Kunz et al. | |

FOREIGN PATENT DOCUMENTS

| | | |
|---|---|---|
| EP | 1 969 935 A1 | 9/2008 |
| EP | 2 120 558 | 11/2009 |
| EP | 2 738 163 A1 | 6/2014 |
| JP | 8-291146 A | 11/1996 |
| WO | 00/46184 A1 | 8/2000 |
| WO | 03/024219 A1 | 3/2003 |
| WO | 03/076415 A1 | 9/2003 |
| WO | 03/093224 A1 | 11/2003 |
| WO | 03/106457 A1 | 12/2003 |
| WO | 2004/005242 A1 | 1/2004 |
| WO | 2004/099160 A1 | 11/2004 |
| WO | 2005/085216 A1 | 9/2005 |
| WO | 2005/089547 A1 | 9/2005 |
| WO | 2005/120234 A2 | 12/2005 |
| WO | 2006/003494 A2 | 1/2006 |
| WO | 2006/043635 A1 | 4/2006 |
| WO | 2008/110314 A1 | 9/2008 |
| WO | 2008/134969 A1 | 11/2008 |
| WO | 2009/049851 A1 | 4/2009 |
| WO | 2009/053448 A1 | 4/2009 |
| WO | 2009/080250 A2 | 7/2009 |
| WO | 2009/099929 A1 | 8/2009 |
| WO | 2010/051926 A2 | 5/2010 |
| WO | 2010/059773 A1 | 5/2010 |
| WO | 2011/095462 A1 | 8/2011 |
| WO | 2012/000896 A2 | 1/2012 |
| WO | 2012/029672 A1 | 3/2012 |
| WO | 2013/144213 A1 | 10/2013 |
| WO | 2014/119617 A1 | 8/2014 |
| WO | 2015/025962 A1 | 2/2015 |
| WO | 2013/018735 A1 | 3/2015 |
| WO | 2015/121802 A1 | 8/2015 |
| WO | 2017/102635 A1 | 6/2017 |

OTHER PUBLICATIONS

Sarvari et al., "Solvent-Free Catalytic Friedel ± Crafts Acylation of Aromatic Compounds with Carboxylic Acids by Using a Novel Heterogeneous Catalyst System: p-Toluenesulfonic Acid/Graphite", Helvetica Chimica Acta, vol. 88, 2005, pp. 2282-2287.

Zarei et al., "Friedel-Crafts acylation of aromatic compounds with carboxylic acids in the presence of P2O5/SiO2 under heterogeneous conditions", Tetrahedron Letters 49 (2008), pp. 6715-6719.

Kobayashi et al., "Remarkable Effect of Lithium Salts in Friedel-Crafts Acylation of 2-Methoxynaphthalene Catalyzed by Metal Triflates", Tetrahedron 56 (2000), pp. 6463-6465.

Hwang et al., "Trifluoromethanesulfonic Acid Catalyzed Novel Friedel-Crafts Acylation of Aromatics with Methyl Benzoate", Tetrahedron 56 (2000), pp. 7199-7203.

Xin et al., "The Surfactant-Promoted Cross-Coupling Reactions of Arylboronic Acids with Carboxylic Anhydrides or Acyl Chlorides in Water", SYNTHESIS 2007, No. 13, pp. 1970-1978.

Epperson et al., "4-Substituted anilides as selective melatonin MT2 receptor agonists", Bioorganic & Medicinal Chemistry Letters 14 (2004), p. 1023 1026.

Freerksen et al., "Oxidative Decyanation of Secondary Nitriles to Ketones", J. Org. Chem. 1983, 48, pp. 4087-4096.

Chardonnens et al., "Sur l'acide 4-benzoyl-phtalique", Helvetica Chimica Acta, vol. XXIX, Fasciculus VI (1946), pp. 1413-1424.

* cited by examiner

4-SUBSTITUTED PHENYLAMINE DERIVATIVES AND THEIR USE TO PROTECT CROPS BY FIGHTING UNDESIRED PHYTOPATHOGENIC MICOORGANISMS

This application is a National Stage Entry of International Application No. PCT/162017/056276, filed Oct. 11, 2017, and entitled "4-Substituted phenylamine derivatives and their use to protect crops by fighting undesired phytopathogenic microorganisms"; which claims priority to Indian Application No. 201611035245, filed Oct. 14, 2016, and entitled "4-Substituted phenylamine derivatives and their use to protect crops by fighting undesired phytopathogenic microorganisms", the contents of which are incorporated by reference herein.

FIELD OF THE INVENTION

The present invention relates to compounds intended to protect crops by fighting undesired phytopathogenic microorganisms. More precisely, the subject of the present invention relates to 4-substituted phenylamine derivatives used to protect crops by fighting undesired phytopathogenic microorganisms.

BACKGROUND OF THE INVENTION

The control of damages to crops caused by phytopathogenic microorganisms is extremely important in achieving high crop efficiency. For instance, plant disease damage to ornamental, vegetable, field, cereal, and fruit crops can cause significant reduction in productivity and thereby result in increased costs to the consumer. Many products are commercially available to control such damages. The need continues for new compounds which are more effective, less costly, less toxic, environmentally safer and/or have different modes of action. Certain phenylamine derivatives are disclosed in literature as microbicidally active ingredients in pesticides. For example, WO2000046184, WO2003093224, WO2003024219, WO2005089547, WO2005120234 and US20110082036 discloses the use of phenylamine derivatives especially phenylamidine, either alone or as part of composition, as fungicides. Certain phenyl benzamides compound, method of producing such compounds and their use for controlling undesired microorganisms is disclosed in WO2004005242.

U.S. Pat. No. 4,173,637 discloses phenylurea compounds and compositions containing these compounds as insecticides. JP08291146 discloses N-substituted phenylsulfonamide compounds having excellent herbicidal activity, especially paddy field herbicides. WO2008110314 discloses fluoroalkyl phenylamidines as fungicidal compounds, method of their preparation and a method for protecting seeds from unwanted microorganisms using such compounds. One other PCT publication WO2011095462 discloses phenylamine derivatives including carboxamides, process for preparing them and insecticidal, acaricidal, nematicidal or molluscidal compositions comprising these derivatives. Certain amidine compounds exhibiting antifungal activity against pathogenic fungi including fungi of the genera *Candida, Aspergillus* and *Trichophyton*, being pharmaceutically useful have been disclosed in WO2013018735.

The effectiveness of the phenylamine derivatives described in the prior art is good, but leaves something to be desired in various cases. Therefore, it is always of high interest in agriculture to use novel pesticidal compounds in order to avoid and/or control the development of microorganisms such as fungal or bacterial pathogens or pests being resistant to known active ingredients. It is therefore of high interest to use novel compounds being more active than those already known, with the aim of decreasing the amounts of active compound to be used, whilst at the same time maintaining an effectiveness at least equivalent to the already known compounds.

We have now found a new family of compounds which possess the above mentioned effects or advantages. A new family of compounds namely, 4-substituted phenylamine derivatives wherein the phenyl ring is substituted according to the invention thus allowing an unexpected and significantly higher activity against undesired microorganisms such as fungal or bacterial pathogens or pests.

SUMMARY OF THE INVENTION

This present invention relates to a novel and inventive 4-substituted phenylamine derivatives of the general formula (I),

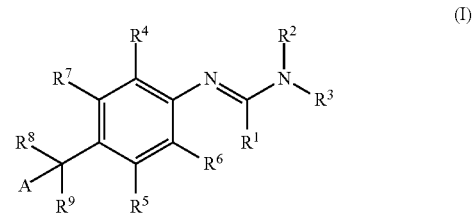

wherein the definition of the substituents is defined in foregoing detailed description.

The 4-substituted phenylamine derivatives of the present invention are novel and inventive even in view of U.S. Pat. No. 8,080,688 and its corresponding EP Application No. 2120558.

U.S. Pat. No. 8,080,688 discloses 3,4-disubstituted phenoxyphenyl amidines represented by general formula

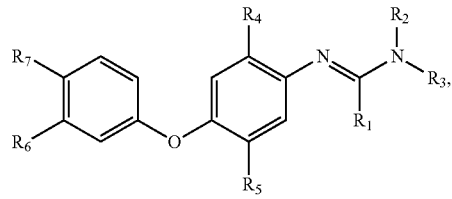

wherein two phenyl rings are linked by "—O—".

Please refer Scheme I, Steps (a-f) at page nos. 18-25 compound (I), and Steps (g-j) at page nos. 27-30 compound (I) of U.S. Pat. No. 8,080,688. Also, refer to examples in Table IV page nos. 48-49.

However, in embodiments on page 18, paragraph 5 and claim 4, the applicant of U.S. Pat. No. 8,080,688 has disclosed 3,4-disubstituted benzylphenyl amidines. The list of 3,4-disubstituted benzylphenyl amidines compounds disclosed in U.S. Pat. No. 8,080,688 is reproduced herein below:

N'-[4-(2,3-Dihydro-1H-inden-5-ylmethyl)-2,5-dimethylphenyl]-N-ethyl-N-methylimidoformamid, N'-{4-[(3,3-Dimethyl-2,3-dihydro-1H-inden-5-yl)methyl]-2,5-dimethylphenyl}-N-ethyl-N-methylimidoformamid, N'-[4-(3-Chlor-4-isopropylbenzyl)-2,5-dimethylphenyl]-N-ethyl-N-methylimidoformamid, N'-[4-(3-Chlor-4-tert-butylbenzyl)-2,5-dimethylphenyl]-N-ethyl-N-methylimidoformamid, N-Ethyl-N'-{4-[(3-hydroxy-3-methyl-2,3-dihydro-1H-inden-5-yl)methyl]-2,5-dimethylphenyl}-N-methylimidoformamid, N'-[4-(3-Chlor-4-methylbenzyl)-2,5-dimethylphenyl]-N-ethyl-N-methylimidoformamid, N'-{2,5-dimethyl-4-[(1,1,3-trimethyl-2,3-dihydro-1H-inden-5-yl)methyl]phenyl}-N-ethyl-N-methylimidoformamid, N'-{2,5-dimethyl-4-[(1,1,3-trimethyl-2,3-dihydro-1H-inden-5-yl)methyl]phenyl}-N-isopropyl-N-methylimidoformamid, N'-{2,5-dimethyl-4-[(1,1,3-trimethyl-2,3-dihydro-1H-inden-5-yl)methyl]phenyl}-N-methyl-N-propylimido-formamid, N'-[2,5-Dimethyl-4-(5,6,7,8-tetrahydronaphthalen-2-ylmethyl)phenyl]-N-ethyl-N-methylimidoformamid, N'-[2,5-Dimethyl-4-(5,6,7,8-tetrahydronaphthalen-2-ylmethyl)phenyl]-N-isopropyl-N-methylimidoformamid, N'-[2,5-Dimethyl-4-(5,6,7,8-tetrahydronaphthalen-2-ylmethyl)phenyl]-N-methyl-N-propylimidoformamid, 2,5-Dimethyl-N-[(1E)-piperidin-1-ylmethylene]-4-(5,6,7,8-tetra-hydronaphthalen-2-ylmethyl)anilin, 4-(4-tert-butyl-3-chlorobenzyl)-2,5-dimethyl-N-[(1E)-piperidin-1-ylmethylene]anilin, N'-(4-{3-Chlor-4-[(trimethylsilyl)methyl]benzyl}-2,5-dimethylphenyl)-N-ethyl-N-methylimidoformamid, N'-[4-(3-Chlor-4-isobutylbenzyl)-2,5-dimethylphenyl]-N-ethyl-N-methylimidoformamid, N'-[4-(4-butyl-3-chlorbenzyl)-2,5-dimethylphenyl]-N-ethyl-N-methylimidoformamid, N'-(2,5-Dimethyl-4-{4-(trifluormethyl)-3-[(trimethylsilyl)methyl]benzyl}phenyl)-N-ethyl-N-methylimidoformamid, and N'-{4-[3-cyclopentyl-4-(trifluormethyl)benzyl]-2,5-dimethylphenyl}-N-ethyl-N-methylimidoformamid.

This disclosure of 3,4-disubstituted benzylphenyl amidines compounds in U.S. Pat. No. 8,080,688 is erroneous and unintentional, for the following reasons: i) that from the language of claim 4, it appears that the applicant intended to claim 3,4-disubstituted phenoxyphenyl amidines and not 3,4-disubstituted benzylphenyl amidines; ii) that 3,4-disubstituted benzylphenyl amidines cannot be prepared by the procedures described in schemes and examples; iii) that in Table IV page nos. 48-49 of U.S. Pat. No. 8,080,688 3,4-disubstituted phenoxyphenyl amidines alone are disclosed.

Thus, in view of this typographical error, which warrants rectification in U.S. Pat. No. 8,080,688 and its corresponding EP Application No. 2120558, the compounds of the present invention are novel.

The inventiveness/non-obviousness of the compounds of the present invention can be seen from the comparative results shown in the example section, wherein it is surprisingly observed that the compounds of the present invention additionally increase the effectiveness for crop protection against attacks by pests, microorganisms, weeds or abiotic stress.

DETAILED DESCRIPTION OF THE INVENTION

Accordingly, the present invention relates to compounds of general formula (I)

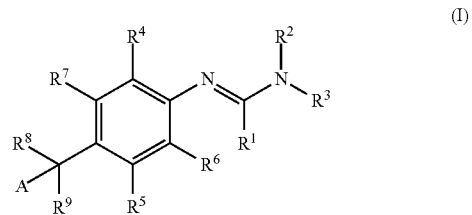

wherein $R^1$ is selected from the group consisting of hydrogen, CN, SR'', S(O)$_n$R'', OR'', $C_{1-12}$-alkyl, $C_{1-12}$-alkoxy, $C_{1-12}$-alkylthio, $C_{2-12}$-alkenyl, $C_{2-12}$-alkynyl, $C_{1-12}$-haloalkyl, $C_{2-12}$-haloalkenyl, $C_{2-12}$-haloalkynyl, $C_{3-8}$-cycloalkyl, $C_{4-8}$-cycloalkenyl, $C_{5-8}$-cycloalkynyl; where in the cyclic ring system one or more carbon atoms may be replaced by heteroatoms selected from the group consisting of N, O, and S(O)$_n$N, O, and S(O)$_n$;

$R^2$ and $R^3$ are independently selected from the group consisting of hydrogen, CN, S(O)$_n$R'', OR', (C=O)—R'', $C_{1-12}$-alkyl, $C_{2-12}$-alkenyl, $C_{2-12}$-alkynyl, $C_{1-12}$-haloalkyl, $C_{2-12}$-haloalkenyl, $C_{2-12}$-haloalkynyl, $C_{3-8}$-cycloalkyl, $C_{4-8}$-cycloalkenyl, $C_{5-8}$-cycloalkynyl, $C_{5-18}$-aryl, $C_{7-19}$-aralkyl, $C_{7-19}$-alkaryl; where in the cyclic ring system one or more carbon atoms may be replaced by heteroatoms selected from the group consisting of N, O, and S(O)$_n$; or $R^1$ and $R^2$, $R^2$ and $R^3$ or $R^1$ and $R^3$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a four to seven membered ring, which for its part may be substituted by one or more X, R', OR', SR', NR'$_2$, SiR'$_3$, COOR', CN, and CONR'$_2$; and wherein each of $R^1$, $R^2$, and $R^3$ may optionally be substituted by one or more groups selected from the group consisting of X, R', OR', SR', NR'$_2$, SiR'$_3$, COOR', CN, and CONR'$_2$;

$R^4$, $R^5$, $R^6$ and $R^7$ are independently selected from the group consisting of hydrogen, X, CN, SCN, SF$_5$, S(O)$_n$R'', SiR'$_3$, OR'', NR'R'', (C=O)—R'', CR'=NR'', $C_{1-12}$-alkyl, $C_{2-12}$-alkenyl, $C_{2-12}$-alkynyl, $C_{1-12}$-haloalkyl, $C_{2-12}$-haloalkenyl, $C_{2-12}$-haloalkynyl, $C_{1-12}$-haloalkoxy, $C_{1-12}$-haloalkylthio, $C_{3-8}$-cycloalkyl, $C_{4-8}$-cycloalkenyl, $C_{5-8}$-cycloalkynyl, $C_{3-8}$-cycloalkyloxy, $C_{3-8}$-cycloalkylthio, $C_{5-18}$-aryl, $C_{7-19}$-aralkyl, $C_{7-19}$-alkaryl; where in the cyclic ring system one or more carbon atoms may be replaced by heteroatoms selected from the group consisting of N, O, and S(O)$_n$; and all of the groups mentioned above may optionally be substituted by one or more groups selected from the group consisting of X, R', OR', SR', NR'$_2$, SiR'$_3$, COOR', CN, and CONR'$_2$; or wherein $R^4$ and $R^7$ or $R^5$ and $R^6$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a four to seven membered ring, which for its part may be substituted by one or more X, R', OR', SR', NR'$_2$, SiR'$_3$, COOR', CN, and CONR'$_2$; and wherein each of $R^4$, $R^5$, $R^6$ and $R^7$ may optionally be substituted by one or more groups selected from the group consisting of X, R', OR', SR', NR'$_2$, SiR'$_3$, COOR', CN, and CONR'$_2$;

$R^8$ and $R^9$ are independently selected from the group consisting of hydrogen, X, CN, SCN, S(O)$_n$R'', OS(O)$_n$R'', SiR'$_3$, OSiR'$_3$, NR'R'', NR'S(O)$_n$R'', (C=O)—R'', CR'=NR'', $C_{1-12}$-alkyl, $C_{2-12}$-alkenyl, $C_{2-12}$-alkynyl, $C_{1-12}$- alkoxy $C_{1-12}$-haloalkyl, $C_{2-12}$-haloalkenyl, $C_{2-12}$-haloalkynyl, $C_{1-12}$-haloalkoxy, $C_{1-12}$-haloalkylthio, $C_{3-8}$-cycloalkyl, $C_{4-8}$-cycloalkenyl, $C_{5-8}$-cycloalkynyl, $C_{3-8}$-cycloalkyloxy, $C_{3-8}$-cycloalkylthio, $C_{5-18}$-aryl, $C_{7-19}$-aralkyl, $C_{7-19}$-alkaryl; where in the cyclic ring system one or more carbon atoms may be replaced by heteroatoms selected from the group consisting of N, O, and $S(O)_n$; and all of the groups mentioned above may be substituted by one or more groups selected from the group consisting of X, R', OR', SR', NR'$_2$, SiR'$_3$, COOR', CN, and CONR'$_2$; or wherein $R^8$ and $R^9$ together with the atom to which they are attached or together with further atoms selected from the group consisting of C, N, O, S and optionally including 1 to 3 ring members selected from the group consisting of C(=O), C(=S), $S(O)_m$ and SiR'$_2$ may form a three to seven membered ring, which for its part may be substituted by one or more X, R', OR', SR', NR'$_2$, SiR'$_3$, COOR', CN, and CONR'$_2$; or wherein $R^8$ and $R^9$ together with the atom to which they are attached may form a group of =C(R'R'''), =S, =NR''';

A is selected from the group consisting of fused or non-fused $C_{6-18}$-aryl, $C_{5-18}$-heteroaryl, wherein one or more carbon atoms are replaced by heteroatoms selected from N, O, S and optionally including 1 to 3 ring members selected from the group consisting of C(=O), C(=S), $S(O)_m$ and SiR'$_2$ optionally substituted by one or more groups of $R^{10}$; with the proviso that heteroaryl does not represent thiazolyl or thiadiazolyl; wherein $R^{10}$ is selected from the group consisting of hydrogen, X, CN, SCN, SF$_5$, R'', OR'', NO$_2$, NR''$_2$, (C=O)—R'', $S(O)_nR''$, $OS(O)_nR''$, NR'$S(O)_nR''$, OSiR'$_3$, $C_{1-8}$-alkyl-$S(O)_nR''$, $C_{1-8}$-alkyl-(C=O)—R'', CR'=NR'', $S(O)_nC_{5-18}$-aryl, $S(O)_nC_{7-19}$-aralkyl, $S(O)C_{7-19}$-alkaryl, $C_{1-12}$-alkyl, $C_{2-12}$-alkenyl, $C_{2-12}$-alkynyl, $C_{1-12}$-haloalkyl, $C_{2-12}$-haloalkenyl, $C_{2-12}$-haloalkynyl, $C_{1-12}$-alkoxy, $C_{1-12}$-alkylthio, $C_{1-12}$-holoalkoxy, $C_{1-12}$-haloalkylthio, $C_{3-12}$-cycloalkyl, $C_{4-8}$-cycloalkenyl, $C_{5-8}$-cycloalkynyl, $C_{3-8}$-cycloalkyloxy, $C_{3-8}$-cycloalkylthio, $C_{7-19}$-aralkyl, $C_{7-19}$-alkaryl; bicyclic $C_{5-12}$-alkyl, $C_{7-12}$-alkenyl; where in the cyclic ring system one or more carbon atoms may be replaced by heteroatoms selected from the group consisting of N, O, and $S(O)_n$; and all of the groups mentioned above may be substituted by one or more groups selected from the group consisting of X, R', OR', SR', NR'$_2$, SiR'$_3$, COOR', CN, and CONR'$_2$;

and wherein each of $R^8$, $R^9$ and $R^{10}$ may optionally be substituted by one or more groups selected from the group consisting of X, R', OR', SR', NR'$_2$, SiR'$_3$, COOR', CN, and CONR'$_2$;

wherein

X represents halogen;

R' represents hydrogen, straight chain or branched chain $C_{1-12}$-alkyl or cyclic $C_{3-10}$-alkyl which are optionally substituted by one or more X;

R'' represents hydrogen; NR'$_2$, OR', straight chain or branched chain $C_{1-12}$-alkyl, $C_{1-12}$-haloalkyl, cyclic $C_{3-8}$-alkyl which are optionally substituted by one or more groups selected from the group consisting of X, R', OR', SR', NR'$_2$, SiR'$_3$, COOR', CN, and CONR'$_2$, $C_{5-18}$-aryl which is optionally substituted by one or more R';

R''' is selected from the groups consisting of hydrogen, R'', CN, OR', (C=O)—R', COOR', CONR'$_2$, straight chain or branched chain $C_{1-12}$-alkyl, $C_{2-12}$-alkenyl, $C_{2-12}$-alkynyl; cyclic $C_{3-8}$-alkyl, $C_{4-8}$-alkenyl, $C_{5-8}$-alkynyl; $C_{5-18}$-aryl, $C_{7-19}$-aralkyl, $C_{7-19}$-alkaryl; where in the cyclic ring system one or more carbon atoms may be replaced by heteroatoms selected from the group consisting of N, O, and $S(O)_n$; and all of the groups mentioned above may be substituted by one or more groups selected from the group consisting of X, R', OR', SR', NR'$_2$, SiR'$_3$, COOR', CN, and CONR'$_2$; or R' and R''' together with the atom to which they are attached or together with further atoms selected from the group consisting of N, O, and $S(O)_n$ may form a three to six membered ring, which for its part may be substituted by one or more X, R', OR', SR', NR'$_2$, SiR'$_3$, COOR', CN, and CONR'$_2$; wherein, m and n represent integers wherein n=0, 1 or 2; and m=1 or 2;

According to one other embodiment, compounds of general formula (Ia) further can be described as

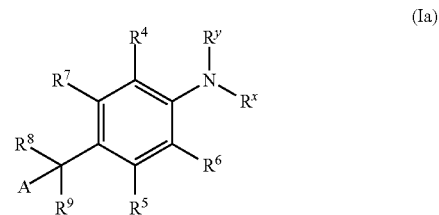

(Ia)

wherein $R^x$ and $R^y$ are independently selected from the group consisting of hydrogen, hydroxy, CN, NO$_2$, COOR', $S(O)_nR''$, OR', (C=O)—R'', $C_1$-$C_{12}$-alkyl, $C_{2-12}$-alkenyl, $C_{2-12}$-alkynyl, $C_{3-8}$-cycloalkyl, $C_{4-8}$-cycloalkenyl, $C_{5-8}$-cycloalkynyl, $C_{5-18}$-aryl, $C_{7-19}$-aralkyl, $C_{7-19}$-alkaryl; where in the cyclic ring system one or more carbon atoms may be replaced by heteroatoms selected from the group consisting of N, O, and $S(O)_n$; or $R^x$ and $R^y$ together with the atom to which they are attached or together with further atoms selected from the group consisting of C, N, O, S and optionally including 1 to 3 ring members selected from the group consisting of C(=O), C(=S), $S(O)_m$ and SiR'$_2$, may form a three to seven membered ring, which for its part may be substituted by one or more X, R', OR', SR', NR'$_2$, SiR'$_2$, COOR', CN, and CONR'$_2$;

and wherein all of the groups of $R^x$ and $R^y$ may optionally be substituted by one or more groups selected from the group consisting of X, R', OR', SR', NR'$_2$, SiR'$_3$, COOR', CN, and CONR'$_2$;

and all other substitutions A and $R^4$ to $R^{10}$ are as defined in one of the above embodiment.

In one another embodiment preferred substitution, $R^1$ of compound of general formula (I) are of hydrogen, $C_{1-6}$-alkyl, $C_{1-6}$-alkoxy, $C_{1-6}$-alkylthio, $C_{1-6}$-haloalkyl, $C_{3-8}$-cycloalkyl.

In one another embodiment more preferred substitution, $R^1$ of compound of general formula (I) is of hydrogen, $C_{1-6}$-alkyl.

In one another embodiment preferred substitution, $R^2$ and $R^3$ of compound of general formula (I) are $C_{1-6}$-alkyl, $C_{2-6}$-alkenyl, $C_{2-6}$-alkynyl, $C_{1-6}$-alkoxy, $C_{1-6}$-alkylthio, $C_{1-6}$-haloalkyl, $C_{3-8}$-cycloalkyl.

In one another embodiment $R^1$ and $R^2$, $R^2$ and $R^3$ or $R^1$ and $R^3$ together with the atoms to which they are attached or together with further atoms selected from the group consisting of C, N, O, S and optionally including 1 to 3 ring members selected from the group consisting of C(=O), C(=S), $S(O)_m$ and SiR'$_2$ may form a four to seven membered ring, which for its part may be substituted by one or more X, R', OR', SR' and CN.

In one another embodiment preferred ring formation structures with the substitutions $R^1$ and $R^2$, $R^2$ and $R^3$ or $R^1$ and $R^3$ together with the atoms to which they are attached are azetidine, pyrrolidine, imidazolidine, oxazolidine, piperidine, morpholine, thiomorpholine, piperazine, 1-methylpiperazine, 1-methylpyrrolidine, 1-methylpiperidine, 3-methyl-1,3-thiazinane.

In one another embodiment preferred substitution, $R^4$ and $R^5$ of compound of general formula (I) are of X, CN, $S(O)_nR''$, NR'R'', (C=O)—R'', CR'=NR'', $C_{1-6}$-alkyl, $C_{2-6}$-alkenyl, $C_{1-6}$-haloalkyl, $C_{1-6}$-alkoxy, $C_{1-6}$-haloalkylthio, $C_{3-8}$-cycloalkyl, $C_{3-8}$-cycloalkylthio.

In one another embodiment preferred substitution, $R^6$ and $R^7$ of compound of general formula (I) are of hydrogen, X, CN, $S(O)_nR''$, NR'R'', (C=O)—R'', CR'=NR'', $C_{1-6}$-alkyl, $C_{2-6}$-alkenyl, $C_{1-6}$-haloalkyl, $C_{1-6}$-alkoxy, $C_{1-6}$-haloalkylthio, $C_{3-8}$-cycloalkyl, $C_{3-8}$-cycloalkylthio.

$R^4$ and $R^7$ or $R^5$ and $R^6$ together with the atom to which they are attached or together with further atoms selected from the group consisting of C, N, O, S and optionally including 1 to 3 ring members selected from the group consisting of C(=O), C(=S), $S(O)_m$ and $SiR'_2$ may form a four to seven membered ring, which for its part may be substituted by one or more X, R', OR', SR', $NR'_2$, $SiR'_3$, COOR', CN, and $CONR'_2$; and wherein each of $R^4$, $R^5$, $R^6$ and $R^7$ may optionally be substituted by one or more groups selected from the group consisting of X, R', OR', SR', $NR'_2$, $SiR'_3$, COOR', CN, and $CONR'_2$.

In one another embodiment preferred substitution, $R^8$ and $R^9$ on compound of general formula (I) are hydrogen, X, CN, $S(O)_nR''$, NR'R'', (C=O)—R'', CR'=NR'', $C_{1-6}$-alkyl, $C_{1-6}$-haloalkyl, $C_{1-6}$-alkoxy, $C_{1-6}$-haloalkoxy, $C_{1-4}$-alkylthio, $C_{1-6}$-haloalkylthio, $C_{3-8}$-cycloalkyl, $C_{3-8}$-cycloalkoxy, $C_{3-8}$-cycloalkylthio.

In one another embodiment $R^8$ and $R^9$ together with the atom to which they are attached or together with further atoms selected from the group consisting of C, N, O, S may form a three to six membered ring, which for its part may be substituted by one or more X, R', OR', SR', $NR'_2$, $SiR'_3$, COOR', CN, and $CONR'_2$.

In one another embodiment preferred substitution, $R^{10}$ on compound of general formula (I) are hydrogen X, CN, SCN, $SF_5$, R'', OR'', $NO_2$, $NR''_2$, $SiR'_3$, (C=O)—R'', $S(O)_nR''$, $C_{1-8}$-alkyl-$S(O)_nR''$, $C_{1-6}$-alkyl-(C=O)—R'', CR'=NR'', $C_{2-6}$-alkenyl, $C_{2-6}$-alkynyl, $C_{1-6}$-haloalkyl, $C_{2-6}$-haloalkenyl, $C_{1-12}$-alkoxy, $C_{1-12}$-alkylthio, $C_{1-12}$-holoalkoxy, $C_{1-12}$-haloalkylthio, $C_{3-8}$-cycloalkyl, $C_{4-8}$-cycloalkenyl, $C_{3-8}$-cycloalkyloxy, $C_{3-8}$-cycloalkylthio.

In one another embodiment two $R^{10}$ together with the atom to which they are attached or together with further atoms selected from the group consisting of C, N, O, S and optionally including 1 to 3 ring members selected from the group consisting of C(=O), C(=S), $S(O)_m$ and $SiR'_2$ may form a four to ten membered ring, which for its part may be substituted by one or more X, R', OR', SR', $NR'_2$, $SiR'_3$, COOR', CN, and $CONR'_2$.

In one another embodiment preferred A is phenyl, napthalenyl, furyl, thienyl, pyrrolyl, isoxazolyl, isothiazolyl, pyrazolyl, oxazolyl, imidazolyl, oxadiazolyl, triazolyl, pyridinyl, pyridazinyl, pyrimidinyl, pyrazinyl, triazinyl, indolyl, benzimidazolyl, indazolyl, benzofuranyl, benzothiophenyl, benzothiazolyl, benzoxazolyl, quinolinyl, isoquinolinyl, quinazolinyl, cinnolyl; substituted with one or more $R^{10}$.

In one another embodiment more preferred A is phenyl, napthalenyl, thienyl, isothiazolyl, pyridinyl, pyridazinyl, pyrimidinyl, pyrazinyl; substituted with one or more $R^{10}$.

In one another embodiment wherein $R^1$ to $R^{10}$ may further optionally substituted by one or more groups selected from the group consisting of X, R'', OR', SR', $NR'_2$, $SiR'_3$, COOR', CN, and $CONR'_2$;

In one another embodiment preferred compound of general formula (I) are

N'-(4-benzyl-2,5-dimethylphenyl)-N-ethyl-N-methylformimidamide;

N-ethyl-N'-(4-(methoxy(phenyl)methyl)-2,5-dimethylphenyl)-N-methylformimidamide;

N'-(4-(3,5-dichlorobenzyl)-2,5-dimethylphenyl)-N-ethyl-N-methylformimidamide;

N'-(4-(4-bromobenzyl)-2,5-dimethylphenyl)-N-ethyl-N-methylformimidamide;

N'-(4-(3,4-dichlorobenzyl)-2,5-dimethylphenyl)-N-ethyl-N-methylformimidamide;

N'-(2,5-dimethyl-4-(3-methylbenzyl)phenyl)-N-ethyl-N-methylformimidamide;

N'-(4-(4-chlorobenzyl)-2,5-dimethylphenyl)-N-ethyl-N-methylformimidamide;

N'-(2,5-dimethyl-4-(4-(methylthio)benzyl)phenyl)-N-ethyl-N-methylformimidamide;

N'-(2,5-dimethyl-4-(4-methylbenzyl)phenyl)-N-ethyl-N-methylformimidamide;

N'-(2-bromo-4-(4-bromobenzyl)-3,6-dimethylphenyl)-N-ethyl-N-methylformimidamide;

N'-(4-(3-chlorobenzyl)-2,5-dimethylphenyl)-N-ethyl-N-methylformimidamide;

N'-(2,5-dimethyl-4-(4-(methylsulfonyl)benzyl)phenyl)-N-ethyl-N-methylformimidamide;

N'-(4-(3-bromobenzyl)-2-chloro-5-methylphenyl)-N-ethyl-N-methylformimidamide;

N'-(4-(3-bromobenzyl)-2,5-dimethylphenyl)-N-ethyl-N-methylformimidamide;

N-ethyl-N'-(4-(2-fluorobenzyl)-2,5-dimethylphenyl)-N-methylformimidamide;

N'-(2-chloro-4-(2-fluorobenzyl)-5-methylphenyl)-N-ethyl-N-methylformimidamide;

N'-(2-chloro-4-(2-chlorobenzyl)-5-methylphenyl)-N-ethyl-N-methylformimidamide;

N'-(4-(2-chlorobenzyl)-2,5-dimethylphenyl)-N-ethyl-N-methylformimidamide;

N-(2,5-dimethyl-4-(4-(methylsulfinyl)benzyl)phenyl)-N-ethyl-N-methylformimidamide;

N'-(2-chloro-4-(3,4-dichlorobenzyl)-5-methylphenyl)-N-ethyl-N-methylformimidamide;

N'-(2-chloro-4-(3,5-dichlorobenzyl)-5-methylphenyl)-N-ethyl-N-methylformimidamide;

N'-(4-(4-bromobenzyl)-2-chloro-5-methylphenyl)-N-ethyl-N-methylformimidamide;

N'-(2,5-dimethyl-4-(2-(methylthio)benzyl)phenyl)-N-ethyl-N-methylformimidamide;

N'-(2,5-dimethyl-4-(2-(methylsulfinyl)benzyl)phenyl)-N-ethyl-N-methylformimidamide;

N'-(2,5-dimethyl-4-(2-(methylsulfonyl)benzyl)phenyl)-N-ethyl-N-methylformimidamide;

N'-(4-(2,5-dimethylbenzyl)-2,5-dimethylphenyl)-N-ethyl-N-methylformimidamide;

N'-(4-(3-bromo-2-fluorobenzyl)-2,5-dimethylphenyl)-N-ethyl-N-methylformimidamide;

N'-(4-(3-chloro-4-fluorobenzyl)-2,5-dimethylphenyl)-N-ethyl-N-methylformimidamide;

N-ethyl-N'-(4-(3-fluorobenzyl)-2,5-dimethylphenyl)-N-methylformimidamide;

N'-(2-chloro-4-(3-fluorobenzyl)-5-methylphenyl)-N-ethyl-N-methylformimidamide;

N'-(2,5-dimethyl-4-((Z)-(methyl imino)(phenyl)methyl)phenyl)-N-ethyl-N-methylformimidamide;
N'-(2,5-dimethyl-4-(2-methylbenzyl)phenyl)-N-ethyl-N-methylformimidamide;
N'-(2,5-dimethyl-4-(2-phenyl-1,3-dithiolan-2-yl)phenyl)-N-ethyl-N-methylformimidamide;
N-(4-(3-chloro-4-fluorobenzyl)-2,5-dimethylphenyl)-1-morpholinomethanimine;
N-(4-(3-chloro-4-fluorobenzyl)-2,5-dimethylphenyl)-1-(piperidin-1-yl)methanimine;
N-(4-(3-bromo-2-fluorobenzyl)-2,5-dimethylphenyl)-1-morpholinomethanimine;
N-(4-(3-bromo-2-fluorobenzyl)-2,5-dimethylphenyl)-1-(piperidin-1-yl)methanimine;
N-(2-chloro-4-(3-fluorobenzyl)-5-methylphenyl)-1-morpholinomethanimine;
N-(2-chloro-4-(3-fluorobenzyl)-5-methylphenyl)-1-(piperidin-1-yl)methanimine;
N-(2-chloro-4-(2-chlorobenzyl)-5-methylphenyl)-1-morpholinomethanimine;
N'-(4-(3-bromo-2-fluorobenzyl)-2,5-dimethylphenyl)-N-methylformimidamide;
N'-(2-chloro-4-(3-fluorobenzyl)-5-methylphenyl)-N-methylformimidamide;
N'-(2-chloro-5-methyl-4-(3-methylbenzyl)phenyl)-N-ethyl-N-methylformimidamide;
N'-(2-chloro-5-methyl-4-(4-methylbenzyl)phenyl)-N-ethyl-N-methylformimidamide;
N-ethyl-N'-(4-(3-methoxybenzyl)-2,5-dimethylphenyl)-N-methylformimidamide;
N'-(2,5-dimethyl-4-(3-(trifluoromethyl)benzyl)phenyl)-N-ethyl-N-methylformimidamide;
N'-(4-(3-cyanobenzyl)-2,5-dimethylphenyl)-N-ethyl-N-methylformimidamide;
N'-(4-(4-cyanobenzyl)-2,5-dimethylphenyl)-N-ethyl-N-methylformimidamide;
N'-(2,5-dimethyl-4-(3-nitrobenzyl)phenyl)-N-ethyl-N-methylformimidamide;
N'-(2,5-dimethyl-4-(2-nitrobenzyl)phenyl)-N-ethyl-N-methylformimidamide;
N'-(2,5-dimethyl-4-(3-(trifluoromethoxy)benzyl)phenyl)-N-ethyl-N-methylformimidamide;
N-ethyl-N'-(4-(3-fluoro-5-(trifluoromethyl)benzyl)-2,5-dimethylphenyl)-N-methylformimidamide;
N'-(2,5-dimethyl-4-(2-methyl-5-(trifluoromethyl)benzyl)phenyl)-N-ethyl-N-methylformimidamide;
N-ethyl-N'-(4-(4-methoxybenzyl)-2,5-dimethylphenyl)-N-methylformimidamide;
N-(4-(2-fluorobenzyl)-2,5-dimethylphenyl)-1-morpholinomethanimine;
N-(4-(4-fluorobenzyl)-2,5-dimethylphenyl)-1-morpholinomethanimine;
N-ethyl-N'-(4-(4-fluorobenzyl)-2,5-dimethylphenyl)-N-methylformimidamide;
N-(4-(2-fluorobenzyl)-2,5-dimethylphenyl)-1-(piperidin-1-yl)methanimine;
N-(4-(2-chlorobenzyl)-2,5-dimethylphenyl)-1-(piperidin-1-yl)methanimine;
N-(4-(4-fluorobenzyl)-2,5-dimethylphenyl)-1-(piperidin-1-yl)methanimine;
N'-(4-(2-fluorobenzyl)-2,5-dimethylphenyl)-N-methoxy-N-methylformimidamide
N'-(4-(2-chlorobenzyl)-2,5-dimethylphenyl)-N-methoxy-N-methylformimidamide
N-(4-(2-chlorobenzyl)-2,5-dimethylphenyl)-1-morpholinomethanimine;
N-cyano-N-(4-(2-fluorobenzyl)-2,5-dimethylphenyl)formimidamide;
N'-(4-(2-chlorobenzyl)-2,5-dimethylphenyl)-N-cyanoformimidamide;
N'-(4-(2-fluorobenzyl)-2,5-dimethylphenyl)-N-isopropylformimidamide;
N'-(4-(2-chlorobenzyl)-2,5-dimethylphenyl)-N-isopropylformimidamide;
N'-(2-chloro-4-(4-cyanobenzyl)-5-methylphenyl)-N-ethyl-N-methylformimidamide;
N'-(2-chloro-4-(4-methoxybenzyl)-5-methylphenyl)-N-ethyl-N-methylformimidamide;
N'-(2-chloro-4-(3-methoxybenzyl)-5-methylphenyl)-N-ethyl-N-methylformimidamide;
N'-(2-chloro-5-methyl-4-(3-nitrobenzyl)phenyl)-N-ethyl-N-methylformimidamide;
N'-(2-chloro-4-(3-cyanobenzyl)-5-methylphenyl)-N-ethyl-N-methylformimidamide;
N'-(4-(difluoro(phenyl)methyl)-2-iodo-3,6-dimethylphenyl)-N-ethyl-N-methylformimidamide;
N'-(4-benzyl-2-chloro-5-methylphenyl)-N-ethyl-N-methylformimidamide;
N'-(2-chloro-5-methyl-4-(2-nitrobenzyl)phenyl)-N-ethyl-N-methylformimidamide;
N'-(2-chloro-4-(4-fluorobenzyl)-5-methylphenyl)-N-ethyl-N-methylformimidamide;
N'-(2-chloro-5-methyl-4-(4-((trifluoromethyl)thio)benzyl)phenyl)-N-ethyl-N-methylformimidamide;
N'-(2-chloro-4-(3-chlorobenzyl)-5-methylphenyl)-N-ethyl-N-methylformimidamide;
N'-(2-chloro-4-(4-chlorobenzyl)-5-methylphenyl)-N-ethyl-N-methylformimidamide;
N'-(2-chloro-5-methyl-4-(3-(trifluoromethyl)benzyl)phenyl)-N-ethyl-N-methylformimidamide;
N'-(4-(2-fluorobenzyl)-2,5-dimethylphenyl)-N-isopropyl-N-methylformimidamide;
N'-(4-(2-chlorobenzyl)-2,5-dimethylphenyl)-N-isopropyl-N-methylformimidamide;
N-allyl-N'-(4-(2-fluorobenzyl)-2,5-dimethylphenyl)-N-methylformimidamide;
N-allyl-N'-(4-(2-chlorobenzyl)-2,5-dimethylphenyl)-N-methylformimidamide;
N-(4-(2-fluorobenzyl)-2,5-dimethylphenyl)-1-thiomorpholinomethanimine;
N-(4-(2-chlorobenzyl)-2,5-dimethylphenyl)-1-thiomorpholinomethanimine;
N-(cyclopropylmethyl)-N-(4-(2-fluorobenzyl)-2,5-dimethylphenyl)-N-methylformimidamide;
N-(cyclopropylmethyl)-N'-(4-(2-fluorobenzyl)-2,5-dimethylphenyl)-N-isopropylformimidamide;
N'-(4-(2-chlorobenzyl)-2,5-dimethylphenyl)-N-(cyclopropylmethyl)-N-isopropylformimidamide;
N'-(4-(2-chlorobenzyl)-2,5-dimethylphenyl)-N-cyano-N-(cyanomethyl)formimidamide;
N-cyano-N-(cyanomethyl)-N'-(4-(2-fluorobenzyl)-2,5-dimethylphenyl)formimidamide;
N'-(2,5-dimethyl-4-(4-((trifluoromethyl)thio)benzyl)phenyl)-N-ethyl-N-methylformimidamide;
N'-(2,5-dimethyl-4-(2-(trifluoromethyl)benzyl)phenyl)-N-ethyl-N-methylformimidamide;
N'-(2,5-dimethyl-4-(4-(trifluoromethyl)benzyl)phenyl)-N-ethyl-N-methylformimidamide;
N'-(2-chloro-4-(4-chloro-3-fluorobenzyl)-5-methylphenyl)-N-ethyl-N-methylformimidamide;
N'-(4-(3,5-bis(trifluoromethyl)benzyl)-2-chloro-5-methylphenyl)-N-ethyl-N-methylformimidamide;

N'-(2,5-dimethyl-4-(4-(trifluoromethyl)benzyl)phenyl)-N-ethyl-N-methylformimidamide;
N'-(2,5-dimethyl-4-(4-(trifluoromethyl)benzyl)phenyl)-N-ethyl-N-methylformimidamide;
N'-(2-chloro-4-(2-chloro-4-fluorobenzyl)-5-methylphenyl)-N-ethyl-N-methylformimidamide;
N'-(2-chloro-4-(2-cyanobenzyl)-5-methylphenyl)-N-ethyl-N-methylformimidamide;
N'-(2-chloro-5-methyl-4-(4-(trifluoromethyl)benzyl)phenyl)-N-ethyl-N-methylformimidamide;
N'-(2-chloro-5-methyl-4-(2-(trifluoromethoxy)benzyl)phenyl)-N-ethyl-N-methylformimidamide;
N'-(2-chloro-5-methyl-4-(2-(trifluoromethyl)benzyl)phenyl)-N-ethyl-N-methylformimidamide;
N'-(2,5-dimethyl-4-(4-methyl-3-(trifluoromethyl)benzyl)phenyl)-N-ethyl-N-methylformimidamide;
N'-(4-(4-chloro-3-fluorobenzyl)-2,5-dimethylphenyl)-N-ethyl-N-methylformimidamide;
N'-(4-(3,5-bis(trifluoromethyl)benzyl)-2,5-dimethylphenyl)-N-ethyl-N-methylformimidamide;
N'-(4-(3-(1-cyanoethyl)benzyl)-2,5-dimethylphenyl)-N-ethyl-N-methylformimidamide;
N'-(4-(4-chloro-3-methylbenzyl)-2,5-dimethylphenyl)-N-ethyl-N-methylformimidamide;
N-ethyl-N'-(4-(4-fluoro-3-methylbenzyl)-2,5-dimethylphenyl)-N-methylformimidamide;
N'-(4-(2-chloro-4-fluorobenzyl)-2,5-dimethylphenyl)-N-ethyl-N-methylformimidamide;
N'-(4-(3-(dimethylamino)benzyl)-2,5-dimethylphenyl)-N-ethyl-N-methylformimidamide;
N'-(4-(2,3-dimethylbenzyl)-2,5-dimethylphenyl)-N-ethyl-N-methylformimidamide;
N'-(4-(3,4-dimethylbenzyl)-2,5-dimethylphenyl)-N-ethyl-N-methylformimidamide;
N'-(4-(3,5-dimethylbenzyl)-2,5-dimethylphenyl)-N-ethyl-N-methylformimidamide;
N'-(4-(2-cyanobenzyl)-2,5-dimethylphenyl)-N-ethyl-N-methylformimidamide;
N'-(2,5-dimethyl-4-(2-(trifluoromethoxy)benzyl)phenyl)-N-ethyl-N-methylformimidamide;
N'-(2,5-dimethyl-4-(4-(trifluoromethoxy)benzyl)phenyl)-N-ethyl-N-methylformimidamide;
N'-(4-(3-chloro-2-fluorobenzyl)-2,5-dimethylphenyl)-N-ethyl-N-methylformimidamide;
N'-(2-chloro-4-(4-fluoro-3-methylbenzyl)-5-methylphenyl)-N-ethyl-N-methylformimidamide;
N'-(2-chloro-4-(4-chloro-3-methylbenzyl)-5-methylphenyl)-N-ethyl-N-methylformimidamide;
N'-(2-chloro-5-methyl-4-(4-(trifluoromethoxy)benzyl)phenyl)-N-ethyl-N-methylformimidamide;
N'-(2-chloro-5-methyl-4-(2-methylbenzyl)phenyl)-N-ethyl-N-methylformimidamide;
N'-(2-chloro-4-(3-chloro-2-fluorobenzyl)-5-methylphenyl)-N-ethyl-N-methylformimidamide;
N'-(2-chloro-5-methyl-4-(3-(trifluoromethoxy)benzyl)phenyl)-N-ethyl-N-methylformimidamide;
N'-(2-chloro-4-(2-chloro-3-fluorobenzyl)-5-methylphenyl)-N-ethyl-N-methylformimidamide;
N'-(2-chloro-4-(3-chloro-2-fluoro-5-(trifluoromethyl)benzyl)-5-methylphenyl)-N-ethyl-N-methylformimidamide;
N'-(4-(cyano(phenyl)methyl)-2,5-dimethylphenyl)-N-ethyl-N-methylformimidamide;
N'-(2-chloro-4-(2,3-dichlorobenzyl)-5-methylphenyl)-N-ethyl-N-methylformimidamide;
N'-(2-chloro-4-(3,5-difluorobenzyl)-5-methylphenyl)-N-ethyl-N-methylformimidamide;
N'-(2-chloro-4-(3,5-dimethylbenzyl)-5-methylphenyl)-N-ethyl-N-methylformimidamide;
N'-(4-(2-chloro-3-fluorobenzyl)-2,5-dimethylphenyl)-N-ethyl-N-methylformimidamide;
N'-(4-(3,5-difluorobenzyl)-2,5-dimethylphenyl)-N-ethyl-N-methylformimidamide;
N'-(4-(2,3-dichlorobenzyl)-2,5-dimethylphenyl)-N-ethyl-N-methylformimidamide;
N'-(4-(3-chloro-2-fluoro-5-(trifluoromethyl)benzyl)-2,5-dimethylphenyl)-N-ethyl-N-methylformimidamide;
N'-(4-(3-chloro-5-fluorobenzyl)-2,5-dimethylphenyl)-N-ethyl-N-methylformimidamide;
N'-(2-chloro-4-(4-chloro-3-(trifluoromethyl)benzyl)-5-methylphenyl)-N-ethyl-N-methylformimidamide;
N'-(2-chloro-4-(3-fluoro-4-(trifluoromethyl)benzyl)-5-methylphenyl)-N-ethyl-N-methylformimidamide;
N'-(2-chloro-4-(3,4-difluorobenzyl)-5-methylphenyl)-N-ethyl-N-methylformimidamide;
N'-(2-chloro-4-(3-fluoro-4-methylbenzyl)-5-methylphenyl)-N-ethyl-N-methylformimidamide;
N'-(2-chloro-4-(3-fluoro-5-methylbenzyl)-5-methylphenyl)-N-ethyl-N-methylformimidamide;
N'-(2,5-dichloro-4-(3-methylbenzyl)phenyl)-N-ethyl-N-methylformimidamide;
N'-(4-(4-chloro-3-(trifluoromethyl)benzyl)-2,5-dimethylphenyl)-N-ethyl-N-methylformimidamide;
N'-(4-(2-chloro-5-fluorobenzyl)-2,5-dimethylphenyl)-N-ethyl-N-methylformimidamide;
N-ethyl-N'-(4-(3-fluoro-4-methylbenzyl)-2,5-dimethylphenyl)-N-methylformimidamide;
N'-(4-(4-chloro-3-(trifluoromethoxy)benzyl)-2,5-dimethylphenyl)-N-ethyl-N-methylformimidamide;
N'-(4-(3,4-difluorobenzyl)-2,5-dimethylphenyl)-N-ethyl-N-methylformimidamide;
N'-(2,5-dichloro-4-(4-methylbenzyl)phenyl)-N-ethyl-N-methylformimidamide;
N'-(2,5-dichloro-4-(3-fluorobenzyl)phenyl)-N-ethyl-N-methylformimidamide;
N'-(2,5-dichloro-4-(2-fluorobenzyl)phenyl)-N-ethyl-N-methylformimidamide;
N'-(2,5-dichloro-4-(2-chlorobenzyl)phenyl)-N-ethyl-N-methylformimidamide;
N'-(2,5-dichloro-4-(2-methylbenzyl)phenyl)-N-ethyl-N-methylformimidamide;
N'-(2,5-dichloro-4-(3-chlorobenzyl)phenyl)-N-ethyl-N-methylformimidamide;
N'-(4-(2,6-dichlorobenzyl)-2,5-dimethylphenyl)-N-ethyl-N-methylformimidamide;
N'-(4-(2-bromobenzyl)-2,5-dimethylphenyl)-N-ethyl-N-methylformimidamide;
N'-(4-(2-chloro-6-fluorobenzyl)-2,5-dimethylphenyl)-N-ethyl-N-methylformimidamide;
N-ethyl-N'-(4-(3-fluoro-5-methoxybenzyl)-2,5-dimethylphenyl)-N-methylformimidamide;
N-ethyl-N'-(4-(5-fluoro-2-methylbenzyl)-2,5-dimethylphenyl)-N-methylformimidamide;
N-ethyl-N'-(4-(3-fluoro-4-(trifluoromethyl)benzyl)-2,5-dimethylphenyl)-N-methylformimidamide;
N'-(4-(2-chloro-5-(trifluoromethyl)benzyl)-2,5-dimethylphenyl)-N-ethyl-N-methylformimidamide;
N'-(4-(2,5-dichlorobenzyl)-2,5-dimethylphenyl)-N-ethyl-N-methylformimidamide;
N'-(4-(2,4-difluorobenzyl)-2,5-dimethylphenyl)-N-ethyl-N-methylformimidamide;
N'-(4-(2,4-dichlorobenzyl)-2,5-dimethylphenyl)-N-ethyl-N-methylformimidamide;

N-ethyl-N'(4-(2-fluorobenzyl)phenyl)-N-methylformimidamide;

N'-(4-(2-chlorobenzyl)phenyl)-N-ethyl-N-methylformimidamide;

N'-(2-chloro-4-(5-fluoro-2-methylbenzyl)-5-methylphenyl)-N-ethyl-N-methylformimidamide;

N'-(2-chloro-4-(2,5-dichlorobenzyl)-5-methylphenyl)-N-ethyl-N-methylformimidamide;

N'-(2-chloro-4-(4-fluoro-2-methylbenzyl)-5-methylphenyl)-N-ethyl-N-methylformimidamide;

N'-(2-chloro-4-(2-chloro-5-(trifluoromethyl)benzyl)-5-methylphenyl)-N-ethyl-N-methylformimidamide;

N'-(2-chloro-4-(3-fluoro-5-methoxybenzyl)-5-methylphenyl)-N-ethyl-N-methylformimidamide;

N-(2-chloro-4-(2,3-dimethylbenzyl)-5-methylphenyl)-N-ethyl-N-methylformimidamide;

N-ethyl-N'-(5-fluoro-2-methyl-4-(3-methylbenzyl)phenyl)-N-methylformimidamide;

N-ethyl-N'-(5-fluoro-4-(3-fluorobenzyl)-2-methylphenyl)-N-methylformimidamide;

N'-(4-(3-chlorobenzyl)-5-fluoro-2-methylphenyl)-N-ethyl-N-methylformimidamide;

N'-(4-(2-chlorobenzyl)-5-fluoro-2-methylphenyl)-N-ethyl-N-methylformimidamide;

N-ethyl-N'-(5-fluoro-2-methyl-4-(4-methylbenzyl)phenyl)-N-methylformimidamide;

N'-(2-chloro-4-(3-chloro-5-fluorobenzyl)-5-methylphenyl)-N-ethyl-N-methylformimidamide;

N'-(2-chloro-4-(4-chloro-3-(trifluoromethoxy)benzyl)-5-methylphenyl)-N-ethyl-N-methylformimidamide;

N'-(2-chloro-4-(2-chloro-5-fluorobenzyl)-5-methylphenyl)-N-ethyl-N-methylformimidamide;

N'-(2-chloro-4-(2,4-dichlorobenzyl)-5-methylphenyl)-N-ethyl-N-methylformimidamide;

N'-(2-chloro-4-(2,4-difluorobenzyl)-5-methylphenyl)-N-ethyl-N-methylformimidamide;

N'-(2-chloro-4-(4-fluoro-3-(trifluoromethyl)benzyl)-5-methylphenyl)-N-ethyl-N-methylformimidamide;

N'-(2,5-dichloro-4-(3-(trifluoromethoxy)benzyl)phenyl)-N-ethyl-N-methylformimidamide;

N'-(2,5-dichloro-4-(3-(trifluoromethyl)benzyl)phenyl)-N-ethyl-N-methylformimidamide;

N'-(2-chloro-4-(2-chloro-6-fluorobenzyl)-5-methylphenyl)-N-ethyl-N-methylformimidamide;

N-ethyl-N'-(5-fluoro-4-(2-fluorobenzyl)-2-methylphenyl)-N-methylformimidamide;

N-ethyl-N'-(5-fluoro-2-methyl-4-(2-methylbenzyl)phenyl)-N-methylformimidamide;

N'-(2-chloro-4-(cyano(4-(trifluoromethyl)phenyl)methyl)-5-methylphenyl)-N-ethyl-N-methylformimidamide;

N'-(2-chloro-4-(cyano(3-(trifluoromethyl)phenyl)methyl)-5-methylphenyl)-N-ethyl-N-methylformimidamide;

N'-(2-chloro-4-(cyano(4-fluorophenyl)methyl)-5-methylphenyl)-N-ethyl-N-methylformimidamide;

N'-(2-chloro-4-((3-chloro-4-fluorophenyl)(cyano)methyl)-5-methylphenyl)-N-ethyl-N-methylformimidamide;

N'-(2-chloro-4-(cyano(p-tolyl)methyl)-5-methylphenyl)-N-ethyl-N-methylformimidamide;

N'-(2-chloro-4-((2-chlorophenyl)(cyano)methyl)-5-methylphenyl)-N-ethyl-N-methylformimidamide;

N'-(2-chloro-4-((4-chlorophenyl)(cyano)methyl)-5-methylphenyl)-N-ethyl-N-methylformimidamide;

N'-(2-chloro-4-(cyano(3-fluorophenyl)methyl)-5-methylphenyl)-N-ethyl-N-methylformimidamide;

N'-(2-chloro-4-(2,6-dichlorobenzyl)-5-methylphenyl)-N-ethyl-N-methylformimidamide;

N-ethyl-N'-(5-fluoro-2-methyl-4-(3-(trifluoromethyl)benzyl)phenyl)-N-methylformimidamide;

N'-(2-cyclopropyl-4-(3-fluorobenzyl)-5-methylphenyl)-N-ethyl-N-methylformimidamide;

N'-(2-cyclopropyl-5-methyl-4-(3-methylbenzyl)phenyl)-N-ethyl-N-methylformimidamide;

N'-(4-(3-chlorobenzyl)-2-cyclopropyl-5-methylphenyl)-N-ethyl-N-methylformimidamide;

N-ethyl-N'-(4-(3-fluoro-5-methylbenzyl)-2,5-dimethylphenyl)-N-methylformimidamide;

N-ethyl-N'-(4-(2-fluoro-4-(trifluoromethyl)benzyl)-2,5-dimethylphenyl)-N-methylformimidamide;

N'-(2,5-dimethyl-4-(pyridin-2-ylmethyl)phenyl)-N-ethyl-N-methylformimidamide;

N'-(2-chloro-4-(2,6-difluorobenzyl)-5-methylphenyl)-N-ethyl-N-methylformimidamide;

N'-(2-chloro-5-methyl-4-(pyridin-3-ylmethyl)phenyl)-N-ethyl-N-methylformimidamide;

N-ethyl-N'-(2-fluoro-5-methyl-4-(3-(trifluoromethyl)benzyl)phenyl)-N-methylformimidamide;

N-ethyl-N'-(2-fluoro-5-methyl-4-(3-(trifluoromethoxy)benzyl)phenyl)-N-methylformimidamide;

N-ethyl-N'-(2-fluoro-5-methyl-4-(2-(trifluoromethoxy)benzyl)phenyl)-N-methylformimidamide;

N'-(4-(3-chlorobenzyl)-2-fluoro-5-methylphenyl)-N-ethyl-N-methylformimidamide;

N-ethyl-N'-(2-fluoro-4-(3-fluorobenzyl)-5-methylphenyl)-N-methylformimidamide;

N-ethyl-N'-(2-fluoro-5-methyl-4-(3-methylbenzyl)phenyl)-N-methylformimidamide;

N-ethyl-N-(2-fluoro-5-methyl-4-(4-methylbenzyl)phenyl)-N-methylformimidamide;

N-ethyl-N'-(2-fluoro-5-methyl-4-(2-methylbenzyl)phenyl)-N-methylformimidamide;

N'-(4-(2-chlorobenzyl)-2-fluoro-5-methylphenyl)-N-ethyl-N-methylformimidamide;

N-ethyl-N'-(2-fluoro-4-(2-fluorobenzyl)-5-methylphenyl)-N-methylformimidamide;

N'-(2,5-dimethyl-4-((Z)-(methylimino)(o-tolyl)methyl)phenyl)-N-ethyl-N-methylformimidamide;

N-ethyl-N'-(4-(3-fluorobenzyl)-5-methyl-2-(methylsulfonyl)phenyl)-N-methylformimidamide;

methyl N-(2-bromo-4-(4-bromobenzyl)-3,6-dimethylphenyl)formimidate

N'-(4-(3-chlorobenzyl)-5-methyl-2-(methylsulfonyl)phenyl)-N-ethyl-N-methylformimidamide;

N'-(2-bromo-3,6-dimethyl-4-(2-methylbenzyl)phenyl)-N-ethyl-N-methylformimidamide;

N'-(2-chloro-4-(2-fluoro-6-(trifluoromethyl)benzyl)-5-methylphenyl)-N-ethyl-N-methylformimidamide;

N'-(2-cyclopropyl-4-(2-fluorobenzyl)-5-methylphenyl)-N-ethyl-N-methylformimidamide;

N'-(2-cyclopropyl-5-methyl-4-(4-methylbenzyl)phenyl)-N-ethyl-N-methylformimidamide;

N'-(4-(2-chlorobenzyl)-2-cyclopropyl-5-methylphenyl)-N-ethyl-N-methylformimidamide;

N'-(2-cyclopropyl-5-methyl-4-(3-(trifluoromethoxy)benzyl)phenyl)-N-ethyl-N-methylformimidamide;

N-ethyl-N'-(2-fluoro-4-(4-methylbenzyl)-5-(trifluoromethyl)phenyl)-N-methylformimidamide;

N'-(4-(2-chlorobenzyl)-2-fluoro-5-(trifluoromethyl)phenyl)-N-ethyl-N-methylformimidamide;

N-ethyl-N'-(2-fluoro-4-(2-fluorobenzyl)-5-(trifluoromethyl)phenyl)-N-methylformimidamide;

N-ethyl-N'-(2-fluoro-4-(2-methylbenzyl)-5-(trifluoromethyl)phenyl)-N-methylformimidamide;

N'-(4-(3-chlorobenzyl)-2-fluoro-5-(trifluoromethyl)phenyl)-N-ethyl-N-methylformimidamide;
N-ethyl-N'-(2-fluoro-4-(3-fluorobenzyl)-5-(trifluoromethyl)phenyl)-N-methylformimidamide;
N-ethyl-N'-(2-fluoro-4-(3-methylbenzyl)-5-(trifluoromethyl)phenyl)-N-methylformimidamide;
N-ethyl-N'-(2-fluoro-5-(trifluoromethyl)-4-(3-(trifluoromethyl)benzyl)phenyl)-N-methylformimidamide;
N-ethyl-N'-(2-fluoro-4-(3-(trifluoromethoxy)benzyl)-5-(trifluoromethyl)phenyl)-N-methylformimidamide;
N-ethyl-N-methyl-N'-(5-methyl-4-(2-methylbenzyl)-2-(methylsulfonyl)phenyl)formimidamide;
N-ethyl-N-methyl-N'-(5-methyl-4-(4-methylbenzyl)-2-(methylsulfonyl)phenyl)formimidamide;
N'-(5-chloro-4-(cyano(5-fluoro-2-methylphenyl)methyl)-2-methylphenyl)-N-ethyl-N-methyl
methyl 2-(2-chloro-4-(((ethyl(methyl)amino)methylene)amino)-5-methylphenyl)-2-(3-chlorophenyl)acetate
N'-(4-(1-(4-bromophenyl)vinyl)-5-chloro-2-methylphenyl)-N-ethyl-N-methylformimidamide;
2-(2-chloro-4-(((ethyl(methyl)amino)methylene)amino)-5-methylphenyl)-2-(3-fluorophenyl)-N,N-dimethylpropanamide;
2-(2-chloro-4-(((ethyl(methyl)amino)methylene)amino)-5-methylphenyl)-2-(5-fluoro-2-methylphenyl)-N,N-dimethylacetamide;
N'-(5-chloro-4-((4-chloro-3-fluorophenyl)(cyano)methyl)-2-methylphenyl)-N-ethyl-N-methylformimidamide;
N'-(2,5-difluoro-4-(2-fluorobenzyl)phenyl)-N-ethyl-N-methylformimidamide;
N'-(4-(3-chlorobenzyl)-2,5-difluorophenyl)-N-ethyl-N-methylformimidamide;
N'-(2,5-difluoro-4-(3-methylbenzyl)phenyl)-N-ethyl-N-methylformimidamide;
N'-(2,5-difluoro-4-(4-methylbenzyl)phenyl)-N-ethyl-N-methylformimidamide;
N'-(4-(2-chlorobenzyl)-5-cyano-2-methylphenyl)-N-ethyl-N-methylformimidamide;
N'-(5-cyano-4-(2-fluorobenzyl)-2-methylphenyl)-N-ethyl-N-methylformimidamide;
N'-(5-cyano-2-methyl-4-(2-methylbenzyl)phenyl)-N-ethyl-N-methylformimidamide;
N'-(4-(3-chlorobenzyl)-5-cyano-2-methylphenyl)-N-ethyl-N-methylformimidamide;
N'-(5-cyano-4-(3-fluorobenzyl)-2-methylphenyl)-N-ethyl-N-methylformimidamide;
N'-(5-cyano-2-methyl-4-(3-methylbenzyl)phenyl)-N-ethyl-N-methylformimidamide;
N'-(5-cyano-2-methyl-4-(4-methylbenzyl)phenyl)-N-ethyl-N-methylformimidamide;
N'-(4-(2-chlorobenzyl)-2,5-difluorophenyl)-N-ethyl-N-methylformimidamide;
N'-(2,5-difluoro-4-(2-methylbenzyl)phenyl)-N-ethyl-N-methylformimidamide;
N'-(5-chloro-4-(2-chlorobenzyl)-2-methylphenyl)-N-ethyl-N-methylformimidamide;
N'-(5-chloro-4-(2-fluorobenzyl)-2-methylphenyl)-N-ethyl-N-methylformimidamide;
N'-(5-chloro-2-methyl-4-(2-methylbenzyl)phenyl)-N-ethyl-N-methylformimidamide;
N'-(5-chloro-4-(3-chlorobenzyl)-2-methylphenyl)-N-ethyl-N-methylformimidamide;
N'-(5-chloro-4-(3-fluorobenzyl)-2-methylphenyl)-N-ethyl-N-methylformimidamide;
N'-(5-chloro-2-methyl-4-(3-methylbenzyl)phenyl)-N-ethyl-N-methylformimidamide;
N'-(5-chloro-2-methyl-4-(4-methylbenzyl)phenyl)-N-ethyl-N-methylformimidamide;
N'-(4-(2-chlorobenzyl)-2-cyclopropyl-5-(trifluoromethyl)phenyl)-N-ethyl-N-methylformimidamide;
N'-(2-cyclopropyl-4-(3-methylbenzyl)-5-(trifluoromethyl)phenyl)-N-ethyl-N-methylformimidamide;
N-(2-cyclopropyl-4-(4-methylbenzyl)-5-(trifluoromethyl)phenyl)-N-ethyl-N-methylformimidamide;
N'-(4-(3-chlorobenzyl)-2-cyclopropyl-5-(trifluoromethyl)phenyl)-N-ethyl-N-methylformimidamide;
N'-(2-cyclopropyl-4-(3-fluorobenzyl)-5-(trifluoromethyl)phenyl)-N-ethyl-N-methylformimidamide;
N'-(2-cyclopropyl-4-(4-cyclopropylbenzyl)-3,6-dimethylphenyl)-N-ethyl-N-methylformimidamide;
N'-(2-cyclopropyl-4-(2-methylbenzyl)-5-(trifluoromethyl)phenyl)-N-ethyl-N-methylformimidamide;
N'-(2,5-difluoro-4-(3-fluorobenzyl)phenyl)-N-ethyl-N-methylformimidamide;
N'-(4-(2-chlorobenzyl)naphthalen-1-yl)-N-ethyl-N-methylformimidamide;
N-ethyl-N-methyl-N'-(4-(2-methylbenzyl)naphthalen-1-yl)formimidamide;
N'-(2-chloro-4-(cyano(3-(trifluoromethyl)phenyl)methyl)-5-methylphenyl)-N-ethyl-N-methylformimidamide hydrochloride;
N-ethyl-N-methyl-N'-(5-methyl-4-(3-methylbenzyl)-2-(methylsulfonyl)phenyl)formimidamide;
N-ethyl-N'-(4-(2-fluorobenzyl)-5-methyl-2-(methylsulfonyl)phenyl)-N-methylformimidamide;
N'-(4-(2-chlorobenzyl)-5-methyl-2-(methylsulfonyl)phenyl)-N-ethyl-N-methylformimidamide;
N-ethyl-N-methyl-N'-(5-methyl-2-(methylsulfonyl)-4-(3-(trifluoromethyl)benzyl)phenyl)formimidamide;
N-ethyl-N-methyl-N'-(5-methyl-2-(methylsulfonyl)-4-(3-(trifluoromethoxy)benzyl)phenyl)formimidamide;
N-ethyl-N'-(5-fluoro-2-methyl-4-(3-(trifluoromethoxy)benzyl)phenyl)-N-methylformimidamide;
N-ethyl-N-methyl-N-(5-methyl-4-(2-methylbenzyl)-2-(methylsulfonyl)phenyl)formimidamide;
N-ethyl-N-methyl-N'-(5-methyl-4-(4-methylbenzyl)-2-(methylsulfonyl)phenyl)formimidamide;
N'-(4-(3-chlorobenzyl)-5-methyl-2-(methylsulfonyl)phenyl)-N-ethyl-N-methylformimidamide;
N-ethyl-N'-(4-(3-fluorobenzyl)-5-methyl-2-(methylsulfonyl)phenyl)-N-methylformimidamide;
N-ethyl-N-methyl-N'-(5-methyl-4-(3-methylbenzyl)-2-(methylsulfonyl)phenyl)formimidamide;
N-ethyl-N'-(4-(2-fluorobenzyl)-5-methyl-2-(methylsulfonyl)phenyl)-N-methylformimidamide;
N'-(4-(2-chlorobenzyl)-5-methyl-2-(methylsulfonyl)phenyl)-N-ethyl-N-methylformimidamide;
N-ethyl-N-methyl-N-(5-methyl-2-(methylsulfonyl)-4-(3-(trifluoromethyl)benzyl)phenyl)formimidamide;
N-ethyl-N-methyl-N'-(5-methyl-2-(methylsulfonyl)-4-(3-(trifluoromethoxy)benzyl)phenyl)formimidamide and
N-ethyl-N'-(5-fluoro-2-methyl-4-(3-(trifluoromethoxy)benzyl)phenyl)-N-methylformimidamide.

* Compound names generated using Chemdraw Professional 16.0

Any of the compounds according to the invention can exist in one or more optical, geometric or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/ or the optical isomers can be separated according to the methods which are known per se by a person ordinary skilled in the art.

Any of the compounds according to the invention can also exist in one or more geometric isomer forms depending on the number of double bonds in the compound. The invention thus relates equally to all geometric isomers and to all possible mixtures, in all proportions. The geometric isomers can be separated according to general methods, which are known per se by a person ordinary skilled in the art.

Any of the compounds according to the invention, can also exist in one or more amorphic or isomorphic or polymorphic forms, depending on their preparation, purification storage and various other influencing factors. The invention thus relates all the possible amorphic, isomorphic and polymorphic forms, in all proportions. The amorphic, isomorphic and polymorphic forms can be prepared and/or separated and/or purified according to general methods, which are known per se by a person ordinary skilled in the art.

In the above description, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers.

"Alkenyl" includes straight-chain or branched alkenes such as ethenyl, 1-propenyl, 2-propenyl, and the different butenyl, pentenyl and hexenyl isomers. "Alkenyl" also includes polyenes such as 1, 2-propadienyl and 2,4-hexadienyl.

"Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Cyclic alkyl" or "cycloalkyl" includes, for example, cyclopropyl, cyclobutyl, cyclopentyl, and cyclohexyl. Cyclic alkenyl includes, for example, cyclopropenyl, cyclobutenyl, cyclopentenyl, and cyclohexenyl. Cyclic alkynyl similarly refers to cyclic pentynyl, hexynyl, heptynyl and octynyl.

The term "aryl" as used herein is a group that contains any carbon-based aromatic group including, but not limited to phenyl, naphthalene, biphenyl, anthracene, and the like. The aryl group can be substituted or unsubstituted. In addition, the aryl group can be a single ring structure or comprise multiple ring structures that are either fused ring structures or attached via one or more bridging groups such as a carbon-carbon bond.

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs.

The term "heterocyclyl" means a cyclic ring system in which at least one ring atom is not carbon and which can contain heteroatoms independently selected from the group comprising of nitrogen, oxygen, sulfur, phosphorous, boron etc.

The term "heterocyclyl" may be further classified as "non-aromatic heterocyle" and "aromatic heterocycle or heteroaryl".

The term "non-aromatic heterocyle" includes fused or unfused three- to fifteen-membered, preferably three- to twelve-membered, saturated or fully or partially unsaturated heterocycle, monocyclic or polycyclic (spiro, fused, bridged, nonfused) heterocycle wherein heteroatom is selected from the group of oxygen, nitrogen and sulphur; and if the ring contains more than one oxygen atom, they are not directly adjacent; Non-limiting examples of non-aromatic heterocyle include oxetanyl, oxiranyl; aziridinyl; thiiranyl, azetidinyl, thiethanyl, dithiethanyl, diazetidinyl, 2-tetrahydrofuranyl; 3-tetrahydrofuranyl; 2-tetrahydrothienyl; 3-tetrahydrothienyl; 2-pyrrolidinyl; 3-pyrrolidinyl; 3-isoxazolidinyl; 4-isoxazolidinyl; 5-isoxazolidinyl; 3-isothiazolidinyl; 4-isothiazolidinyl; 2-tetrahydropyranyl; 4-tetrahydropyranyl. This definition also applies to heterocyclyl as a part of a composite substituent, for example heterocyclylalkyl (heterocycle radicals including an alkyl portion as defined above) etc., unless specifically defined elsewhere.

The term "heteroarylaryl" as used herein is a group that contains fused or unfused three to fifteen membered, preferably three to twelve membered, more preferably 5 or 6 membered; monocyclic or polycyclic unsaturated ring system, containing heteroatoms selected from the group of oxygen, nitrogen, sulphur, phosphorous, boron etc.

Non-limiting examples of 5 membered heteroaryl groups include 2-furyl; 3-furyl; 2-thienyl; 3-thienyl; 2-pyrrolyl; 3-pyrrolyl; 3-isoxazolyl; 4-isoxazolyl; 5-isoxazolyl; 3-isothiazolyl; 4-isothiazolyl; 5-isothiazolyl; 3-pyrazolyl; 4-pyrazolyl; 5-pyrazolyl; 2-oxazolyl; 4-oxazolyl; 5-oxazolyl; 2-thiazolyl; 4-thiazolyl; 5-thiazolyl; 2-imidazolyl; 4-imidazolyl; 1,2,4-oxadiazol-3-yl; 1,2,4-oxadiazol-5-yl; 1,2,4-thiadiazol-3-yl; 1,2,4-thiadiazol-5-yl; 1,2,4-triazol-3-yl; 1,3,4-oxadiazol-2-yl; 1,3,4-thiadiazol-2-yl and 1,3,4-triazol-2-yl; 1-pyrrolyl; 1-pyrazolyl; 1,2,4-triazol-1-yl; 1-imidazolyl; 1,2,3-triazol-1-yl; 1,3,4-triazol-1-yl and the like.

Non-limiting examples of 6 membered heteroaryl groups include 2-pyridinyl; 3-pyridinyl; 4-pyridinyl; 3-pyridazinyl; 4-pyridazinyl; 2-pyrimidinyl; 4-pyrimidinyl; 5-pyrimidinyl; 2-pyrazinyl; 1,3,5-triazin-2-yl; 1,2,4-triazin-3-yl; 1,2,4,5-tetrazin-3-yl and the like.

Non-limiting examples of benzofused 5-membered heteroaryl include indol-1-yl; indol-2-yl; indol-3-yl; indol-4-yl; indol-5-yl; indol-6-yl; indol-7-yl; benzimidazol-1-yl; benzimidazol-2-yl; benzimidazol-4-yl; benzimidazol-5-yl; indazol-1-yl; indazol-3-yl; indazol-4-yl; indazol-5-yl; indazol-6-yl; indazol-7-yl; indazol-2: yl; 1-benzofuran-2-yl; 1-benzofuran-3-yl; 1-benzofuran-4-yl; 1-benzofuran-5-yl; 1-benzofuran-6-yl; 1-benzofuran-7-yl; 1-benzothiophen-2-yl; 1-benzothiophen-3-yl; 1-benzothiophen-4-yl; 1-benzothiophen-5-yl; 1-benzothiophen-6-yl; 1-benzothiophen-7-yl; 1,3-benzothiazol-2-yl; 1,3-benzothiazol-4-yl; 1,3-benzothiazol-5-yl; 1,3-benzothiazol-6-yl; 1,3-benzothiazol-7-yl; 1,3-benzoxazol-2-yl; 1,3-benzoxazol-4-yl; 1,3-benzoxazol-5-yl; 1,3-benzoxazol-6-yl; 1,3-benzoxazol-7-yl and the liked.

Non-limiting examples of benzofused 6-membered heteroaryl include quinolin-2-yl; quinolin-3-yl; quinolin-4-yl; quinolin-5-yl; quinolin-6-yl; quinolin-7-yl; quinolin-8-yl; isoquinolin-1-yl; isoquinolin-3-yl; isoquinolin-4-yl; isoquinolin-5-yl; isoquinolin-6-yl; isoquinolin-7-yl; isoquinolin-8-yl and the like.

The term "aralkyl" refers to aryl hydrocarbon radicals including an alkyl portion as defined above. Examples include benzyl, phenylethyl, and 6-naphthylhexyl. As used herein, the term "aralkenyl" refers to aryl hydrocarbon radicals including an alkenyl portion, as defined above, and an aryl portion, as defined above. Examples include styryl, 3-(benzyl) prop-2-enyl, and 6-napthylhex-2-enyl.

The term "alkaryl" refers to an aryl group which bears an alkyl group; as used herein, the term "alkaryl" includes both substituted and unsubstituted groups. One example of an alkaryl group is the 4-methylphenyl radical.

"Alkoxy" includes, for example, methoxy, ethoxy, n-propyloxy, isopropyloxy and the different butoxy, pentoxy and hexyloxy isomers.

"Alkylthio" includes branched or straight-chain alkylthio moieties such as methylthio, ethylthio, and the different propylthio, butylthio, pentylthio and hexylthio isomers.

The term "halogen", either alone or in compound words such as "haloalkyl", includes fluorine, chlorine, bromine or iodine.

The total number of carbon atoms in a substituent group is indicated by the "$C_{i-j}$" prefix where i and j are numbers from 1 to 21. For example, $C_{1-3}$ alkoxy designates methoxy through propoxy. In the above recitations, when a compound of formula (I) is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e. g. $(R)_{i-j}$, then the number of substituents may be selected from the integers between i and j inclusive.

When a group contains a substituent which can be hydrogen, for example $R^1$ or $R^2$, then, when this substituent is taken as hydrogen, it is recognized that this is equivalent to said group being unsubstituted.

The present invention further relates to a composition for controlling unwanted microorganisms comprising at least one of the compounds of the formula (I) and one or more inert carrier. The inert carrier further comprises agriculturally suitable auxiliaries, solvents, diluents, surfactants and/or extenders and the like.

The present invention further relates to a composition for controlling unwanted microorganisms, comprising at least one of the compounds of the formula (I) and/or one or more active compatible compound selected from fungicides, bactericides, acaricides, insecticides, nematicides, herbicides, biopesticides, plant growth regulators, antibiotics, fertilizers and/or mixtures thereof.

The present invention further relates to a composition wherein the concentration of compounds having general formula (I) ranges from 1 to 90% by weight with respect to the total weight of the composition, preferably from 5 to 50% by weight with respect to the total weight of the composition.

The present invention also relates to a method for controlling unwanted microorganisms, wherein compounds of the formula (I) are applied to the microorganisms and/or in their habitat.

The present invention further provides a method for protecting seed against unwanted microorganisms by using seed treated with at least one compound of the formula (I).

The compounds of the formula (I) can possess potent microbicidal activity and can be used for the control of unwanted microorganisms, such as fungi, insects, mites, nematodes and bacteria, in agricultural or horticultural crop protection and in the protection of such materials.

The compounds of the formula (I) can possess very good fungicidal properties and can be used in crop protection, for example for control of Plasmodiophoromycetes, Ownycetes, Chytridiomycetes, Zygotnycetes, Ascomycetes, Basidiomycetes and Deuteromycetes.

The compounds of the formula (I) can be used as nematicides in crop protection, for example, for control of Rhabditida, Dorylamida, and Tryplonchida.

The compounds of the formula (I) can be used as insecticides in crop protection, for example, for control of Lepidoptera, Coleoptera, Hemiptera, Homoptera, Thysanoptera, Diptera, Orthoptera & Isoptera.

The compounds of the formula (I) can be used as acaricides in crop protection, for example, for control of Eriophyoidea, Tetranychoidea, Eupodoidea and Tarsonemidae.

The compounds of the formula (I) can be used as bactericides in crop protection, for example, for control of Pseudomonadaceae, Rhizobiaceae, Enterobacteriaceae, Corynebacteriaceae and Streptomycetaceae.

The compounds of the formula (I) can be used as herbicides and can be effective against a broad spectrum of economically important mono- and dicotyledonous harmful plants. Monocotyledonous broad-leaved weed species may include *Avena, Lolium, Alopecurus, Phalaris, Echinochloa, Digitaria, Setaria* and *Cyperus* species from the annual group and perennial species *Agropyron, Cynodon, Imperata* and Sorghum and also perennial *Cyperus* species. Dicotyledonous broad-leaved weed species may include Galium, Viola, Veronica, *Lamium, Stellaria, Amaranthus, Sinapis, Ipomoea, Sida, Matricaria* and *Abutilon* on the annual side, and also *Convolvulus, Cirsium, Rumex* and *Artemisia* in the case of the perennial broad-leaved weeds. Harmful plants that occur in rice, such as, for example, *Echinochloa, Sagittaria, Alisma, Eleocharis, Scirpus* and *Cyperus*, can be controlled by the compounds of formula (I).

The compounds of the formula (I) can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The compounds of the formula (I) can be used for controlling or preventing against phytopathogenic fungi, bacteria, insects, nematodes, mites of agricultural crops and or horticultural crops.

The compounds of the formula (I) can be used in crop protection, wherein the agricultural crops are cereals, corn, rice, soybean and other leguminous plants, fruits and fruit trees, nuts and nut trees, citrus and citrus trees, any horticultural plants, cucurbitaceae, oleaginous plants, tobacco, coffee, tea, cacao, sugar beet, sugar cane, cotton, potato, tomato, onions, peppers and other vegetables, and ornamentals.

According to the invention, as defined above a carrier is a natural or synthetic, organic or inorganic substance with which the active ingredients are mixed or combined for better applicability, in particular for application to plants or plant parts or seed. The carrier, which may be solid or liquid, are generally inert and should be suitable for use in agriculture.

Useful solid carriers include for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally, suitable are oligo- or polymers, for example those derived from vinylic monomers, from acrylic acid, from EO and/or PO alone or in combination with, for example, (poly) alcohols or (poly) amines. It is also possible to use lignin and its sulphonic acid derivatives, unmodified and modified celluloses, aromatic and/or aliphatic sulphonic acids and also their adducts with formaldehyde.

The active ingredients can be applied as such or converted to the customary formulations or in the form of their formulations or the use forms prepared therefrom, such as ready-to-use solutions, emulsions, water- or oil-based suspensions, powders, wettable powders, pastes, soluble powders, soluble tablets, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, nursery boxes, broadcasting, dusting, foaming, spreading-on and the like. It is also possible to deploy the active ingredients by the ultra-low volume method or to inject the active ingredient preparation or the active ingredient itself into the soil. It is also possible to treat the seed of the plants.

The active ingredients can be further converted to the nanoformulation with intent to further improve water solubility, thermal stability, bioavailability, sensory attributes, and physiological performance.

Furthermore, the choice of the type of formulation will depend on the specific use.

The formulations mentioned can be prepared in a manner known per se, for example by mixing the active ingredients with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

The present invention includes not only formulations which are already ready for use and can be deployed with a suitable apparatus to the plant or the seed, but also commercial concentrates which have to be diluted with water prior to use.

The auxiliaries used may be those substances which are suitable for imparting particular properties to the composition itself and/or to preparations derived therefrom (for example spray liquors, seed dressings), such as certain technical properties and/or also particular biological properties. Typical auxiliaries include extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally be be substituted, etherified and/or esterified), the ketones (such as acetone, cyclohexanone), esters (including fats and oils) and (poly) ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral, vegetable oils and methylated seed oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compounds of the formula (I) may additionally comprise further components, for example surfactants. Suitable surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70% by weight.

The formulations described above can be used for controlling unwanted microorganisms, in which the compositions comprising compounds of the formula (I) are applied to the microorganisms and/or in their habitat.

Compounds of the formula (I) according to this invention, as well as salts, N-oxides, metal complexes, stereoisomers or polymorphs can be used as such or in formulations thereof and can be mixed with known mixing partners in order to broaden, for example, the activity spectrum or to prevent development of resistance. Useful mixing partners include, for example, known fungicides, insecticides, acaricides, nematicides, biopesticides and bactericides. A mixture with other known active ingredients, such as herbicides, or with fertilizers and growth regulators, safeners and/or semiochemicals, is also possible.

Examples for such chemical ingredients are given herein in a not limiting way. Some of them are specified herein by their common names that are known and described, for example in *The Pesticide Manual* 17th Ed., or can be searched in the internet (e.g. under www.alanwood.net/pesticides). Others are described by their systematic name following the IUPAC rules for nomenclature.

All named mixing partners of the classes (A) to (O) as described below can, if their functional groups enable this, optionally form salts with suitable bases or acids, appear as stereoisomers, even if not specifically mentioned in each case, or as polymorphs. They are also understood as being included herein. These examples are A) Inhibitors of the ergosterol biosynthesis, for example (A01) aldimorph, (A02) azaconazole, (A03) bitertanol, (A04) bromuconazole, (A05) cyproconazole, (A06) diclobutrazole, (A07) difenoconazole, (A08) diniconazole, (A09) diniconazole-M, (A10) dodemorph, (A11) dodemorph acetate, (A12) epoxiconazole, (A13) etaconazole, (A14) fenarimol, (A15) fenbuconazole, (A16) fenhexamid, (A17) fenpropidin, (A18) fenpropimorph, (A19) fluquinconazole, (A20) flurprimidol, (A21) flusilazole, (A22) flutriafol, (A23) furconazole, (A24) furconazole-cis, (A25) hexaconazole, (A26) imazalil, (A27) imazalil sulfate, (A28) imibenconazole, (A29) ipconazole, (A30) metconazole, (A31) myclobutanil, (A32) naftifine, (A33) nuarimol, (A34) oxpoconazole, (A35) paclobutrazol, (A36) pefürazoate, (A37) penconazole, (A38) piperalin, (A39) prochloraz, (A40) propiconazole, (A41) prothioconazole, (A42) pyributicarb, (A43) pyrifenox, (A44) quinconazole, (A45) simeconazole, (A46) spiroxamine, (A47) tebuconazole, (A48) terbinafine, (A49) tetraconazole, (A50) triadimefon, (A51) triadimenol, (A52) tridemorph, (A53) triflumizole, (A54) triforine, (A55) triticonazole, (A56) uniconazole, (A57) uniconazole-p, (A58) viniconazole, (A59) voriconazole, (A60) 1-(4-chlorophenyl)-2-(1H-1,2,4-triazol-1-yl)cycloheptanol, (A61) methyl 1-(2,2-dimethyl-2,3-dihydro-1H-inden-1-yl)-1H-imidazole-5-carboxylate, (A62) N'-{5-(difluoromethyl)-2-methyl-4-[3-(trimethylsilyl) propoxy] phenyl}-N-ethyl-N-methylimidoformamide, (A63) N-ethyl-N-methyl-N'-{2-methyl-5-(trifluoromethyl)-4-[3-(trimethylsilyl)propoxy]phenyl}imidoformamide, (A64) O-[1-(4-methoxyphenoxy)-3,3-dimethylbutan-2-yl]-1H-imidazole-1-carbothioate, (A65) Pyrisoxazole, (A66) 2-{[3-(2-chlorophenyl)-2-(2,4-difluorophenyl)oxiran-2-yl] methyl}-2,4-dihydro-3H-1,2,4-triazole-3-thione, (A67) 1-{[3-(2-chlorophenyl)-2-(2,4-difluorophenyl)oxiran-2-yl] methyl}-1H-1,2,4-triazol-5-yl thiocyanate, (A68) 5-(allylsulfanyl)-1-{[3-(2-chlorophenyl)-2-(2,4-difluorophenyl)oxiran-2-yl]methyl}-1H-1,2,4-triazole, (A69) 2-[1-(2,4-dichlorophenyl)-5-hydroxy-2,6,6-trimethylheptan-4-yl]-2,4-dihydro-3H-1,2,4-triazole-3-thione, (A70) 2-{[rel (2R,3S)-3-(2-chlorophenyl)-2-(2,4-difluorophenyl) oxiran-2-yl]methyl}-2,4-dihydro-3H-1,2,4-triazole-3-thione, (A71) 2-{[rel(2R,3R)-3-(2-chlorophenyl)-2-(2,4-difluorophenyl) oxiran-2-yl]methyl}-2,4-dihydro-3H-1,2,4-triazole-3-thione, (A72) 1-{[rel(2R,3S)-3-(2-chlorophenyl)-2-(2,4-difluorophenyl)oxiran-2-yl]methyl}-1H-1,2,4-triazol-5-yl thiocyanate, (A73) 1-{[rel(2R,3R)-3-(2-chlorophenyl)-2-(2, 4-difluorophenyl)oxiran-2-yl]methyl}-1H-1,2,4-triazol-5-yl thiocyanate, (A74) 5-(allylsulfanyl)-1-{[rel(2R,3S)-3-(2-chlorophenyl)-2-(2,4-difluorophenyl)oxiran-2-yl]methyl}-1H-1,2,4-triazole, (A75) 5-(allylsulfanyl)-1-{[rel(2R,3R)-3-(2-chlorophenyl)-2-(2,4-difluorophenyl) oxiran-2-yl] methyl}-1H-1,2,4-triazole, (A76) 2-[(2S,4S,5S)-1-(2,4-dichlorophenyl)-5-hydroxy-2,6,6-trimethylheptan-4-yl]-2, 4-dihydro-3H-1,2,4-triazole-3-thione, (A77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (A78) 2-[(2R, 4R,5R)-1-(2,4-dichlorophenyl)-5-hydroxy-2,6,6-trimethylheptan-4-yl]-2,4-dihydro-3H-1,2,4-triazole-3-thione, (A79) 2-[(2 S,4R,5R)-1-(2,4-dichlorophenyl)-5-hydroxy-2,6,6-trimethylheptan-4-yl]-2,4-dihydro-3H-1,2,4-triazole-3-thione, (A80) 2-[(2S,4S,5R)-1-(2,4-dichlorophenyl)-5-hydroxy-2,6,6-trimethylheptan-4-yl]-2, 4-dihydro-3H-1,2,4-triazole-3-thione, (A81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (A82) 2-[(2R, 4R,5S)-1-(2,4-dichlorophenyl)-5-hydroxy-2,6,6-trimethylheptan-4-yl]-2,4-dihydro-3H-1,2,4-triazole-3-thione, (A83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (A84) 2-[4-(4-chlorophenoxy)-2-(trifluoromethyl)phenyl]-1-(1H-1,2,4-triazol-1-yl)propan-2-ol, (A85) 2-[4-(4-chlorophenoxy)-2-(trifluoromethyl) phenyl]-1-(1H-1,2,4-triazol-1-yl)butan-2-ol, (A86) 2-[4-(4-chlorophenoxy)-2-(trifluoromethyl)phenyl]-1-(1H-1,2,4-triazol-1-yl)pentan-2-ol, (A87) 2-[2-chloro-4-(4-chlorophenoxy)phenyl]-1-(1H-1,2,4-triazol-1-yl)butan-2-ol, (A88) 2-[2-chloro-4-(2,4-dichlorophenoxy)phenyl]-1-(1H-1,2,4-triazol-1-yl)propan-2-ol, (A89) (2R)-2-(1-chlorocyclopropyl)-4-[(1R)-2,2-dichlorocyclopropyl]-1-(1H-1,2,4-triazol-1-yl)butan-2-ol, (A90) (2R)-2-(1-chlorocyclopropyl)-4-[(1S)-2,2-dichlorocyclopropyl]-1-(1H-1,2,4-triazol-1-yl)butan-2-ol, (A91) (2 S)-2-(1-chlorocyclopropyl)-4-[(1S)-2,2-dichlorocyclopropyl]-1-(1H-1,2,4-triazol-1-yl)butan-2-ol, (A92) (2 S)-2-(1-chlorocyclopropyl)-4-[(1R)-2,2-dichlorocyclopropyl]-1-(1H-1,2,4-triazol-1-yl)butan-2-ol, (A93) (1S,2R,5R)-5-(4-chlorobenzyl)-2-(chloromethyl)-2-methyl-1-(1H-1,2,4-triazol-1-ylmethyl)cyclopentanol, (A94) (1R,2S,5S)-5-(4-chlorobenzyl)-2-(chloromethyl)-2-methyl-1-(1H-1,2,4-triazol-1-ylmethyl)cyclopentanol, (A95) 5-(4-chlorobenzyl)-2-(chloromethyl)-2-methyl-1-(1H-1,2,4-triazol-1-ylmethyl)cyclopentanol.

B) Inhibitors of the respiratory chain at complex I or II, for example (B01) bixafen, (B02) boscalid, (B03) carboxin, (B04) cypropamide, (B05) diflumetorim, (B06) fenfuram, (B07) fluopyram, (B08) flutolanil, (B09) fluxapyroxad, (B10) furametpyr, (B11) furmecyclox, (B12) isopyrazam (mixture of syn-epimeric racemate 1RS,4SR,9RS and anti-epimeric racemate 1RS,4SR,9SR), (B13) isopyrazam (anti-epimeric racemate 1RS,4SR,9SR), (B14) isopyrazam (anti-epimeric enantiomer 1R,4S,9S), (B15) isopyrazam (anti-epimeric enantiomer 1S,4R,9R), (B16) isopyrazam (syn-epimeric racemate 1RS,4SR,9RS), (B17) isopyrazam (syn-epimeric enantiomer 1R,4S,9R), (B18) isopyrazam (syn-epimeric enantiomer 1S,4R,9S), (B19) mepronil, (B20) oxycarboxin, (B21) penflufen, (B22) penthiopyrad, (B23) pydiflumetofen, (B24) sedaxane, (B25) thifluzamide, (B26) 1-methyl-N-[2-(1,1,2,2-tetrafluoroethoxy)phenyl]-3-(trifluoromethyl)-1H-pyrazole-4-carboxamide, (B27) 3-(difluoromethyl)-1-methyl-N-[2-(1,1,2,2-tetrafluoroethoxy)phenyl]-1H-pyrazole-4-carboxamide, (B28) 3-(difluoromethyl)-N-[4-fluoro-2-(1,1,2,3,3,3-hexafluoropropoxy)phenyl]-1-methyl-1H-pyrazole-4-carboxamide, (B29) N-[1-(2,4-dichlorophenyl)-1-m ethoxypropan-2-yl]-3-(difluoromethyl)-1-methyl-1H-pyrazole-4-carboxamide, (B30) 5,8-difluoro-N-[2-(2-fluoro-4-{[4-(trifluoromethyl)pyridin-2-yl]oxy}phenyl)ethyl]quinazolin-4-amine, (B31) benzovindiflupyr, (B32) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (B33) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (B34) 3-(difluoromethyl)-1-methyl-N-(1,1,3-trimethyl-2,3-dihydro-1H-inden-4-yl)-1H-pyrazole-4-carboxamide, (B35) 1,3,5-trimethyl-N-(1,1,3-trimethyl-2,3-dihydro-1H-inden-4-yl)-1H-pyrazole-4-carboxamide, (B36) 1-methyl-3-(trifluoromethyl)-N-(1,1,3-trimethyl-2,3-dihydro-1H-inden-4-yl)-1H-pyrazole-4-carboxamide, (B37) 1-methyl-3-(trifluoromethyl)-N-[(3R)-1,1,3-trimethyl-2,3-dihydro-1H-inden-4-yl]-1H-pyrazole-4-carboxamide, (B38) 1-methyl-3-(trifluoromethyl)-N-[(3S)-1,1,3-trimethyl-2,3-dihydro-1H-inden-4-yl]-1H-pyrazole-4-carboxamide, (B39) 3-(difluoromethyl)-1-methyl-N-[(3S)-1,1,3-trimethyl-2,3-dihydro-1H-inden-4-yl]-1H-pyrazole-4-carboxamide, (B40) 3-(difluoromethyl)-1-methyl-N-[(3R)-1,1,3-trimethyl-2,3-dihydro-1H-inden-4-yl]-1H-pyrazole-4-carboxamide, (B41) 1,3,5-trimethyl-N-[(3R)-1,1,3-trimethyl-2,3-dihydro-1H-inden-4-yl]-1H-pyrazole-4-carboxamide, (B42) 1,3,5-trimethyl-N-[(3S)-1,1,3-trimethyl-2,3-dihydro-1H-inden-4-yl]-1H-pyrazole-4-carboxamide, (B43) benodanil, (B44) 2-chloro-N-(1,1,3-trimethyl-2,3-dihydro-1H-inden-4-yl)pyridine-3-carboxamide, (B45) Isofetamid, (B46) 1-methyl-3-(trifluoromethyl)-N-[2'-(trifluoromethyl)biphenyl-2-yl]-1H-pyrazole-4-carboxamide, (B47) N-(4'-chlorobiphenyl-2-yl)-3-(difluoromethyl)-1-methyl-1H-pyrazole-4-carboxamide, (B48) N-(2',4'-dichlorobiphenyl-2-yl)-3-(difluoromethyl)-1-methyl-1H-pyrazole-4-carboxamide, (B49) 3-(difluoromethyl)-1-methyl-N-[4'-(trifluoromethyl)biphenyl-2-yl]-1H-pyrazole-4-carboxamide, (B50) N-(2',5'-difluorobiphenyl-2-yl)-1-methyl-3-(trifluoromethyl)-1H-pyrazole-4-carboxamide, (B51) 3-(difluoromethyl)-1-methyl-N-[4'-(prop-1-yn-1-yl)biphenyl-2-yl]-1H-pyrazole-4-carboxamide, (B52) 5-fluoro-1,3-dimethyl-N-[4'-(prop-1-yn-1-yl)biphenyl-2-yl]-1H-pyrazole-4-carboxamide, (B53) 2-chloro-N-[4'-(prop-1-yn-1-yl)biphenyl-2-yl]nicotinamide, (B54) 3-(difluoromethyl)-N-[4'-(3,3-dimethylbut-1-yn-1-yl)biphenyl-2-yl]-1-methyl-1H-pyrazole-4-carboxamide, (B55) N-[4'-(3,3-dimethylbut-1-yn-1-yl)biphenyl-2-yl]-5-fluoro-1,3-dimethyl-1H-pyrazole-4-carboxamide, (B56) 3-(difluoromethyl)-N-(4'-ethynylbiphenyl-2-yl)-1-methyl-1H-pyrazole-4-carboxamide, (B57) N-(4'-ethynylbiphenyl-2-yl)-5-fluoro-1,3-dimethyl-1H-pyrazole-4-carboxamide, (B58) 2-chloro-N-(4'-ethynylbiphenyl-2-yl)nicotinamide, (B59) 2-chloro-N-[4'-(3,3-dimethylbut-1-yn-1-yl)biphenyl-2-yl]nicotinamide, (B60) 4-(difluoromethyl)-2-methyl-N-[4'-(trifluoromethyl)biphenyl-2-yl]-1,3-thiazole-5-carboxamide, (B61) 5-fluoro-N-[4'-(3-hydroxy-3-methylbut-1-yn-1-yl)biphenyl-2-yl]-1,3-dimethyl-1H-pyrazole-4-carboxamide, (B62) 2-chloro-N-[4'-(3-hydroxy-3-methylbut-1-yn-1-yl)biphenyl-2-yl]nicotinamide, (B63) 3-(difluoromethyl)-N-[4'-(3-methoxy-3-methylbut-1-yn-1-yl)biphenyl-2-yl]-1-methyl-1H-pyrazole-4-carboxamide, (B64) 5-fluoro-N-[4'-(3-methoxy-3-methylbut-1-yn-1-yl)biphenyl-2-yl]-1,3-dimethyl-1H-pyrazole-4-carboxamide, (B65) 2-chloro-N-[4'-(3-methoxy-3-methylbut-1-yn-1-yl)biphenyl-2-yl]nicotinamide, (B66) 1,3-dimethyl-N-(1,1,3-trimethyl-2,3-dihydro-1H-inden-4-yl)-1H-pyrazole-4-carboxamide, (B67) 1,3-dimethyl-N-[(3R)-1,1,3-trimethyl-2,3-dihydro-1H-inden-4-yl]-1H-pyrazole-4-carboxamide, (B68) 1,3-dimethyl-N-[(3S)-1,1,3-trimethyl-2,3-dihydro-1H-inden-4-yl]-1H-pyrazole-4-carboxamide, (B69) 3-(difluoromethyl)-N-methoxy-1-methyl-N-[1-(2,4,6-trichlorophenyl)propan-2-yl]-1H-pyrazole-4-carboxamide, (B70) 3-(difluoromethyl)-N-(7-fluoro-1,1,3-trimethyl-2,3-dihydro-1H-inden-4-yl)-1-methyl-1H-pyrazole-4-carboxamide, (B71) 3-(difluoromethyl)-N-[(3,R)-7-fluoro-1,1,3-trimethyl-2,3-dihydro-1H-inden-4-yl]-1-methyl-1H-pyrazole-4-carboxamide, (B72) 3-(difluoromethyl)-N-[(3S)-7-fluoro-1,1,3-trimethyl-2,3-dihydro-1H-inden-4-yl]-1-methyl-1H-pyrazole-4-carboxamide.

C) Inhibitors of the respiratory chain at complex III, for example (C01) ametoctradin, (C02) amisulbrom, (C03) azoxystrobin, (C04) cyazofamid, (C05) coumethoxystrobin, (C06) coumoxystrobin, (C07) dimoxystrobin, (C08) enoxastrobin, (C09) famoxadone, (C10) fenamidone, (C11) fenaminstrobin, (C12) flufenoxystrobin, (C13) fluoxastrobin, (C14) kresoxim-methyl, (C15) metominostrobin, (C16) mandestrobin, (C17) orysastrobin, (C18) picoxystrobin, (C19) pyraclostrobin, (C20) pyrametostrobin, (C21) pyraoxystrobin, (C22) pyribencarb, (C23) triclopyricarb, (C24) trifloxystrobin, (C25) (2E)-2-(2-{[6-(3-chloro-2-methylphenoxy)-5-fluoropyrimidin-4-yl]oxy}phenyl)-2-(methoxyimino)-N-methylacetamide, (C26) (2E)-2-(methoxyimino)-N-methyl-2-(2-[[({(1E)-1-[3-(trifluoromethyl)phenyl]ethylidene}amino)oxy]methyl}phenyl) acetamide, (C27) (2E)-2-(methoxyimino)-N-methyl-2-{2-[(E)-({1-[3-(trifluoromethyl)phenyl]ethoxy}imino)methyl]phenyl}acetamide, (C28) (2E)-2-{2-[({[(1E)-1-(3-{[(1E)-1-fluoro-2-phenylvinyl]oxy}phenyl)ethylidene]amino}oxy)methyl]phenyl}-2-(methoxyimino)-N-methylacetamide, (C29) Fenaminostrobin, (C30) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (C31) methyl (2E)-2-{2-[(cyclopropyl[(4-methoxyphenyl)imino]methyl}sulfanyl)methyl]phenyl}-3-methoxyacrylate, (C32) N-(3-ethyl-3,5,5-trimethylcyclohexyl)-3-formamido-2-hydroxybenzamide, (C33) 2-{2-[(2,5-dimethylphenoxy)methyl]phenyl}-2-methoxy-N-methylacetamide, (C34) 2-{2-[(2,5-dimethylphenoxy)methyl]phenyl}-2-methoxy-N-methylacetamide, (C35) (2E,3Z)-5-{[1-(4-chlorophenyl)-1H-pyrazol-3-yl]oxy}-2-(methoxyimino)-N,3-dimethylpent-3-enamide.

D) Inhibitors of the mitosis and cell division, for example (D01) benomyl, (D02) carbendazim, (D03) chlorfenazole, (D04) diethofencarb, (D05) ethaboxam, (D06) fluopicolide, (D07) fiiberidazole, (D08) pencycuron, (D09) thiabendazole, (D10) thiophanate-methyl, (D11) thiophanate, (D12) zoxamide, (D13) 5-chloro-7-(4-methylpiperidin-1-yl)-6-(2,4,6-trifluorophenyl)[1,2,4]triazolo[1,5-a]pyrimidine, (D14) 3-chloro-5-(6-chloropyridin-3-yl)-6-methyl-4-(2,4,6-trifluorophenyl) pyridazine.

E) Compounds capable to have a multisite action, for example (E01) bordeaux mixture, (E02) captafol, (E03) captan, (E04) chlorothalonil, (E05) copper hydroxide, (E06) copper naphthenate, (E07) copper oxide, (E08) copper oxychloride, (E09) copper (2+) sulfate, (E10) dichlofluanid, (E11) dithianon, (E12) dodine, (E13) dodine free base, (E14) ferbam, (E15) fluorofolpet, (E16) folpet, (E17) guazatine, (E18) guazatine acetate, (E19) iminoctadine, (E20) iminoctadine albesilate, (E21) iminoctadine triacetate, (E22) mancopper, (E23) mancozeb, (E24) maneb, (E25) metiram, (E26) metiram zinc, (E27) oxine-copper, (E28) propamidine, (E29) propineb, (E30) sulfur and sulfur preparations including calcium polysulfide, (E31) thiram, (E32) tolylfluanid, (E33) zineb, (E34) ziram, (E35) anilazine.

F) Compounds capable to induce a host defence, for example (F01) acibenzolar-S-methyl, (F02) isotianil, (F03) probenazole, (F04) tiadinil, (F05) laminarin.

G) Inhibitors of the amino acid and/or protein biosynthesis, for example (G01) andoprim, (G02) blasticidin-S, (G03) cyprodinil, (G04) kasugamycin, (G05) kasugamycin hydrochloride hydrate, (G06) mepanipyrim, (G07) pyrimethanil, (G08) 3-(5-fluoro-3,3,4,4-tetramethyl-3,4-dihydroisoquinolin-1-yl)quinoline, (G09)oxytetracycline, (G10) streptomycin.

H) Inhibitors of the ATP production, for example (H01) fentin acetate, (H02) fentin chloride, (H03) fentinhydroxide, (H04) silthiofam.

I) Inhibitors of the cell wall synthesis, for example (I01) benthiavalicarb, (I02) dimethomorph, (I03) flumorph, (I04) iprovalicarb, (I05) mandipropamid, (I06) polyoxins, (I07) polyoxorim, (I08) validamycin A, (I09) valifenalate, (I10) polyoxin B, (I11) (2E)-3-(4-tert-butylphenyl)-3-(2-chloropyridin-4-yl)-1-(morpholin-4-yl)prop-2-en-1-one, (I12) (2Z)-3-(4-tert-butylphenyl)-3-(2-chloropyridin-4-yl)-1-(morpholin-4-yl)prop-2-en-1-one.

J) Inhibitors of the lipid and membrane synthesis, for example (J01) biphenyl, (J02) chloroneb, (J03) dicloran, (J04) edifenphos, (J05) etridiazole, (J06) iodocarb, (J07) iprobenfos, (J08) isoprothiolane, (J09) propamocarb, (J10) propamocarb hydrochloride, (J11) prothiocarb, (J12) pyrazophos, (J13) quintozene, (J14) tecnazene, (J15) tocloface-methyl.

K) Inhibitors of the melanin biosynthesis, for example (K01) carpropamid, (K02) diclocymet, (K03) fenoxanil, (K04) phthalide, (K05) pyroquilon, (K06) tolprocarb, (K07) tricyclazole.

L) Inhibitors of the nucleic acid synthesis, for example (L01) benalaxyl, (L02) benalaxyl-M (kiralaxyl), (L03) bupirimate, (L04) clozylacon, (L05) dimethirimol, (L06) ethirimol, (L07) furalaxyl, (L08) hymexazol, (L09) metalaxyl, (L10) metalaxyl-M (mefenoxam), (L11) ofurace, (L12) oxadixyl, (L13) oxolinic acid, (L14)octhilinone.

M) Inhibitors of the signal transduction, for example (M01) chlozolinate, (M02) fenpiclonil, (M03) fludioxonil, (M04) iprodione, (M05) procymidone, (M06) quinoxyfen, (M07) vinclozolin, (M08) proquinazid.

N) Compounds capable to act as an uncoupler, for example (N01) binapacryl, (N02) dinocap, (N03) ferimzone, (N04) fluazinam, (N05) meptyldinocap.

O) Further compounds, for example (O01) benthiazole, (O02) bethoxazin, (O03) capsimycin, (O04) carvone, (O05) chinomethionat, (O06) pyriofenone (chlazafenone), (O07) cufraneb, (O08) cyflufenamid, (O09) cymoxanil, (O10) cyprosulfamide, (O11) dazomet, (O12) debacarb, (O13) dichlorophen, (O14) dichlobentiazox, (O15) diclomezine, (O16) difenzoquat, (O17) difenzoquat metilsulfate, (O18) diphenylamine, (O19) ecomate, (O20) fenpyrazamine, (O21) fenhexamine, (O22) flumetover, (O23) fluoroimide, (O24) flusulfamide, (O25) flutianil, (O26) fosetyl-aluminium, (O27) fosetyl-calcium, (O28) fosetyl-sodium, (O29) hexachlorobenzene, (O30) irumamycin, (O31) isothianil, (O32) methasulfocarb, (O33) methyl isothiocyanate, (O34) metrafenone, (O35) mildiomycin, (O36) natamycin, (O37) nickel dimethyldithiocarbamate, (O38) nitrothal-isopropyl, (O39) oxamocarb, (O40) oxyfenthiin, (O41) pentachlorophenol and salts, (O42) phenothrin, (O43) picarbutrazox (O44) phosphorous acid and its salts, (O45) propamocarb-fosetylate, (O46) propanosine-sodium, (O47) pyrimorph, (O48) pyraziflumid (O49) pyrrolnitrine, (O50) tebufloquin, (O51) tecloftalam, (O52) tolnifanide, (O53) triazoxide, (O54) trichlamide, (O55) zarilamid, (O56) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (O57) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (O58) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (O59) oxathiapiprolin, (O60) 1-(4-methoxyphenoxy)-3,3-dimethylbutan-2-yl-1H-imidazole-1-carboxylate, (O61) 2,3,5,6-tetrachloro-4-(methylsulfonyl)pyridine, (O62) 2,3-dibutyl-6-chlorothieno[2,3-d]pyrimidin-4(3H)-one, (O63) 2,6-dimethyl-1H,5H-[1,4]dithiino[2,3-c:5,6-c']dipyrrole-1,3,5,7 (2H,6H)-tetrone, (O64) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (O65) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (O66) 2-[5-methyl-3-(trifluoromethyl)-1H-pyrazol-yl]-1-{4-[4-(5-phenyl-4,5-dihydro-1,2-oxazol-3-yl)-1,3-thiazol-2-yl]piperidin-1-yl}ethanone, (O67) 2-butoxy-6-iodo-3-propyl-4H-chromen-4-one, (O68) 2-chloro-5-[2-chloro-1-(2,6-difluoro-4-methoxyphenyl)-4-methyl-1H-imidazol-5-yl]pyridine, (O69) 2-phenylphenol and salts, (O70) 3-(4,4,5-trifluoro-3,3-dimethyl-3,4-dihydroisoquinolin-1-yl)quinoline, (O71) 3,4,5-trichloropyridine-2,6-dicarbonitrile, (O72) 3-chloro-5-(4-chlorophenyl)-4-(2,6-difluorophenyl)-6-methylpyridazine, (O73) 4-(4-chlorophenyl)-5-(2,6-difluorophenyl)-3,6-dimethylpyridazine, (O74) 3-chloro-4-(2,6-difluorophenyl)-6-methyl-5-phenylpyridazine, (O75) 5-amino-1,3,4-thiadiazole-2-thiol, (O76) 5-chloro-N'-phenyl-N'-(prop-2-yn-1-yl)thiophene-2-sulfonohydrazide, (O77) 5-fluoro-2-[(4-fluorobenzyl)oxy]pyrimidin-4-amine, (O78) 5-fluoro-2-[(4-methylbenzyl)oxy]pyrimidin-4-amine, (O79) 5-methyl-6-octyl[1,2,4]triazolo[1,5-a]pyrimidin-7-amine, (O80) ethyl (2Z)-3-amino-2-cyano-3-phenylacrylate, (O81) N'-(4-{[3-(4-chlorobenzyl)-1,2,4-thiadiazol-5-yl] oxy}-2,5-di methylphenyl)-N-ethyl-N-methylimidoformamide, (O82) N-(4-chlorobenzyl)-3-[3-methoxy-4-(prop-2-yn-1-yloxy)phenyl]propanamide, (O83) N-[(4-chlorophenyl)(cyano)methyl]-3-[3-methoxy-4-(prop-2-yn-1-yloxy)phenyl]propanamide, (O84) N-[(5-bromo-3-chloropyridin-2-yl)methyl]-2,4-dichloronicotinamide, (O85) N-[1-(5-bromo-3-chloropyridin-2-yl)ethyl]-2,4-dichloronicotinamide, (O86) N-[1-(5-bromo-3-chloropyridin-2-yl)ethyl]-2-fluoro-4-iodonicotinamide, (O87) N-{(E)-[(cyclopropylmethoxy)imino][6-(difluoromethoxy)-2,3-difluorophenyl]methyl}-2-phenylacetamide, (O88) N—{(Z)-[(cyclopropylmethoxy)imino][6-(difluoromethoxy)-2,3-difluorophenyl]methyl}-2-phenylacetamide, (O89) N'-{4-

[(3-tert-butyl-4-cyano-1,2-thiazol-5-yl)oxy]-2-chloro-5-methylphenyl}-N-ethyl-N-methylimidoformamide, (O90) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (O91) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (O92) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (O93) pentyl {6-[({[(1-methyl-1H-tetrazol-5-yl)(phenyl)methylene]amino}oxy)methyl]pyridin-2-yl}carbamate, (O94) phenazine-1-carboxylic acid, (O95) quinolin-8-ol, (O96) quinolin-8-ol sulfate (2:1), (O97) tert-butyl {6-[({[(1-methyl-1H-tetrazol-5-yl)(phenyl)methylene]amino}oxy)methyl]pyridin-2-yl}carbamate, (O98) (5-bromo-2-methoxy-4-methylpyridin-3-yl)(2,3,4-trimethoxy-6-methylphenyl) methanone, (O99) N-[2-(4-{[3-(4-chlorophenyl)prop-2-yn-1-yl]oxy}-3-methoxyphenyl)thyl]-N2-(methylsulfonyl)valinamide, (O100) 4-oxo-4-[(2-phenylethyl)amino]butanoic acid, (O101) but-3-yn-1-yl {6-[({[(Z)-(1-methyl-1H-tetrazol-5-yl)(phenyl)methylene]amino}oxy)methyl]pyridin-2-yl}carbamate, (O102) 4-amino-5-fluoropyrimidin-2-ol (tautomeric form: 4-amino-5-fluoropyrimidin-2(1H)-one), (O103) propyl 3,4,5-trihydroxybenzoate, (O104) [3-(4-chloro-2-fluorophenyl)-5-(2,4-difluorophenyl)-1,2-oxazol-4-yl](pyridin-3-yl)methanol, (O105) (S)-[3-(4-chloro-2-fluorophenyl)-5-(2,4-difluorophenyl)-1,2-oxazol-4-yl](pyridin-3-yl)methanol, (O106) (R)-[3-(4-chloro-2-fluorophenyl)-5-(2,4-difluorophenyl)-1,2-oxazol-4-yl](pyridin-3-yl)methanol, (O107) 2-fluoro-6-(trifluoromethyl)-N-(1,1,3-trimethyl-2,3-dihydro-1H-inden-4-yl)benzamide, (O108) 2-(6-benzylpyridin-2-yl)quinazoline, (O109) 2-[6-(3-fluoro-4-methoxyphenyl)-5-methylpyridin-2-yl]quinazoline, (O110) 3-(4,4-difluoro-3,3-dimethyl-3,4-dihydroisoquinolin-1-yl)quinoline, (O111) Abscisic acid, (O112) N'-[5-bromo-6-(2,3-dihydro-1H-inden-2-yloxy)-2-methylpyridin-3-yl]-N-ethyl-N-methylimidoformamide, (O113) N'-{5-bromo-6-[1-(3,5-difluorophenyl)ethoxy]-2-methylpyridin-3-yl}-N-ethyl-N-methylimidoformamide, (O114) N'-{5-bromo-6-[(1R)-1-(3,5-difluorophenyl)ethoxy]-2-methylpyridin-3-yl}-N-ethyl-N-methylimidoformamide, (O115) N'-{5-bromo-6-[(1S)-1-(3,5-difluorophenyl)ethoxy]-2-methylpyridin-3-yl}-N-ethyl-N-methylimidoformamide, (O116) N'-{5-bromo-6-[(cis-4-isopropylcyclohexyl)oxy]-2-methylpyridin-3-yl}-N-ethyl-N-methylimidoformamide, (O117) N'-{5-bromo-6-[(trans-4-isopropylcyclohexyl)oxy]-2-methylpyridin-3-yl}-N-ethyl-N-methylimidoformamide, (O118) N-cyclopropyl-3-(difluoromethyl)-5-fluoro-N-(2-isopropylbenzyl)-1-methyl-1H-pyrazole-4-carboxamide, (O119) N-cyclopropyl-N-(2-cyclopropylbenzyl)-3-(difluoromethyl)-5-fluoro-1-methyl-1H-pyrazole-4-carboxamide, (O120) N-(2-tert-butylbenzyl)-N-cyclopropyl-3-(difluoromethyl)-5-fluoro-1-methyl-1H-pyrazole-4-carboxamide, (O121) N-(5-chloro-2-ethylbenzyl)-N-cyclopropyl-3-(difluoromethyl)-5-fluoro-1-methyl-1H-pyrazole-4-carboxamide, O122) N-(5-chloro-2-isopropylbenzyl)-N-cyclopropyl-3-(difluoromethyl)-5-fluoro-1-methyl-1H-pyrazole-4-carboxamide, (O123) N-cyclopropyl-3-(difluoromethyl)-N-(2-ethyl-5-fluorobenzyl)-5-fluoro-1-methyl-1H-pyrazole-4-carboxamide, (O124) N-cyclopropyl-3-(difluoromethyl)-5-fluoro-N-(5-fluoro-2-isopropylbenzyl)-1-methyl-1H-pyrazole-4-carboxamide, (O125) N-cyclopropyl-N-(2-cyclopropyl-5-fluorobenzyl)-3-(difluoromethyl)-5-fluoro-1-methyl-1H-pyrazole-4-carboxamide, (O126) N-(2-cyclopentyl-5-fluorobenzyl)-N-cyclopropyl-3-(difluoromethyl)-5-fluoro-1-methyl-1H-pyrazole-4-carboxamide, (O127) N-cyclopropyl-3-(difluoromethyl)-5-fluoro-N-(2-fluoro-6-isopropylbenzyl)-1-methyl-1H-pyrazole-4-carboxamide, (O128) N-cyclopropyl-3-(difluoromethyl)-N-(2-ethyl-5-methylbenzyl)-5-fluoro-1-methyl-1H-pyrazole-4-carboxamide, (O129) N-cyclopropyl-3-(difluoromethyl)-5-fluoro-N-(2-isopropyl-5-methylbenzyl)-1-methyl-1H-pyrazole-4-carboxamide, (O130) N-cyclopropyl-N-(2-cyclopropyl-5-methylbenzyl)-3-(difluoromethyl)-5-fluoro-1-methyl-1H-pyrazole-4-carboxamide, (O131) N-(2-tert-butyl-5-methylbenzyl)-N-cyclopropyl-3-(difluoromethyl)-5-fluoro-1-methyl-1H-pyrazole-4-carboxamide, (O132) N-[5-chloro-2-(trifluoromethyl)benzyl]-N-cyclopropyl-3-(difluoromethyl)-5-fluoro-1-methyl-1H-pyrazole-4-carboxamide, (O133) N-cyclopropyl-3-(difluoromethyl)-5-fluoro-1-methyl-N-[5-methyl-2-(trifluoromethyl)benzyl]-1H-pyrazole-4-carboxamide, (O134) N-[2-chloro-6-(trifluoromethyl)benzyl]-N-cyclopropyl-3-(difluoromethyl)-5-fluoro-1-methyl-1H-pyrazole-4-carboxamide, (O135) N-[3-chloro-2-fluoro-6-(trifluoromethyl)benzyl]-N-cyclopropyl-3-(difluoromethyl)-5-fluoro-1-methyl-1H-pyrazole-4-carboxamide, (O136) N-cyclopropyl-3-(difluoromethyl)-N-(2-ethyl-4,5-dimethylbenzyl)-5-fluoro-1-methyl-1H-pyrazole-4-carboxamide, (O137) N-cyclopropyl-3-(difluoromethyl)-5-fluoro-N-(2-isopropylbenzyl)-1-methyl-1H-pyrazole-4-carbothioamide, (O138) N'-(2,5-dimethyl-4-phenoxyphenyl)-N-ethyl-N-methylimidoformamide, (O139) N'-{4-[(4,5-dichloro-1,3-thiazol-2-yl)oxy]-2,5-dimethylphenyl}-N-ethyl-N-methyl imidoformamide, (O140) N-(4-chloro-2,6-difluorophenyl)-4-(2-chloro-4-fluorophenyl)-1,3-dimethyl-1H-pyrazol-5-amine, (O141) 9-fluoro-2,2-dimethyl-5-(quinolin-3-yl)-2,3-dihydro-1,4-benzoxazepine, (O142) 2-{2-fluoro-6-[(8-fluoro-2-methylquinolin-3-yl)oxy]phenyl}propan-2-ol, (O143) 2-{2-[(7,8-difluoro-2-methylquinolin-3-yl)oxy]-6-fluorophenyl}propan-2-ol, (O144) 4-(2-chloro-4-fluorophenyl)-N-(2-fluorophenyl)-1,3-dimethyl-1H-pyrazol-5-amine, (O145) 4-(2-chloro-4-fluorophenyl)-N-(2,6-difluorophenyl)-1,3-dimethyl-1H-pyrazol-5-amine, (O146) 4-(2-chloro-4-fluorophenyl)-N-(2-chloro-6-fluorophenyl)-1,3-dimethyl-1H-pyrazol-5-amine, (O147) 4-(2-bromo-4-fluorophenyl)-N-(2-chloro-6-fluorophenyl)-1,3-dimethyl-1-pyrazol-5-amine, (O148) N-(2-bromo-6-fluorophenyl)-4-(2-chloro-4-fluorophenyl)-1,3-dimethyl-1H-pyrazol-5-amine, (O149) 4-(2-bromo-4-fluorophenyl)-N-(2-bromophenyl)-1,3-dimethyl-1H-pyrazol-5-amine, (O150) 4-(2-bromo-4-fluorophenyl)-N-(2-bromo-6-fluorophenyl)-1,3-dimethyl-1H-pyrazol-5-amine, (O151) 4-(2-bromo-4-fluorophenyl)-N-(2-chlorophenyl)-1,3-dimethyl-1H-pyrazol-5-amine, (O152) N-(2-bromophenyl)-4-(2-chloro-4-fluorophenyl)-1,3-dimethyl-1H-pyrazol-5-amine, (O153) 4-(2-chloro-4-fluorophenyl)-N-(2-chlorophenyl)-1,3-dimethyl-1H-pyrazol-5-amine, (O154) 4-(2-bromo-4-fluorophenyl)-N-(2,6-difluorophenyl)-1,3-dimethyl-1H-pyrazol-5-amine, (O155) 4-(2-bromo-4-fluorophenyl)-N-(2-fluorophenyl)-1,3-dimethyl-1H-pyrazol-5-amine, (O156) N'-(4-{3-[(difluoromethyl)sulfanyl]phenoxy}2,5-dimethylphenyl)-N-ethyl-N-methylimidoformamide, (O157) N'-(2,5-dimethyl-4-{3-[(1,1,2,2-tetrafluoroethyl)sulfanyl]phenoxy}phenyl)-N-ethyl-N-methylimidoformamide, (O158) N'-(2,5-dimethyl-4-{3-[(2,2,2-trifluoroethyl)sulfanyl]phenoxy}phenyl)-N-ethyl-N-methylimidoformamide, (O159) N'-(2,5-dimethyl-4-{3-[(2,2,3,3-tetrafluoropropyl)sulfanyl]phenoxy}phenyl)-N-ethyl-N-methylimidoformamide, (O160) N'-(2,5-dimethyl-4-{3-[(pentafluoroethyl)sulfanyl]phenoxy}phenyl)-N-ethyl-N-methylimidoformamide, (O161) N'-(4-{[3-(difluoromethoxy)phenyl]sulfanyl}-2,5-dimethylphenyl)-N-ethyl-N-methylimidoformamide, (O162) N'-(2,5-dimethyl-4-{[3-(1,1,2,2-tetrafluoroethoxy)phenyl]sulfanyl}phenyl)-N-ethyl-N-methylimidoformamide, (O163) N'-(2,5-dimethyl-4-{[3-(2,2,2-trifluoroethoxy)phenyl]sulfanyl}phenyl)-N-ethyl-N-methylimidoformamide, (O164) N'-(2,5-dimethyl-4-{[3-(2,2,3,3-tetrafluoropropoxy)phenyl]sulfanyl}phenyl)-N-ethyl-N-methylimidoformamide, (O165) N'-(2,5-dimethyl-4-{[3-(pentafluoroethoxy)phenyl]sulfanyl}phenyl)-N-ethyl-N-methylimidoformamide, (O166) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (O167) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (O168) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (O169) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (O170) 2-{3-[2-(1-{[3,5-bis(difluoromethyl)-1H-pyrazol-1-yl]acetyl}piperidin-4-yl)-1,3-thiazol-4-yl]-dihydro-1,2-oxazol-5-yl}-3-chlorophenyl methanesulfonate, (O171) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (O172) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (O173) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (O174) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (O175) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (O176) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (O177) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (O178) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (O179) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (O180) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (O181) (3S,6S,7R,8R)-8-benzyl-3-{3-[(isobutyryloxy)methoxy]-4-methoxypicolinamido}-6-methyl-4,9-dioxo-1,5-dioxonan-7-yl isobutyrate.

As described above the compound of formula (I) can be mixed with one or more active compatible compound selected from insecticides/acaricides/nematicides class. which are specified herein by their common names that are known and described, for example in *The Pesticide Manual* 17th Ed., or can be searched in the internet (e.g. under www.alanwood.net/pesticides).

(1) Acetylcholinesterase (AChE) inhibitors such as carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb or organophosphates, such as acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as cyclodiene organochlorines, for example chlordane and endosulfan or phenylpyrazoles (fiproles), for example ethiprole and fipronil.

(3) Sodium channel modulators/voltage-dependent sodium channel blockers, such as pyrethroids, for example acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans-isomer), prallethrin, pyrethrins (pyrethrum), resmethrin, silafluofen, tefluthrin, tetramethrin, tetramethrin [(1R)-isomers)], tralomethrin and transfluthrin or DDT or methoxychlor.

(4) Nicotinic acetylcholine receptor (nAChR) competitive modulators, such as neonicotinoids, for example acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, such as spinosyns, for example spinetoram and spinosad.

(6) Glutamate-gated chloride channel (GluCl) allosteric modulators, such as avermectins/milbemycins, for example abamectin, emamectin benzoate, lepimectin and milbemectin.

(7) Juvenile hormone mimics such as juvenile hormone analogues, for example hydroprene, kinoprene and methoprene or fenoxycarb or pyriproxyfen.

(8) Active compounds with unknown or non-specific mechanisms of action, such as alkyl halides for example as methyl bromide and other alkyl halides or chloropicrin or fluorides or borates or tartar emetic or methyl isocyanate generators.

(9) Chordotonal organ TRPV channel modulators such as pyridine azomethine derivatives, for example pymetrozine and pyrifluquinazon or flonicamid.

(10) Mite growth inhibitors, for example clofentezine, hexythiazox and diflovidazin or etoxazole.

(11) Microbial disruptors of insect gut midgut, for example *Bacillus thuringiensis* subspecies *israelensis, Bacillus thuringiensis* subspecies *aizawai, Bacillus thuringiensis* subspecies *kurstaki, Bacillus thuringiensis* subspecies *tenebrionis* and *Bacillus sphaericus* and BT crop proteins: Cry1Ab, Cry1Ac, Cry1Fa, Cry1A 105, Cry2Ab, Vip3a, mCry3A, Cry3Ab, Cry3Bb, Cry34Ab1/Cry35Ab1.

(12) Inhibitors of mitochondrial ATP synthase such as organotin miticides, for example azocyclotin, cyhexatin and fenbutatin oxide or diafenthiuron or propargite or tetradifon.

(13) Uncouplers of oxidative phosphorylation acting via disruption of the proton gradient, for example chlorfenapyr, DNOC and sulfluramid.

(14) Nicotinic acetylcholine receptor (nAChR) channel blockers, such as bensultap, cartap-hydrochloride, thiocyclam and thiosultap-sodium.

(15) Inhibitors of chitin biosynthesis, type 0, such as bistrifluoron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, such as buprofezin.

(17) Molting disruptors (particularly in Dipteran), such as cyromazine.

(18) Ecdysone receptor agonists, such as chromafenozide, halofenozide, methoxyfenozide and tebufenozide.

(19) Octopamine receptor agonists, such as amitraz.

(20) Mitochondrial complex III electron transport inhibitors such as hydramethylnon or acequinocyl or fluacrypyrim or bifenazate.

(21) Mitochondrial complex I electron transport inhibitors, for example, METI acaricides and insecticides, for example fenazaquin, fenpyroximate, pyrimidifen, pyridaben, tebufenpyrad and tolfenpyrad or rotenone (Derris).

(22) Voltage-dependent sodium channel blockers such as indoxacarb or metaflumizone.

(23) Inhibitors of acetyl CoA carboxylase, such as tetronic and tetramic acid derivatives, for example spirodiclofen, spiromesifen and spirotetramat.

(24) Mitochondrial complex IV electron transport inhibitors, such as phosphides, for example aluminum phosphide, calcium phosphide, zinc phosphide and phosphine or cyanides.

(25) Mitochondrial complex II electron transport inhibitors such as beta-ketonitrile derivatives, for example cyenopyrafen and cyflumetofen or carboxanilides.

(28) Ryanodine receptor modulators such as diamides, for example chlorantraniliprole, cyantraniliprole and flubendiamide.

(29) Chordotonal organ modulators on undefined target site such as flonicamid.

Further active ingredients with unknown or indeterminate mode of action, such as afidopyropen, afoxolaner, azadirachtin, benclothiaz, benzoximate, bifenazate, broflanilide, bromopropylate, chinomethionat, cryolite, cyclaniliprole, cycloxaprid, cyhalodiamide, dicloromezotiaz, dicofol, diflovidazin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, triflumezopyrim and iodomethane; furthermore, preparations based on *Bacillus firmus* (1-1582, BioNeem, Votivo), and the following known active compounds: 1-{2-fluoro-4-methyl-5-[(2,2,2-trifluoroethyl)sulfinyl]phenyl}-3-(trifluoromethyl)-1H-1,2,4-triazol-5-amine (known from WO2006043635), {1'-[(2E)-3-(4-chlorophenyl)prop-2-ene-1-yl]-5-fluorospiro[indole-3,4'-piperidine]-1(2H)-yl}(2-chloropyridin-4-yl)methanone (known from WO2003106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006003494), 3-(2,5-dimethylphenyl)-4-hydroxy-8-methoxy-1,8-diazaspiro[4.5]dec-3-en-2-one (known from WO2009049851), 3-(2,5-dimethylphenyl)-8-methoxy-2-oxo-1,8-diazaspiro[4.5]dec-3-en-4-yl ethylcarbonate (known from WO2009049851), 4-(but-2-in-1-yloxy)-6-(3,5-dimethylpiperidin-1-yl)-5-fluoropyrimidine (known from WO2004099160), 4-(but-2-in-1-yloxy)-6-(3-chlorophenyl)pyrimidine (known from WO2003076415), PF1364 (CAS-Reg. No. 1204776-60-2), methyl-2-[2-({[3-bromo-1-(3-chloropyridin-2-yl)-1H-pyrazol-5-yl]carbonyl}amino)-5-chloro-3-methylbenzoyl]-2-methylhydrazincarboxylate (known from WO2005085216), methyl-2-[2-({[3-bromo-1-(3-chloropyridin-2-yl)-1H-pyrazol-5-yl]carbonyl}amino)-5-cyano-3-methylbenzoyl]-2-ethylhydrazincarboxylate (known from WO2005085216), methyl-2-[2-({[3-bromo-1-(3-chloro-pyridin-2-yl)-1H-pyrazol-5-yl]carbonyl}amino)-5-cyano-3-methylbenzoyl]-2-methylhydrazincarboxylate (known from WO2005085216), methyl-2-[3,5-dibromo-2-({[3-bromo-1-(3-chloro-pyridin-2-yl)-1H-pyrazol-5-yl]carbonyl}amino)benzoyl]-2-ethylhydrazincarboxylate (known from WO2005085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009080250), N-[(2E)-1-[(6-chloropyridine-3-yl)methyl]pyridin-2(1H)-ylidene]-2,2,2-trifluoroacetamide (known from WO2012029672), 1-[(2-chloro-1,3-thiazol-5-yl)methyl]-4-oxo-3-phenyl-4H-pyrido[1,2-a]pyrimidin-1-ium-2-olate (known from WO2009099929), 1-[(6-chloropyrid in-3-yl)methyl]-4-oxo-3-phenyl-4H-pyrido[1,2-a]pyrimidin-1-ium-2-olate (known from WO2009099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008134969), butyl-[2-(2,4-dichlorophenyl)-3-oxo-4-oxaspiro[4.5]dec-1-en-1-yl] carbonate (disclosed in CN102060818), 3(E)-3-[1-[(6-chloro-3-pyridyl)methyl]-2-pyridylidene]-1,1,1-trifluoropropan-2-one (known from WO2013144213), N-(methylsulfonyl)-6-[2-(pyridin-3-yl)-1,3-thiazol-5-yl]pyridine-2-carboxamide (known from WO2012000896), N-[3-(benzylcarbamoyl)-4-chlorophenyl]-1-methyl-3-(pentafluoroethyl)-4-(trifluoromethyl)-1H-pyrazole-5-carboxamide (known from WO2010051926).

The compounds of formula (I) may be used to treat several fungal pathogens. Non-limiting examples of pathogens of fungal diseases which can be treated in accordance with the invention include:

diseases caused by powdery mildew pathogens, for example *Blumeria* species, for example *Blumeria graminis; Podosphaera* species, for example *Podosphaera leucotricha; Sphaerotheca* species, for example *Sphaerotheca*

*fuliginea; Uncinula* species, for example *Uncinula necator; Erysiphe* species, for example *Erysiphe cichoracearu;* diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis* order *Puccinia striiformis; Uromyces* species, for example *Uromyces appendiculatus;* diseases caused by pathogens from the group of the Oomycetes, for example *Albugo* species, for example *Albugo candida; Bremia* species, for example *Bremia lactucae; Peronospora* species, for example *Peronospora pisi* or *P. brassicae; Phytophthora* species, for example *Phytophthora infestans; Plasmopara* species, for example *Plasmopara viticola; Pseudoperonospora* species, for example *Pseudoperonospora humuli* or *Pseudoperonospora cubensis; Pythium* species, for example *Pythium ultimum;* leaf blotch diseases and leaf wilt diseases caused, for example, by *Alternaria* species, for example *Alternaria solani; Cercospora* species, for example *Cercospora beticola; Cladiosporium* species, for example *Cladiosporium cucumerinum; Cochliobolus* species, for example *Cochliobolus sativus* (conidial form: *Drechslera,* syn: *Helminthosporium*) or *Cochliobolus miyabeanus; Colletotrichum* species, for example *Colletotrichum lindemuthaniwn; Cycloconiwn* species, for example *Cycloconium oleaginwn; Diaporthe* species, for example *Diaporthe citri; Elsinoe* species, for example *Elsinoe fawcettii; Gloeosporiwn* species, for example *Gloeosporium laeticolor; Glomerella* species, for example *Glomerella cingulata; Guignardia* species, for example *Guignardia bidwelli; Leptosphaeria* species, for example *Leptosphaeria maculans; Magnaporthe* species, for example *Magnaporthe grisea; Microdochium* species, for example *Microdochium nivale; Mycosphaerella* species, for example *Mycosphaerella graminicola, Mycosphaerella arachidicola* or *Mycosphaerella fijiensis; Phaeosphaeria* species, for example *Phaeosphaeria nodorum; Pyrenophora* species, for example *Pyrenophora teres* or *Pyrenophora tritici repentis; Ramularia* species, for example *Ramularia collo-cygni* or *Ramularia areola; Rhynchosporium* species, for example *Rhynchosporium secalis; Septoria* species, for example *Septoria apii* or *Septoria lycopersici; Stagonospora* species, for example *Stagonospora nodorum; Typhula* species, for example *Typhula incarnata; Venturia* species, for example *Venturia inaequalis;* root and stem diseases caused, for example, by *Corticium* species, for example *Corticium gramineartun; Fusarium* species, for example *Fusarium oxysporum; Gaeumannoznyces* species, for example *Gaeumannoinyces graminis; Plasmodiophora* species, for example *Plasmodiophora brassicae; Rhizoctonia* species, for example *Rhizoctonia solani; Sarocladium* species, for example *Sarocladium oryzae; Sclerotium* species, for example *Sclerotium oryzae; Tapesia* species, for example *Tapesia acuformis; Thielaviopsis* species, for example *Thielaviopsis basicola; Ganoderma* species, for example *Ganoderma lucidum;* ear and panicle diseases (including corn cobs) caused, for example, by *Alternaria* species, for example *Alternaria* spp.; *Aspergillus* species, for example *Aspergillus flavus; Cladosporium* species, for example *Cladosporium cladosporioides; Claviceps* species, for example *Claviceps purpurea; Fusarium* species, for example *Fusarium culmorum; Gibberella* species, for example *Gibberella zeae; Monographella* species, for example *Monographella nivalis; Stagnospora* species, for example *Stagnospora nodorum;* diseases caused by smut fungi, for example *Sphacelotheca* species, for example *Sphacelotheca reiliana; Tilletia* species, for example *Tilletia caries* or *Tilletia controversa; Urocystis* species, for example *Urocystis occulta; Ustilago* species, for example *Ustilago nuda;* fruit rot caused, for example, by *Aspergillus* species, for example *Aspergillus flavus; Botrytis* species, for example *Botrytis cinerea; Penicillium* species, for example *Penicillium expansum* or *Penicillium purpurogenum; Rhizopus* species, for example *Rhizopus stolonifer; Sclerotinia* species, for example *Sclerotinia sclerotiorum; Verticilium* species, for example *Verticilium alboatrum;* seed- and soil-borne rot and wilt diseases, and also diseases of seedlings, caused, for example, by *Alternaria* species, for example *Alternaria brassicicola; Aphanomyces* species, for example *Aphanomyces euteiches; Ascochyta* species, for example *Ascochyta lentis; Aspergillus* species, for example *Aspergillus flavus; Cladosporium* species, for example *Cladosporium herbarum; Cochliobolus* species, for example *Cochliobolus sativus* (conidial form: *Drechslera, Bipolaris* Syn: *Helminthosporium*); *Colletotrichum* species, for example *Colletotrichum coccodes; Fusarium* species, for example *Fusarium culmorum; Gibberella* species, for example *Gibberella zeae; Macrophomina* species, for example *Macrophomina phaseolina; Microdochium* species, for example *Microdochium nivale; Monographella* species, for example *Monographella nivalis; Penicillium* species, for example *Penicillium expansum; Phoma* species, for example *Phoma lingam; Phomopsis* species, for example *Phomopsis sojae; Phytophthora* species, for example *Phytophthora cactorum; Pyrenophora* species, for example *Pyrenophora graminea; Pyricularia* species, for example *Pyricularia oryzae; Pythium* species, for example *Pythium ultimum; Rhizoctonia* species, for example *Rhizoctonia solani; Rhizopus* species, for example *Rhizopus oryzae; Sclerotium* species, for example *Sclerotium rolfsii; Septoria* species, for example *Septoria nodorum; Typhula* species, for example *Typhula incarnata; Verticillium* species, for example *Verticillium dahliae;* cancers, galls and witches' broom caused, for example, by *Nectria* species, for example *Nectria galligena;* wilt diseases caused, for example, by *Monilinia* species, for example *Monilinia laxa;* deformations of leaves, flowers and fruits caused, for example, by *Exobasidium* species, for example *Exobasidium vexans; Taphrina* species, for example *Taphrina deformans;* degenerative diseases in woody plants, caused, for example, by *Esca* species, for example *Phaeomoniella chlamydospora, Phaeoacremonium aleophilum* or *Fomitiporie mediterranea; Ganoderma* species, for example *Ganoderma boninense;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora; Ralstonia* species, for example *Ralstonia solanacearum;*

Fungal diseases on roots and the stem base caused, for example, by black root rot (*Calonectria crotalariae*), charcoal rot (*Macrophomina phaseolina*), *Fusarium* blight or wilt, root rot, and pod and collar rot (*Fusarium oxysporum, Fusarium orthoceras, Fusarium semitectum, Fusarium equiseti*), *Mycoleptodiscus* root rot (*Mycoleptodiscus terrestris*), *Neocosmospora* (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), *Pythium* rot (*Pythium aphanidermatum, Pythium irregulars, Pythium debaryanwn, Pythium myriotylum, Pythium ultimum*), *Rhizoctonia* root rot, stem decay, and damping-off (*Rhizoctonia solani*), *Sclerotinia* stem decay (*Sclerotinia sclerotiorum*), *Sclerotinia* southern blight (*Sclerotinia rolfsii*), *Thielaviopsis* root rot (*Thielaviopsis basicola*).

Plants which can be treated in accordance with the invention include the following: *Rosaceae* sp (for example pome fruits such as apples, pears, apricots, cherries, almonds and *peaches*), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (*for example banana trees* and *plantations*), *Rubiaceae* sp. (for example coffee), *Theaceae* sp., *Sterculiceae* sp., *Rutaceae* sp. (for example lemons, oranges and grapefruit); *Vitaceae* sp. (for example grapes); *Solanaceae* sp. (for example tomatoes, peppers), *Liliaceae* sp., *Asteraceae* sp. (for example lettuce), *Unibelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Poaceae/Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); *Malvaceae* (for example cotton); useful plants and ornamental plants for gardens and wooded areas; and genetically modified varieties of each of these plants.

All plants and plant parts can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts are understood to mean all parts and organs of plants above and below the ground, such as shoot, leaf, flower and root, examples of which include leaves, needles, stalks, stems, flowers, fruit bodies, fruits and seeds, and also roots, tubers and rhizomes. The plant parts also include harvested material and vegetative and generative propagation material, for example cuttings, tubers, rhizomes, slips and seeds.

The invention furthermore includes a method for treating seed, particularly seeds (dormant, primed, pregerminated or even with emerged roots and leaves) treated with at least one of the compounds of the formula (I) and compositions thereof. The inventive seeds are used in methods for protection of seeds and emerged plants from the seeds from phytopathogenic harmful fungi. In these methods, seed treated with at least one inventive active ingredient is used.

It is also desirable to optimize the amount of the active ingredient used so as to provide the best possible protection for the seeds, the germinating plants and emerged seedlings from attack by phytopathogenic fungi, but without damaging the plants themselves by the active ingredient used. In particular, methods for the treatment of seed should also take into consideration the intrinsic phenotypes of transgenic plants in order to achieve optimum protection of the seed and the germinating plant with a minimum of crop protection compositions being employed.

The present invention therefore also relates to a method for protecting seeds, germinating plants and emerged seedlings against attack by animal pests and/or phytopathogenic harmful microorganisms by treating the seeds with an inventive composition. The invention also relates to the use of the compositions according to the invention for treating seeds for protecting the seeds, the germinating plants and emerged seedlings against animal pests and/or phytopathogenic microorganisms. The invention further relates to seeds which has been treated with an inventive composition for protection from animal pests and/or phytopathogenic microorganisms.

One of the advantages of the present invention is that the treatment of the seeds with these compositions not only protects the seed itself, but also the resulting plants after emergence, from animal pests and/or phytopathogenic harmful microorganisms. In this way, the immediate treatment of the crop at the time of sowing or shortly thereafter protect plants as well as seed treatment in prior to sowing. It is likewise considered to be advantageous that the inventive active ingredients or compositions can be used especially also for transgenic seed, in which case the plant which grows from this seed is capable of expressing a protein which acts against pests, herbicidal damage or abiotic stress. The treatment of such seeds with the inventive active ingredients or compositions, for example an insecticidal protein, can result in control of certain pests. Surprisingly, a further synergistic effect can be observed in this case, which additionally increases the effectiveness for protection against attack by pests, microorganisms, weeds or abiotic stress.

The compounds of the formula (I) are suitable for protection of seed of any plant variety which is used in agriculture, in the greenhouse, in forests or in horticulture. More particularly, the seed is that of cereals (such as wheat, barley, rye, millet and oats), oilseed rape, maize, cotton, soybean, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice.

As also described below, the treatment of transgenic seed with the inventive active ingredients or compositions is of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus*, *Rhizobium*, *Pseudomonas*, *Serratia*, *Trichoderma*, *Clavibacter*, *Glomus* or *Gliocladium*. These heterologous genes preferably originate from *Bacillus* sp., in which case the gene product is effective against the European corn borer and/or the Western corn rootworm. Particularly preferably, the heterologous genes originate from *Bacillus thuringiensis*.

In the context of the present invention, the inventive composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pregerminated seeds, or seeds sown on nursery trays, tapes or paper.

When treating the seeds, it generally has to be ensured that the amount of the inventive composition applied to the seed and/or the amount of further additives is selected such that the germination of the seed is not impaired, or that the resulting plant is not damaged. This must be ensured particularly in the case of active ingredients which can exhibit phytotoxic effects at certain application rates.

The compounds of the formula (I) can be applied directly, i.e. without containing any other components and without having been diluted. In general, it is preferable to apply the compositions to the seed in the form of a suitable formulation. Suitable formulations and methods for seed treatment are known to those skilled in the art. The compounds of the formula (I) can be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

In the treatment of seeds to facilitate plantability seeds can be coated with polymer. The polymer coating is comprised of a binder, a wax and a pigment, and one or more stabilizers in an amount effective to stabilize the suspension. The binder can be a polymer selected from the group consisting of vinyl acetate-ethylene copolymer, vinyl acetate homopolymer, vinyl acetate-acrylic copolymer, vinylacrylic, acrylic, ethylene-vinyl chloride, vinyl ether maleic anhydride, or butadiene styrene. Other similar polymers can be used.

These formulations are prepared in a known manner, by mixing the active ingredients or active ingredient combinations with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants. In this case, additional synergistic effects may also occur in interaction with the substances formed by expression.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds. The application rates of each single active ingredient are generally between 0.001 and 15 g per kilogram of seed, preferably between 0.01 and 5 g per kilogram of seed.

When using the compounds of the formula (I) as fungicides, the application rates can be varied within a relatively wide range, depending on the kind of application. The application rate of the inventive active ingredients is:
in the case of treatment of plant parts, for example leaves: from 0.1 to 10000 g/ha, preferably from 10 to 1000 g/ha, more preferably from 30 to 300 g/ha (in the case of application by watering or dripping, it is even possible to reduce the application rate, especially when inert substrates such as rockwool or perlite are used);

in the case of seed treatment: from 0.1 to 200 g per 100 kg of seed, preferably from 1 to 150 g per 100 kg of seed, more preferably from 2.5 to 25 g per 100 kg of seed, even more preferably from 2.5 to 12.5 g per 100 kg of seed;

in the case of soil treatment: from 0.1 to 10000 g/ha, preferably from 1 to 5000 g/ha.

These application rates are merely by way of example and are not limiting for the purposes of the invention.

In some cases, the compounds of the formula (I) can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (Mycoplasma-like organisms) and RLO (Rickettsia-like organisms).

The compounds of the formula (I) intervene in physiological processes of plants and can therefore also be used as plant growth regulators. Plant growth regulators may exert various effects on plants. The effect of the substances depends essentially on the time of application in relation to the developmental stage of the plant, the plant variety and also on the amounts of active ingredient applied to the plants or their environment and on the type of application. In each case, growth regulators should have a particular desired effect on the crop plants.

Growth regulating effects, comprise earlier germination, better emergence, more developed root system and/or improved root growth, increased ability of tillering, more productive tillers, earlier flowering, increased plant height and/or biomass, shorting of sterns, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectolitre weight as well as to improved product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, amino acid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxines, less aflatoxines, geosmin level, phenolic aromas, lacchase, polyphenol oxidases and peroxidases, nitrate content etc.

Plant growth-regulating compounds can be used, for example, to slow down the vegetative growth of the plants. Such growth depression is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, vegetative growth depression allows denser planting, and it is thus possible to achieve higher yields based on the soil surface. Another advantage of the smaller plants obtained in this way is that the crop is easier to cultivate and harvest.

Reduction of the vegetative plant growth may also lead to increased or improved yields because the nutrients and assimilates are of more benefit to flower and fruit formation than to the vegetative parts of the plants.

Alternatively, growth regulators can also be used to promote vegetative growth. This is of great benefit when harvesting the vegetative plant parts. However, promoting vegetative growth may also promote generative growth in that more assimilates are formed, resulting in more or larger fruits.

Furthermore, beneficial effects on growth or yield can be achieved through improved nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Likewise, growth regulators can be used to alter the composition of the plants, which in turn may result in an improvement in quality of the harvested products. Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Furthermore, growth regulators can modulate plant senescence, which may result in prolonged green leaf area duration, a longer grain filling phase, improved yield quality, etc.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"). In addition, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to synchronize maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

The compounds of the formula (I) also exhibit a potent strengthening effect in plants. Accordingly, they can be used for mobilizing the defenses of the plant against attack by undesirable microorganisms.

Plant-strengthening (resistance-inducing) substances in the present context are substances capable of stimulating the defence system of plants in such a way that the treated plants, when subsequently inoculated with undesirable microorganisms, develop a high degree of resistance to these microorganisms.

Further, in context with the present invention plant physiology effects comprise the following:

Abiotic stress tolerance, comprising tolerance to high or low temperatures, drought tolerance and recovery after drought stress, water use efficiency (correlating to reduced water consumption), flood tolerance, ozone stress and UV tolerance, tolerance towards chemicals like heavy metals, salts, pesticides etc.

Biotic stress tolerance comprising increased fungal resistance and increased resistance against nematodes, viruses and bacteria. In context with the present invention, biotic stress tolerance preferably comprises increased fungal resistance and increased resistance against nematodes.

Increased plant vigor, comprising plant health/plant quality and seed vigor, reduced stand failure, improved appearance, increased recovery after periods of stress, improved pigmentation (e.g. chlorophyll content, stay-green effects, etc.) and improved pholosynthetic efficiency.

In addition, the compounds of the formula (I) can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferaturn, F. poae, F. pseudograminearum, F. sam-bucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicaium, P. citrinum, P. expansum, P. claviforme, P. roqueforti, Claviceps* spec., such as *C. purpurea, C. fusiformis, C. paspali, C. africana, Stachybotrys* spec. and others.

The compounds of the formula (I) can also be used in the protection of materials, for protection of industrial materials against attack and destruction by phytopathogenic fungi.

In addition, the compounds of the formula (I) can be used as antifouling compositions, alone or in combinations with other active ingredients.

Industrial materials in the present context are understood to mean inanimate materials which have been prepared for use in industry. For example, industrial materials which are to be protected by inventive compositions from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compounds of the formula (I) may prevent adverse effects, such as rotting, decay, discoloration, decolouration or formation of mould.

In the case of treatment of wood the compounds of the formula (I) may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition according to the invention; this includes for example direct application, spraying, dipping, injection or any other suitable means.

In addition, the compounds of the formula (I) can be used to protect objects which come into contact with saltwater or brackish water, especially hulls, screens, nets, buildings, moorings and signalling systems, from fouling.

The compounds of the formula (I) can also be employed for protecting storage goods. Storage goods are understood to mean natural substances of vegetable or animal origin or processed products thereof which are of natural origin, and for which long-term protection is desired.

Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive compositions may prevent adverse effects, such as rotting, decay, discoloration, decoloration or formation of mould.

Microorganisms capable of degrading or altering the industrial materials include, for example, bacteria, fungi, yeasts, algae and slime organisms. The compounds of the formula (I) preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomiunt*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

In addition, the compounds of the formula (I) also have very good antimycotic effects. They have a very broad antimycotic activity spectrum, especially against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The enumeration of these fungi by no means constitutes a restriction of the mycotic spectrum covered, and is merely of illustrative character.

The compounds can be used also to control important fungal pathogens in fish and crustacea farming, e.g. *saprolegnia diclina* in trouts, *saprolegnia parasitica* in crayfish.

The compounds of the formula (I) can therefore be used both in medical and in non-medical applications.

The compounds of the formula (I) can be used as such, in the form of their formulations or the use forms prepared therefrom, such as ready-to-use solutions, suspensions, wettable powders, pastes, soluble powders, dusts and granules. Application is accomplished in a customary manner, for example by watering, spraying, atomizing, broadcasting, dusting, foaming, spreading-on and the like. It is also possible to deploy the active ingredients by the ultra-low volume method or to inject the active ingredient preparation/the active ingredient itself into the soil. It is also possible to treat the seed of the plants.

It is possible to treat all plants and their parts in accordance with the invention, preferably with wild plant species and plant cultivars, or those obtained by conventional biological breeding methods, such as crossing or protoplast fusion, and also parts thereof. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference-RNAi-technology or microRNA-miRNA-technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved pholosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as tobacco plants, with altered post-translational protein modification patterns.

Accordingly compounds of present invention have been illustrated in table 1 and 2.

The following tables illustrate in a non-limiting manner examples of compounds according to the invention. In the following examples, M+1 (or M−1) means the molecular ion peak, plus or minus 1 a.m.u. (atomic mass unit) respectively, as observed in mass spectroscopy $^1$H-NMR data of selected examples are written in form of $^1$H-NMR-peak lists. To each signal peak are listed the δ-value in ppm and the no of proton in round brackets.

For calibrating chemical shift for $^1$H spectra, we use tetramethylsilane and/or the chemical shift of the solvent used, especially in the case of spectra measured in DMSO, Therefore in NMR peak lists, tetramethylsilane peak can occur but not necessarily.

The $^1$H-NMR peak lists are similar to classical $^1$H-NMR prints and contains therefore usually 15 all peaks, which are listed at classical NMR-interpretation.

Additionally they can show like classical $^1$H-NMR prints signals of solvents, stereoisomers of the target compounds, which are also object of the invention, and/or peaks of impurities.

Table 1 provides compounds of general formula (I)

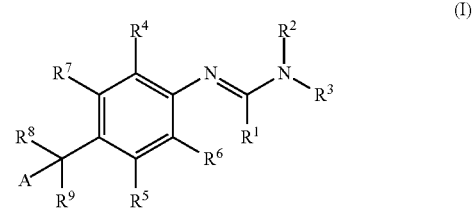

(I)

| Sr. No. | Compound Name | Analytical Data |
|---|---|---|
| 1. | N'-(4-benzyl-2,5-dimethylphenyl)-N-ethyl-N-methylformimidamide | $^1$H-NMR (400 MHz, DMSO-d6) δ 7.51 (bs, 1H), 7.27-7.23 (m, 2H), 7.16-7.09 (m, 3H), 6.85 (s, 1H), 6.54 (s, 1H), 3.84 (s, 2H), 2.90 (s, 3H), 2.09 (s, 6H), 1.10 (t, 3H); (M + 1): 281.5 |
| 2. | N-ethyl-N'-(4-(methoxy(phenyl)methyl)-2,5-dimethylphenyl)-N-methylformimidamide | Example 20 |
| 3. | N'-(4-(3,5-dichlorobenzyl)-2,5-dimethylphenyl)-N-ethyl-N-methylformimidamide | Example: 1 |
| 4. | N'-(4-(4-bromobenzyl)-2,5-dimethylphenyl)-N-ethyl-N-methylformimidamide | Example: 2 |
| 5. | N'-(4-(3,4-dichlorobenzyl)-2,5-dimethylphenyl)-N-ethyl-N-methylformimidamide | Example: 3 |

-continued

| Sr. No. | Compound Name | Analytical Data |
|---|---|---|
| 6. | N'-(2,5-dimethyl-4-(3-methylbenzyl)phenyl)-N-ethyl-N-methylformimidamide | Example: 4 |
| 7. | N'-(4-(4-chlorobenzyl)-2,5-dimethylphenyl)-N-ethyl-N-methylformimidamide | $^1$H-NMR (400 MHz, DMSO-d6) δ 7.66-7.43 (1H), 7.31-7.29 (m, 2H), 7.11 (d, 2H), 6.85 (s, 1H), 6.54 (s, 1H), 3.82 (s, 2H), 3.47-3.32 (2H), 2.90 (s, 3H), 2.09 (s, 3H), 2.06 (s, 3H), 1.10 (t, 3H); (M + 1): 316.2 |
| 8. | N'-(2,5-dimethyl-4-(4-(methylthio)benzyl)phenyl)-N-ethyl-N-methylformimidamide | Example: 6 |
| 9. | N'-(2,5-dimethyl-4-(4-methylbenzyl)phenyl)-N-ethyl-N-methylformimidamide | $^1$H-NMR (400 MHz, DMSO-d6) δ 7.56 (s, 1H), 7.04 (d, 2H), 6.97 (d, 2H), 6.82 (s, 1H), 6.53 (s, 1H), 3.79 (d, 2H), 3.33 (d, 2H), 2.90 (s, 3H), 2.23 (s, 3H), 2.11 (s, 6H), 1.13 (t, 3H); (M + 1): 295.30 |
| 10. | N'-(2-bromo-4-(4-bromobenzyl)-3,6-dimethylphenyl)-N-ethyl-N-methylformimidamide | $^1$H-NMR (400 MHz, DMSO-d6) δ 7.46-7.43 (m, 2H), 7.30 (d, 1H), 7.05 (d, 2H), 6.96 (s, 1H), 3.91 (s, 2H), 3.41 (d, 1H), 3.29-3.20 (m, 1H), 2.91 (s, 3H), 2.22-2.18 (m, 3H), 2.07 (d, 3H), 1.08-1.18 (m, 3H); (M + 1): 438.2 |
| 11. | N'-(4-(3-chlorobenzyl)-2,5-dimethylphenyl)-N-ethyl-N-methylformimidamide | $^1$H-NMR (400 MHz, DMSO-d6) δ 7.56 (bs, 1H), 7.30-7.20 (m, 2H), 7.17-7.14 (m, 2H), 6.87 (s, 1H), 6.56 (s, 1H), 3.90-3.85 (m, 2H), 3.39 (s, 1H), 3.30 (s, 1H), 2.91 (s, 3H), 2.11 (s, 3H), 2.07 (s, 3H), 1.09-1.15 (m, 3H); (M + 1): 316.4 |
| 12. | N'-(2,5-dimethyl-4-(4-(methylsulfonyl)benzyl)phenyl)-N-ethyl-N-methylformimidamide; | $^1$H-NMR (400 MHz, DMSO-d6) δ 7.81 (dd, 2H), 7.68-7.44 (1H), 7.36 (d, 2H), 6.90 (s, 1H), 6.57 (s, 1H), 3.95 (s, 2H), 3.34 (d, 2H), 3.16 (s, 3H), 2.91 (s, 3H), 2.09 (s, 6H), 1.11 (t, 3H); (M + 1): 359.30 |
| 13. | N'-(4-(3-bromobenzyl)-2-chloro-5-methylphenyl)-N-ethyl-N-methylformimidamide | $^1$H-NMR (400 MHz, DMSO-d6) δ 7.64 (bs, 1H), 7.38-7.34 (m, 1H), 7.29-7.22 (m, 2H), 7.14-7.11 (m, 2H), 6.78 (s, 1H), 3.87 (s, 2H), 3.45-3.36 (m, 2H), 2.97-2.90 (m, 3H), 2.09 (s, 3H), 1.13 (s, 3H); (M + 1): 380.8 |
| 14. | N'-(4-(3-bromobenzyl)-2,5-dimethylphenyl)-N-ethyl-N-methylformimidamide | $^1$H-NMR (400 MHz, DMSO-d6) δ 7.58 (s, 1H), 7.34 (d, 1H), 7.25-7.20 (m, 2H), 7.14-7.10 (m, 1H), 6.87 (s, 1H), 6.56 (s, 1H), 3.84 (s, 2H), 3.35 (s, 2H), 2.91 (s, 3H), 2.10 (s, 3H), 2.06 (d, 3H), 1.10 (t, 3H); (M + 1): 361.1 |
| 15. | N-ethyl-N'-(4-(2-fluorobenzyl)-2,5-dimethylphenyl)-N-methylformimidamide | $^1$H-NMR (400 MHz, DMSO-d6) δ 7.58 (s, 1H),7.26-6.99 (m, 4H), 6.78 (s, 1H), 6.56 (s, 1H), 3.83 (s, 2H), 3.60-3.36 (2H), 2.90 (s, 3H), 2.15-2.04 (m, 6H), 1.10 (t, 3H); (M + 1): 298.6 |
| 16. | N'-(2-chloro-4-(2-fluorobenzyl)-5-methylphenyl)-N-ethyl-N-methylformimidamide | $^1$H-NMR (400 MHz, DMSO-d6) δ 7.64 (d,1H), 7.29-7.24 (m, 1H), 7.19-7.06 (m, 3H), 6.97 (s, 1H), 6.79 (s, 1H), 3.86 (s, 2H), 3.40 (s, 2H), 2.93 (d, 3H), 2.14 (s, 3H), 1.12 (t, 3H); (M + 1): 319.2 |
| 17. | N'-(2-chloro-4-(2-chlorobenzyl)-5-methylphenyl)-N-ethyl-N-methylformimidamide | $^1$H-NMR (400 MHz, DMSO-d6) δ 7.65 (d, 1H), 7.47-7.44 (m, 1H), 7.26 (dt, 2H), 7.04-7.01 (m, 1H), 6.83 (d, 2H), 3.93 (s, 2H), 3.40 (s, 2H), 2.97-2.90 (m, 3H), 2.14 (d, 3H), 1.11 (t, 3H); (M + 1): 336.18 |
| 18. | N'-(4-(2-chlorobenzyl)-2,5-dimethylphenyl)-N-ethyl-N-methylformimidamide | $^1$H-NMR (400 MHz, DMSO-d6) δ 7.60-7.56 (m, 1H), 7.46-7.42 (m, 1H), 7.26-7.20 (m, 2H), 6.96-6.91 (m, 1H), 6.69 (s, 1H), 6.59 (s, 1H), 3.90 (s, 2H), 3.70-3.39 (1H), 3.28-3.10 (1H), 2.91 (s, 3H), 2.10 (s, 6H), 1.16-1.12 (m, 3H); (M + 1):314.8 |
| 19. | N'-(2,5-dimethyl-4-(4-(methylsulfinyl)benzyl)phenyl)-N-ethyl-N-methylformimidamide | $^1$H-NMR (400 MHz, DMSO-d6) δ 7.57-7.55 (m, 3H), 7.30 (d, 2H), 6.88 (s, 1H), 6.55 (s, 1H), 3.90 (s, 2H), 3.35 (s, 1H), 2.90 (s, 3H), 2.69 (s, 3H), 2.09 (d, 6H), 1.10 (t, 3H); (M + 1): 343.1 |
| 20. | N'-(2-chloro-4-(3,4-dichlorobenzyl)-5-methylphenyl)-N-ethyl-N-methylformimidamide | $^1$H-NMR (400 MHz, DMSO-d6) δ 7.64 (d,1H), 7.53 (d, 1H), 7.36 (d, 1H), 7.09-7.12 (m, 2H), 6.79 (s, 1H), 3.87 (s, 2H), 3.44-3.34 (m, 2H), 2.93 (d, 3H), 2.09 (s, 3H), 1.11 (t, 3H); (M + 1): 371.1 |
| 21. | N'-(2-chloro-4-(3,5-dichlorobenzyl)-5-methylphenyl)-N-ethyl-N-methylformimidamide | $^1$H-NMR (400 MHz, DMSO-d6) δ 7.65 (d, 1H), 7.42 (t, 1H), 7.15 (s, 3H), 6.79 (s, 1H), 3.89 (s, 2H), 3.30-3.25 (1H), 3.30 (s, 1H), 2.97 (s, 3H), 2.08 (s, 3H), 1.12 (t, 3H); (M + 1): 370.1 |
| 22. | N'-(4-(4-bromobenzyl)-2-chloro-5-methylphenyl)-N-ethyl-N-methylformimidamide | $^1$H-NMR (400 MHz, DMSO-d6) δ 7.63 (d, 1H), 7.48-7.44 (m, 2H), 7.09-7.06 (m, 3H), 6.78 (s, 1H), 3.83 (s, 2H), 3.42-3.36 (m, 1H), 3.29 (s, 1H), 2.96-2.90 (m, 3H), 2.08 (d, 3H), 1.11 (t, 3H); (M + 1): 380.2 |

-continued

| Sr. No. | Compound Name | Analytical Data |
|---|---|---|
| 23. | N'-(2,5-dimethyl-4-(2-(methylthio)benzyl)phenyl)-N-ethyl-N-methylformimidamide | $^1$H-NMR (400 MHz, DMSO-d6) δ 7.59 (brs, 1H), 7.26-7.19 (m, 2H), 7.03 (td, H), 6.76 (d, 1H), 6.67 (s, 1H), 6.58 (s, 1H), 3.79 (s, 2H), 3.39-3.46 (m, 2H), 2.91 (s, 3H), 2.45 (s, 3H), 2.07 (d, 6H), 1.11 (t, 3H); (M + 1): |
| 24. | N'-(2,5-dimethyl-4-(2-(methylsulfinyl)benzyl)phenyl)-N-ethyl-N-methylformimidamide | $^1$H-NMR (400 MHz, DMSO-d6) δ 7.87 (d, 1H), 7.61-7.57 (m, 1H), 7.47-7.40 (m, 2H), 7.00 (d, 1H), 6.68 (s, 1H), 6.59 (s, 1H), 3.90 (dd, 2H), 3.40-3.36 (m, 2H), 2.90 (s, 3H), 2.55 (s, 3H), 2.12-2.06 (m, 6H), 1.10 (t, 3H); (M + 1): |
| 25. | N'-(2,5-dimethyl-4-(2-(methylsulfonyl)benzyl)phenyl)-N-ethyl-N-methylformimidamide | $^1$H-NMR (400 MHz, DMSO-d6) δ 7.96 (d, 1H), 7.70-7.53 (m, 3H), 7.47 (t, 1H), 6.99 (d 1H), 6.71 (s, 1H), 6.62 (s, 1H), 4.32 (s, 2H), 3.35 (s, 1H), 3.18 (s, 3H), 2.91 (s, 3H), 2.07-2.05 (m, 6H), 1.11 (t, 3H); (M + 1): |
| 26. | N'-(4-(2,5-dimethylbenzyl)-2,5-dimethylphenyl)-N-ethyl-N-methylformimidamide | $^1$H-NMR (400 MHz, DMSO-d6) δ 7.60 (s, 1H), 7.04-6.88 (m, 2H), 6.61 (d,2H), 5.74 (d, 1H), 3.76-3.72 (m, 21-0, 3.35 (s, 2H), 2.89 (d, 3H) 2.22 (s, 12H), 1.12 (t, 3H); (M + 1): 309.4 |
| 27. | N'-(4-(3-bromo-2-fluorobenzyl)-2,5-dimethylphenyl)-N-ethyl-N-methylformimidamide | $^1$H-NMR (400 MHz, DMSO-d6) δ 7.58-7.52 (m, 2H), 7.07-6.99 (m, 2H), 6.79 (s, 1H), 6.57 (s, 1H), 3.87 (s, 2H), 3.35 (s, 2H), 2.90 (s, 3H), 2.10 (s, 3H), 2.07 (s, 3H), 1.10 (t, 3H); (M + 1): 378.4 |
| 28. | N'-(4-(3-chloro-4-fluorobenzyl)-2,5-dimethylphenyl)-N-ethyl-N-methylformimidamide | $^1$H-NMR (400 MHz, DMSO-d6) δ 7.58 (s, 1H), 7.31-7.30 (m, 2H), 7.09 (dq, 1H), 6.86 (s, 1H), 6.56 (s, 1H), 3.83 (s, 2H), 3.35 (s, 1H), 3.28 (d, 1H), 2.90 (s, 3H), 2.10 (s, 3H), 2.06 (s, 3H), 1.10 (t, 3H); (M + 1): 334.1 |
| 29. | N-ethyl-N'-(4-(3-fluorobenzyl)-2,5-dimethylphenyl)-N-methylformimidamide | $^1$H-NMR (400 MHz, DMSO-d6) δ 7.64 (d, J = 45.5 Hz, 1H), 7.24-7.28 (m, 1H), 7.06-7.19 (m, 3H), 6.97 (s, 1H), 6.80 (s, 1H), 3.86 (s, 2H), 3.35-3.42 (m, 1H), 3.29 (s, 1H), 2.93 (d, J = 27.1 Hz, 3H), 2.14 (s, 6H), 1.11 (t, J = 6.9 Hz, 3H); (M + 1): 299.4 |
| 30. | N'-(2-chloro-4-(3-fluorobenzyl)-5-methylphenyl)-N-ethyl-N-methylformimidamide | $^1$H-NMR (400 MHz, DMSO-d6) δ 7.70 (s, 1H), 7.31 (td, 1H), 7.09 (s, 1H), 7.02-6.90 (m, 3H), 6.78 (s, 1H), 3.88 (s, 2H), 3.42-3.42 (m, 1H), 3.29 (s, 1H), 2.93 (d, 3H), 2.10 (s, 3H), 1.11 (t, 3H); (M + 1): 320.1 |
| 31. | N'-(2,5-dimethyl-4-((methylimino)(phenyl)methyl)phenyl)-N-ethyl-N-methylformimidamide | $^1$H-NMR (400 MHz, DMSO-d6) δ 7.72-7.62 (m, 1H), 7.53-7.49 (m, 2H), 7.40-7.32 (m, 3H), 6.73 (s, 1H), 6.68 (s, 1H), 3.48 (s, 2H), 3.10-3.04 (m, 3H), 2.94 (s, 3H), 2.13 (d, 3H), 1.91 (d, 3H), 1.13 (t, 3H); (M + 1): 308.4 |
| 32. | N'-(2,5-dimethyl-4-(2-methylbenzyl)phenyl)-N-ethyl-N-methylformimidamide | $^1$H-NMR (400 MHz, DMSO-d6) δ 7.59 (s, 1H), 7.17-7.14 (m, 1H), 7.10-7.03 (m, 2H), 6.80-6.77 (m, 1H), 6.59 (d, 2H), 3.78 (d, 2H), 3.42-3.35 (m, 1H), 3.29 (s, 1H), 2.90 (s, 3H), 2.22 (s, 3H), 2.09 (s, 3H), 2.04 (s, 3H), 1.10 (t, 3H); (M + 1): 295.1 |
| 33. | N'-(2,5-dimethyl-4-(2-phenyl-1,3-dithiolan-2-yl)phenyl)-N-ethyl-N-methylformimidamide | $^1$H-NMR (400 MHz, DMSO-d6) δ 7.79 (s, 1H), 7.64 (s, 1H), 7.39-7.37 (m, 2H), 7.27-7.23 (m, 2H), 7.20-7.15 (m, 1H), 6.52 (s, 1H), 3.48-3.44 (m, 3H), 3.37-3.32 (m,3H), 2.91 (s, 3H), 2.20 (s, 3H), 1.74 (s, 3H), 1.11 (t, 3H); (M + 1): |
| 34. | N-(4-(3-chloro-4-fluorobenzyl)-2,5-dimethylphenyl)-1-morpholinomethanimine | $^1$H-NMR (400 MHz, DMSO-d6) δ 7.61 (s, 1H), 7.31-7.25 (m, 2H), 7.09 (dq, 1H), 6.88 (s, 1H), 6.60 (s, 1H), 3.83 (s, 2H), 3.62-3.59 (m, 4H), 3.44 (s, 4H), 2.08 (d, 6H); (M + 1): 362.2 |
| 35. | N-(4-(3-chloro-4-fluorobenzyl)-2,5-dimethylphenyl)-1-(piperidin-1-yl)methanimine | $^1$H-NMR (400 MHz, DMSO-d6) δ 7.53 (s, 1H), 7.31-7.23 (m, 2H), 7.08 (dq, 2.3 Hz, 1H), 6.86 (s, 1H), 6.56 (s, 1H), 3.82 (s, 2H), 3.45-3.34 (m, 4H), 2.07 (d, 6H), 1.62-1.58 (m, 2H), 1.52-1.46 (m, 4H); (M + 1): 369.9 |
| 36. | N-(4-(3-bromo-2-fluorobenzyl)-2,5-dimethylphenyl)-1-morpholinomethanimine | Example: 16 |
| 37. | N-(4-(3-bromo-2-fluorobenzyl)-2,5-dimethylphenyl)-1-(piperidin-1-yl)methanimine | $^1$H-NMR (400 MHz, DMSO-d6) δ 7.54-7.50 (m, 2H), 7.07-6.98 (m, 2H), 6.79 (s, 1H), 6.58 (s, 1H), 3.87 (s, 2H), 3.46-3.35 (m, 4H), 2.08 (d, 6H), 1.63-1.58 (m, 2H), 1.52-1.46 (m, 4H); (M + 1): 404.2 |
| 38. | N-(2-chloro-4-(3-fluorobenzyl)-5-methylphenyl)-1-morpholinomethanimine | $^1$H-NMR (400 MHz, DMSO-d6) δ 7.71 (s, 1H), 7.32 (td, 1H), 7.11 (s, 1H), 7.03-6.91 (m, 3H), 6.82 (s, 1H), 3.89 (s, 2H), 3.62-3.60 (m, 4H), 3.55-3.40 (m, 4H), 2.11 (s, 3H); (M + 1): 347.8 |

-continued

| Sr. No. | Compound Name | Analytical Data |
|---|---|---|
| 39. | N-(2-chloro-4-(3-fluorobenzyl)-5-methylphenyl)-1-(piperidin-1-yl)methanimine | $^1$H-NMR (400 MHz, DMSO-d6) δ 7.64 (s, 1H), 7.31 (td, 1H), 7.09 (s, 1H), 7.02-6.90 (m, 3H), 6.79 (s, 1H), 3.88 (s, 2H), 3.52-3.33 (m, 4H), 2.10 (s, 3H), 1.62-1.58 (m, 2H),1.50 (s, 4H); (M + 1): 346.5 |
| 40. | N-(2-chloro-4-(2-chlorobenzyl)-5-methylphenyl)-1-morpholinomethanimine | $^1$H-NMR (400 MHz, DMSO-d6) δ 7.73 (s, 1H), 7.48-7.45 (m, 1H), 7.27 (dt, 2H), 7.03 (dd, 1H), 6.85 (d, 2H), 3.94 (s, 2H), 3.61 (t, 4H), 3.53-3.43 (m, 4H), 2.13 (s, 3H); (M + 1): 363. |
| 41. | N'-(4-(3-bromo-2-fluorobenzyl)-2,5-dimethylphenyl)-N-methylformimidamide | $^1$H-NMR (400 MHz, DMSO-d6) δ 7.47-7.45 (m, 2H), 7.11-7.01 (m, 3H), 6.80 (s, 1H), 6.54 (s, 1H), 3.88 (s, 2H), 2.77 (s, 3H), 2.07-2.12 (m, 6H); (M + 1): 351.1 |
| 42. | N'-(2-chloro-4-(3-fluorobenzyl)-5-methylphenyl)-N-methylformimidamide | $^1$H-NMR (400 MHz, DMSO-d6) δ 7.60 (d, 1H), 7.31 (td, 1H), 7.15 (s, 1H), 7.09 (s, 1H), 7.02-6.92 (m, 3H), 6.72 (s, 1H), 3.88 (s, 2H), 2.77 (d, 3H), 2.10 (s, 3H); (M + 1): 291.8 |
| 43. | N'-(2-chloro-5-methyl-4-(3-methylbenzyl)phenyl)-N-ethyl-N-methylformimidamide | $^1$H-NMR (400 MHz, DMSO-d6) δ 7.63 (d, 1H), 7.15 (t, 1H), 7.04 (s, 1H), 6.98 (d, 1H), 6.91 (t, 2H), 6.77 (s, 1H), 3.81 (s, 2H), 3.40 (s, 2H), 2.93 (s, 3H), 2.23 (d, 3H), 2.12 (d, 3H), 1.11 (t, 3H); (M + 1): 314.8 |
| 44. | N'-(2-chloro-5-methyl-4-(4-methylbenzyl)phenyl)-N-ethyl-N-methylformimidamide | $^1$H-NMR (400 MHz, DMSO-d6) δ 7.63 (d, 1H), 7.22-7.12 (m, 1H), 7.16-7.10 (m, 2H),7.02- 6.99 (m, 2H), 6.76 (s, 1H), 3.80 (s, 2H), 3.35-3.42 (m 2H), 2.93 (s, 3H), 2.24 (s, 3H), 2.08 (s, 3H), 1.11 (t, 3H); (M + 1): 316.2 |
| 45. | N-ethyl-N'-(4-(3-methoxybenzyl)-2,5-dimethylphenyl)-N-methylformimidamide | $^1$H-NMR (400 MHz, DMSO-d6) δ 7.57 (s, 1H), 7.16 (t, 1H), 6.84 (s, 1H), 6.73-6.70 (m, 1H), 6.67-6.65 (m, 2H), 6.54 (s, 1H), 3.79 (s, 2H), 3.69 (d, 3H), 3.35-3.29 (m, 2H), 2.90 (s, 3H), 2.08 (s, 6H), 1.13-1.08 (m, 3H); (M + 1): 311.2 |
| 46. | N'-(2,5-dimethyl-4-(3-(trifluoromethyl)benzyl)phenyl)-N-ethyl-N-methylformimidamide | $^1$H-NMR (400 MHz, DMSO-d6) δ 7.75 (s, 1H), 7.63-7.37 (m, 4H), 6.93 (s, 1H), 6.67 (s, 1H), 3.96 (s, 2H), 3.62-3.37 (2H), 2.87-2.96 (m, 3H), 2.13 (s, 3H), 2.08 (s, 3H), 1.12 (t, 3H); (M + 1): 349.2 |
| 47. | N'-(4-(3-cyanobenzyl)-2,5-dimethylphenyl)-N-ethyl-N-methylformimidamide | $^1$H-NMR (400 MHz, DMSO-d6) δ 7.64-7.45 (m, 5H), 6.88 (s, 1H), 6.56 (s, 1H), 3.89 (s, 2H), 3.45-3.34 (m, 2H), 2.90 (s, 3H), 2.10 (s, 3H), 2.07 (s, 3H), 1.10 (t, 3H); (M + 1): 306.2 |
| 48. | N'-(4-(4-cyanobenzyl)-2,5-dimethylphenyl)-N-ethyl-N-methylformimidamide | $^1$H-NMR (400 MHz, DMSO-d6) δ 7.73-7.71 (m, 2H), 7.59 (s, 1H), 7.29 (d, 2H), 6.88 (s, 1H), 6.57 (s, 1H), 3.93 (s, 2H), 3.51-3.33 (1H), 3.30-3.15 (1H), 2.91 (s, 3H), 2.10 (s, 3H), 2.05 (s, 3H), 1.10 (t, 3H); (M + 1): 306.17 |
| 49. | N'-(2,5-dimethyl-4-(3-nitrobenzyl)phenyl)-N-ethyl-N-methylformimidamide | $^1$H-NMR (400 MHz, DMSO-d6) δ 8.06-8.02 (m, 1H), 7.92 (s, 1H), 7.64-7.54 (m, 3H), 6.92 (s, 1H), 6.60 (s, 1H), 3.99 (s, 2H), 3.35 (m, 2H), 2.92 (s, 3H), 2.10 (s, 6H), 1.11 (t, 3H); (M + 1): 326.2 |
| 50. | N'-(2,5-dimethyl-4-(2-nitrobenzyl)phenyl)-N-ethyl-N-methylformimidamide | $^1$H-NMR (400 MHz, DMSO-d6) δ 7.95 (dd, 1H), 7.61-7.47 (m, 3H), 7.14 (d, 1H), 6.61 (d, 2H), 4.09 (s, 2H), 3.35 (m, 2H), 2.90 (s, 3H), 2.04 (s, 6H), 1.10 (t, 3H); (M + 1): 326.2 |
| 51. | N'-(2,5-dimethyl-4-(3-(trifluoromethoxy)benzypphenyl)-N-ethyl-N-methylformimidamide | $^1$H-NMR (400 MHz, DMSO-d6) δ 7.58 (s, 1H), 7.41-7.36 (m, 1H), 7.15-7.02 (m, 3H), 6.88 (s, 1H), 6.55 (s, 1H), 3.92 (d, 2H), 3.35 (m, 2H), 2.92 (d, 3H), 2.09-2.06 (s, 6H), 1.10 (t, 3H); (M + 1): 364.2 |
| 52. | N-ethyl-N'-(4-(3-fluoro-5-(trifluoromethyl)benzyl)-2,5-dimethylphenyl)-N-methylformimidamide | $^1$H-NMR (400 MHz, DMSO-d6) δ 7.61 (s, 1H), 7.47 (d, 1H), 7.32 (s, 1H), 7.23 (d, 1H), 6.90 (s, 1H), 6.58 (s, 1H), 3.96 (s, 2H), 3.35 (m, 2H), 2.96 (s, 3H), 2.09 (s, 6H), 1.11 (t, 3H); (M + 1): 367.17 |
| 53. | N'-(2,5-dimethyl-4-(2-methyl-5-(trifluoromethyl)benzyl)phenyl)-N-ethyl-N-methylformimidamide | $^1$H-NMR (400 MHz, DMSO-d6) δ 7.63 (s, 1H), 7.43 (dd, 2H), 7.07 (s, 1H), 6.63 (s, 2H), 3.86 (s, 2H), 3.37 (s, 2H), 2.91 (s, 3H), 2.32 (s, 3H), 2.10-2.03 (s, 6H), 1.11 (t, 3H); (M + 1): 362.4 |
| 54. | N-ethyl-N'-(4-(4-methoxybenzyl)-2,5-dimethylphenyl)-N-methylformimidamide | $^1$H-NMR (400 MHz, DMSO-d6) δ 7.56 (s, 1H), 7.00 (d, 2H), 6.83-6.79 (m, 3H), 6.53 (s, 1H), 3.75 (s, 2H), 3.69 (s, 3H), 3.35 (d, 1H), 3.28 (d, 1H), 2.90 (s, 3H), 2.09 (s, 6H), 1.10 (t, 3H); (M + 1): 311.14 |
| 55. | N-(4-(2-fluorobenzyl)-2,5-dimethylphenyl)-1-morpholinomethanimine | $^1$H-NMR (400 MHz, DMSO-d6) δ 7.61 (s, 1H), 7.26-7.20 (m, 1H), 7.17-7.12 (m, 1H), 7.08 (td, 1H), 7.01 (td, 1H), 6.79 (s, 1H), 6.60 (s, 1H), 3.83 (s, 2H), 3.62-3.59 (m, 4H), 3.45 (d, 4H), 2.11 (s, 3H), 2.06 (s, 3H); (M + 1): 326.2 |

-continued

| Sr. No. | Compound Name | Analytical Data |
|---|---|---|
| 56. | N-(4-(4-fluorobenzyl)-2,5-dimethylphenyl)-1-morpholinomethanimine | $^1$H-NMR (400 MHz, DMSO-d6) δ 7.60 (s, 1H), 7.13-7.12 (m, 4H), 6.85 (s, 1H), 6.58 (s, 1H), 3.82 (s, 2H), 3.60 (t, 4H), 3.43 (s, 4H), 2.08 (s, 6H); (M + 1): 326.4 |
| 57. | N-ethyl-N'-(4-(4-fluorobenzyl)-2,5-dimethylphenye-N-methylformimidamide | $^1$H-NMR (400 MHz, DMSO-d6) δ 7.54 (s, 1H), 7.14-7.03 (m, 4H), 6.84 (s, 1H), 6.56 (d, 1H), 3.81 (s, 2H), 3.35-3.29 (m, 2H), 2.90 (s, 3H), 2.08 (s, 6H), 1.10 (t, 3H); (M + 1): 398.1 |
| 58. | N-(4-(2-fluorobenzyl)-2,5-dimethylphenyl)-1-(piperidin-1-yl)methanimine | $^1$H-NMR (400 MHz, DMSO-d6) δ 7.53 (s, 1H), 7.24-7.21 (m, 1H), 7.16-7.12 (m, 1H), 7.08 (td, 1H), 7.01 (dd, 1H), 6.78 (s, 1H), 6.57 (s, 1H), 3.83 (s, 2H), 3.45-3.36 (m, 4H), 2.11 (s, 3H), 2.06 (s, 3H), 1.62-1.58 (m, 2H), 1.52-1.47 (m, 4H); (M + 1): 325.2 |
| 59. | N-(4-(2-chlorobenzyl)-2,5-dimethylphenyl)-1-(piperidin-1-yl)methanimine | $^1$H-NMR (400 MHz, DMSO-d6) δ 7.55 (s, 1H), 7.45-7.43 (m, 1H), 7.24-7.20 (m, 2H), 6.93 (dd, 1H), 6.69 (s, 1H), 6.60 (s, 1H), 3.90 (s, 2H), 3.46-3.36 (m, 4H), 2.08 (s, 3H), 2.05 (s, 3H), 1.64-1.38 (m, 2H), 1.53-1.47 (m, 4H); (M + 1): 341.2 |
| 60. | N-(4-(4-fluorobenzyl)-2,5-dimethylphenyl)-1-(piperidin-1-yl)methanimine | $^1$H-NMR (400 MHz, DMSO-d6) δ 7.52 (s, 1H), 7.13-7.03 (m, 4H), 6.84 (s, 1H), 6.55 (s, 1H), 3.82 (d, 2H), 3.46-3.34 (m, 4H), 2.08 (s, 6H), 1.62-1.58 (m, 2H), 1.52-1.46 (m, 4H); (M + 1): 325.18 |
| 61. | N'-(4-(2-fluorobenzyl)-2,5-dimethylphenyl)-N-methoxy-N-methylformimidamide | $^1$H-NMR (400 MHz, DMSO-d6) δ 7.86 (s, 1H), 7.26-7.21 (m, 1H), 7.18-7.01 (m, 3H), 6.82 (s, 1H), 6.66 (s, 1H), 3.85 (s, 2H), 3.68 (s, 3H), 3.09 (s, 3H), 2.12 (s, 3H), 2.08 (s, 3H); (M + 1): 301.2 |
| 62. | N'-(4-(2-chlorobenzyl)-2,5-dimethylphenyl)-N-methoxy-N-methylformimidamide | $^1$H-NMR (400 MHz, DMSO-d6) δ 7.88 (s, 1H), 7.46-7.41 (m, 1H), 7.24 (dd, 2H), 6.96 (dd, 1H), 6.72 (s, 1H), 6.69 (s, 1H), 3.92 (s, 2H), 3.69 (s, 3H), 3.10 (d, 3H), 2.11 (s, 3H), 2.07 (s, 3H); (M + 1): 318.3 |
| 63. | N-(4-(2-chlorobenzyl)-2,5-dimethylphenyl)-1-morpholinomethanimine | $^1$H-NMR (400 MHz, DMSO-d6) δ 7.63 (s, 1H), 7.45-7.43 (m, 1H), 7.23 (dd, 2H), 6.93 (dd, 1H), 6.70 (s, 1H), 6.63 (s, 1H), 3.90 (s, 2H), 3.61 (t, 4H), 3.44 (s, 4H), 2.08 (s, 3H), 2.06 (s, 3H); (M + 1): 343.4 |
| 64. | N-cyano-N'-(4-(2-fluorobenzyl)-2,5-dimethylphenyl)formimidamide | $^1$H-NMR (400 MHz, DMSO-d6) δ 8.60 (d, 1H), 7.30-7.04 (m, 5H), 6.93 (d, 2H), 3.91-3.89 (m, 2H), 2.21 (s, 3H), 2.08 (s, 3H); (M + 1): 282.14 |
| 65. | N'-(4-(2-chlorobenzyl)-2,5-dimethylphenyl)-N-cyanoformimidamide | $^1$H-NMR (400 MHz, DMSO-d6) δ 8.61 (s, 1H), 7.48-7.45 (m, 1H), 7.29-7.28 (m, 3H), 7.01-6.98 (m, 2H), 6.81 (d, 1H), 3.98-3.95 (m, 2H), 2.15 (s, 6H); (M + 1): 299.1 |
| 66. | N'-(4-(2-fluorobenzyl)-2,5-dimethylphenyl)-N-isopropylformimidamide | $^1$H-NMR (400 MHz, DMSO-d6) δ 7.41 (s, 1H), 7.26-7.20 (m, 1H), 7.17-7.00 (m, 3H), 6.82-6.77 (m, 2H), 6.50 (s, 1H), 3.98 (s, 1H), 3.82 (s, 2H), 2.11 (s, 3H), 2.05 (s, 3H), 1.15-1.11 (m, 6H); (M + 1): 300.2 |
| 67. | N'-(4-(2-chlorobenzyl)-2,5-dimethylphenyl)-N-isopropylformimidamide | $^1$H-NMR (400 MHz, DMSO-d6) δ 7.44 (dt, 2H), 7.24-7.20 (m, 2H), 6.95 (dd, 1H), 6.83 (s, 1H), 6.68 (s, 1H), 6.53 (s, 1H), 3.93 (s, 1H), 3.89 (s, 2H), 2.06 (s, 6H), 1.20-1.15 (d, 6H); (M + 1): 315.4 |
| 68. | N'-(2-chloro-4-(4-cyanobenzyl)-5-methylphenyl)-N-ethyl-N-methylformimidamide | $^1$H-NMR (400 MHz, DMSO-d6) δ 7.70-7.58 (m, 3H), 7.52-7.50 (m, 2H), 7.12 (s, 1H), 6.79 (s, 1H), 3.93 (s, 2H), 3.47-3.36 (m, 2H), 2.93 (s, 3H), 2.09 (s, 3H), 1.11 (t, 3H); (M + 1): 325.8 |
| 69. | N'-(2-chloro-4-(4-methoxybenzyl)-5-methylphenyl)-N-ethyl-N-methylformimidamide | $^1$H-NMR (400 MHz, DMSO-d6) δ 7.63 (d, 1H), 7.21-7.17 (m, 1H), 7.05 (s, 1H), 6.77-6.73 (m, 2H), 6.68-6.66 (m, 2H), 3.82 (s, 2H), 3.69 (s, 3H), 3.32-3.24 (1H), 2.93 (d, 3H), 2.11 (s, 3H), 1.11 (t, 3H); (M + 1): 331.4 |
| 70. | N'-(2-chloro-4-(3-methoxybenzyl)-5-methylphenyl)-N-ethyl-N-methylformimidamide | ($^1$H-NMR (400 MHz, DMSO-d6) δ 7.62 (d, 1H), 7.04-7.01 (m, 3H), 6.85-6.82 (m, 2H), 6.76 (s, 1H), 3.77 (s, 2H), 3.70 (s, 3H), 3.38 (s, 2H), 2.93 (s, 3H), 2.11 (s, 3H), 1.11 (t, 3H); (M + 1): 331.5 |
| 71. | N'-(2-chloro-5-methyl-4-(3-nitrobenzyl)phenyl)-N-ethyl-N-methylformimidamide | $^1$H-NMR (400 MHz, DMSO-d6) δ 8.05 (dt, 1H), 7.95 (s, 1H), 7.71 (s, 1H), 7.61-7.56 (m, 3H), 7.17 (s, 1H), 6.80 (s, 1H), 4.03 (s, 2H), 3.36 (s, 1H), 2.94 (s, 3H), 2.10 (s, 3H), 1.12 (t, 3H); (M + 1): 345.8 |
| 72. | N'-(2-chloro-4-(3-cyanobenzyl)-5-methylphenyl)-N-ethyl-N-methylformimidamide | $^1$H-NMR (400 MHz, DMSO-d6) δ 7.70-7.65 (m, 2H), 7.58 (s, 1H), 7.45-7.52 (m, 2H), 7.12 (s, 1H), 6.79 (s, 1H), 3.93 (s, 2H), 3.36-3.42 (m, 2H), 2.93 (d, 3H), 2.09 (s, 3H), 1.11 (t, 3H); (M + 1): 326.2 |

-continued

| Sr. No. | Compound Name | Analytical Data |
|---|---|---|
| 73. | N'-(4-(difluoro(phenyl)methyl)-2-iodo-3,6-dimethylphenyl)-N-ethyl-N-methylformimidamide | $^1$H-NMR (400 MHz, DMSO-d6) δ 7.53-7.43 (m, 4H), 7.39-7.37 (m, 3H), 3.57-3.30 (m, 2H), 2.83 (s, 3H), 2.32 (s, 3H), 2.12 (s, 3H), 1.19 (t, 3H); (M + 1): 443.05 |
| 74. | N'-(4-benzyl-2-chloro-5-methylphenyl)-N-ethyl-N-methylformimidamide | $^1$H-NMR (400 MHz, DMSO-d6) δ 7.63 (d, 1H), 7.27 (t, 2H), 7.19-7.11 (m, 3H), 7.05 (s, 1H), 6.77 (s, 1H), 3.85 (s, 2H), 3.40 (s, 2H), 2.93 (s, 3H), 2.13 (s, 3H), 1.11 (t, 3H); (M + 1): 290.9 |
| 75. | N'-(2-chloro-5-methyl-4-(2-nitrobenzyl)phenyl)-N-ethyl-N-methylformimidamide | $^1$H-NMR (400 MHz, DMSO-d6) δ 7.98 (dd, 1H), 7.72-7.62 (m, 2H), 7.49-7.53 (m, 1H), 7.21 (d, 1H), 6.82 (d, 2H), 4.13 (s, 2H), 3.35-3.42 (m, 2H), 2.94 (d, 3H), 2.09 (s, 3H), 1.12 (t, 3H); (M + 1): 346.06 |
| 76. | N'-(2-chloro-4-(4-fluorobenzyl)-5-methylphenyl)-N-ethyl-N-methylformimidamide | $^1$H-NMR (400 MHz, DMSO-d6) δ 7.69-7.57 (m, 1H), 7.40-7.22 (m, 1H), 7.19-7.04 (m, 6H), 6.77 (s, 1H), 3.84 (s, 2H), 3.42-3.37 (m, 2H), 2.93 (d, 3H), 2.10 (s, 3H), 1.11 (t, 3H); (M + 1): 319.2 |
| 77. | N'-(2-chloro-5-methyl-4-(4-((trifluoromethyl)thio)benzyl)phenyl)-N-ethyl-N-methylformimidamide | $^1$H-NMR (400 MHz, DMSO-d6) δ 7.69-7.58 (m, 3H), 7.27 (t, 2H), 7.13 (s, 1H), 6.78 (s, 1H), 3.95 (d, 2H), 3.46-3.35 (m, 2H), 2.93 (s, 3H), 2.09 (s, 3H), 1.11 (t, 3H); (M + 1): 401.4 |
| 78. | N'-(2-chloro-4-(3-chlorobenzyl)-5-methylphenyl)-N-ethyl-N-methylformimidamide | $^1$H-NMR (400 MHz, DMSO-d6) δ 7.64 (d, 1H), 7.33-7.23 (m, 2H), 7.15-7.08 (m, 3H), 6.78 (s, 1H), 3.88 (s, 2H), 3.42-3.35 (m, 1H), 2.94 (d, 3H), 2.08 (s, 3H), 1.12 (t, 3H); (M + 1): 336.2 |
| 79. | N'-(2-chloro-4-(4-chlorobenzyl)-5-methylphenyl)-N-ethyl-N-methylformimidamide | $^1$H-NMR (400 MHz, DMSO-d6) δ7.63 (d, 1H), 7.33 (d, 2H), 7.13 (d, 2H), 7.08 (s, 1H), 6.78 (s, 1H), 3.85 (s, 2H), 3.35-3.42 (m, 2H), 2.93 (s, 3H), 2.09 (s, 3H), 1.11 (t, 3H); (M + 1): 335.1 |
| 80. | N'-(2-chloro-5-methyl-4-(3-(trifluoromethyl)benzyp)phenyl)-N-ethyl-N-methylformimidamide | $^1$H-NMR (400 MHz, DMSO-d6) δ 7.70-7.41 (m, 5H), 7.13 (s, 1H), 6.79 (s, 1H), 3.98 (s, 2H), 3.35-3.42 (m, 2H), 2.94 (s, 3H), 2.10 (s, 3H), 1.12 (t, 3H); (M + 1): 368.6 |
| 81. | N'-(4-(2-fluorobenzyl)-2,5-dimethylphenyl)-N-isopropyl-N-methylformimidamide | $^1$H-NMR (400 MHz, DMSO-d6) δ 7.65 (s, 1H), 7.26-7.20 (m, 1H), 7.17-7.14 (m, 1H), 7.12-7.10 (m, 1H), 7.01 (td, 1H), 6.78 (s, 1H), 6.57 (s, 1H), 3.82 (s, 2H), 3.80-3.65 (1H), 2.81 (s, 3H), 2.10 (s, 3H), 2.06 (s, 3H), 1.15 (s, 6H); (M + 1): 328.8 |
| 82. | N'-(4-(2-chlorobenzyl)-2,5-dimethylphenyl)-N-isopropyl-N-methylformimidamide | $^1$H-NMR (400 MHz, DMSO-d6) δ 7.67 (s, 1H), 7.45-7.43 (m, 1H), 7.24-7.20 (m, 2H), 6.94 (dd, 1H), 6.69 (s, 1H), 6.60 (s, 1H), 3.91 (d, 2H), 3.86-3.58 (1H), 2.81 (s, 3H), 2.07 (s, 6H), 1.16-1.12 (m, 6H); (M + 1): 329.2 |
| 83. | N-allyl-N'-(4-(2-fluorobenzyl)-2,5-dimethylphenyl)-N-methylformimidamide | $^1$H-NMR (400 MHz, DMSO-d6) δ 7.62 (s, 1H), 7.23 (ddd, 1H), 7.17-7.12 (m, 1H), 7.08 (td, 1H), 7.01 (td, 1H), 6.79 (s, 1H), 6.58 (s, 1H), 5.84 (dt, 2H), 5.21-5.17 (m, 1H), 3.92-3.89 (m, 2H), 3.83 (s, 2H), 2.88 (s, 3H), 2.11 (s, 3H), 2.07 (s, 3H); (M + 1): 311.2 |
| 84. | N-allyl-N'-(4-(2-chlorobenzyl)-2,5-dimethylphenyl)-N-methylformimidamide | $^1$H-NMR (400 MHz, DMSO-d6) δ 7.64 (s, 1H), 7.45-7.43 (m, 1H), 7.25-7.20 (m, 2H), 6.94 (dd, 1H), 6.70 (s, 1H), 6.61 (s, 1H), 5.88-5.81 (m, 2H), 5.22-5.17 (m, 1H), 3.94 (s, 2H), 3.89-3.80 (m, 2H), 2.88 (s, 3H), 2.07 (d, 6H); (M + 1): 327 |
| 85. | N-(4-(2-fluorobenzyl)-2,5-dimethylphenyl)-1-thiomorpholinomethanimine | $^1$H-NMR (400 MHz, DMSO-d6) δ 7.58 (s, 1H), 6.98-7.25 (m, 4H), 6.79 (s, 1H), 6.60 (s, 1H), 3.83-3.67 (m, 6H), 2.61-2.59 (m, 4H), 2.11 (s, 3H), 2.06 (s, 3H); (M + 1): 343.2 |
| 86. | N-(4-(2-chlorobenzyl)-2,5-dimethylphenyl)-1-thiomorpholinomethanimine | $^1$H-NMR (400 MHz, DMSO-d6) δ 7.60 (s, 1H), 7.45-7.44 (m, 1H), 7.23 (dd, 2H), 6.96-6.94 (m, 1H), 6.70 (s, 1H), 6.63 (s, 1H), 3.90 (s, 2H), 3.73 (d, 4H), 2.62-2.59 (m, 4H), 2.07 (s, 6H); (M + 1): 359.1 |
| 87. | N-(cyclopropylmethyl)-N'-(4-(2-fluorobenzyl)-2,5-dimethylphenyl)-N-methylformimidamide | $^1$H-NMR (400 MHz, DMSO-d6) δ 7.59 (s, 1H), 7.23-7.20 (m, 4H), 6.77 (s, 1H), 6.55 (s, 1H), 3.82 (s, 2H), 3.04 (d, 5H), 2.10-2.06 (m, 6H), 1.21 (s, 1H), 0.49-0.44 (m, 2H), 0.21 (s, 2H); (M + 1): 325.4 |
| 88. | N-(cyclopropylmethyl)-N'-(4-(2-fluorobenzyl)-2,5-dimethylphenyl)-N-isopropylformimidamide | $^1$H-NMR (400 MHz, DMSO-d6) δ 7.75-7.53 (1H), 7.24-6.99 (m, 4H), 6.78 (s, 1H), 6.55 (s, 1H), 3.83 (s, 2H), 3.57 (1H), 3.20 (s, 2H), 2.09 (d, 6H), 1.22 (d, 6H), 1.17-0.98 (1H), 0.46-0.27 (m, 4H); (M + 1): 353.4 |

-continued

| Sr. No. | Compound Name | Analytical Data |
|---|---|---|
| 89. | N'-(4-(2-chlorobenzyl)-2,5-dimethylphenyl)-N-(cyclopropylmethyl)-N-isopropylformimidamide | $^1$H-NMR (400 MHz, DMSO-d6) δ 7.65 (s, 1H), 7.44-7.41 (m, 1H), 7.24-7.21 (m, 2H), 6.94 (dd, 1H), 6.68 (s, 1H), 6.57 (s, 1H), 3.89 (s, 2H), 3.82-3.57 (m, 1H), 3.21 (d, 2H), 2.07-2.00 (s, 6H), 1.23-1.19 (m, 6H), 1.00 (m, 1H), 0.45 (d, 2H), 0.29 (d, 2H); (M + 1): 369.2 |
| 90. | N'-(4-(2-chlorobenzyl)-2,5-dimethylphenyl)-N-cyano-N-(cyanomethyl)formimidamide | $^1$H-NMR (400 MHz, CHLOROFORM-D) δ 8.16 (s, 1H), 7.43 (dd, 1H), 7.25-7.18 (m, 2H), 7.05 (s, 1H), 6.95-6.91 (m, 2H), 4.59 (s, 2H), 4.05 (s, 2H), 2.31 (s, 3H), 2.15 (s, 3H); (M + 1): 337.4 |
| 91. | N-cyano-N-(cyanomethyl)-N'-(4-(2-fluorobenzyl)-2,5-dimethylphenyl)formimidamide | $^1$H-NMR (400 MHz, CHLOROFORM-D) δ 8.14 (bs, 1H), 7.24 (d, 1H), 7.10-6.99 (m, 5H), 4.58 (s, 2H), 3.97 (s, 2H), 2.29 (s, 6H); (M + 1): 321.2 |
| 92. | N'-(2,5-dimethyl-4-(4-((trifluoromethyl)thio)benzyl)phenyl)-N-ethyl-N-methylformimidamide | $^1$H-NMR (400 MHz, CHLOROFORM-D) δ 7.52 (d, 2H), 7.43 (s, 1H), 7.15 (d, 2H), 6.89 (s, 1H), 6.60 (s, 1H), 3.93 (s, 2H), 3.38 (m, 2H), 3.03 (s, 3H), 2.27 (s, 3H), 2.12 (s, 3H), 1.26-1.20 (m, 3H); (M + 1): 381.16 |
| 93. | N'-(2,5-dimethyl-4-(2-(trifluoromethyl)benzyl)phenyl)-N-ethyl-N-methylformimidamide | $^1$H-NMR (400 MHz, DMSO-d6) δ 7.72 (bs, 1H), 7.52 (t, 1H), 7.40 (t, 1H), 6.96 (d, 1H), 6.70 (s, 1H), 6.61 (s, 1H), 4.00 (s, 2H), 3.35 (m, 2H), 2.91 (s, 3H), 2.05 (d, 6H), 1.11 (t, 3H); (M + 1): 349.2 |
| 94. | N'-(2,5 -dimethyl-4-(4-(trifluoromethyl)benzyl)phenyl)-N-ethyl-N-methylformimidamide | $^1$H-NMR (400 MHz, DMSO-d6) δ 7.64-7.60 (m, 3H), 7.31 (d, 2H), 6.88 (s, 1H), 6.56 (s, 1H), 3.93 (s, 2H), 3.35-3.39 (m, 2H), 2.90 (s, 3H), 2.08 (s, 6H), 1.10 (t, 3H); (M + 1): 348.4 |
| 95. | N'-(2-chloro-4-(4-chloro-3-fluorobenzyl)-5-methylphenyl)-N-ethyl-N-methylformimidamide | $^1$H-NMR (400 MHz, DMSO-d6) δ 7.95 (s, 1H), 7.69-7.58 (m, 1H), 7.50-7.46 (m, 1H), 7.18 (d, 1H), 6.87-6.78 (m, 2H), 4.13 (s, 2H), 3.47-3.28 (m, 2H), 2.84 (s, 3H), 2.03 (s, 3H), 1.11 (t, 3H); (M + 1): 353.10 |
| 96. | N'-(4-(3,5-bis(trifluoromethyl)benzyl)-2-chloro-5-methylphenyl)-N-ethyl-N-methylformimidamide | $^1$H-NMR (400 MHz, DMSO-d6) δ 7.92 (s, 1H), 7.81 (s, 2H), 7.66 (d, 1H), 7.19 (s, 1H), 6.81 (s, 1H), 4.09 (s, 2H), 3.42-3.33 (m, 2H), 2.93 (s, 3H), 2.09 (s, 3H), 1.11 (t, 3H); (M + 1): 437.15 |
| 97. | N'-(2,5-dimethyl-4-(4-(trifluoromethyl)benzyl)phenyl)-N-ethyl-N-methylformimidamide | $^1$H-NMR (400 MHz, DMSO-d6) δ 7.64 (s, 1H), 7.40-7.26 (m, 3H), 7.09 (s, 1H), 6.78 (s, 1H), 3.91 (s, 2H), 3.42-3.32 (m, 2H), 2.93 (s, 3H), 2.38 (s, 3H), 2.09 (s, 3H), 1.11 (t, 3H); (M + 1): 383.2 |
| 98. | N'-(2,5-dimethyl-4-(4-(trifluoromethyl)benzyl)phenyl)-N-ethyl-N-methylformimidamide | $^1$H-NMR (400 MHz, DMSO-d6) δ 7.64 (s, 1H), 7.39 (t, 1H), 7.11-7.06 (m, 2H), 6.93 (s, 1H), 6.56 (d, 1H), 3.76 (s, 2H), 3.19-3.10 (m, 2H), 2.67 (s, 3H), 1.86 (s, 3H), 0.92 (t, 3H); (M + 1): 387.10 |
| 99. | N'-(2-chloro-4-(2-chloro-4-fluorobenzyl)-5-methylphenyl)-N-ethyl-N-methylformimidamide | $^1$H-NMR (400 MHz, DMSO-d6) δ 7.66 (bs, 1H), 7.46 (dd, 1H), 7.16 (td, 1H), 7.06 (dd 1H), 6.83 (d, 1H), 3.90 (s, 2H), 3.42-3.33 (m, 2H), 2.94 (s, 3H), 2.11 (s, 3H), 1.12 (t, 3H); (M + 1): 352.95 |
| 100. | N'-(2-chloro-4-(2-cyanobenzyl)-5-methylphenyl)-N-ethyl-N-methylformimidamide | $^1$H-NMR (400 MHz, DMSO-d6) δ 7.83 (dd, 1H), 7.72-7.61 (m, 2H), 7.42 (t, 1H), 7.19 (d, 1H), 6.93 (s, 1H), 6.83 (s, 1H), 4.07 (s, 2H), 3.38 (m, 2H), 2.94 (s, 3H), 2.13 (s, 3H), 1.12 (t, 3H); (M + 1): 326.50 |
| 101. | N'-(2-chloro-5-methyl-4-(4-(trifluoromethyl)benzyl)phenyl)-N-ethyl-N-methylformimidamide | $^1$H-NMR (400 MHz, DMSO-d6) δ 7.75-7.35 (m, 5H), 7.12 (d, 1H), 6.96-6.75 (m, 1H), 4.09-3.78 (m, 2H), 3.53-3.24 (m, 2H), 3.04 (s, 3H), 2.63-2.42 (s, 3H), 2.29-1.87 (m, 3H), 1.32-1.07 (m, 3H); (M + 1): 369.50 |
| 102. | N'-(2-chloro-5-methyl-4-(2-(trifluoromethoxy)benzyl)phenyl)-N-ethyl-N-methylformimidamide | $^1$H-NMR (400 MHz, DMSO-d6) δ 7.65 (bs, 1H), 7.38-7.26 (n, 3H), 7.09 (d, 1H), 6.96 (s, 1H), 6.81 (s, 1H), 3.89 (s, 2H), 3.43-3.32 (m, 1H), 2.94 (s, 3H), 2.09 (s, 3H), 1.12 (t, 3H); (M + 1): 385.75 |
| 103. | N'-(2-chloro-5-methyl-4-(2-(trifluoromethyl)benzyl)phenyl)-N-ethyl-N-methylformimidamide | $^1$H-NMR (400 MHz, DMSO-d6) δ 7.79-7.88 (m, 1H), 7.71-7.75 (m, 2H), 7.55-7.63 (m, 2H), 7.44 (t, 1H), 7.04 (d, 1H), 6.85 (d, 2H), 4.03 (s, 2H), 3.34-3.46 (m, 2H), 2.94 (d, 3H), 2.06 (s, 3H), 1.12 (t, 3H); (M + 1): |
| 104. | N'-(2,5-dimethyl-4-(4-methyl-3-(trifluoromethyl)benzyl)phenyl)-N-ethyl-N-methylformimidamide | $^1$H-NMR (400 MHz, DMSO-d6) δ 7.59 (bs, 1H), 7.38 (s, 1H), 7.28 (dd, 2H), 6.86 (s, 1H), 6.56 (s, 1H), 3.88 (s, 2H), 3.35-3.27 (m, 2H), 2.90 (s, 3H), 2.37 (s, 3H), 2.08 (s, 6H), 1.10 (t, 3H); (M + 1): 363.4 |
| 105. | N-(4-(4-chloro-3-fluorobenzyl)-2,5-dimethylphenyl)-N-ethyl-N-methylformimidamide | $^1$H-NMR (400 MHz, DMSO-d6) δ 7.59 (bs, 1H), 7.46 (t, 1H), 7.11 (m, 1H), 6.95 (dd, 1H), 6.86 (s, 1H), 6.56 (s, 1H), 3.84 (s, 2H), 3.35-3.28 (m, 2H), 2.90 (s, 3H), 2.08 (s, 6H), 1.10 (t, 3H); (M + 1): 333.15 |
| 106. | N'-(4-(3,5-bis(trifluoromethyl)benzyl)-2,5-dimethylphenyl)-N-ethyl-N-methylformimidamide | $^1$H-NMR (400 MHz, DMSO-d6) δ 7.91 (s, 1H), 7.77 (s, 2H), 7.62 (bs, 1H), 6.92 (s, 1H), 6.60 (s, 1H), 4.07 (s, 2H), 3.36 (m, 2H), 2.91 (s, 3H), 2.11 (s, 6H), 1.11 (t, 3H); (M + 1): 417.4 |

-continued

| Sr. No. | Compound Name | Analytical Data |
|---|---|---|
| 107. | N'-(4-(3-(1-cyanoethyl)benzyl)-2,5-dimethylphenyl)-N-ethyl-N-methylformimidamide | ¹H-NMR (400 MHz, DMSO-d6) δ 7.56 (bs, 1H), 7.30-7.26 (m, 1H), 7.18 (d, 2H), 7.03 (d, 1H), 6.85 (s, 1H), 6.54 (s, 1H), 4.23 (q, 1H), 3.84 (s, 2H), 3.34 (m, 2H), 2.89(s, 3H), 2.08 (s, 6H), 1.48 (d, 3H), 1.09 (t, 3H); (M + 1): 334.4 |
| 108. | N'-(4-(4-chloro-3-methylbenzyl)-2,5-dimethylphenyl)-N-ethyl-N-methylformimidamide | ¹H-NMR (400 MHz, DMSO-d6) δ 7.57 (bs, 1H), 7.27 (d, 1H), 7.08 (d, 1H), 6.91 (dd, 1H), 6.84 (s, 1H), 6.54 (s, 1H), 3.78 (s, 2H), 3.35 (m, 2H), 2.90 (s, 3H), 2.25 (s, 3H), 2.08 (s, 6H), 1.10 (t, 3H); (M + 1): 329.2 |
| 109. | N-ethyl-N-(4-(4-fluoro-3-methylbenzyl)-2,5-dimethylphenyl)-N-methylformimidamide | ¹H-NMR (400 MHz, DMSO-d6) δ 7.56 (bs, 1H), 7.01-6.83 (m, 4H), 6.53 (s, 1H), 3.79 (s, 2H), 3.35 (m, 2H), 2.89 (s, 3H), 2.15 (s, 3H), 2.10-2.07 (m, 6H), 1.09 (t, 3H); (M + 1): 313.35 |
| 110. | N'-(4-(2-chloro-4-fluorobenzyl)-2,5-dimethylphenyl)-N-ethyl-N-methylformimidamide | ¹H-NMR (400 MHz, DMSO-d6) δ 7.60 (bs, 1H), 7.43 (dd, 1H), 7.12 (td, 1H), 6.96 (dd, 1H), 6.64 (d, 2H), 3.86 (s, 2H), 3.35 (m, 2H), 2.91 (s, 3H), 2.07 (s, 6H), 1.10 (t, 3H); (M + 1): 333.2 |
| 111. | N'-(4-(3-(dimethylamino)benzyl)-2,5-dimethylphenyl)-N-ethyl-N-methylformimidamide | ¹H-NMR (400 MHz, DMSO-d6) δ 7.56 (bs, 1H), 7.06-7.01 (m, 1H), 6.82 (s, 1H), 6.57-6.49 (m, 3H), 6.35 (d, 1H), 3.76 (s, 2H), 3.37 (m, 2H), 2.90-2.86 (m, 3H), 2.83 (s, 6H), 2.14 (s, 6H), 1.12 (t, 3H); (M + 1): 324.2 |
| 112. | N'-(4-(2,3-dimethylbenzyl)-2,5-dimethylphenyl)-N-ethyl-N-methylformimidamide | ¹H-NMR (400 MHz, DMSO-d6) δ 7.59 (bs, 1H), 7.00-6.92 (m, 2H), 6.66 (d, 1H), 6.56 (d, 2H), 3.78 (s, 2H), 3.48-3.32 (m, 2H), 2.90 (s, 3H), 2.24 (s, 3H), 2.14 (s, 6H), 2.04 (s, 3H), 1.10 (t, 3H); (M + 1): 309.15 |
| 113. | N'-(4-(3,4-dimethylbenzyl)-2,5-dimethylphenyl)-N-ethyl-N-methylformimidamide | ¹H-NMR (400 MHz, DMSO-d6) δ 7.58 (bs, 1H), 7.02-6.98 (m, 1H), 6.89-6.78 (m, 3H), 6.53 (s, 1H), 3.74 (s, 2H), 3.51-3.29 (m, 2H), 2.90 (s, 3H), 2.14 (s, 6H), 2.08 (s, 6H), 1.10 (t, 3H); (M + 1): 309.1 |
| 114. | N'-(4-(3,5-dimethylbenzyl)-2,5-dimethylphenyl)-N-ethyl-N-methylformimidamide | ¹H-NMR (400 MHz, DMSO-d6) δ 7.57 (bs, 1H), 6.83 (s, 1H), 6.76 (s, 1H), 6.69 (s, 2H), 6.53 (s, 1H), 3.73 (s, 2H), 3.49-3.20 (m, 2H), 2.90 (s, 3H), 2.21 (s, 6H), 2.08 (s, 6H), 1.10 (t, 3H); (M + 1): 309.15 |
| 115. | N'-(4-(2-cyanobenzyl)-2,5-dimethylphenyl)-N-ethyl-N-methylformimidamide | ¹H-NMR (400 MHz, DMSO-d6) δ 7.81 (dd, 1H), 7.60 (td, 2H), 7.39 (t, 1H), 7.13 (d, 1H), 6.74 (s, 1H), 6.60 (s, 1H), 4.03 (s, 2H), 3.47-3.20 (m, 2H), 2.91 (s, 3H), 2.10 (s, 3H), 2.07 (s, 3H), 1.10 (t, 3H); (M + 1): 306.05 |
| 116. | N'-(2,5-dimethyl-4-(2-(trifluoromethoxy)benzyl)phenyl)-N-ethyl-N-methylformimidamide | ¹H-NMR (400 MHz, DMSO-d6) δ 7.59 (bs, 1H), 7.33-7.25 (m, 3H), 7.01 (d, 1H), 6.76 (s, 1H), 6.58 (s, 1H), 3.86 (s, 2H), 3.47-3.20 (m, 2H), 2.90 (s, 3H), 2.07 (s, 6H), 1.10 (t, 3H); (M + 1): 365.05 |
| 117. | N'-(2,5-dimethyl-4-(4-(trifluoromethoxy)benzyl)phenyl)-N-ethyl-N-methylformimidamide | ¹H-NMR (400 MHz, DMSO-d6) δ 7.58 (bs, 1H), 7.28-7.20 (m, 4H), 6.87 (s, 1H), 6.55 (s, 1H), 3.86 (s, 2H), 3.47-3.20 (m, 2H), 2.90 (s, 3H), 2.10 (s, 3H), 2.08 (s, 3H), 1.10 (t, 3H); (M + 1): 365.1 |
| 118. | N'-(4-(3-chloro-2-fluorobenzyl)-2,5-dimethylphenyl)-N-ethyl-N-methylformimidamide | ¹H-NMR (400 MHz, DMSO-d6) δ 7.58 (bs, 1H), 7.42-7.38 (m, 1H), 7.11 (t, 1H), 7.00- 6.96 (m, 1H), 6.79 (s, 1H), 6.57 (s, 1H), 3.87 (s, 2H), 3.47-3.21 (m, 2H), 2.92 (s, 3H), 2.09 (s, 6H), 1.10 (t, 3H), (M + 1): 333.6 |
| 119. | N'-(2-chloro-4-(4-fluoro-3-methylbenzyl)-5-methylphenyl)-N-ethyl-N-methylformimidamide | ¹H-NMR (400 MHz, DMSO-d6) δ 7.68 (bs, 1H), 7.12-7.02 (m, 3H), 6.95-6.91 (m, 1H), 6.76 (s, 1H), 3.79 (s, 2H), 3.41 (q, 2H), 2.89 (s, 3H), 2.16 (s, 3H), 2.10 (s, 3H), 1.14-1.09 (m, 3H); (M + 1): 333.20 |
| 120. | N'-(2-chloro-4-(4-chloro-3-methylbenzyl)-5-methylphenyl)-N-ethyl-N-methylformimidamide | ¹H-NMR (400 MHz, DMSO-d6) δ 7.70 (bs, 1H), 7.30 (d, 1H), 7.11-7.01 (m, 2H), 6.94 (dd, 1H), 6.78 (s, 1H), 3.82 (s, 2H), 3.42 (m, 2H), 2.91 (s, 3H), 2.27 (s, 3H), 2.10 (s, 3H), 1.12 (t, 3H); (M + 1): 350.90 |
| 121. | N'-(2-chloro-5-methyl-4-(4-(trifluoromethoxy)benzyl)phenyl)-N-ethyl-N-methylformimidamide | ¹H-NMR (400 MHz, DMSO-d6) δ 7.64 (bs, 1H), 7.25 (dd, 4H), 7.11 (s, 1H), 6.77 (d, 1H), 3.89 (s, 2H), 3.41-3.30 (m, 2H), 2.93 (s, 3H), 2.10 (s, 3H), 1.11 (t, 3H); (M + 1): 385.1 |
| 122. | N'-(2-chloro-5-methyl-4-(2-methylbenzyl)phenyl)-N-ethyl-N-methylformimidamide | ¹H-NMR (400 MHz, DMSO-d6) δ 7.66 (bs, 1H), 7.20-7.17 (m, 1H), 7.15-7.08 (m, 2H), 6.86-6.80 (m, 2H), 6.73 (s, 1H), 3.80 (s, 2H), 3.42-3.29 (m, 2H), 2.94 (s, 3H), 2.19 (s, 3H), 2.13 (s, 3H), 1.12 (t, 3H); (M + 1): 315.1 |
| 123. | N-(2-chloro-4-(3-chloro-2-fluorobenzyl)-5-methylphenyl)-N-ethyl-N-methylformimidamide | ¹H-NMR (400 MHz, DMSO-d6) δ 7.65 (bs, 1H), 7.46-7.42 (m, 1H), 7.15 (t, 1H), 7.05-7.01 (m, 2H), 6.80 (d, 1H), 3.91 (s, 2H), 3.42-3.30 (m, 2H), 2.94 (s, 3H), 2.13 (s, 3H), 1.12 (t, 3H); (M + 1): 353.4 |

| Sr. No. | Compound Name | Analytical Data |
| --- | --- | --- |
| 124. | N'-(2-chloro-5-methyl-4-(3-(trifluoromethoxy)benzyl)phenyl)-N-ethyl-N-methylformimidamide | $^1$H-NMR (400 MHz, DMSO-d6) δ 7.65 (bs, 1H), 7.43-7.37 (m, 1H), 7.19-7.10 (m, 4H), 6.78 (d, 1H), 3.93 (s, 2H), 3.42-3.30 (m, 2H), 2.93 (s, 3H), 2.12 (s, 3H), 1.11 (t, 3H); (M + 1): 385.4 |
| 125. | N'-(2-chloro-4-(2-chloro-3-fluorobenzyl)-5-methylphenyl)-N-ethyl-N-methylformimidamide | $^1$H-NMR (400 MHz, DMSO-d6) δ 7.66 (bs, 1H), 7.34-7.27 (m, 2H), 6.88-6.83 (m, 3H), 3.98 (s, 2H), 3.42-3.39 (m, 2H), 2.94 (s, 3H), 2.11 (s, 3H), 1.12 (t, 3H); (M + 1): 354.1 |
| 126. | N'-(2-chloro-4-(3-chloro-2-fluoro-5-(trifluoromethyl)benzyl)-5-methylphenyl)-N-ethyl-N-methylformimidamide | $^1$H-NMR (400 MHz, DMSO-d6) δ 7.97 (dd, 1H), 7.66 (bs, 1H), 7.45 (d, 1H), 7.06 (s, 1H), 6.83 (s, 1H), 4.01 (s, 2H), 3.38 (m, 2H), 2.97-2.91 (m, 3H), 2.13 (s, 3H), 1.12 (t, 3H); (M + 1): 421.1 |
| 127. | N'-(4-(cyano(phenyl)methyl)-2,5-dimethylphenyl)-N-ethyl-N-methylformimidamide | $^1$H-NMR (400 MHz, DMSO-d6) δ 7.59 (S, 1H), 7.41-7.37 (m, 2H), 7.33-7.27 (m, 3H), 7.07 (s, 1H), 6.62 (s, 1H), 5.72 (s, 1H), 3.39-3.25 (m, 2H), 2.90 (s, 3H), 2.08 (s, 6H), 1.10 (t, 3H); (M + 1): 306.10 |
| 128. | N'-(2-chloro-4-(2,3-dichlorobenzyl)-5-methylphenyl)-N-ethyl-N-methylformimidamide | $^1$H-NMR (400 MHz, DMSO-d6) δ 7.66 (bs, 1H), 7.53 (dd, 1H), 7.29 (t, 1H), 6.98 (dd, 1H), 6.85 (d, 2H), 3.99 (s, 2H), 3.38-3.31 (m, 2H), 2.94 (s, 3H), 2.11 (s, 3H), 1.12 (t, 3H); (M + 1): 370.0 |
| 129. | N'-(2-chloro-4-(3,5-difluorobenzyl)-5-methylphenyl)-N-ethyl-N-methylformimidamide | $^1$H-NMR (400 MHz, DMSO-d6) δ 7.65 (bs, 1H), 7.13 (s, 1H), 7.04 (tt, 1H), 6.82-6.79 (m, 3H), 3.89 (s, 2H), 3.42 (s, 1H), 3.31-3.22 (m, 2H), 2.97-2.90 (m, 3H), 2.09 (s, 3H), 1.12 (t, 3H); (M + 1): 336.8 |
| 130. | N'-(2-chloro-4-(3,5-dimethylbenzyl)-5-methylphenyl)-N-ethyl-N-methylformimidamide | $^1$H-NMR (400 MHz, DMSO-d6) δ 7.64 (bs, 1H), 7.03 (s, 1H), 6.80-6.71 (m, 4H), 3.76 (s, 2H), 3.43-3.24 (m, 2H), 2.93 (s, 3H), 2.20 (s, 6H), 2.11 (s, 3H), 1.10-1.15 (m, 3H); (M + 1): 329.1 |
| 131. | N'-(4-(2-chloro-3-fluorobenzyl)-2,5-dimethylphenyl)-N-ethyl-N-methylformimidamide | $^1$H-NMR (400 MHz, DMSO-d6) δ 7.59 (bs,1H), 7.30-7.2 3(m, 2H), 6.79-6.77 (m, 1H), 6.69 (s, 1H), 6.60 (s, 1H), 3.93 (s, 2H), 3.50-3.22 (m, 2H), 2.90 (s, 3H), 2.08 (s, 6H), 1.10 (t, 3H); (M + 1): 333.55 |
| 132. | N-(4-(3,5-difluorobenzyl)-2,5-dimethylphenyl)-N-ethyl-N-methylformimidamide | $^1$H-NMR (400 MHz, DMSO-d6) δ 7.59 (bs, 1H), 7.00 (tt, 1H), 6.88 (s, 1H), 6.80-6.75 (m, 2H), 6.56 (s, 1H), 3.86 (s, 2H), 3.36-3.22 (m, 2H), , 2.90 (s, 3H), 2.10 (s, 3H), 2.07 (s, 3H), 1.10 (t, 3H); (M + 1): 317.15 |
| 133. | N'-(4-(2,3-dichlorobenzyl)-2,5-dimethylphenyl)-N-ethyl-N-methylformimidamide | $^1$H-NMR (400 MHz, DMSO-d6) δ 7.60 (bs, 1H), 7.52-7.48 (m, 1H), 7.28-7.24 (m, 1H), 6.89 (dd, 1H), 6.69 (s, 1H), 6.61 (s, 1H), 3.95 (s, 2H), 3.48-3.23 (m, 2H), 2.91 (s, 3H), 2.08 (s, 6H), 1.11 (t, 3H); (M + 1): 349.1 |
| 134. | N'-(4-(3-chloro-2-fluoro-5-(trifluoromethyl)benzyl)-2,5-dimethylphenyl)-N-ethyl-N-methylformimidamide | $^1$H-NMR (400 MHz, DMSO-d6) δ7.94 (dd, 1H), 7.61 (bs, 1H), 7.37 (dd, 1H), 6.81 (s, 1H), 6.60 (s, 1H), 3.97 (s, 2H), 3.38-3.25 (m, 2H), 2.90 (s, 3H), 2.12 (s, 6H), 1.14 (t, 3H); (M + 1): 401.25 |
| 135. | N'-(4-(3-chloro-5-fluorobenzyl)-2,5-dimethylphenyl)-N-ethyl-N-methylformimidamide | $^1$H-NMR (400 MHz, DMSO-d6) δ 7.60 (bs, 1H), 7.21 (dt, 1H), 6.98 (s, 1H), 6.95-6.90 (m, 1H), 6.88 (s, 1H), 6.57 (s, 1H), 3.86 (s, 2H), 3.47-3.21 (m, 2H), 2.90 (s, 3H), 2.10 (s, 3H), 2.07 (s, 3H), 1.10 (t, 3H); (M + 1): 333.15 |
| 136. | N'-(2-chloro-4-(4-chloro-3-(trifluoromethyl)benzyl)-5-methylphenyl)-N-ethyl-N-methylformimidamide | $^1$H-NMR (400 MHz, DMSO-d6) δ 7.70-7.59 (m, 3H), 7.39 (d, 1H), 7.14 (s, 1H), 6.80 (s, 1H), 3.96 (s, 2H), 3.41-3.26 (m, 2H), 2.94 (s, 3H), 2.08 (s, 3H), 1.12 (t, 3H); (M + 1): 403.15 |
| 137. | N'-(2-chloro-4-(3-fluoro-4-(trifluoromethyl)benzyl)-5-methylphenyl)-N-ethyl-N-methylformimidamide | $^1$H-NMR (400 MHz, DMSO-d6) δ 7.71-7.59 (m, 2H), 7.25 (d, 1H), 7.16-7.13 (m, 2H), 6.80 (s, 1H), 3.98 (s, 2H), 3.42 (m, 2H), 3.00 (s, 3H), 2.09 (s, 3H), 1.12 (t, 3H); (M + 1): 387.15 |
| 138. | N'-(2-chloro-4-(3,4-difluorobenzyl)-5-methylphenyl)-N-ethyl-N-methylformimidamide | $^1$H-NMR (400 MHz, DMSO-d6) δ 7.64 (bs, 1H), 7.33 (dd, 1H), 7.18-7.14 (m, 1H), 7.10 (s, 1H), 6.95 (s, 1H), 6.78 (s, 1H), 3.86 (s, 2H), 3.41 (m, 2H), 2.97 (s, 3H), 2.10 (s, 3H), 1.11 (t, 3H); (M + 1): 337.15 |
| 139. | N'-(2-chloro-4-(3-fluoro-4-methylbenzyl)-5-methylphenyl)-N-ethyl-N-methylformimidamide | $^1$H-NMR (400 MHz, DMSO-d6) δ 7.63 (bs, 1H), 7.17 (t, 1H), 7.07 (s, 1H), 6.84 (d, 2H), 6.77 (s, 1H), 3.83 (s, 2H), 3.40-3.25 (m, 2H), 2.93 (s, 3H), 2.17 (s, 3H), 2.10 (s, 3H), 1.11 (t, 3H); (M + 1): 337.15 |
| 140. | N'-(2-chloro-4-(3-fluoro-5-methylbenzyl)-5-methylphenyl)-N-ethyl-N-methylformimidamide | $^1$H-NMR (400 MHz, DMSO-d6) δ 7.64 (bs, 1H), 7.08 (s, 1H), 6.83 (d, 1H), 6.78 (s, 2H), 6.69 (d, 1H), 3.83 (s, 2H), 3.40 (m, 2H), 2.93 (s, 3H), 2.27 (s, 3H), 2.10 (s, 3H), 1.11 (t, 3H); (M + 1): 333.2 |
| 141. | N'-(2,5-dichloro-4-(3-methylbenzyl)phenyl)-N-ethyl-N-methylformimidamide | $^1$H-NMR (400 MHz, DMSO-d6) δ 7.76 (bs, 1H), 7.27 (s, 1H), 7.16 (t, 1H), 7.12-7.07 (m, 1H), 7.02 (m, 3H), 3.91 (s, 2H), 3.33-3.45 (m, 2H), 2.95 (s, 3H), 2.24 (s, 3H), 1.09-1.15 (m, 3H); (M + 1): 335.15 |

-continued

| Sr. No. | Compound Name | Analytical Data |
|---|---|---|
| 142. | N'-(4-(4-chloro-3-(trifluoromethyp)benzyl)-2,5-dimethylphenyl)-N-ethyl-N-methylformimidamide | ¹H-NMR (400 MHz, DMSO-d6) δ 7.59-7.55 (m, 3H), 7.34 (dd, 1H), 6.85 (s, 1H), 6.54 (s, 1H), 3.90 (s, 2H), 3.29 (m, 2H), 2.87 (s, 3H), 2.05 (s, 6H), 1.07 (t, 3H); (M + 1): 383.2 |
| 143. | N'-(4-(2-chloro-5-fluorobenzyl)-2,5-dimethylphenyl)-N-ethyl-N-methylformimidamide | ¹H-NMR (400 MHz, DMSO-d6) δ 7.61 (bs, 1H), 7.50 (dd, 1H), 7.11 (td, 1H), 6.71-6.67 (m, 2H), 6.61 (s, 1H), 3.89 (s, 2H), 3.49-3.21 (m, 2H), 2.94 (s, 3H), 2.07 (s, 6H), 1.11 (t, 3H); (M + 1): 333.2 |
| 144. | N-ethyl-N'-(4-(3-fluoro-4-methylbenzyl)-2,5-dimethylphenyl)-N-methylformimidamide | ¹H-NMR (400 MHz, DMSO-d6) δ 7.57 (bs, 1H), 7.14 (t, 1H), 6.84-6.79 (m, 3H), 6.54 (s, 1H), 3.79 (s, 2H), 3.48-3.29 (m, 2H), 2.90 (s, 3H), 2.18 (s, 3H), 2.12 (s, 6H), 1.10 (t, 3H); (M + 1): 313.25 |
| 145. | N'-(4-(4-chloro-3-(trifluoromethoxy)benzyl)-2,5-dimethylphenyl)-N-ethyl-N-methylformimidamide | ¹H-NMR (400 MHz, DMSO-d6) δ 7.60-7.54 (m, 2H), 7.28 (s, 1H), 7.13 (dd, 1H), 6.87 (s, 1H), 6.56 (s, 1H), 3.89 (s, 2H), 3.50-3.27 (m, 2H), 2.90 (s, 3H), 2.12 (s, 6H), 1.10 (t, 3H); (M + 1): 399.2 |
| 146. | N'-(4-(3,4-difluorobenzyl)-2,5-dimethylphenyl)-N-ethyl-N-methylformimidamide | ¹H-NMR (400 MHz, DMSO-d6) δ 7.5 (bs, 1H), 7.30 (dd, 1H), 7.10 (t, 1H), 6.92-6.85 (m, 2H), 6.55 (s, 1H), 3.82 (s, 2H), 3.44-3.20 (m, 2H), 2.88 (s, 3H), 2.12 (s, 6H), 1.14 (t, 3H); (M + 1): 317.3 |
| 147. | N'-(2,5-dichloro-4-(4-methylbenzyl)phenyl)-N-ethyl-N-methylformimidamide | ¹H-NMR (400 MHz, DMSO-d6) δ 7.72 (bs, 1H), 7.22 (s, 1H), 7.08-7.02 (m, 5H), 3.87 (s, 2H), 3.35 (s, 2H), 2.92 (s, 3H), 2.21 (s, 3H), 1.06-1.12 (m, 3H); (M + 1): 335.1 |
| 148. | N'-(2,5-dichloro-4-(3-fluorobenzyl)phenyl)-N-ethyl-N-methylformimidamide | ¹H-NMR (400 MHz, DMSO-d6) δ 7.77 (bs, 1H), 7.35 (s, 1H), 7.34-7.30 (m, 1H), 7.10 (d, 1H), 7.04-6.99 (m, 3H), 3.98 (s, 2H), 3.46 (s, 2H), 2.99 (s, 3H), 1.15-1.09 (m, 3H); (M + 1): 339.05 |
| 149. | N'-(2,5-dichloro-4-(2-fluorobenzyl)phenyl)-N-ethyl-N-methylformimidamide | ¹H-NMR (400 MHz, DMSO-d6) δ 7.77 (bs, 1H), 7.32-7.28 (m, 1H), 7.19-7.10 (m, 5H), 3.98 (s, 2H), 3.46-3.40 (m, 2H), 3.03 (s, 3H), 1.09-1.15 (m, 3H); (M + 1): 339.1 |
| 150. | N'-(2,5-dichloro-4-(2-chlorobenzyl)phenyl)-N-ethyl-N-methylformimidamide | ¹H-NMR (400 MHz, DMSO-d6) δ 7.79 (bs, 1H), 7.47 (dt, 1H), 7.32-7.26 (m, 2H), 7.16-7.13 (m, 1H), 7.10-7.05 (m, 2H), 4.05 (s, 2H), 3.39 (m, 2H), 3.00 (s, 3H), 1.09-1.15 (m, 3H); (M + 1): 356.9 |
| 151. | N'-(2,5-dichloro-4-(2-methylbenzyl)phenyl)-N-ethyl-N-methylformimidamide | ¹H-NMR (400 MHz, DMSO-d6) δ 7.79 (bs, 1H), 7.20-7.08 (m, 4H), 6.90-6.93 (m, 2H), 3.92 (s, 2H), 3.44-3.34 (m, 2H), 2.96 (s, 3H), 2.20 (s, 3H), 1.09-1.15 (m, 3H); (M + 1): 335 |
| 152. | N'-(2,5-dichloro-4-(3-chlorobenzyl)phenyl)-N-ethyl-N-methylformimidamide | ¹H-NMR (400 MHz, DMSO-d6) δ 7.77 (bs, 1H), 7.37 (s, 1H), 7.09-7.35 (m, 5H), 3.97 (s, 2H), 3.46-3.36 (m, 2H), 2.99 (m, 3H), 1.09-1.15 (m, 3H); (M + 1): 357.3 |
| 153. | N'-(4-(2,6-dichlorobenzyl)-2,5-dimethylphenyl)-N-ethyl-N-methylformimidamide | ¹H-NMR (400 MHz, DMSO-d6) δ 7.60-7.49 (m, 3H), 7.35 (dd, 1H), 6.62 (d, 1H), 6.10 (s, 1H), 4.06 (s, 2H), 3.46-3.21 (m, 2H), 2.89 (s, 3H), 2.32-2.29 (s, 3H), 1.92 (s, 3H), 1.12 (t, 3H); (M + 1): 349.1 |
| 154. | N'-(4-(2-bromobenzyl)-2,5-dimethylphenyl)-N-ethyl-N-methylformimidamide | ¹H-NMR (400 MHz, DMSO-d6) δ 7.61 (dd, 2H), 7.27 (td, 1H), 7.14 (td, 1H), 6.91 (dd, 1H), 6.67 (s, 1H), 6.60 (s, 1H), 3.88 (s, 2H), 3.46-3.24 (m, 2H), 2.91 (s, 3H), 2.07 (s, 6H), 1.11 (t, 3H); (M + 1): 361 |
| 155. | N'-(4-(2-chloro-6-fluorobenzyl)-2,5-dimethylphenyl)-N-ethyl-N-methylformimidamide | ¹H-NMR (400 MHz, DMSO-d6) δ 7.59-7.50 (m, 1H), 7.40-7.33 (m, 2H), 7.29-7.23 (m, 1H), 6.60 (s, 1H), 6.28 (s, 1H), 3.92 (s, 2H), 3.44-3.27 (m, 2H), 2.89 (s, 3H), 2.27 (s, 3H), 1.96 (s, 3H), 1.10 (t, 3H), (M + 1): 333.15 |
| 156. | N-ethyl-N'-(4-(3-fluoro-5-methoxybenzyl)-2,5-dimethylphenyl)-N-methylformimidamide | ¹H-NMR (400 MHz, DMSO-d6) δ 7.58 (bs, 1H), 6.85 (s, 1H), 6.61 (dt, 1H), 6.55 (s, 1H), 6.51 (s, 1H), 6.43 (d, 1H), 3.80 (s, 2H), 3.67 (s, 3H), 3.35-3.18 (m, 2H), 2.90 (s, 3H), 2.10 (s, 6H), 1.14-1.08 (t, 3H); (M + 1): 329.6 |
| 157. | N-ethyl-N'-(4-(5-fluoro-2-methylbenzyl)-2,5-dimethylphenyl)-N-methylformimidamide | ¹H-NMR (400 MHz, DMSO-d6) δ 7.59 (bs, 1H), 7.19 (dd, 1H), 6.90 (td, 1H), 6.65 (s, 1H), 6.61 (s, 1H), 6.49 (dd, 1H), 3.76 (s, 2H), 3.35-3.27 (m, 2H), 2.91 (s, 3H), 2.23 (s, 3H), 2.05 (s, 6H), 1.11 (t, 3H); (M + 1): 313.6 |
| 158. | N-ethyl-N'-(4-(3-fluoro-4-(trifluoromethyl)benzyl)-2,5-dimethylphenyl)-N-methylformimidamide | ¹H-NMR (400 MHz, DMSO-d6) δ 7.66 (t, 1H), 7.59 (bs, 1H), 7.20 (d, 1H), 7.12 (d, 1H), 6.90 (s, 1H), 6.57 (s, 1H), 3.94 (s, 2H), 3.35-3.13 (n, 2H), 2.90 (s, 3H), 2.10 (s, 3H), 2.07 (s, 3H), 1.10 (t, 3H), (M + 1): 367.55 |
| 159. | N'-(4-(2-chloro-5-(trifluoromethyl)benzyl)-2,5-dimethylphenyl)-N-ethyl-N-methylformimidamide | ¹H-NMR (400 MHz, DMSO-d6) δ 7.72-7.60 (m, 3H), 7.26 (d, 1H), 6.69 (s, 1H), 6.63 (s, 1H), 3.99 (s, 2H), 3.50-3.32 (m, 2H), 2.91 (s, 3H), 2.03-2.11 (m, 6H), 1.09-1.14 (m, 3H); (M + 1): 384.1 |

-continued

| Sr. No. | Compound Name | Analytical Data |
|---|---|---|
| 160. | N'-(4-(2,5-dichlorobenzyl)-2,5-dimethylphenyl)-N-ethyl-N-methylformimidamide | $^1$H-NMR (400 MHz, DMSO-d6) δ 7.62 (bs, 1H), 7.52-7.48 (m, 1H), 7.31 (dd, 1H), 6.90 (d, 1H), 6.72 (s, 1H), 6.62 (s, 1H), 3.89 (s, 2H), 3.53-3.33 (m, 2H), 2.91 (s, 3H), 2.08 (s, 6H), 1.15 (t, 3H); (M + 1): 350 |
| 161. | N'-(4-(2,4-difluorobenzyl)-2,5-dimethylphenyl)-N-ethyl-N-methylformimidamide | $^1$H-NMR (400 MHz, DMSO-d6) δ 7.63 (bs, 1H), 7.21-7.15 (m, 1H), 7.06-7.00 (m, 1H), 6.97 (td, 1H), 6.76 (s, 1H), 6.56 (s, 1H), 3.79 (s, 2H), 3.53-3.33 (m, 2H), 2.87 (s, 3H), 2.11 (s, 3H), 2.07 (s, 3H), 1.14 (t, 3H); (M + 1): 317.4 |
| 162. | N'-(4-(2,4-dichlorobenzyl)-2,5-dimethylphenyl)-N-ethyl-N-methylformimidamide | $^1$H-NMR (400 MHz, DMSO-d6) δ 7.63 (m, 2H), 7.32 (dd, 1H), 6.95-6.92 (m, 1H), 6.69 (s, 1H), 6.60 (s, 1H), 3.87 (s, 2H), 3.35-3.27 (m, 2H), 2.91 (s, 3H), 2.06 (s, 6H), 1.11 (t, 3H); (M + 1): 350 |
| 163. | N-ethyl-N'-(4-(2-fluorobenzyl)phenyl)-N-methylformimidamide | $^1$H-NMR (400 MHz, DMSO-d6) δ 7.69 (bs, 1H), 7.28-7.20 (m, 2H), 7.15-7.07 (m, 2H), 7.02 (d, 2H), 6.79 (d, 2H), 3.88 (d, 2H), 3.35-3.14 (m, 2H), 2.86 (s, 3H), 1.08 (t, 3H); (M + 1): 271.35 |
| 164. | N'-(4-(2-chlorobenzyl)phenyl)-N-ethyl-N-methylformimidamide | $^1$H-NMR (400 MHz, DMSO-d6) δ 7.69 (bs, 1H), 7.41 (dd, 1H), 7.20-7.31 (m, 3H), 7.01 (d, 2H), 6.80 (d, 2H), 3.97 (s, 2H), 3.35-3.18 (m, 2H), 2.87 (s, 3H), 1.09 (t, 3H); (M + 1): 287.45 |
| 165. | N'-(2-chloro-4-(5-fluoro-2-methylbenzyl)-5-methylphenyl)-N-ethyl-N-methylformimidamide | $^1$H-NMR (400 MHz, DMSO-d6) δ 7.73 (bs, 1H), 7.22 (dd, 1H), 6.94 (td, 1H), 6.82 (d, 2H), 6.59 (dd, 1H), 3.81 (s, 2H), 3.43-3.34 (m, 2H), 2.91 (s, 3H), 2.18 (s, 3H), 2.11 (s, 3H), 1.12 (t, 3H); (M + 1): 333.30 |
| 166. | N'-(2-chloro-4-(2,5-dichlorobenzyl)-5-methylphenyl)-N-ethyl-N-methylformimidamide | $^1$H-NMR (400 MHz, DMSO-d6) δ 7.74 (bs, 1H), 7.54-7.50 (m, 1H), 7.38-7.32 (m, 1H), 7.03-6.99 (m, 1H), 6.89 (s, 1H), 6.84 (s, 1H), 3.93 (s, 2H), 3.31-3.42 (m, 2H), 2.87 (s, 3H), 2.11 (s, 3H), 1.10 (t, 3H); (M + 1): 370.30 |
| 167. | N'-(2-chloro-4-(4-fluoro-2-methylbenzyl)-5-methylphenyl)-N-ethyl-N-methylformimidamide | $^1$H-NMR (400 MHz, DMSO-d6) δ 7.71 (bs, 1H), 7.05 (dd, 2H), 6.92 (td, 1H), 6.86 (dd, 1H), 6.82 (s, 1H), 3.77 (s, 2H), 3.41-3.30 (m, 2H), 2.90 (s, 3H), 2.20 (s, 3H), 2.12 (s, 3H), 1.12 (t, 3H); (M + 1): 334.10 |
| 168. | N'-(2-chloro-4-(2-chloro-5-(trifluoromethyl)benzyl)-5-methylphenyl)-N-ethyl-N-methylformimidamide | $^1$H-NMR (400 MHz, DMSO-d6) δ 7.74-7.62 (m, 3H), 7.38 (s, 1H), 6.86 (s, 2H), 4.03 (s, 2H), 3.49-3.31 (m, 2H), 2.91 (s, 3H), 2.12 (s, 3H), 1.12 (t, 3H); (M + 1): 404.25 |
| 169. | N'-(2-chloro-4-(3-fluoro-5-methoxybenzyl)-5-methylphenyl)-N-ethyl-N-methylformimidamide | $^1$H-NMR (400 MHz, DMSO-d6) δ 7.70 (bs, 1H), 7.09 (s, 1H), 6.78 (s, 1H), 6.67-6.60 (m, 1H), 6.54 (s, 1H), 6.47 (d, 1H), 3.83 (s, 2H), 3.71 (s, 3H), 3.49-3.42 (m, 2H), 2.91 (s, 3H), 2.10 (s, 3H), 1.12 (t, 3H); (M + 1): 349.20 |
| 170. | N'-(2-chloro-4-(2,3-dimethylbenzyl)-5-methylphenyl)-N-ethyl-N-methylformimidamide | $^1$H-NMR (400 MHz, DMSO-d6) δ 7.71 (bs, 1H), 7.03 (d, 1H), 6.99 (t, 1H), 6.81 (s, 1H), 6.73 (d, 1H), 6.66 (s, 1H), 3.81 (s, 2H), 3.41-3.33 (m, 2H), 2.90 (s, 3H), 2.25 (s, 3H), 2.15 (s, 3H), 2.07 (s, 3H), 1.12 (t, 3H); (M + 1): 329.55 |
| 171. | N-ethyl-N'-(5-fluoro-2-methyl-4-(3-methylbenzyl)phenyl)-N-methylformimidamide | $^1$H-NMR (400 MHz, DMSO-d6) δ 7.69 (bs, 1H), 7.14 (t, 1H), 6.98-6.93 (m, 4H), 6.61 (d, 1H), 3.77 (s, 2H), 3.31-3.39 (m, 2H), 2.89 (s, 3H), 2.23 (s, 3H), 2.08 (s, 3H), 1.10 (t, 3H); (M + 1): 299.55 |
| 172. | N-ethyl-N'-(5-fluoro-4-(3-fluorobenzyl)-2-methylphenyl)-N-methylformimidamide | $^1$H-NMR (400 MHz, DMSO-d6) δ 7.69 (bs, 1H), 7.33-7.27 (m, 1H), 7.02-6.96 (m, 4H), 6.63 (d, 1H), 3.85 (s, 2H), 3.40-3.31 (m, 2H), 2.90 (s, 3H), 2.09 (s, 3H), 1.10 (t, 3H); (M + 1): 303.55 |
| 173. | N'-(4-(3-chlorobenzyl)-5-fluoro-2-methylphenyl)-N-ethyl-N-methylformimidamide | $^1$H-NMR (400 MHz, DMSO-d6) δ 7.69 (bs, 1H), 7.29 (t, 1H), 7.24-7.20 (m, 2H), 7.14 (d, 1H), 6.99 (d, 1H), 6.64 (d, 1H), 3.84 (s, 2H), 3.29-3.41 (m, 2H), 2.89 (s, 3H), 2.09 (s, 3H), 1.10 (t, 3H); (M + 1): 319.50 |
| 174. | N'-(4-(2-chlorobenzyl)-5-fluoro-2-methylphenyl)-N-ethyl-N-methylformimidamide | $^1$H-NMR (400 MHz, DMSO-d6) δ 7.71 (bs, 1H), 7.44-7.40 (m, 1H), 7.28-7.21 (m, 2H), 7.18-7.15 (m, 1H), 6.84 (d, 1H), 6.65 (d, 1H), 3.94 (s, 2H), 3.40-3.38 (m, 2H), 2.90 (s, 3H), 2.07 (s, 3H), 1.11 (t, 3H); (M + 1): 319.15 |
| 175. | N-ethyl-N'-(5-fluoro-2-methyl-4-(4-methylbenzyl)phenyl)-N-methylformimidamide | $^1$H-NMR (400 MHz, DMSO-d6) δ 7.68 (bs, 1H), 7.09-7.02 (m, 4H), 6.92 (d, 1H), 6.61 (d, 1H), 3.76 (s, 2H), 3.39-3.32 (m, 2H), 2.89 (s, 3H), 2.23 (s, 3H), 2.07 (s, 3H), 1.10 (t, 3H); (M + 1): 299.60 |
| 176. | N'-(2-chloro-4-(3-chloro-5-fluorobenzyl)-5-methylphenyl)-ethyl-N-methylformimidamide | $^1$H-NMR (400 MHz, DMSO-d6) δ 7.71 (bs, 1H), 7.24 (dt, 1H), 7.14 (s, 1H), 7.02 (s, 1H), 6.96-6.94 (m, 1H), 6.79 (s, 1H), 3.90 (s, 2H), 3.42-3.31 (m, 2H), 2.91 (s, 3H), 2.09 (s, 3H), 1.12 (t, 3H); (M + 1): 354.25 |

-continued

| Sr. No. | Compound Name | Analytical Data |
|---|---|---|
| 177. | N'-(2-chloro-4-(4-chloro-3-(trifluoromethoxy)benzyl)-5-methylphenyl)-N-ethyl-N-methylformimidamide | $^1$H-NMR (400 MHz, DMSO-d6) δ 7.70 (bs, 2H), 7.32 (s, 1H), 7.15 (dd, 1H), 7.13 (s, 1H), 6.79 (s, 1H), 3.93 (s, 2H), 3.42-3.31 (m, 2H), 2.90 (d, 3H), 2.08 (s, 3H), 1.11 (t, 3H): (M + 1): 420.00 |
| 178. | N'-(2-chloro-4-(2-chloro-5-fluorobenzyl)-5-methylphenyl)-N-ethyl-N-methylformimidamide | $^1$H-NMR (400 MHz, DMSO-d6) δ 7.72 (bs, 1H), 7.52 (dd, 1H), 7.15 (td, 1H), 6.88 (s, 1H), 6.82 (dd, 2H), 3.93 (s, 2H), 3.43-3.41 (m, 2H), 2.91 (s, 3H), 2.12 (s, 3H), 1.12 (t, 3H); (M + 1): 354.30 |
| 179. | N'-(2-chloro-4-(2,4-dichlorobenzyl)-5-methylphenyl)-N-ethyl-N-methylformimidamide | $^1$H-NMR (400 MHz, DMSO-d6) δ 7.72 (bs, 1H), 7.63 (d, 1H), 7.36 (dd, 1H), 7.02 (d, 1H), 6.87 (s, 1H), 6.83 (s, 1H), 3.91 (s, 2H), 3.35-3.31 (m, 2H), 2.91 (s, 3H), 2.10 (s, 3H), 1.12 (t, 3H); (M + 1): 370.80 |
| 180. | N'-(2-chloro-4-(2,4-difluorobenzyl)-5-methylphenyl)-N-ethyl-N-methylformimidamide | $^1$H-NMR (400 MHz, DMSO-d6) δ7.70 (bs, 1H), 7.24-7.18 (m, 1H), 7.14-7.08 (m, 1H), 7.01 (td, 1H), 6.97(s, 1H), 6.80 (s, 1H), 3.83 (s, 2H), 3.42-3.27 (m, 2H), 2.90 (s, 3H), 2.13 (s, 3H), 1.11 (t, 3H); (M + 1): 338.10 |
| 181. | N'-(2-chloro-4-(4-fluoro-3-(trifluoromethypbenzyl)-5-methylphenyl)-N-ethyl-N-methylformimidamide | $^1$H-NMR (400 MHz, DMSO-d6) δ 7.70 (bs, 1H), 7.52 (d, 1H), 7.48-7.39 (m, 2H), 7.13 (s, 1H), 6.79 (s, 1H), 3.95 (s, 2H), 3.42-3.32 (m, 2H), 2.90 (s, 3H), 2.09 (s, 3H), 1.12 (t, 3H); (M + 1): 388.15 |
| 182. | N'-(2,5-dichloro-4-(3-(trifluoromethoxy)benzyl)phenyl)-N-ethyl-N-methylformimidamide | $^1$H-NMR (400 MHz, DMSO-d6) δ 7.82 (bs, 1H), 7.42 (t, 1H), 7.39 (s, 1H), 7.09-7.22 (m, 4H), 4.02 (s, 2H), 3.46-3.31 (m, 2H), 2.92 (s, 3H), 1.15-1.09 (m, 3H); (M + 1): 406.90 |
| 183. | N'-(2,5-dichloro-4-(3-(trifluoromethyl)benzyl)phenyl)-N-ethyl-N-methylformimidamide | $^1$H-NMR (400 MHz, DMSO-d6) δ 7.83 (bs, 1H), 7.57-7.51 (m, 3H), 7.49-7.41 (m, 1H), 7.41 (s, 1H), 7.11 (d, 1H), 4.07 (s, 2H), 3.44-3.31 (m, 2H), 2.92 (s, 3H), 1.15-1.09 (t, 3H); (M + 1): 390.00 |
| 184. | N'-(2-chloro-4-(2-chloro-6-fluorobenzyl)-5-methylphenyl)-N-ethyl-N-methylformimidamide | $^1$H-NMR (400 MHz, DMSO-d6) δ 7.70 (bs, 1H), 7.43-7.37 (m, 2H), 7.32-7.26 (m, 1H), 6.83 (s, 1H), 6.43 (s, 1H), 3.95 (s, 2H), 3.39-3.30 (s, 2H), 2.89 (s, 3H), 2.29 (s, 3H), 1.11 (m, 3H); (M + 1): 354.25 |
| 185. | N-ethyl-N'-(5-fluoro-4-(2-fluorobenzyl)-2-methylphenyl)-N-methylformimidamide | $^1$H-NMR (400 MHz, DMSO-d6) δ 7.69 (bs, 1H), 7.28-7.07 (m, 4H), 6.90 (d, 1H), 6.63 (d, 1H), 3.85 (s, 2H), 3.41-3.30 (m, 2H), 2.88 (s, 3H), 2.08 (s, 3H), 1.10 (t, 3H); (M + 1): 303.10 |
| 186. | N-ethyl-N'-(5-fluoro-2-methyl-4-(2-methylbenzyl)phenyl)-N-methylformimidamide | $^1$H-NMR (400 MHz, DMSO-d6) δ 7.71 (bs, 14H), 7.15-7.05 (m, 3H), 7.01-6.98 (m, 1H), 6.76 (d, 1H), 6.64 (d, 1H), 3.81 (s, 2H), 3.40-3.27 (m, 2H), 2.90 (m, 3H), 2.22 (s, 3H), 2.05 (s, 3H), 1.08 (t, 3H); (M + 1): 299.10 |
| 187. | N'-(2-chloro-4-(cyano(4-(trifluoromethyl)phenyl)methyl)-5-methylphenyl)-N-ethyl-N-methylformimidamide | $^1$H-NMR (400 MHz, DMSO-d6) δ 7.80 (s, 2H), 7.54-7.52 (m, 2H) ,7.29 (s, 1H), 6.88 (d, 2 H), 5.99 (s, 1H), 3.46-3.33 (m, 2H), 2.92 (s, 3H), 2.13 (s, 3H), 1.13 (t, 3H); (M + 1): 394.20 |
| 188. | N'-(2-chloro-4-(cyano(3-(trifluoromethyl)phenyl)methyl)-5-methylphenyl)-N-ethyl-N-methylformimidamide | $^1$H-NMR (400 MHz, DMSO-d6) δ 7.77-7.61 (m, 5H), 7.29 (s, 1H), 6.89 (d, 1H), 5.99 (s, 1H), 3.38-3.33 (m, 2H), 2.92 (s, 3H), 2.13 (s, 3H), 1.13 (t, 3H); (M + 1): 394.25 |
| 189. | N'-(2-chloro-4-(cyano(4-fluorophenypmethyl)-5-methylphenyl)-N-ethyl-N-methylformimidamide | $^1$H-NMR (400 MHz, DMSO-d6) δ 7.70 (s, 1H), 7.34 (dd, 2H), 7.28-7.22 (m, 3H), 6.86 (d, 1H), 5.83 (s, 1H), 3.45-3.32 (m, 2H), 2.92 (s, 3H), 2.13 (s, 3H), 1.13 (t, 3H); (M + 1): 344.15 |
| 190. | N'-(2-chloro-4-((3-chloro-4-fluorophenyl)(cyano)methyl)-5-methylphenyl)-N-ethyl-N-methylformimidamide | $^1$H-NMR (400 MHz, DMSO-d6) δ 7.71 (s, 1H), 7.51-7.45 (m, 2H), 7.35-7.30 (m, 2H), 6.88 (d, 1H), 5.86 (s, 1H), 3.44-3.33 (m, 2H), 2.95 (d, 3H), 2.12 (s, 3H), 1.13 (t, 3H); (M + 1): 378.15 |
| 191. | N'-(2-chloro-4-(cyano(p-tolypmethyl)-5-methylphenyl)-N-ethyl-N-methylformimidamide | $^1$H-NMR (400 MHz, DMSO-d6) δ 7.69 (s, 1H), 7.23-7.16 (m, 5H), 6.85 (s, 1H), 5.74 (s, 1H), 3.44-3.30 (m, 2H), 2.95 (d, 3H), 2.28 (s, 3H), 2.14 (s, 3H), 1.12 (t, 3H); (M + 1): 340.55 |
| 192. | N'-(2-chloro-4-((2-chlorophenyl)(cyano)methyl)-5-methylphenyl)-N-ethyl-N-methylformimidamide | $^1$H-NMR (400 MHz, DMSO-d6) δ 7.72 (s, 1H), 7.58-7.55 (m, 1H), 7.47-7.43 (m, 2H), 7.40-7.36 (m, 1H), 7.01 (s, 1H), 6.91 (d, 1H), 5.88 (s, 1H), 3.44-3.33 (m, 2H), 2.92 (s, 3H), 2.17 (s, 3H), 1.10 (t, 3H); (M − 1): 357.90 |
| 193. | N'-(2-chloro-4-((4-chlorophenyl)(cyano)methyl)-5-methylphenyl)-N-ethyl-N-methylformimidamide | $^1$H-NMR (400 MHz, DMSO-d6) δ 7.70 (s, 1H), 7.49-7.47 (m, 2H), 7.32 (d, 2H), 7.26 (s, 1H), 6.87 (d, 1H), 5.85 (s, 1H), 3.46-3.34 (m, 2H), 2.92 (s, 3H), 2.14 (s, 3H), 1.13 (t, 3H); (M + 1): 360.15 |
| 194. | N'-(2-chloro-4-(cyano(3-fluorophenyl)methyl)-5-methylphenyl)-N-ethyl-N-methylformimidamide | $^1$H-NMR (400 MHz, DMSO-d6) δ 7.70 (s, 1H), 7.48 (td, 1H), 7.28 (s, 1H), 7.23-7.19 (m, 1H), 7.16 (d, 1H), 7.11 (dd, 1H), 6.87 (d, 1H), 5.86 (s, 1H), 3.38-3.32 (m, 2H), 2.92 (s, 3H), 2.14 (s, 3H), 1.13 (t, 3H); (M + 1): 344.20 |

| Sr. No. | Compound Name | Analytical Data |
| --- | --- | --- |
| 195. | N'-(2-chloro-4-(2,6-dichlorobenzyl)-5-methylphenyl)-N-ethyl-N-methylformimidamide | ¹H-NMR (400 MHz, DMSO-d6) δ 7.70 (bs, 1H), 7.57 (s, 1H), 7.54 (s, 1H), 7.40-7.36 (m, 1H), 6.85 (s, 1H), 6.24 (s, 1H), 4.08 (s, 2H), 3.40-3.31 (m, 2H), 2.89 (m, 3H), 2.31 (s, 3H), 1.11 (t, 3H); (M + 1): 370.60 |
| 196. | N-ethyl-N'-(5-fluoro-2-methyl-4-(3-(trifluoromethyl)benzyl)phenyl)-N-methylformimidamide | ¹H-NMR (400 MHz, DMSO-d6) δ 7.70 (bs, 1H), 7.55-7.47 (m, 4H), 7.02 (d, 1H), 6.64 (d, 1H), 3.94 (s, 2H), 3.40-3.37 (m, 2H), 2.90 (s, 3H), 2.10 (s, 3H), 1.10 (t, 3H); (M + 1): 353.35 |
| 197. | N'-(2-cyclopropyl-4-(3-fluorobenzyl)-5-methylphenyl)-N-ethyl-N-methylformimidamide | ¹H-NMR (400 MHz, DMSO-d6) δ 7.60 (bs, 1H), 7.25-7.30 (m, 1H), 6.94-6.98 (m, 1H), 6.92 (d, 1H), 6.84 (dd, 1H), 6.52 (s, 1H), 6.48 (s, 1H), 3.83 (s, 2H), 3.27-3.35 (m, 2H), 2.91 (s, 3H), 2.22-2.32 (m, 1H), 2.04 (s, 3H), 1.11 (t, 3H), 0.78-0.83 (m, 2H), 0.51-0.55 (m, 2H); (M + 1): 325.40 |
| 198. | N'-(2-cyclopropyl-5-methyl-4-(3-methylbenzyl)phenyl)-N-ethyl-N-methylformimidamide | ¹H-NMR (400 MHz, DMSO-d6) δ 7.59 (bs, 1H), 7.11 (t, 1H) 6.95-6.93 (m, 1H), 6.88 (s, 1H), 6.84 (d, 1H), 6.50 (s, 1H), 6.46 (s, 1H), 3.77-3.60 (m, 5H), 2.91 (s, 3H), 2.26-2.28 (m, 1H), 2.22 (s, 3H), 2.05 (s, 3H), 1.11 (t, 3H), 0.78-0.82 (m, 2H), 0.50-0.54 (m, 2H); (M + 1): 321.55 |
| 199. | N'-(4-(3-chlorobenzyl)-2-cyclopropyl-5-methylphenyl)-N-ethyl-N-methylformimidamide | ¹H-NMR (400 MHz, DMSO-d6) δ 7.61 (bs, 1H), 7.27 (t, 1H), 7.21-7.19 (m, 1H), 7.07 (d, 1H), 7.04 (d, 1H), 6.52 (s, 1H), 6.49 (s, 1H), 3.83 (s, 2H), 3.50-3.32 (m, 2H), 2.91 (s, 3H), 2.23-2.32 (m, 1H), 2.04 (s, 3H), 1.11 (t, 3H), 0.83-0.79 (m, 2H), 0.55-0.51 (m, 2H); (M + 1): 342.10 |
| 200. | N-ethyl-N'-(4-(3-fluoro-5-methylbenzyl)-2,5-dimethylphenyl)-N-methylformimidamide | ¹H-NMR (400 MHz, DMSO-d6) δ 7.58 (bs, 1H), 6.85 (s, 1H), 6.79 (d, 1H), 6.77 (s, 1H), 6.64 (d, 1H), 6.55 (s, 1H), 3.80 (s, 2H), 3.47-3.20 (m, 2H), 2.90 (s, 3H), 2.24 (s, 3H), 2.09 (s, 6H), 1.10 (t, 3H); (M + 1): 313.6 |
| 201. | N-ethyl-N'-(4-(2-fluoro-4-(trifluoromethyl)benzyl)-2,5-dimethylphenyl)-N-methylformimidamide | ¹H-NMR (400 MHz, DMSO-d6) δ 7.63-7.48 (m, 3H), 7.21 (t, 1H), 6.81 (s, 1H), 6.58 (s, 1H), 3.91 (s, 2H), 3.34 (m, 2H), 2.90 (s, 3H), 2.08 (s, 6H), 1.14-1.08 (m, 3H); (M + 1): 367.4 |
| 202. | N'-(2,5-dimethyl-4-(pyridin-2-ylmethyl)phenyl)-N-ethyl-N-methylformimidamide | ¹H-NMR (400 MHz, DMSO-d6) δ 8.39-8.36 (m, 2H), 7.58 (bs, 2H), 7.27 (ddd, 1H), 6.86 (s, 1H), 6.55 (s, 1H), 3.85 (s, 2H), 3.36-3.22 (m, 2H), 2.90 (s, 3H), 2.13 (s, 6H), 1.10 (t, 3H); (M + 1): 333.55 |
| 203. | N'-(2-chloro-4-(2,6-difluorobenzyl)-5-methylphenyl)-N-ethyl-N-methylformimidamide | ¹H-NMR (400 MHz, DMSO-d6) δ 7.69 (bs, 1H), 7.42-7.29 (m, 1H), 7.15-7.08 (m, 2H), 6.79 (s, 1H), 6.72 (s, 1H), 3.86 (s, 2H), 3.41-3.28 (m, 2H), 2.89 (s, 3H), 2.24 (s, 3H), 1.11 (t, 3H); (M + 1): 388.00 |
| 204. | N'-(2-chloro-5-methyl-4-(pyridin-3-ylmethyl)phenyl)-N-ethyl-N-methylformimidamide | ¹H-NMR (400 MHz, DMSO-d6) δ 8.41-8.38 (m, 2H), 7.64 (d, 1H), 7.49 (dt, 1H), 7.29 (dd, 1H), 7.10 (s, 1H), 6.79 (s, 1H), 3.88 (s, 2H), 3.42-3.29 (m, 1H), 2.90 (s, 3H), 2.12 (s, 3H), 1.11 (t, 3H); (M + 1): 302.50 |
| 205. | N-ethyl-N'-(2-fluoro-5-methyl-4-(3-(trifluoromethypbenzyl)phenyl)-N-methylformimidamide | ¹H-NMR (400 MHz, DMSO-d6) δ 7.72 (brs, 1H), 7.56-7.27 (m, 4H), 6.86 (d, 1H), 6.76 (d, 1H), 3.94 (s, 2H), 3.48-3.25 (m, 2H), 2.85 (s, 3H), 2.05 (s, 3H), 1.20-0.98 (m, 3H); (M + 1): 353.50 |
| 206. | N-ethyl-N'-(2-fluoro-5-methyl-4-(3-(trifluoromethoxy)benzyl)phenyl)-N-methylformimidamide | ¹H-NMR (400 MHz, DMSO-d6) δ 7.74 (bs, 1H), 7.41 (t, 1H), 7.18-7.15 (m, 2H), 7.09 (s, 1H), 6.88 (d, 1H), 6.78 (d, 1H), 3.92 (s, 2H), 3.37-3.29 (m, 2H), 2.92 (s, 3H), 2.08 (s, 3H), 1.16-1.09 (m, 3H); (M + 1): 369.5 |
| 207. | N-ethyl-N'-(2-fluoro-5-methyl-4-(2-(trifluoromethoxy)benzyl)phenyl)-N-methylformimidamide | ¹H-NMR (400 MHz, DMSO-d6) δ 7.75 (bs, 1H), 7.36-7.28 (m, 3H), 7.08 (d, 1H), 6.81 (d, 1H), 6.71 (d, 1H), 3.89 (s, 2H), 3.42-3.41 (m, 2H), 2.92 (s, 3H), 2.07 (s, 3H), 1.11 (t, 3H); (M + 1): 369.5 |
| 208. | N'-(4-(3-chlorobenzyl)-2-fluoro-5-methylphenyl)-N-ethyl-N-methylformimidamide | ¹H-NMR (400 MHz, DMSO-d6) δ 7.75 (bs, 1H), 7.30 (t, 1H), 7.24 (dt, 1H), 7.15 (s, 1H), 7.10 (d, 1H), 6.87 (d, 1H), 6.78 (d, 1H), 3.87 (s, 2H), 3.36-3.29 (m, 2H), 2.92 (s, 3H), 2.08 (s, 3H), 1.10 (t, 3H); (M + 1): 319.5 |
| 209. | N-ethyl-N'-(2-fluoro-4-(3-fluorobenzyl)-5-methylphenyl)-N-methylformimidamide | ¹H-NMR (400 MHz, DMSO-d6) δ 7.74 (bs, 1H), 7.31 (td, 1H), 7.04-6.84 (m, 5H), 3.87 (s, 2H), 3.38-3.30 (m, 2H), 2.91 (s, 3H), 2.10 (s, 3H), 1.10 (t, 3H); (M + 1): 303.55 |
| 210. | N-ethyl-N'-(2-fluoro-5-methyl-4-(3-methylbenzyl)phenyl)-N-methylformimidamide | ¹H-NMR (400 MHz, DMSO-d6) δ 7.73 (bs, 1H), 7.15 (t, 1H), 6.98 (d, 1H), 6.93-6.89 (m, 2H), 6.82-6.75 (m, 2H), 3.80 (s, 2H), 3.35-3.30 (m, 2H), 2.95-2.88 (s, 3H), 2.23 (s, 3H), 2.11 (s, 3H), 1.10 (t, 3H); (M + 1): 299.5 |

-continued

| Sr. No. | Compound Name | Analytical Data |
|---|---|---|
| 211. | N-ethyl-N'-(2-fluoro-5-methyl-4-(4-methylbenzyl)phenyl)-N-methylformimidamide | $^1$H-NMR (400 MHz, DMSO-d6) δ 7.73 (bs, 1H), 7.07 (d, 2H), 7.00 (d, 2H), 6.79-6.74 (m, 2H), 3.78 (s, 2H), 3.39-3.30 (m, 2H), 2.88 (s, 3H), 2.22 (s, 3H), 2.08 (s, 3H), 1.10 (t, 3H); (M + 1): 299.5 |
| 212. | N-ethyl-N'-(2-fluoro-5-methyl-4-(2-methylbenzyl)phenyl)-N-methylformimidamide | $^1$H-NMR (400 MHz, DMSO-d6) δ 7.75 (bs, 1H), 7.19-7.17 (m, 1H), 7.14-7.09 (m, 2H), 6.86-6.84 (m, 1H), 6.81 (d, 1H), 6.47 (d, 1H), 3.79 (s, 2H), 3.28-3.21 (m, 2H), 2.92 (s, 3H), 2.18 (s, 3H), 2.12 (s, 3H), 1.11 (t, 3H); (M + 1): 299.6 |
| 213. | N'-(4-(2-chlorobenzyl)-2-fluoro-5-methylphenyl)-N-ethyl-N-methylformimidamide | $^1$H-NMR (400 MHz, DMSO-d6) δ 7.76 (bs, 1H), 7.30 (t, 1H), 7.24 (dt, 1H), 7.15 (s, 1H), 7.10 (d, 1H), 6.87 (d, 1H), 6.78 (d,1H), 3.87 (s, 2H), 3.36-3.29 (m, 2H), 2.92 (s, 3H), 2.08 (s, 3H), 1.10 (t, 3H); (M + 1): 320.05 |
| 214. | N-ethyl-N'-(2-fluoro-4-(2-fluorobenzyl)-5-methylphenyl)-N-methylformimidamide | $^1$H-NMR (400 MHz, DMSO-d6) δ 7.74 (bs, 1H), 7.29-7.23 (m, 1H), 7.19-7.14 (m, 1H), 7.13-7.05 (m, 2H), 6.79 (d, 1H), 6.72 (d, 1H), 3.85 (s, 2H), 3.39-3.30 (m, 2H), 2.95 (s, 3H), 2.15 (s, 3H), 1.10 (t, 3H); (M + 1): 303.55 |
| 215. | N'-(2,5-dimethyl-4-((Z)-(methyl imino)(o-tolyl)methyl)phenyl)-N-ethyl-N-methylformimidamide | $^1$H-NMR (400 MHz, DMSO-d6) δ 7.63 (bs, 1H), 7.29-6.97 (m, 4H), 6.73 (d, 1H), 6.64 (d, 1H), 3.41-3.34 (m, 2H), 3.08-3.04 (s, 3H), 2.95 (s, 3H), 2.42 (s, 3H), 2.14 (s, 3H), 2.00 (s, 3H), 1.14 (td, 3H); (M + 1): 322.25 |
| 216. | N-ethyl-N'-(4-(3-fluorobenzyl)-5-methyl-2-(methylsulfonyl)phenyl)-N-methylformimidamide | $^1$H-NMR (400 MHz, DMSO-d6) δ 7.89 (bs, 1H), 7.53 (s, 1H), 7.38-7.31 (m, 1H), 7.01-7.06 (m, 1H), 6.98-6.92 (m, 3H), 3.99 (s, 2H), 3.46-3.44 (m, 5H), 2.94 (s, 3H), 2.22 (s, 3H), 1.18 (t, 3H); (M + 1): 363.45 |
| 217. | methyl N-(2-bromo-4-(4-bromobenzyl)-3,6-dimethylphenyl)formimidate | $^1$H-NMR (400 MHz, DMSO-d6) δ 7.78 (bs, 1H), 7.47-7.44 (m, 2H), 7.08-7.04 (m, 3H), 3.93 (s, 2H), 3.85 (s, 3H), 2.20 (s, 3H), 2.06 (s, 3H); (M + 1): 411.85 |
| 218. | N'-(4-(3-chlorobenzyl)-5-methyl-2-(methylsulfonyl)phenyl)-N-ethyl-N-methylformimidamide | $^1$H-NMR (400 MHz, DMSO-d6) δ 7.89 (bs, 1H), 7.54 (s, 1H), 7.34 (t, 1H), 7.26-7.28 (m, 1H), 7.17 (s, 1H), 7.10 (d, 1H), 6.97 (d, 1H), 3.99 (s, 2H), 3.47-3.35 (m, 5H), 2.94 (s, 3H), 2.21 (s, 3H), 1.18 (t, 3H); (M + 1): 379.40 |
| 219. | N'-(2-bromo-3,6-dimethyl-4-(2-methylbenzyl)phenyl)-N-ethyl-N-methylformimidamide | $^1$H-NMR (400 MHz, DMSO-d6) δ 7.37 (bs, 1H), 7.17 (d, 1H), 7.13-7.09 (m, 2H), 6.77-6.71 (m, 2H), 3.91 (s, 2H), 3.39-3.28 (m, 2H), 2.90 (s, 3H), 2.24 (s, 3H), 2.18 (s, 3H), 2.00 (s, 3H), 1.11 (s, 3H); (M + 1): 374.45 |
| 220. | N'-(2-chloro-4-(2-fluoro-6-(trifluoromethyl)benzyl)-5-methylphenyl)-N-ethyl-N-methylformimidamide | $^1$H-NMR (400 MHz, DMSO-d6) δ 7.72-7.61 (m, 4H), 6.85 (d, 1H), 6.24 (s, 1H), 3.99 (s, 2H), 3.42-3.31 (m, 2H), 2.90 (s, 3H), 2.31 (s, 3H), 1.13 (t, 3H); (M + 1): 387.40 |
| 221. | N'-(2-cyclopropyl-4-(2-fluorobenzyl)-5-methylphenyl)-N-ethyl-N-methylformimidamide | $^1$H-NMR (400 MHz, DMSO-d6) δ 7.62 (bs, 1H), 7.27-7.21 (m, 1H), 7.18-7.13 (m, 1H), 7.11-7.06 (m, 1H), 6.97 (td, 1H), 6.55 (s, 1H), 6.43 (s, 1H), 3.83 (s, 2H), 3.44-3.34 (m, 2H), 2.93 (s, 3H), 2.27-2.22 (m, 1H), 2.09 (s, 3H), 1.12 (t, 3H), 0.86-0.76 (m, 2H), 0.48 (m, 2H); (M + 1): 325.60 |
| 222. | N'-(2-cyclopropyl-5-methyl-4-(4-methylbenzyl)phenyl)-N-ethyl-N-methylformimidamide | $^1$H-NMR (400 MHz, DMSO-d6) δ 7.58 (bs, 1H), 7.03 (d, 2H), 6.94 (d, 2H), 6.50 (s, 1H), 6.46 (s, 1H), 3.75 (s, 2H), 3.45-3.35 (m, 2H), 2.91 (s, 3H), 2.26-2.20 (m, 4H), 2.04 (s 3H), 1.11 (t, 3H), 0.82-0.77 (m, 2H), 0.53-0.47 (m, 2H); (M + 1): 321.65 |
| 223. | N'-(4-(2-chlorobenzyl)-2-cyclopropyl-5-methylphenyl)-N-ethyl-N-methylformimidamide | $^1$H-NMR (400 MHz, DMSO-d6) δ 7.61 (s, 1H), 7.45-7.41 (m, 1H), 7.24-7.19 (m, 2H), 6.89-6.86 (m, 1H), 6.56 (s, 1H), 6.33 (s, 1H), 3.88 (s, 2H), 3.46-3.26 (m, 2H), 2.92 (s, 3H), 2.25-2.20 (m, 1H), 2.04 (s, 3H), 1.11 (t, 3H), 0.79-0.75 (m, 2H), 0.44-0.41 (m, 2H); (M + 1): 341.55 |
| 224. | N'-(2-cyclopropyl-5-methyl-4-(3-(trifluoromethoxy)benzyl)phenyl)-N-ethyl-N-methylformimidamide | $^1$H-NMR (400 MHz, DMSO-d6) δ 7.62 (bs, 1H), 7.38 (t, 1H), 7.15-7.10 (m, 2H), 7.03 (s, 1H), 6.54 (s, 1H), 6.48 (s, 1H), 3.88 (s, 2H), 3.50-3.31 (m, 2H), 2.92 (s, 3H), 2.32-2.28 (m, 1H), 2.05 (s, 3H), 1.11 (t, 3H), 0.84-0.78 (m, 2H), 0.52-0.49 (m, 2H); (M + 1): 391.55 |
| 225. | N-ethyl-N'-(2-fluoro-4-(4-methylbenzyl)-5-(trifluoromethyl)phenyl)-N-methylformimidamide | $^1$H-NMR (400 MHz, DMSO-d6) δ 7.92 (bs, 1H), 7.32 (t, 1H), 7.11 (d, 2H), 7.04-6.98 (m, 3H), 4.00 (s, 2H), 3.47-3.36 (m, 2H), 2.92 (s, 3H), 2.26 (s, 3H), 1.16-1.09 (m, 3H); (M + 1): 353.55 |
| 226. | N'-(4-(2-chlorobenzyl)-2-fluoro-5-(trifluoromethyl)phenyl)-N-ethyl-N-methylformimidamide | $^1$H-NMR (400 MHz, DMSO-d6) δ 7.93 (bs, 1H), 7.51-7.41 (m, 1H), 7.40-7.35 (m, 1H), 7.33-7.27 (m, 2H), 7.06-7.03 (m, 1H), 6.76 (d, 1H), 4.14 (s, 2H), 3.47-3.33 (m, 2H), 2.91 (s, 3H), 1.15 (t, 3H); (M + 1): 374.35 |

-continued

| Sr. No. | Compound Name | Analytical Data |
|---|---|---|
| 227. | N-ethyl-N'-(2-fluoro-4-(2-fluorobenzyl)-5-(trifluoromethyl)phenyl)-N-methylformimidamide | $^1$H-NMR (400 MHz, DMSO-d6) δ 7.92 (bs, 1H), 7.37-7.32 (m, 1H), 7.31-7.21 (m, 1H), 7.21-7.16 (m, 1H), 7.15-7.11 (m, 1H), 7.08-7.04 (m, 1H), 6.92 (d, 1H), 4.07 (s, 2H), 3.44-3.31 (m, 2H), 2.91 (s, 3H), 1.14 (t, 3H); (M + 1): 357.55 |
| 228. | N-ethyl-N'-(2-fluoro-4-(2-methylbenzyl)-5-(trifluoromethyl)phenyl)-N-methylformimidamide | $^1$H-NMR (400 MHz, DMSO-d6) δ 7.92 (bs, 1H), 7.36 (t, 1H), 7.22-7.13 (m, 3H), 6.93-6.90 (m, 1H), 6.62 (d, 1H), 4.01 (s, 2H), 3.54-3.45 (m, 2H), 2.91 (s, 3H), 2.15 (s, 3H), 1.14 (t, 3H); (M + 1): 353.55 |
| 229. | N'-(4-(3-chlorobenzyl)-2-fluoro-5-(trifluoromethyl)phenyl-N-ethyl-N-methylformimidamide | $^1$H-NMR (400 MHz, DMSO-d6) δ 7.94 (bs, 1H), 7.37-7.27 (m, 3H), 7.19 (s, 1H), 7.15-7.09 (m, 2H), 4.07 (s, 2H), 3.48-3.36 (m, 2H), 2.93 (s, 3H), 1.16 (t, 3H); (M + 1): 374.35 |
| 230. | N-ethyl-N'-(2-fluoro-4-(3-fluorobenzyl)-5-(trifluoromethyl)phenyl)-N-methylformimidamide | $^1$H-NMR (400 MHz, DMSO-d6) δ 7.94 (bs, 1H), 7.38-7.32 (m, 2H), 7.12 (d, 1H), 7.07-7.02 (m, 1H), 6.98-6.92 (m, 2H), 4.08 (s, 2H), 3.48-3.36 (m, 2H), 3.02 (s, 3H), 1.16 (t, 3H); (M + 1): 357.55 |
| 231. | N-ethyl-N'-(2-fluoro-4-(3-methylbenzyl)-5-(trifluoromethyl)phenyl)-N-methylformimidamide | $^1$H-NMR (400 MHz, DMSO-d6) δ 7.94 (bs, 1H), 7.36-7.31 (m, 1H), 7.19 (t, 1H),7.05-6.91 (m, 4H), 4.01 (s, 2H), 3.48-3.36 (m, 2H), 2.94 (s, 3H), 2.26 (s, 3H), 1.16 (s, 3H); (M + 1): 353.55 |
| 232. | N-ethyl-N'-(2-fluoro-5-(trifluoromethyl)-4-(3-(trifluoromethyl)benzyl)phenyl)-N-methylformimidamide | $^1$H-NMR (400 MHz, DMSO-d6) δ 7.95 (bs, 1H), 7.60-7.52 (m, 2H), 7.49 (s, 1H), 7.43 (d, 1H), 7.36 (t, 1H), 7.16 (d, 1H), 4.17 (s, 2H), 3.48-3.36 (m, 2H), 2.93 (s, 3H), 1.16 (t, 3H); (M + 1): 407.50 |
| 233. | N-ethyl-N'-(2-fluoro-4-(3-(trifluoromethoxy)benzyl)-5-(trifluoromethyl)phenyl)-N-methylformimidamide | $^1$H-NMR (400 MHz, DMSO-d6) δ 7.94 (bs, 1H), 7.44 (t, 1H), 7.35 (t, 1H), 7.22 (d, 1H), 7.17-7.12 (m, 3H), 4.12 (s, 2H), 3.48-3.36 (m, 2H), 2.91 (s, 3H), 1.16 (t, 3H); (M + 1): 423.50 |
| 234. | N-ethyl-N-methyl-N'-(5-methyl-4-(2-methylbenzyl)-2-(methylsulfonyl)phenyl)formimidamide | $^1$H-NMR (400 MHz, DMSO-d6) δ 7.89 (bs, 1H), 7.29 (s, 1H), 7.21 (dd, 1H), 7.17-7.09 (m, 2H), 6.99 (d, 1H), 6.86 (d, 1H), 3.90 (s, 2H), 3.45-3.35 (m, 5H), 2.91 (s, 3H), 2.25 (s, 3H), 2.22 (s, 3H), 1.19 (t, 3H); (M + 1): 359.50 |
| 235. | N-ethyl-N-methyl-N'-(5-methyl-4-(4-methylbenzyl)-2-(methylsulfonyl)phenyl)formimidamide | $^1$H-NMR (400 MHz, DMSO-d6) δ 7.87 (bs, 1H), 7.51 (s, 1H), 7.10 (d, 2H),), 7.01 (d, 2H), 6.94 (d, 1H), 3.90 (s, 2H), 3.35-3.47 (m, 5H), 2.94 (s, 3H), 2.26 (s, 3H), 2.22 (s, 3H), 1.13-1.18 (t, 3H); (M + 1): 359.45 |
| 236. | N'-(5-chloro-4-(cyano(5-fluoro-2-methylphenyl)methyl)-2-methylphenyl)-N-ethyl-N-methylformimidamide | $^1$H-NMR (400 MHz, DMSO-d6) δ 7.73 (s, 1H), 7.33 (dd, 2 H), 7.16 (td, 1H), 7.08 (d, 1H), 6.96-7.02 (m, 1H), 5.86 (s, 1H), 3.46-3.34 (m, 2H), 2.98 (s, 3H), 2.23 (s, 3H), 2.16 (s, 3H), 1.08 (t, 3H); (M − 1): 356.00 |
| 237. | methyl 2-(2-chloro-4-(((ethyl(methyl)amino)methylene)amino)-5-methylphenyl)-2-(3-chlorophenyl)acetate | $^1$H-NMR (400 MHz, DMSO-d6) δ 7.69 (s, 1H) 7.39-7.32 (m, 2H), 7.29 (s, 1H), 7.20 (dt, 1H), 6.91 (d, 2H), 5.37 (s, 1H), 3.67 (s, 3H), 3.42-3.33 (m, 2H), 2.94 (s, 3H), 2.11 (s, 3H), 1.11 (t, 3H); (M + 1): 394.75 |
| 238. | N'-(4-(1-(4-bromophenyl)vinyl)-5-chloro-2-methylphenyl)-N-ethyl-N-methylformimidamide | $^1$H-NMR (400 MHz, DMSO-d6) δ 7.73 (s, 1H), 7.52-7.48 (m, 2H), 7.19-7.15 (m, 2H), 7.05 (s, 1H), 6.89 (d, 1H), 5.84 (s, 1H), 5.24 (s, 1H), 3.45-3.34 (m, 2H), 2.96 (s, 3H), 2.17 (s, 3H), 1.13 (t, 3H); (M + 1): 391.00 |
| 239. | 2-(2-chloro-4-(((ethyl(methyl)amino)methylene)amino)-5-methylphenyl)-2-(3-fluorophenyl)-N,N-dimethylpropanamide | $^1$H-NMR (400 MHz, DMSO-d6) δ 7.74 (s, 1H), 7.37-7.31 (m, 1H), 7.08 (td, 1H), 6.99-7.03 (m, 2H), 6.92 (d, 2H), 3.35-3.46 (m, 2H), 3.16 (s, 3H), 2.99 (s, 3H), 2.72 (s, 3H), 2.09 (s, 3H), 1.93 (s, 1.12 (t, 3H); (M + 1): 404.50 |
| 240. | 2-(2-chloro-4-(((ethyl(methyl)amino)methylene)amino)-5-methylphenyl)-2-(5-fluoro-2-methylphenyl)-N,N-dimethylacetamide | $^1$H-NMR (400 MHz, DMSO-d6) δ 7.73 (s, 1H), 7.25 (dd, 1H), 7.04-6.92 (m, 2H), 6.73 (s, 1H), 6.56 (dd, 1H), 5.50 (s, 1H), 3.44-3.23 (m, 2H), 3.08 (s, 3H), 2.78 (s, 3H), 2.65 (s, 3H), 2.17 (s, 3H), 2.10 (s, 3H), 1.12 (t, 3H); (M + 1): 405.05 |
| 241. | N'-(5-chloro-4-((4-chloro-3-fluorophenyl)(cyano)methyl)-2-methylphenyl)-N-ethyl-N-methylformimidamide | $^1$H-NMR (400 MHz, DMSO-d6) δ 7.92 (s, 1H), 7.55-7.45 (m 2H), 7.38-7.28 (m, 2H), 7.01-6.92 (m, 1H), 5.92 (s, 1H), 3.52-3.40 (m, 2H), 3.08 (s, 3H), 2.88 (s, 3H), 2.18 (s, 3H), 1.12-1.05 (m, 3H) |
| 242. | N'-(2,5-difluoro-4-(2-fluorobenzyl)phenyl)-N-ethyl-N-methylformimidamide | $^1$H-NMR (400 MHz, DMSO-d6) δ 7.85 (bs, 1H), 7.31-7.12 (m, 4H), 6.96-6.85 (m, 2H), 3.89 (s, 2H), 3.43-3.32 (m, 2H), 2.95 (s, 3H), 1.07 (t, 3H); (M + 1): 307.5 |
| 243. | N'-(4-(3-chlorobenzyl)-2,5-difluorophenyl)-N-ethyl-N-methylformimidamide | $^1$H-NMR (400 MHz, DMSO-d6) δ 7.83 (bs, 1H), 7.33-7.29 (m, 1H), 7.25 (t, 2H), 7.16 (d, 1H), 7.07 (dd, 1H), 6.89-6.83 (m, 1H), 3.86 (s, 2H), 3.44-3.33 (m, 2H), 2.93 (s, 3H), 1.13-1.06 (m, 3H); (M + 1): 324 |

-continued

| Sr. No. | Compound Name | Analytical Data |
|---|---|---|
| 244. | N'-(2,5-difluoro-4-(3-methylbenzyl)phenyl)-N-ethyl-N-methylformimidamide | $^1$H-NMR (400 MHz, DMSO-d6) δ 7.83(bs, 1H), 7.08-7.05 (m, 4H), 6.96 (dd, 1H), 6.84 (dd, 1H), 3.79 (s, 2H), 3.42-3.32 (m, 2H), 2.93 (s, 3H), 2.29 (s, 3H), 1.06 (t, 3H); (M + 1): 303.55 |
| 245. | N'-(2,5-difluoro-4-(4-methylbenzyl)phenyl)-N-ethyl-N-methylformimidamide | $^1$H-NMR (400 MHz, DMSO-d6) δ 7.83 (bs, 1H), 7.16 (t, 1H), 7.00-6.96 (m, 4H), 6.85 (dd, 1H), 3.80 (s, 2H), 3.42-3.33 (m, 2H), 2.93 (s, 3H), 2.24 (s, 3H), 1.13-1.06 (m, 3H); (M + 1): 303.55 |
| 246. | N'-(4-(2-chlorobenzyl)-5-cyano-2-methylphenyl)-N-ethyl-N-methylformimidamide | $^1$H-NMR (400 MHz, DMSO-d6) δ 7.77 (bs, 1H), 7.50-7.45 (m, 1H), 7.34-7.22 (m, 3H), 7.18-7.16 (m, 1H), 6.98 (s, 1H), 4.14 (s, 2H), 3.45-3.36 (m, 2H), 3.00 (s, 3H), 2.17 (s, 3H), 1.14 (t, 3H); (M + 1): 326.4 |
| 247. | N'-(5-cyano-4-(2-fluorobenzyl)-2-methylphenyl)-N-ethyl-N-methylformimidamide | $^1$H-NMR (400 MHz, DMSO-d6) δ 7.77 (bs, 1H), 7.32-7.27 (m, 1H), 7.23-7.13 (m, 4H), 7.10 (s, 1H), 4.05 (s, 2H), 3.40 (m, 2H), 2.96 (s, 3H), 2.19 (s, 3H), 1.14 (t, 3H); (M + 1): 310.35 |
| 248. | N'-(5-cyano-2-methyl-4-(2-methylbenzyl)phenyl)-N-ethyl-N-methylformimidamide | $^1$H-NMR (400 MHz, DMSO-d6) δ 7.80 (bs, 1H), 7.25-7.12 (m, 4H), 6.95 (t, 2H), 4.02 (s, 2H), 3.41 (m, 2H), 2.96 (s, 3H), 2.25 (s, 3H), 2.17 (s, 3H), 1.14 (t, 3H); (M + 1): 306.55 |
| 249. | N'-(4-(3-chlorobenzyl)-5-cyano-2-methylphenyl)-N-ethyl-N-methylformimidamide | $^1$H-NMR (400 MHz, DMSO-d6) δ 7.77 (bs, 1H), 7.34 (td, 1H), 7.29-7.27 (m, 2H), 7.23 (d, 2H), 7.19 (m, 1H), 4.04 (s, 2H), 3.40 (m, 2H), 2.99 (s, 3H), 2.22 (s, 3H), 1.14 (t, 3H); (M + 1): 327 |
| 250. | N'-(5-cyano-4-(3-fluorobenzyl)-2-methylphenyl)-N-ethyl-N-methylformimidamide | $^1$H-NMR (400 MHz, DMSO-d6) δ 7.79 (bs,1H), 7.40-6.98 (m, 6H), 4.00 (s, 2H), 3.45-3.33 (m, 2H), 3.04 (m, 3H), 2.26 (s, 3H), 1.12 (t, 3H); (M + 1): 310.5 |
| 251. | N'-(5-cyano-2-methyl-4-(3-methylbenzyl)phenyl)-N-ethyl-N-methylformimidamide | $^1$H-NMR (400 MHz, DMSO-d6) δ 7.75(bs, 1H), 7.39-7.00 (m, 6H), 4.00 (s, 2H), 3.50-3.35 (m, 2H), 3.04 (s, 3H), 2.33 (s, 6H), 1.24 (t, 3H); (M + 1): 306.6 |
| 252. | N'-(5-cyano-2-methyl-4-(4-methylbenzyl)phenyl)-N-ethyl-N-methylformimidamide | $^1$H-NMR (400 MHz, DMSO-d6) δ 7.76 (bs, 1H), 7.40-7.09 (m, 6H), 3.97 (s, 2H), 3.44-3.36 (m, 2H), 2.95 (s, 3H), 2.30 (s, 6H), 1.24 (t, 3H); (M + 1): 306.6 |
| 253. | N'-(4-(2-chlorobenzyl)-2,5-difluorophenyl)-N-ethyl-N-methylformimidamide | $^1$H-NMR (400 MHz, DMSO-d6) δ 7.84 (bs, 1H), 7.46-7.43 (m, 1H), 7.31-7.20 (m, 3H), 6.86 (dd, 2H), 3.96 (s, 2H), 3.43-3.34 (m, 2H), 2.94 (s, 3H), 1.06 (t, 3H); (M + 1): 324 |
| 254. | N'-(2,5-difluoro-4-(2-methylbenzyl)phenyl)-N-ethyl-N-methylformimidamide | $^1$H-NMR (400 MHz, DMSO-d6) δ 7.84 (bs, 1H), 7.17-7.09 (m, 3H), 7.04-7.01 (m, 1H), 6.89 (dd, 1H), 6.72 (dd, 1H), 3.84 (s, 2H), 3.42-3.33 (m, 2H), 2.93 (s, 3H), 2.29 (s, 3H), 1.06 (t, 3H); (M + 1): 303.55 |
| 255. | N'-(5-chloro-4-(2-chlorobenzyl)-2-methylphenyl)-N-ethyl-N-methylformimidamide | $^1$H-NMR$^1$H-NMR (400 MHz, DMSO-d6) δ 7.70 (bs, 1H), 7.49-7.24 (m, 3H), 7.04-6.87 (m, 3H), 4.03 (s, 2H), 3.42-3.34 (m, 2H), 2.99 (s, 3H), 2.33 (m, 3H), 1.24-1.11 (m, 3H); (M + 1): 336.45 |
| 256. | N'-(5-chloro-4-(2-fluorobenzyl)-2-methylphenyl)-N-ethyl-N-methylformimidamide | $^1$H-NMR (400 MHz, DMSO-d6) δ 7.68 (bs, 1H), 7.30-7.24 (m, 1H), 7.20-7.06 (m, 3H), 6.97 (d, 1H), 6.86 (d, 1H), 3.96 (s, 2H), 3.34 (s, 2H), 2.95 (s, 3H), 2.14 (s, 3H), 1.13 (t, 3H); (M + 1): 319.5 |
| 257. | N'-(5-chloro-2-methyl-4-(2-methylbenzyl)phenyl)-N-ethyl-N-methylformimidamide | $^1$H-NMR (400 MHz, DMSO-d6) δ 7.70 (bs, 1H), 7.39-7.07 (m, 2H), 6.91-6.87 (m, 3H), 6.77 (s, 1H), 3.95 (s, 2H), 3.35 (m, 2H), 2.95 (s, 3H), 2.20 (s, 3H), 2.04 (s, 3H), 1.24 (t, 3H); (M + 1): 316.05 |
| 258. | N'-(5-chloro-4-(3-chlorobenzyl)-2-methylphenyl)-N-ethyl-N-methylformimidamide | $^1$H-NMR (400 MHz, DMSO-d6) δ 7.72 (bs, 1H), 7.30 (t, 1H), 7.24-7.22 (m, 1H), 7.18 (s, 1H), 7.13 (d, 1H), 7.08 (s, 1H), 6.86 (s, 1H), 3.94 (s, 2H), 3.40-3.25 (m, 2H), 2.93 (s, 3H), 2.13 (s, 3H), 1.11 (t, 3H); (M + 1): 336.45 |
| 259. | N'-(5-chloro-4-(3-fluorobenzyl)-2-methylphenyl)-N-ethyl-N-methylformimidamide | $^1$H-NMR (400 MHz, DMSO-d6DMSO-d6) δ 7.71 (bs, 1H), 7.30 (td, 1H), 7.07 (s, 1H), 7.01-6.92 (m, 3H), 6.86 (s, 1H), 3.95 (s, 2H), 3.40-3.24 (m, 2H), 2.93 (s, 3H), 2.11 (s, 3H), 1.16 (t, 3H); (M + 1): 319.5 |
| 260. | N'-(5-chloro-2-methyl-4-(3-methylbenzyl)phenyl)-N-ethyl-N-methylformimidamide | $^1$H-NMR (400 MHz, DMSO-d6) δ 7.70 (bs, 1H), 7.16-7.12 (m, 1H), 7.02 (s, 1H), 7.00-6.93 (m, 3H), 6.84 (s, 1H), 3.87 (s, 2H), 3.40-3.24 (m, 2H), 2.96 (s, 3H), 2.26 (s, 3H), 2.10 (s, 3H), 1.11 (t, 3H); (M + 1): 316.05 |
| 261. | N'-(5-chloro-2-methyl-4-(4-methylbenzyl)phenyl)-N-ethyl-N-methylformimidamide | $^1$H-NMR (400 MHz, DMSO-d6) δ 7.70 (bs, 1H), 7.05 (dd, 4H), 6.99 (d, 1H), 6.83 (s, 1H), 3.87 (s, 2H), 3.37-3.24 (m, 2H), 2.96 (s, 3H), 2.24 (s, 3H), 2.08 (s, 3H), 1.10 (t, 3H); (M + 1): 315.5 |
| 262. | N'-(4-(2-chlorobenzyl)-2-cyclopropyl-5-(trifluoromethyl)phenyl)-N-ethyl-N-methylformimidamide | $^1$H-NMR (400 MHz, DMSO-d6) δ 7.80 (bs, 1H), 7.49-7.47 (m, 1H), 7.29-7.25 (m, 2H), 7.09 (s, 1H), 6.87 (d, 1H), 6.44 (s, 1H), 4.10 (s, 2H), 3.47-3.37 (m, 2H), 2.98 (s, 3H), 2.34-2.15 (m, 1H), 1.13 (t, 3H), 0.89 (d, 2H), 0.49 (d, 2H); (M + 1): 395.05 |

-continued

| Sr. No. | Compound Name | Analytical Data |
|---|---|---|
| 263. | N'-(2-cyclopropyl-4-(3-methylbenzyl)-5-(trifluoromethyl)phenyl)-N-ethyl-N-methylformimidamide | ¹H-NMR (400 MHz, DMSO-d6) δ 7.75 (bs,1H), 7.17-6.84 (n, 5H), 6.62 (s, 1H), 4.00 (s, 2H), 3.42 (n, 2H), 2.97 (s, 3H), 2.41-2.30 (m, 1H), 2.25 (s, 3H), 1.34-1.12 (t, 3H), 0.86-0.93 (m, 2H), 0.59-0.52 (m, 2H); (M + 1): 375.55 |
| 264. | N'-(2-cyclopropyl-4-(4-methylbenzyl)-5-(trifluoromethyl)phenyl)-N-ethyl-N-methylformimidamide | ¹H-NMR (400 MHz, DMSO-d6) δ 7.75 (bs, 1H), 7.06 (d, 2H), 7.01-6.98 (m, 1H), 6.94 (d, 2H), 6.60 (s, 1H), 3.94 (s, 2H), 3.43-3.34 (m, 2H), 2.95 (s, 3H), 2.39 (m, 1H), 2.25 (s, 3H), 1.12 (t, 3H), 0.91-0.87 (m, 2H), 0.57-0.53 (m, 2H); (M + 1): 375.6 |
| 265. | N'-(4-(3-chlorobenzyl)-2-cyclopropyl-5-(trifluoromethyl)phenyl)-N-ethyl-N-methylformimidamide | ¹H-NMR (400 MHz, DMSO-d6) δ 7.77 (bs, 1H), 7.31-7.27 (m, 1H), 7.23 (dd, 1H), 7.08 (s, 1H), 7.01 (d, 2H), 6.67 (s, 1H), 4.01 (s, 2H), 3.46-3.34 (m, 2H), 2.96 (s, 3H), 2.41 (m, 1H), 1.13 (t, 3H), 0.94-0.89 (m, 2H), 0.62-0.58 (m, 2H); (M + 1): 396 |
| 266. | N'-(2-cyclopropyl-4-(3-fluorobenzyl)-5-(trifluoromethyl)phenyl)-N-ethyl-N-methylformimidamide | ¹H-NMR (400 MHz, DMSO-d6) δ 7.77 (bs, 1H), 7.30 (td, 1H), 7.03-6.97 (m, 1H), 6.89 (d, 1H), 6.86-6.83 (m, 1H), 6.66 (s, H), 4.02 (s, 2H), 3.46-3.34 (m, 2H), 2.96 (d, 3H), 2.40 (d, 1H), 1.13 (t, 3H), 0.93-0.89 (m, 2H), 0.61-0.58 (m, 2H); (M + 1): 379.55 |
| 267. | N'-(2-cyclopropyl-4-(4-cyclopropylbenzyl)-3,6-dimethylphenyl)-N-ethyl-N-methylformimidamide | ¹H-NMR (400 MHz, DMSO-d6) δ 7.41 (bs, 1H), 6.97 (d, 4H), 6.76 (s, 1H), 3.79 (s, 2H), 3.33 (s, 2H), 2.93 (s, 3H), 2.19 (s, 3H), 2.01 (s, 3H), 1.88-1.81 (m, 1H), 1.58-1.54 (m, 1H), 1.13 (t, 3H), 0.92-0.85 (m, 4H), 0.62-0.58 (m, 2H), 0.26 (td, 2H); (M + 1): 361.65 |
| 268. | N'-(2-cyclopropyl-4-(2-methylbenzyl)-5-(trifluoromethyl)phenyl)-N-ethyl-N-methylformimidamide | ¹H-NMR (400 MHz, DMSO-d6) δ 7.80 (bs, 1H), 7.20-7.07 (m, 4H), 6.77 (d, 1H), 6.33 (s, 1H), 3.97 (s, 2H), 3.46-3.37 (m, 2H), 2.98 (s, 3H), 2.36 (m, 1H), 2.18 (s, 3H), 1.24-1.13 (m, 3H), 0.84-0.89 (m, 2H), 0.40 (dd, 2H); (M + 1): 375.45 |
| 269. | N'-(2,5-difluoro-4-(3-fluorobenzyl)phenyl)-N-ethyl-N-methylformimidamide | ¹H-NMR (400 MHz, DMSO-d6) δ 7.84 (bs, 1H), 7.37-7.31 (m, 1H), 7.10-7.00 (m, 4H), 6.91-6.85 (m, 1H), 3.89 (s, 2H), 3.46-3.36 (m, 2H), 2.95 (s, 3H), 1.15 (t, 3H); (M + 1): 307.5 |
| 270. | N'-(4-(2-chlorobenzyl)naphthalen-1-yl)-N-ethyl-N-methylformimidamide | ¹H-NMR (400 MHz, DMSO-d6) δ 8.49 (bs, 1H), 7.86-7.76 (m, 2H), 7.52-7.39 (m, 3H), 7.31-7.14 (m, 2H), 7.05-6.73 (m, 3H), 4.42 (s, 2H), 3.58-3.38 (m, 2H), 3.18 (s, 3H), 1.18 (t, 3H); (M + 1): 337.45 |
| 271. | N-ethyl-N-methyl-N'-(4-(2-methylbenzyl)naphthalen-1-yl)formimidamide | ¹H-NMR (400 MHz, DMSO-d6) δ 8.47 (s, 1H), 7.87-7.74 (m, 2H), 7.47-7.41 (m, 2H), 7.24-7.21 (m, 1H), 7.12 (t, 1H), 7.03 (t, 1H), 6.94 (d, 1H), 6.80 (d, 2H), 4.29 (s, 2H), 3.44-3.34 (m, 2H), 3.08 (s, 3H), 2.33 (s, 3H), 1.17 (m, 3H); (M + 1): 317.6 |
| 272. | N'-(2-chloro-4-(cyano(3-(trifluoromethyl)phenyl)methyl)-5-methylphenyl)-N-ethyl-N-methylformimidamide hydrochloride | ¹H-NMR (400 MHz, CHLOROFORM-D) δ 12.71 (s, 1H), 8.18 (bs, 1H), 7.70-7.41 (m, 6H), 5.46 (s, 1H), 3.80-3.2 (m, 2H), 2.85 (s, 3H), 2.51 (s, 3H), 1.18 (t, 3H); (M + 1): 394.05 |
| 273. | N-ethyl-N-methyl-N'-(5-methyl-4-(3-methylbenzyl)-2-(methylsulfonyl)phenyl)formimidamide | ¹H-NMR (400 MHz, DMSO-d6) δ 7.88 (bs, 1H), 7.53 (s, 1H), 7.38-7.31 (m, 1H), 7.01-7.06 (m, 1H), 6.98-6.91 (m, 3H), 3.99 (s, 2H), 3.46-3.34 (m, 5H), 2.94 (s, 3H), 2.22 (s, 3H), 2.10 (s, 3H); 1.13-1.18 (m, 3H); (M + 1): 359.45 |
| 274. | N-ethyl-N'-(4-(2-fluorobenzyl)-5-methyl-2-(methylsulfonyl)phenyl)-N-methylformimidamide | ¹H-NMR (400 MHz, DMSO-d6) δ 7.88 (bs, 1H), 7.46 (s, 1H), 7.33-7.27 (m, 1H), 7.22-7.09 (m, 3H), 6.97 (d, 1H), 3.96 (s, 2H), 3.47-3.33 (m, 5H), 2.94 (s, 3H), 2.26 (s, 3H), 1.18 (t, 3H); (M + 1): 363.45 |
| 275. | N'-(4-(2-chlorobenzyl)-5-methyl-2-(methylsulfonyl)phenyl)-N-ethyl-N-methylformimidamide | ¹H-NMR (400 MHz, DMSO-d6) δ 7.89 (bs, 1H), 7.48-7.45 (m, 1H), 7.32-7.28 (m, 3H), 7.08-7.06 (m, 1H), 6.98 (d, 1H), 4.01 (s, 2H), 3.46-3.35 (m, 2H), 3.30 (s, 3H), 2.94 (m, 3H), 2.23 (s, 3H), 1.17 (t, 3H); (M + 1): 379.45 |
| 276. | N-ethyl-N-methyl-N'-(5-methyl-2-(methylsulfonyl)-4-(3-(trifluoromethyl)benzyl)pbenyl)formimidamide | ¹H-NMR (400 MHz, DMSO-d6) δ 7.89 (bs, 1H), 7.57-7.49 (m, 4H), 7.40 (d, 1H), 6.96 (d, 1H), 4.07 (s, 2H), 3.46-3.38 (m, 5H), 2.94 (s, 3H), 2.20 (s, 3H), 1.12-1.17 (t, 3H); (M + 1): 413.45 |
| 277. | N-ethyl-N-methyl-N'-(5-methyl-2-(methylsulfonyl)-4-(3-(trifluoromethoxy)benzyl)phenyl)formimidamide | ¹H-NMR (400 MHz, DMSO-d6) δ 7.89 (bs, 1H), 7.53 (s, 1H), 7.42 (t, 1H), 7.19 (d, 1H), 7.14-7.10 (m, 2H), 6.95 (d, 1H), 4.02 (s, 2H), 3.46-3.32 (m, 5H), 2.94 (s, 3H), 2.19 (s, 3H), 1.17 (t, 3H); (M + 1): 429.50 |
| 278. | N-ethyl-N'-(5-fluoro-2-methyl-4-(3-(trifluoromethoxy)benzyl)phenyl)-N-methylformimidamide | ¹H-NMR (400 MHz, DMSO-d6) δ 7.70 (bs, 1H), 7.40 (t, 1H), 7.20 (d, 1H), 7.17-7.14 (m, 2H), 7.00 (d, 1H), 6.40 (d, 1H), 3.89 (s, 2H), 3.40-3.34 (m, 2H), 2.90 (s, 3H), 2.09 (s, 3H), 1.10 (t, 3H); (M + 1): 369.40 |

* Compound names generated using Chemdraw Professional 16.0

Table 2 provides compounds of general formula (Ia) wherein $R^x$, $R^y$, $R^4$, $R^5$, $R^6$, $R^7$, $R^8$, $R^9$ and A have been defined.

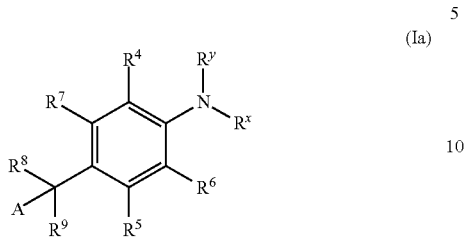

(Ia)

| Sr No. | Compound Name | Analytical Data |
|---|---|---|
| 1. | N'-(2-bromo-4-(4-chlorobenzoyl)-3,6-dimethylphenyl)-N-ethyl-N-methylformimidamide | $^1$H-NMR (400 MHz, DMSO-d6) δ 7.70 (dt, 2H), 7.58-7.62 (m, 2H), 7.42 (bs, 1H), 7.08 (s, 1H), 3.46 - 3.30 (s, 2H), 2.95 (s, 3H), 2.22 (s, 3fl), 2.09 (s, 3H), 1.11-1.20 (m, 3H); (M + 1): 408.8 |
| 2. | N'-(4-cyclopropyl-2,5-dimethylphenyl)-N-ethyl-N-methylformimidamide | $^1$H-NMR (400 MHz, DMSO-d6) δ 7.54 (bs, 1H), 6.63 (s, 1H), 6.52 (s, 1H), 3.48-3.19 (m, 2H), 2.89 (s, 3H), 2.24 (s, 3H), 2.08 (s, 3H), 1.78-1.74 (m, 1H), 1.10 (t, 3H), 0.83-0.78 (m, 2H), 0.48 (td, 2H); (M + 1): 231.2 |
| 3. | N'-(4-bromo-2-cyclopropyl-5-(trifluoromethyl)phenyl)-N-ethyl-N-methylformimidamide | $^1$H-NMR (400 MHz, DMSO-d6) δ 7.75 (bs, 1H), 7.14 (s, 1H), 7.00 (s, 1H), 3.45-3.34 (m, 2H), 2.97 (s, 3H), 2.46-2.41 (m, 1H), 1.15 (s, 3H), 0.96 (m, 2H), 0.75-0.71 (m, 2H), (M + 1): 350.95 |
| 4. | N'-(4-bromo-2-fluoro-5-methylphenyl)-N-ethyl-N-methylformimidamide | $^1$H-NMR (400 MHz, DMSO-d6) δ 7.74 (bs, 1H), 7.32 (s, 1H), 7.01-6.97 (m, 1H), 3.44-3.32 (m, 2H), 2.98 (m, 3H), 2.23 (s, 3H), 1.14-1.07 (m, 3H); (M + 1): 275 |
| 5. | N'-(4-bromo-2,5-difluorophenyl)-N-ethyl-N-methylformimidamide | $^1$H-NMR (400 MHz, DMSO-d6) δ 7.85 (bs, 1H), 7.50-7.46 (m, 1H), 7.14-7.07 (m, 1H), 3.39 (m, 2H), 3.00 (s, 3H), 1.17-1.07- (m, 3H); (M + 1): 279 |
| 6. | N'-(4-bromo-5-chloro-2-methylphenyl)-N-ethyl-N-methylformimidamide | $^1$H-NMR (400 MHz, DMSO-d6) δ 7.71 (bs, 1H), 7.42 (s, 1H), 7.03 (s, 1H), 3.33-3.43(sm, 2H), 2.94 (s, 3H), 2.13 (s, 3H), 1.12 (t, 3H); (M + 1): 290 |
| 7. | N'-(4-bromo-5-cyano-2-methylphenyl)-N-ethyl-N-methylformimidamide | (M + 1): 280.20 |
| 8. | N'-(2,5-dimethylphenyl)-N-ethyl-N-methylformimidamide | (M + 1): 190.2 |
| 9. | 4-(4-chlorobenzyl)-2,5-dimethylaniline | (M + 1): 245.80 |
| 10. | 2,5-dimethyl-4-(4-(methylthio)benzyl)aniline | (M + 1): 257.6 |
| 11. | 4-(3,5-dichlorobenzyl)-2,5-dimethylaniline | (M + 1): 280.2 |
| 12. | 2-bromo-4-(4-bromobenzyl)-3,6-dimethylaniline | $^1$H-NMR (400 MHz, DMSO-d6) δ 7.43 (d, J = 8.4 Hz, 2H), 7.02 (d, J = 8.4 Hz, 2H), 6.83 (s, 1H), 4.84 (s, 2H), 3.84 (s, 2H), 2.14 (s, 3H), 2.10 (s, 3H) |
| 13. | 4-(3-chlorobenzyl)-2,5-dimethylaniline | $^1$H-NMR (400 MHz, DMSO-d6) δ 7.27 (t, J = 7.7 Hz, 1H), 7.18-7.22 (m, 1H), 7.05-7.08 (m, 2H), 6.71 (s, 1H), 6.41 (s, 1H), 4.61 (s, 2H), 3.76 (s, 2H), 1.97 (d, J = 14.5 Hz, 6H) |
| 14. | 4-(2-fluorobenzyl)-2,5-dimethylaniline | $^1$H-NMR (400 MHz, DMSO-d6) δ 7.21 (ddd, J = 15.3, 5.6, 1.8 Hz, 1H), 7.04-7.15 (m, 2H), 6.98 (td, J = 7.7, 1.6 Hz, 1H), 6.62 (s, 1H), 6.41 (s, 1H), 4.59 (s, 2H), 3.74 (s, 2H), 2.02 (s, 3H), 1.96 (d, J = 11.3 Hz, 3H) |
| 15. | 4-(3-bromobenzyl)-2,5-dimethylaniline | $^1$H-NMR (400 MHz, DMSO-d6) δ 7.32-7.34 (m, 1H), 7.18-7.22 (m, 2H), 7.09 (d, J = 7.8 Hz, 1H), 6.70 (s, 1H), 6.40 (s, 1H), 4.60 (s, 2H), 3.75 (s, 2H), 1.98 (s, 6H) |

-continued

| Sr No. | Compound Name | Analytical Data |
|---|---|---|
| 16. | 4-(2-chlorobenzyl)-2,5-dimethylaniline | $^1$H-NMR (400 MHz, DMSO-d6) δ 7.43 (dd, J = 5.6, 3.6 Hz, 1H), 7.21 (dd, J = 5.8, 3.5 Hz, 2H), 6.91 (dd, J = 5.4, 3.7 Hz, 1H), 6.50 (d, J = 42.8 Hz, 2H), 4.63 (s, 2H), 3.82 (s, 2H), 1.98 (d, J = 17.3 Hz, 6H) |
| 17. | 2-chloro-4-(2-chlorobenzyl)-5-methylaniline | $^1$H-NMR (400 MHz, DMSO-d6) δ 7.45 (dd, J = 6.6, 1.8 Hz, 2H), 7.07 (d, J = 8.4 Hz, 2H), 6.94 (s, 1H), 6.59 (s, 1H), 5.10 (s, 2H), 3.76 (s, 2H), 2.01 (s, 3H) |
| 18. | 2-chloro-4-(2-fluorobenzyl)-5-methylaniline | $^1$H-NMR (400 MHz, DMSO-d6) δ 7.22-7.26 (m, 1H), 7.03-7.18 (m, 3H), 6.83 (s, 1H), 6.61 (s, 1H), 5.10 (s, 2H), 3.78 (s, 2H), 2.06 (s, 3H) |
| 19. | 4-(3-fluorobenzyl)-2,5-dimethylaniline | $^1$H-NMR (400 MHz, DMSO-d6) δ 7.27 (dd, J = 14.4, 7.8 Hz, 1H), 6.91-6.97 (m, 2H), 6.84 (d, J = 10.4 Hz, 1H), 6.70 (s, 1H), 6.40 (s, 1H), 4.60 (s, 2H), 3.76 (s, 2H), 2.00 (dd, J = 14.5, 5.2 Hz, 6H) |
| 20. | 4-(3-chloro-4-fluorobenzyl)-2,5-dimethylaniline | $^1$H-NMR (400 MHz, DMSO-d6) δ 7.19-7.29 (m, 2H), 7.04-7.08 (m, 1H), 6.69 (s, 1H), 6.40 (s, 1H), 4.61 (s, 2H), 3.73 (s, 2H), 1.97 (s, 6H) |
| 21. | N'-(4-bromo-2,5-dimethylphenyl)-N-ethyl-N-methylformimidamide | (M + 1): 269.2 |
| 22. | N-(2-chloro-5-methyl-4-(4-((trifluoromethyl)thio)benzyl)phenyl)formamide | $^1$H-NMR (400 MHz, DMSO-d6) δ 9.80-9.77 (m, 1H), 8.30 (d, 1H), 7.90 (s, 1H), 7.63 (d, 2H), 7.33-7.26 (m, 3H), 4.00 (s, 2H), 2.15 (d, 3H); (M + 1): 357.90 |
| 23. | N-(4-(2-fluorobenzyl)-2,5-dimethylphenyl)acetamide | $^1$H-NMR (400 MHz, DMSO-d6) δ 9.17 (s, 1H), 7.24-7.04 (m, 5H), 6.86 (s, 1H), 3.87 (s, 2H), 2.14 (s, 3H), 2.08 (s, 3H), 2.01 (s, 3H); (M + 1): 272.3 |
| 24. | N'-(4-bromo-2-cyclopropyl-5-methylphenyl)-N-ethyl-N-methylformimidamide | $^1$H-NMR (400 MHz, DMSO-d6) δ 7.65 (bs, 1H), 6.76 (s, 1H), 6.72 (s, 1H), 3.40-3.20 (m, 2H), 2.90 (s, 3H), 2.28-2.18 (m, 4H), 1.11 (t, 3H), 0.86-0.82 (m, 2H), 0.59-0.52 (m, 2H); (M + 1): 296.75 |
| 25. | N'-(2-cyclopropyl-5-methyl-4-(4,4,5,5-tetramethyl-1,3,2-dioxaborolan-2-yl)phenyl)-N-ethyl-N-methylformimidamide | $^1$H-NMR (400 MHz, DMSO-d6) δ 7.65 (bs, 1H), 6.94 (s, 1H), 6.53 (s, 1H), 3.39-3.41 (m, 2H), 2.91 (s, 3H), 2.34 (s, 3H), 2.27-2.19 (m, 1H), 1.29-1.22 (m, 12H), 1.12 (t, 3H), 0.79-0.85 (m, 2H), 0.47-0.51 (m, 2H); (M + 1): 343.25 |

* Compound names generated using Chemdraw Professional 16.0

Compounds of the present invention as defined by general formula (I) and/or in table 1 and 2 may be prepared, in known manner, in a variety of ways as described in Schemes 1-4.

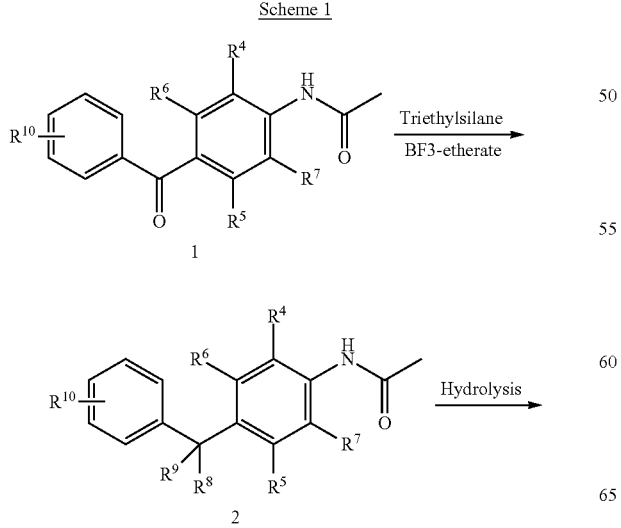

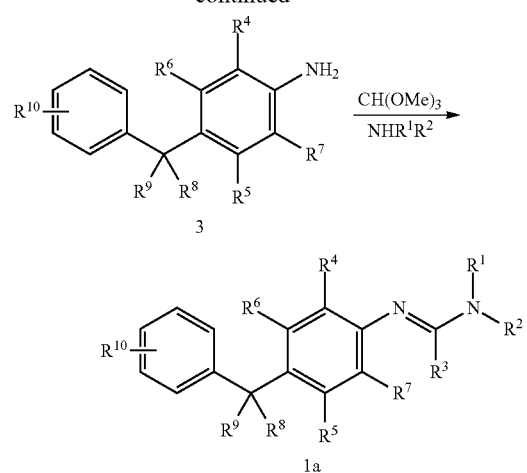

Compound of formula 1a can be synthesized by treating compound of formula 3 with trimethylortoformate and PTSA followed by the reaction with different secondary amines (HNR$^1$R$^2$) as mentioned in US20110130282.

Compound 1 is an important intermediate for the synthesis of compound of formula 1a. There are various methods described in the literature to synthesis compound formula 1 such as Method 1:

From corresponding benzoyl chloride using catalyst $ZnCl_2$ or $AlCl_3$ in the presence of dichloromethane as described in Helvitachimica Act XXIX (1946), page No 1413-1424, and Tetrahedron, 56 (2000), page no 7199-7203

Method 2:

From corresponding benzoic acid in the presence of acid catalyst such as (a) trifluoromethane sulphonic acid as described in Tetrahedron, 56 (2000), pages 7199-7203; (b) Graphite and methane sulphonic acid as described in Synthesis 13 (2004), page no 2165-2168; (c) Graphite and p-toluene sulphonic acid as described in Helvetiva Chimica act 88 (2005) page no 2282-2287; (d) 1-perfluorobutanesulphonic acid as described in Synthesis 10 (2000), page no 1427-1430.

Method 3:

From corresponding derivative of benzoic acid in the presence of metal triflates such as copper triflate, gallium triflate or antimonium triflate or ytterbium triflate or scandium triflate or bismuth triflate as described in Green chemistry, 4 (2002), page no 129-133 or in Tetrahedron, 56 (2000), page no 6 63-6465 or Bull chemical society of Jpn 73 (2000), page no 2325-2333.

Method 4:

From corresponding substituted benzoic acid in the presence of $P_2O_5$ as such or adsorbed on silica gel as described in Tetrahedron letters 49 (2008), page no 6715-6719.

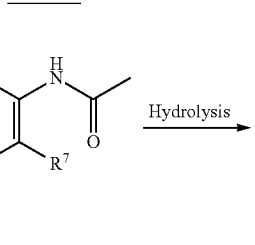

Scheme 2

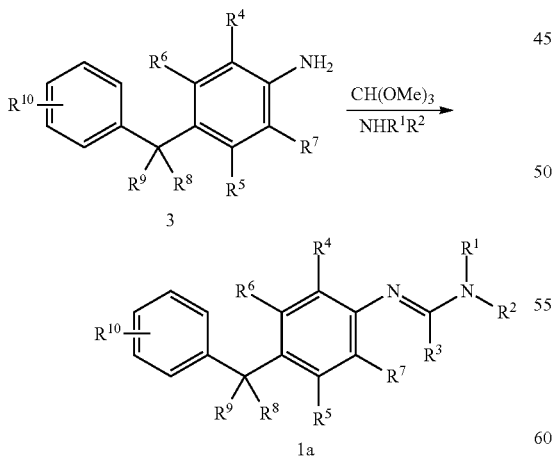

Compound of formula 1a can be synthesized using properly substituted 2a and following the same methods as described in scheme 1. The corresponding intermediate 2a can be synthesized from phenyl acetonitrile in presence of bases like Sodium hydroxide, or Sodium tert. Butoxide, or sodium hydride followed by oxidation with $H_2O_2$/mCPBA in presence of aq KOH as described in (J. Org. Chem 1983, 48, 4097-98, *J. Org. Chem.* 1983, 48, 4087-4096)

Scheme 3

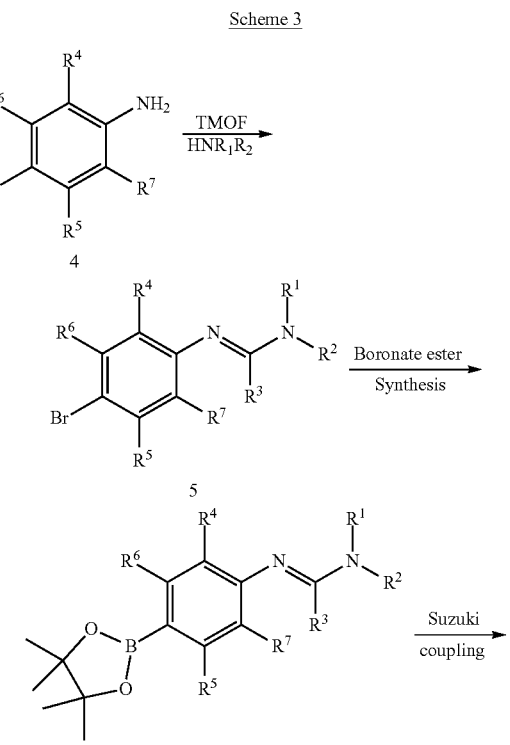

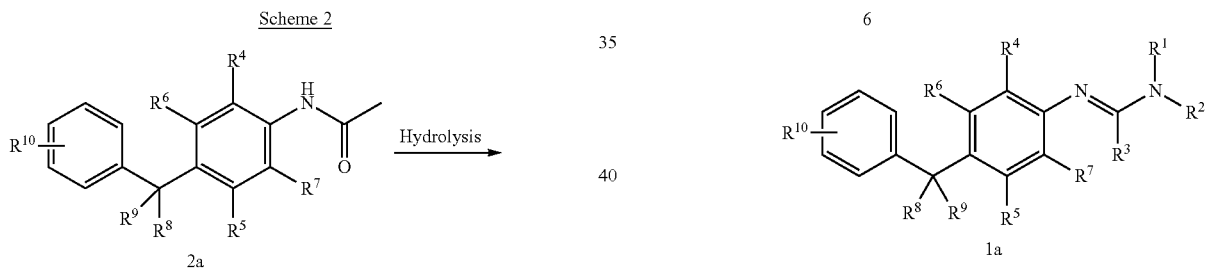

The compound of formula 1a can also be synthesised using Suzuki reaction by treating compound of formula 6 with the corresponding substituted benzyl halide as mentioned in Bioorganic & Medicinal Chemistry Letters, 14 (4), page no 1023-1026; 2004.

Compounds of formula 6 can be synthesised by treating the bromo derivative 5 with Bis(pinacolato)diboran using palladium acetate and $PdCl_2$(dppf) DCM complex in dioxane with good yield.

Scheme 4

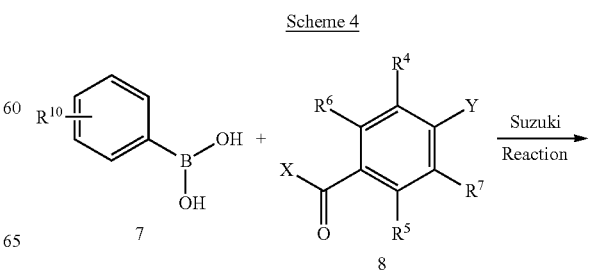

-continued

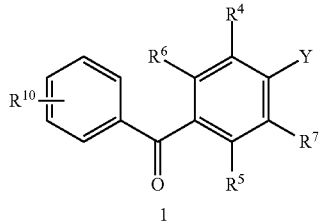

1

The compound of formula 1 can be synthesized by treating phenylboronic acid derivative having formula 7 with a compound of formula 8, wherein X is an activator of carboxylic acid for example chloride, and Y represents the precursor of an amine group such as a nitro group or NHCOCH$_3$ group in the presence of a base like sodium carbonate, a palladium based catalyst and a surfactant such as sodium dodecyl sulphate as described in Synthesis, 13, (2007), page no 1970-1980.

The present invention is further illustrated in the following non-limiting examples. Structures of novel compounds were confirmed by NMR and/or other appropriate analysis as given below.

Example 1

Preparation of N'-(4-(3,5-dichlorobenzyl)-2,5-dimethylphenyl)-N-ethyl-N-methylformimidamide Step A: N-(4-(3,5-dichlorobenzyl)-2,5-dimethylphenyl)acetamide Triethylsilane (2.78 ml, 17.40 mmol) was added to a suspension of N-(4-(3,5-dichlorobenzoyl)-2,5-dimethylphenyl)acetamide (0.9 g, 2.68 mmol) in dichloromethane (15 ml) at 0° C. The reaction mixture was stirred for 10 minutes. Boron trifluoride etherate (2.090 g, 14.72 mmol) was added dropwise to this reaction mixture. The reaction mixture was stirred for 36 hours at room temperature. After the completion of the reaction, the reaction mixture was neutralised with solid sodium bicarbonate and then extracted with dichloromethane (3×200 ml). The combined organic phases were dried over anhydrous Na$_2$SO$_4$. The mixture was filtered and concentrated under reduced pressure. The residue was then purified by column chromatography on silica gel using Hexane: Ethyl acetate as eluent to give the desired N-(4-(3,5-dichlorobenzyl)-2,5-dimethylphenyl)acetamide (0.7 g) as a solid. LCMS (M+H) 323.23

Step B: 4-(3,5-dichlorobenzyl)-2,5-dimethylaniline

To a suspension of N-(4-(3,5-dichlorobenzyl)-2,5-dimethylphenyl)acetamide (0.9 g, 2.79 mmol) in water (10 ml): ethanol (10 ml), sodium hydroxide (3.35 g, 84 mmol) was charged and the reaction mixture was heated to reflux (100° C.). for 36 hours. After the completion of the reaction, the reaction mixture was extracted with dichloromethane. The combined organic phases were dried over anhydrous Na$_2$SO$_4$. The mixture was then filtered and evaporated under reduced pressure. The residue was then purified by column chromatography on silica gel using Hexane: Ethyl acetate as eluent to give the desired 4-(3,5-dichlorobenzyl)-2,5-dimethylaniline (0.4 g) as a gum. LCMS (M+H) 281.29

Step C: Preparation of N'-(4-(3,5-dichlorobenzyl)-2,5-dimethylphenyl)-N-ethyl-N-methylformimidamide A solution of 4-(3,5-dichlorobenzyl)-2,5-dimethylaniline (0.500 g, 1.784 mmol) in trimethyl orthoformate (10.00 ml) with p-toluenesulfonic acid monohydrate (0.017 g, 0.089 mmol) was stirred at 103° C. for 4 hours. The reaction mixture was concentrated under reduced pressure to get the intermediate which was then taken in 1,4-dioxane (10 ml). N-ethylmethylamine (1.551 ml, 17.84 mmol) was added and the reaction mixture was heated to 103° C. for 2 hours. After completion of the reaction, the reaction mixture was concentrated under reduced pressure to get the residue, which was then purified by column chromatography on silica gel using Hexane: Ethyl acetate as eluent to give the desired N'-(4-(3,5-dichlorobenzyl)-2,5-dimethylphenyl)-N-ethyl-N-methylformimidamide (0.210 g) as a gum. LCMS (M+H) 350.35, $^1$H-NMR (400 MHz, DMSO-d6) δ 7.61 (bs, 1H), 7.40 (t, 1H), 7.12 (d, 2H), 6.90 (s, 1H), 6.58 (s, 1H), 3.87 (s, 2H), 3.49-3.32 (bs, 2H), 2.92 (s, 3H), 2.12 (s, 3H), 2.07 (s, 3H), 1.11 (t, 3H)

Example 2

Preparation of N'-(4-(4-bromobenzyl)-2,5-dimethylphenyl)-N-ethyl-N-methylformimidamide Step A: Preparation of N-(4-(4-bromobenzyl)-2,5-dimethylphenyl)acetamide Triethylsilane (3.02 g, 26.0 mmol) was added to a suspension N-(4-(4-bromobenzoyl)-2,5-dimethylphenyl)acetamide (1.5 g, 4.33 mmol) in dichloromethane (30 ml) at 0° C. After stirring the reaction for 10 minutes, Boron trifluoride etherate (3.69 g, 26.0 mmol) was added dropwise to this reaction mixture. After the completion of addition, the reaction mixture was stirred for 36 hours at room temperature. After the completion of the reaction, the reaction mixture was neutralised with solid sodium bicarbonate and then extracted with dichloromethane (3×200 ml). The combined organic phases were dried over anhydrous Na$_2$SO$_4$. The mixture was filtered and concentrated under reduced pressure. The mixture was then filtered and evaporated under reduced pressure. The residue was then purified by column chromatography on silica gel using Hexane: Ethyl acetate as eluent to give the desired N-(4-(4-bromobenzyl)-2,5-dimethylphenyl)acetamide (0.7 g) as a gum. LCMS (M+H) 333.24

Step B: Preparation of 4-(4-bromobenzyl)-2,5-dimethylaniline

To a suspension of (4-amino-2,5-dimethylphenyl)(4-bromophenyl)methanone (0.7 g, 2.301 mmol) in ethanol (21 ml)-water (9 ml), potassium hydroxide (3.87 g, 69.0 mmol) was charged and reaction mixture was heated to reflux (100° C.). for 36 hours. After the completion of the reaction, the reaction mixture was cooled to room temperature and extracted with dichloromethane. The combined organic phases were dried over anhydrous Na$_2$SO$_4$. The mixture was then filtered and evaporated under reduced pressure. The residue was then purified by column chromatography on silica gel using Hexane: Ethyl acetate as eluent to give the desired 4-(4-bromobenzyl)-2,5-dimethylaniline (0.45 g) as a gum. LCMS (M+H) 291.20

Step C: Preparation of N'-(4-(4-bromobenzyl)-2,5-dimethylphenyl)-N-ethyl-N-methylformimidamide A solution 4-(4-bromobenzyl)-2,5-dimethylaniline (0.4 g, 1.378 mmol) in trimethyl orthoformate (15.00 ml) with p-toluenesulfonic acid monohydrate (0.013 g, 0.069 mmol) was stirred at 103° C. for 4 hours. The reaction mixture was concentrated under reduced pressure to get an intermediate which was then taken in 1,4-dioxane (15 ml). N-ethylmethylamine (1.198 ml, 13.78 mmol) was added and the reaction mixture was heated at 103° C. for 2 hours. After completion of the reaction, the reaction mixture was concentrated under reduced pressure to get the residue, which was then purified by column chromatography on silica gel using Hexane:Ethyl acetate as eluent to give the desired N'-(4-(4-bromobenzyl)-2,5-dimethylphenyl)-N-ethyl-N-methylformimidamide (0.4 g) as a gum. $^1$H-NMR (400 MHz, CHLOROFORM-D) δ 7.42 (bs, 1H), 7.35 (d, 2H), 6.98 (d, 2H), 6.86 (s, 1H), 6.58 (s, 1H), 3.84 (s, 2H), 3.59-3.18 (bs, 2H), 3.01 (s, 3H), 2.21 (s, 3H), 2.18 (s, 3H), 1.21 (t, 3H)

Example 3

N'-(4-(3,4-dichlorobenzyl)-2,5-dimethylphenyl)-N-ethyl-N-methylformimidamide

Step A: Preparation of N-(4-(3,4-dichlorobenzyl)-2,5-dimethylphenyl)acetamide

Triethylsilane (1.245 g, 10.71 mmol) was added to a suspension N-(4-(3,4-dichlorobenzoyl)-2,5-dimethylphenyl)acetamide (0.6 g, 1.785 mmol) in dichloromethane (30 ml) at 0° C. After stirring the reaction mixture for 10 minutes, boron trifluoride etherate (1.520 g, 10.71 mmol) was added dropwise to this reaction mixture. After the complete addition, reaction mixture was stirred for 36 hours at room temperature. After the completion of the reaction, the reaction mixture was neutralised with solid sodium bicarbonate and then extracted with dichloromethane (3×200 ml). The combined organic phases were dried over anhydrous Na$_2$SO$_4$. The mixture was filtered and concentrated under reduced pressure. The mixture was then filtered and evaporated under reduced pressure. The residue was then purified by column chromatography on silica gel using Hexane: Ethyl acetate as eluent to give the desired N-(4-(3,4-dichlorobenzyl)-2,5-dimethylphenyl)acetamide (0.4 g) as a gum. LCMS (M+H) 323.23

Step B: Preparation of 4-(3,4-dichlorobenzyl)-2,5-dimethylaniline

To a suspension of (4-amino-2,5-dimethylphenyl)(3,4-dichlorophenyl)methanone (0.5 g, 1.700 mmol) in ethanol (10 ml)-water (3 ml), potassium hydroxide (2.86 g, 51.0 mmol) was charged and reaction mixture was heated to reflux (100° C.). for 36 hours. After the completion of the reaction, the reaction mixture was cooled to room temperature and extracted with dichloromethane. The combined organic phases were dried over anhydrous Na$_2$SO$_4$. The mixture was then filtered and evaporated under reduced pressure. The residue was then purified by column chromatography on silica gel using Hexane: Ethyl acetate as eluent to give the desired 4-(3,4-dichlorobenzyl)-2,5-dimethylaniline (0.2 g) as a gum. LCMS (M+H) 281.20

Step C: Preparation of N-(4-(3,4-dichlorobenzyl)-2,5-dimethylphenyl)-N-ethyl-N-methylformimidamide A solution 4-(3,4-dichlorobenzyl)-2,5-dimethylaniline (0.150 g, 0.535 mmol) in trimethyl orthoformate (10.00 ml) with p-toluenesulfonic acid monohydrate (5.09 mg, 0.027 mmol) was stirred at 103° C. for 4 hours. The reaction mixture was concentrated under reduced pressure to get an intermediate which was then taken in 1,4-dioxane (10 ml). N-ethylmethylamine (0.465 ml, 5.35 mmol) was added and reaction mixture was heated at 103° C. for 2 hours. After completion of the reaction, the reaction mixture was concentrated under reduced pressure to get the residue, which was then purified by column chromatography on silica gel using Hexane:Ethyl acetate as eluent to give the desired N'-(4-(3,4-dichlorobenzyl)-2,5-dimethylphenyl)-N-ethyl-N-methylformimidamide (0.13 g) as a gum. $^1$H-NMR (400 MHz, DMSO-d6) δ 7.60 (bs, 1H), 7.52 (d, 1H), 7.33 (d, 1H), 7.09 (dd, 8.0 Hz, 1H), 6.88 (s, 1H), 6.57 (s, 1H), 3.85 (s, 2H), 3.48-3.30 (bs, 2H), 2.91 (s, 3H), 2.11 (s, 3H), 2.07 (s, 3H), 1.11 (t, 3H).

Example 4

N'-(2,5-dimethyl-4-(3-methylbenzyl)phenyl)-N-ethyl-N-methyl formimidamide

Step A:
N-(2,5-dimethyl-4-(3-methylbenzyl)phenyl)acetamide

Triethylsilane (2.98 g, 25.6 mmol) was added to a suspension N-(2,5-dimethyl-4-(3-methylbenzoyl)phenyl)acetamide (1.5 g, 5.33 mmol) in dichloromethane (30 ml) at 0° C. After stirring for 10 minutes, boron trifluoride etherate (4.16 g, 29.3 mmol) was added dropwise to this reaction mixture. After the complete addition, reaction mixture was stirred for 36 hours at room temperature. After the completion of the reaction, the reaction mixture was neutralised with solid sodium bicarbonate and then extracted with dichloromethane (3×200 ml). The combined organic phases were dried over anhydrous Na$_2$SO$_4$. The mixture was filtered and concentrated under reduced pressure. The residue was then purified by column chromatography on silica gel using Hexane: Ethyl acetate as eluent to give the desired N-(2,5-dimethyl-4-(3-methylbenzyl)phenyl)acetamide (0.8 g) as a gum. LCMS (M+H) 268.37

Step B: Preparation of 2,5-dimethyl-4-(3-methylbenzyl)aniline

To a suspension of N-(2,5-dimethyl-4-(3-methylbenzyl)phenyl)acetamide (0.7 g, 2.62 mmol) in ethanol (21 ml)-water (9 ml), potassium hydroxide (4.41 g, 79 mmol) was charged and reaction mixture was heated to reflux (100° C.). for 36 hours. After the completion of the reaction, the reaction mixture was cooled to room temperature and extracted with dichloromethane. The combined organic phases were dried over anhydrous Na$_2$SO$_4$. The mixture was then filtered and evaporated under reduced pressure. The residue was then purified by column chromatography on silica gel using Hexane: Ethyl acetate as eluent to give the desired 2,5-dimethyl-4-(3-methylbenzyl)aniline (0.4 g) as a gum. LCMS (M+H) 226.34

Step C: Preparation of N'-(2,5-dimethyl-4-(3-methylbenzyl)phenyl)-N-ethyl-N-methylformimidamide A solution of 2,5-dimethyl-4-(3-methylbenzyl)aniline (0.3 g, 1.331 mmol) in trimethyl orthoformate (10 ml) with p-toluenesulfonic acid monohydrate (0.013 g, 0.067 mmol) was stirred at 103° C. for 4 hours. The reaction mixture was concentrated under reduced pressure to get an intermediate which was then taken in 1,4-dioxane (10 ml). N-ethylmethylamine (1.157 ml, 13.31 mmol) was added and reaction mixture was heated at 103° C. for 2 hours. After completion of the reaction, the reaction mixture was concentrated under reduced pressure to get the residue, which was then purified by column chromatography on silica gel using Hexane: Ethyl acetate as eluent to give the desired N'-(2,5-dimethyl-4-(3-methylbenzyl)phenyl)-N-ethyl-N-methylformimidamide (0.160 g) as a gum. $^1$H-NMR (400 MHz, DMSO-d6) δ 7.58 (bs, 1H), 7.13 (t, 7.6 Hz, 1H), 6.96 (d, 7.9 Hz, 1H), 6.92 (s, 1H), 6.89 (d, 1H), 6.85 (s, 1H), 6.54 (s, 1H), 3.79 (s, 2H), 3.42 (bs, 2H), 2.91 (s, 3H), 2.24 (s, 3H), 2.10 (2s, 6H), 1.11 (t, 3H)

Example 5

N'-(4-(4-chlorobenzyl)-2,5-dimethylphenyl)-N-ethyl-N-methylformimidamide

Step A: Preparation of N-(4-(4-chlorobenzyl)-2,5-dimethylphenyl)acetamide triethylsilane (4.16 g, 35.8 mmol) was added to a suspension N-(4-(4-chlorobenzoyl)-2,5-dimethylphenyl)acetamide (1.8 g, 5.96 mmol) in dichloromethane (40 ml) at 0° C. After stirring the reaction mixture for 10 minutes, boron trifluoride etherate (5.08 g, 35.8 mmol) was added dropwise to this reaction mixture. After complete addition reaction mixture was stirred for 36 hours at room temperature. After the completion of the reaction, the reaction mixture was neutralised with solid sodium bicarbonate and then extracted with dichloromethane (3×200 ml). The combined organic phases were dried over anhydrous Na$_2$SO$_4$. The mixture was filtered and concentrated under reduced pressure. The mixture was then filtered and evaporated under reduced pressure. The residue was then purified by column chromatography on silica gel using Hexane: Ethyl acetate as eluent to give the desired N-(4-(4-chlorobenzyl)-2,5-dimethylphenyl) acetamide (1.5 g) as a solid. LCMS (M+H) 288.79.

Step B: Preparation of 4-(4-chlorobenzyl)-2,5-dimethylaniline

To a suspension of N-(4-(4-chlorobenzyl)-2,5-dimethylphenyl)acetamide (1.3 g, 4.52 mmol) in ethanol (21 ml)-water (9 ml), potassium hydroxide (7.60 g, 136 mmol) was charged and reaction mixture was heated to reflux (100° C.). for 36 hours. After the completion of the reaction, the reaction mixture was cooled to room temperature and extracted with dichloromethane. The combined organic phases were dried over anhydrous Na$_2$SO$_4$. The mixture was then filtered and evaporated under reduced pressure. The residue was then purified by column chromatography on silica gel using Hexane: Ethyl acetate as eluent to give the desired 4-(4-chlorobenzyl)-2,5-dimethylaniline (0.8 g) as a solid. LCMS (M+H) 246.75

Step C: Preparation of N'-(4-(4-chlorobenzyl)-2,5-dimethylphenyl)-N-ethyl-N-methylformimidamide A solution 4-(4-chlorobenzyl)-2,5-dimethylaniline (0.7 g, 2.85 mmol) in trimethyl orthoformate (10.00 ml) with p-toluenesulfonic acid monohydrate (0.027 g, 0.142 mmol) was stirred at 103° C. for 4 hours. The reaction mixture was concentrated under reduced pressure to get an intermediate which was then taken in 1,4-dioxane (10 ml). N-ethylmethylamine (2.476 ml, 28.5 mmol) was added and the reaction mixture was heated to 103° C. for 2 hours. After completion of the reaction, the reaction mixture was concentrated under reduced pressure to get the residue, which was then purified by column chromatography on silica gel using Hexane: Ethyl acetate as eluent to give the desired N'-(4-(4-chlorobenzyl)-2,5-dimethylphenyl)-N-ethyl-N-methylformimidamide (0.3 g) as a gum. $^1$H-NMR (400 MHz, DMSO-d6) δ 7.66-7.43 (bs, 1H), 7.30 (d, 2H), 7.14-7.08 (d, 2H), 6.85 (s, 1H), 6.54 (s, 1H), 3.82 (s, 2H), 3.47-3.32 (bs, 2H), 2.99-2.79 (s, 3H), 2.09 (s, 3H), 2.06 (s, 3H), 1.10 (t, 3H)

Example 6

N'-(2,5-dimethyl-4-(4-(methylthio)benzyl)phenyl)-N-ethyl-N-methyl Formimidamide

Step A: Preparation of N-(2,5-dimethyl-4-(4-(methylthio)benzyl)phenyl) acetamide Triethylsilane (3.78 g, 32.5 mmol) was added to a suspension N-(2,5-dimethyl-4-(4-(methylthio)benzoyl)phenyl) acetamide (1.7 g, 5.42 mmol) in dichloromethane (30 ml) at 0° C. After stirring the reaction for 10 minutes boron trifluoride etherate (4.62 g, 32.5 mmol) was added dropwise to this reaction mixture. After the complete addition the reaction mixture was stirred for 36 hours at room temperature. After the completion of the reaction, the reaction mixture was neutralised with solid sodium bicarbonate and then extracted with dichloromethane (3×200 mL). The combined organic phases were dried over anhydrous Na$_2$SO$_4$. The mixture was filtered and concentrated under reduced pressure. The residue was then purified by column chromatography on silica gel using Hexane: Ethyl acetate as eluent to give the desired N-(2,5-dimethyl-4-(4-(methylthio)benzyl)phenyl)acetamide (0.7 g) as a gum. LCMS (M+H) 297.90

Step B: Preparation of 2,5-dimethyl-4-(4-(methylthio)benzyl)aniline

To a suspension of N-(2,5-dimethyl-4-(4-(methylthio)benzyl)phenyl)acetamide (0.7 g, 2.338 mmol) in ethanol (21 ml)-water (9 ml), potassium hydroxide (3.93 g, 70.1 mmol) was charged and reaction mixture was heated to reflux (100° C.). for 36 hours. After the completion of the reaction, the reaction mixture was cooled to room temperature and extracted with dichloromethane. The combined organic phases were dried over anhydrous Na$_2$SO$_4$. The mixture was then filtered and evaporated under reduced pressure. The residue was then purified by column chromatography on silica gel using Hexane: Ethyl acetate as eluent to give the desired 2,5-dimethyl-4-(4-(methylthio)benzyl)aniline (0.4 g,) as a solid. LCMS (M+H) 256.90

Step C: Preparation of N'-(2,5-dimethyl-4-(4-(methylthio)benzyl)phenyl)-N-ethyl-N-methylformimidamide A solution 2,5-dimethyl-4-(4-(methylthio)benzyl)aniline (0.3 g, 1.166 mmol) in trimethyl orthoformate (10 ml) with p-toluenesulfonic acid monohydrate (0.011 g, 0.058 mmol) was stirred at 103° C. for 4 hours. The reaction mixture was concentrated under reduced pressure to get an intermediate which was then taken in 1,4-dioxane (10.00 ml). N-ethylmethylamine (1.013 ml, 11.66 mmol) was added and the reaction mixture was heated at 103° C. for 2 hours. After completion of the reaction, the reaction mixture was concentrated under reduced pressure to get the residue, which was then purified by column chromatography on silica gel using Hexane:Ethyl acetate as eluent to give the desired N'-(2,5-dimethyl-4-(4-(methylthio)benzyl)phenyl)-N-ethyl-N-methylformimidamide (0.21 g) as a gum. $^1$H-NMR (400 MHz, DMSO-d6) δ 7.59-7.44 (bs, 1H), 7.12 (d, 2H), 7.01 (d, 2H), 6.83-6.78 (s, 1H), 6.51 (s, 1H), 3.75 (s, 2H), 3.42-3.30 (bs, 2H), 2.87 (s, 3H), 2.39 (s, 3H), 2.06 (s, 3H), 2.05 (s, 3H), 1.07 (t, 3H)

Example 7

N'-(2,5-dimethyl-4-(4-methylbenzyl)phenyl)-N-ethyl-N-methyl Formimidamide

Step A: Preparation of N-(2,5-dimethyl-4-(4-methylbenzyl)phenyl)acetamide

Triethylsilane (3.47 g, 29.9 mmol) was added to a suspension N-(2,5-dimethyl-4-(4-methylbenzoyl)phenyl)acetamide (1.4 g, 4.98 mmol) in dichloromethane (30 ml) at 0° C. After stirring the reaction mixture for 10 minutes, boron trifluoride etherate (4.24 g, 29.9 mmol) was added dropwise to this reaction mixture. After the completion of the addition, reaction mixture was stirred for 36 hours at room temperature. After the completion of the reaction, the reaction mixture was neutralised with solid sodium bicarbonate and then extracted with dichloromethane (3×200 mL). The combined organic phases were dried over anhydrous Na$_2$SO$_4$. The mixture was filtered and concentrated under reduced pressure. The mixture was then filtered and evaporated under reduced pressure. The residue was then purified by column chromatography on silica gel using Hexane: Ethyl acetate as eluent to give the desired N-(2,5-dimethyl-4-(4-methylbenzyl)phenyl)acetamide (0.9 g) as a solid. LCMS (M+H) 268.37

Step B: Preparation of 2,5-dimethyl-4-(4-methylbenzyl)aniline

To a suspension of N-(2,5-dimethyl-4-(4-methylbenzyl)phenyl)acetamide (0.7 g, 2.62 mmol) in ethanol (21 ml)-water (9 ml), potassium hydroxide (4.41 g, 79 mmol) was charged and reaction mixture was heated to reflux (100° C.). for 36 hours. After the completion of the reaction, the reaction mixture was cooled to room temperature and extracted with dichloromethane. The combined organic phases were dried over anhydrous Na$_2$SO$_4$. The mixture was then filtered and evaporated under reduced pressure. The residue was then purified by column chromatography on silica gel using Hexane: Ethyl acetate as eluent to give the desired 2,5-dimethyl-4-(4-methylbenzyl)aniline (0.28 g) as a gum. LCMS (M+H) 226.37

Step C: Preparation of N'-(2,5-dimethyl-4-(4-methylbenzyl)phenyl)-N-ethyl-N-methylformimidamide A solution 2,5-dimethyl-4-(4-methylbenzyl)aniline (0.3 g, 1.331 mmol) in trimethyl orthoformate (10 ml) with p-toluenesulfonic acid monohydrate (0.013 g, 0.067 mmol) was stirred at 103° C. for 4 hours. The reaction mixture was concentrated under reduced pressure to get an intermediate which was then taken in 1,4-dioxane (10 ml). N-ethylmethylamine (1.157 ml, 13.31 mmol) was added and the reaction mixture was heated at 103° C. for 2 hours. After completion of the reaction, the reaction mixture was concentrated under reduced pressure to get the residue, which was then purified by column chromatography on silica gel using Hexane: Ethyl acetate as eluent to give the desired N'-(2,5-dimethyl-4-(4-methylbenzyl)phenyl)-N-ethyl-N-methylformimidamide (0.160 g) as a gum. $^1$H-NMR (400 MHz, DMSO-d6) δ 7.56 (bs, 1H), 7.04 (d, 2H), 6.97 (d, 2H), 6.82 (s, 1H), 6.53 (s, 1H), 3.79 (s, 2H), 3.33 (bs, 2H), 2.90 (s, 3H), 2.23 (s, 3H), 2.14-2.04 (2s, 6H), 1.10 (t, 3H)

Example 8

N'-(2-bromo-4-(4-bromobenzyl)-3,6-dimethylphenyl)-N-ethyl-N-methylformimidamide

Step A and Step B were carried out as described in above examples.

Step C: Preparation of N'-(2-bromo-4-(4-bromobenzyl)-3,6-dimethylphenyl)-N-ethyl-N-methylformimidamide A solution 4-(bromo-(4-bromophenyl)methyl)-2,5-dimethylaniline (0.5 g, 1.355 mmol) in trimethyl orthoformate (30.0 ml) with p-toluenesulfonic acid monohydrate (0.013 g, 0.068 mmol) was stirred at 103° C. for 4 hours. The reaction mixture was concentrated under reduced pressure to get an intermediate which was then taken in 1,4-dioxane (30 ml). N-ethylmethylamine (1.178 ml, 13.55 mmol) was added and reaction mixture was heated at 103° C. for 2 hours. After completion of the reaction, the reaction mixture was concentrated under reduced pressure to get the residue, which was then purified by column chromatography on silica gel using Hexane: Ethyl acetate as eluent to give the desired N'-(2-bromo-4-(4-bromobenzyl)-3,6-dimethylphenyl)-N-ethyl-N-methylformimidamide (0.2 g) as a gum. $^1$H-NMR (400 MHz, DMSO-d6) δ 7.45 (d, 2H), 7.40-7.23 (bs, 1H), 7.05 (d, 2H), 6.96 (s, 1H), 3.96-3.86 (s, 2H), 3.50-3.36 (bs, 1H), 3.29-3.19 (bs, 1H), 2.91 (s, 3H), 2.18 (s, 3H), 2.05 (s, 3H), 1.11 (bs, 3H)

Example 9

N'-(4-(3-chlorobenzyl)-2,5-dimethylphenyl)-N-ethyl-N-methylformimidamide

Step A: Preparation of N-(4-(3-chlorobenzyl)-2,5-dimethylphenyl)acetamide

Triethylsilane (8.05 g, 69.3 mmol) was added to a suspension of N-(4-(3-chlorobenzoyl)-2,5-dimethylphenyl)acetamide (3.8 g, 12.59 mmol) in dichloromethane (40 ml) at 0° C. After stirring the reaction mixture for 10 minutes, boron trifluoride ethyl etherate (8.04 g, 56.7 mmol) was added dropwise to this reaction mixture. After the addition the reaction mixture was stirred for 36 hours at room temperature. After the completion of the reaction, the reaction mixture was neutralised with solid sodium bicarbonate and then extracted with dichloromethane (3×200 ml). The combined organic phases were dried over anhydrous Na$_2$SO$_4$. The mixture was filtered and concentrated under reduced pressure. The residue was then purified by column chromatography on silica gel using Hexane: Ethyl acetate as eluent to give the desired N-(4-(3-chlorobenzyl)-2,5-dimethylphenyl)acetamide (2.5 g) as a solid. LCMS (M+H) 288.79

Step B: Preparation of 4-(3-chlorobenzyl)-2,5-dimethylaniline

To a suspension of N-(4-(3-chlorobenzyl)-2,5-dimethylphenyl)acetamide (4.6 g, 15.98 mmol) in ethanol (80 ml)-water (20 ml), potassium hydroxide (26.9 g, 480 mmol) was charged and reaction mixture was heated to reflux (100° C.). for 36 hours. After the completion of the reaction, the reaction mixture was cooled to room temperature and extracted with dichloromethane. The combined organic phases were dried over anhydrous $Na_2SO_4$. The mixture was then filtered and evaporated under reduced pressure. The residue was then purified by column chromatography on silica gel using Hexane: Ethyl acetate as eluent to give the desired 4-(3-chlorobenzyl)-2,5-dimethylaniline (2.5 g) as a solid. LCMS (M+H) 246.75

Step C: Preparation of N'-(4-(3-chlorobenzyl)-2,5-dimethylphenyl)-N-ethyl-N-methylformimidamide A solution of 4-(3-chlorobenzyl)-2,5-dimethylaniline (0.8 g, 3.26 mmol) in trimethyl orthoformate (30.0 ml) with p-toluenesulfonic acid monohydrate (0.031 g, 0.163 mmol) was stirred at 103° C. for 4 hours. The reaction mixture was concentrated under reduced pressure to get an intermediate, which was then taken in 1,4-dioxane (30 ml). N-ethylmethylamine (2.83 ml, 32.6 mmol) was added and the reaction mixture heated at 103° C. for 2 hours. After completion of the reaction, the reaction mixture was concentrated under reduced pressure to get the residue, which was then purified by column chromatography on silica gel using Hexane: Ethyl acetate as eluent to give the desired N'-(4-(3-chlorobenzyl)-2,5-dimethylphenyl)-N-ethyl-N-methylformimidamide (0.3 g) as a gum. $^1$H-NMR (400 MHz, DMSO-d6) δ 7.68-7.42 (bs, 1H), 7.28 (d, 1H), 7.21 (dd, 1H), 7.11 (s, 1H), 7.08 (d, 1H), 6.87 (s, 1H), 6.56 (s, 1H), 3.85 (s, 2H), 3.49-3.34 (bs, 1H), 3.32-3.19 (bs, 1H), 2.91 (s, 3H), 2.11 (s, 3H), 2.07 (s, 3H), 1.10 (t, 3H)

Example 10

N'-(2,5-dimethyl-4-(4-(methylsulfonyl)benzyl)phenyl)-N-ethyl-N-methyl Formimidamide Step A and Step B were carried out as described in above examples.

Step C: Preparation of N'-(2,5-dimethyl-4-(4-(methylsulfonyl)benzyl)phenyl)-N-ethyl-N-methylformimidamide To a solution of 2,5-dimethyl-4-(4-(methylsulfonyl)benzyl)aniline (0.3 g, 1.037 mmol) in trimethyl orthoformate (15 ml) was added p-toluenesulfonic acid monohydrate (0.020 g, 0.104 mmol) and heated at 100° C. for 4 hours. After the completion of the reaction, the volatiles were evaporated. The residue was taken in 1,4-dioxane (15.00 ml) and added N-ethylmethylamine (0.270 ml, 3.11 mmol). The reaction mixture was heated at 100° C. for 4 hours, After completion of the reaction, the dioxane was evaporated and residue was subjected to purification by prep HPLC to give N'-(2,5-dimethyl-4-(4-(methylsulfonyl)benzyl)phenyl)-N-ethyl-N-methylformimidamide (240 mg) as gum. 1H NMR (400 MHz, DMSO-d6) δ=7.81 (d, 2H,), 7.55 (bs, 1H), 7.36 (d, 2H,),6.89 (s, 1H), 6.56 (s, 1H), 3.95 (s, 2H), 3.35-3.29 (m, 2H), 3.15 (s, 3H), 2.90 (s, 3H), 2.10 (s, 3H), 2.08 (s, 3H), 1.10 (t, 3H,); LCMS (M+H) 359.15

Example 11

N'-(2,5-dimethyl-4-(4-(methylsulfinyl)benzyl)phenyl)-N-ethyl-N-methyl Formimidamide Step A and Step B were carried out as described in above examples.

Step C: Preparation of N'-(2,5-dimethyl-4-(4-(methylsulfinyl)benzyl)phenyl)-N-ethyl-N-methylformimidamide To a solution of N'-(2,5-dimethyl-4-(4-(methylthio)benzyl)phenyl)-N-ethyl-N-methylformimidamide (0.3 g, 0.919 mmol) in ethanol (5 ml) was added oxone (0.282 g, 0.919 mmol) and heated at 65° C. for 2 hours. After the completion of the reaction the reaction mixture was filtered, the filtrate was evaporated to get a residue which was then purified column to give N'-(2,5-dimethyl-4-(4-(methylsulfinyl)benzyl)phenyl)-N-ethyl-N-methylformimidamide (0.25 g); 1H NMR (400 MHz, DMSO-d6) δ 7.57-7.55 (m, 3H), 7.29 (d, 2H,), 6.88 (s, 1H), 6.55 (s, 1H), 3.90 (s, 2H), 3.35-3.29 (m, 2H), 2.90 (s, 3H), 2.68 (s, 3H), 2.09 (s, 3H), 2.08 (s, 3H), 1.10 (t, 3H,); LCMS (M+H) 343.20

Example 12

N'-[4-(3-bromo-2-fluorobenzyl)-2,5-dimethylphenyl]-N-methylimidoformamide

Step A and Step B were carried out as described in above examples.

Step C: Preparation of N'-(4-(3-bromo-2-fluorobenzyl)-2,5-dimethylphenyl)-N-methylformimidamide To a solution of 4-(3-bromo-2-fluorobenzyl)-2,5-dimethylaniline (1.5 g, 4.87 mmol) in trimethyl orthoformate (10 ml) was added p-toluenesulfonic acid monohydrate (0.926 g, 4.87 mmol) and stirred for 4 hours at 103° C. Then reaction mixture was concentrated under reduced pressure to get an intermediate. To this intermediate was added 1,4-dioxane (10.00 ml) and methylamine (20.02 ml, 40.0 mmol). The reaction mixture was again heated to 103° C. for 2.0 hours. After completion of the reaction, the reaction mixture was concentrated under reduced pressure to get crude product. This crude product was purified over flash chromatography using Hexane: Ethyl acetate to get desired N'-(4-(3-bromo-2-fluorobenzyl)-2,5-dimethylphenyl)-N-methylformimidamide (400 mg) as a gum. $^1$H-NMR (400 MHz, DMSO-d6) δ 7.61 (s, 1H), 7.56-7.49 (m, 1H), 7.05 (t, 1H), 7.03-6.96 (m, 1H), 6.81 (s, 1H), 6.61 (s, 1H), 3.88 (s, 2H), 3.64-3.57 (m, 4H), 3.54-3.34 (4H), 2.11 (s, 3H), 2.07 (s, 3H)

Example 13

N'-[2-chloro-4-(3-fluorobenzyl)-5-methylphenyl]-N-methylimidoformamide

Step A and Step B were carried out as described in above examples.

Step C: Preparation of N'-(2-chloro-4-(3-fluorobenzyl)-5-methylphenyl)-N-methylformimidamide To a solution of 2-chloro-4-(3-fluorobenzyl)-5-methylaniline (1.0 g, 4.00 mmol) in trimethyl orthoformate (10 ml)

was added p-toluenesulfonic acid monohydrate (0.038 g, 0.200 mmol) and was stirred for 4 hours at 103° C. Then reaction mixture was concentrated under reduced pressure to get an intermediate. To this intermediate was added 1,4-dioxane (10.00 ml) and methylamine (20.02 ml, 40.0 mmol). The reaction mixture was again heated to 103° C. for 2 hours. After completion of the reaction, the reaction mixture was concentrated under reduced pressure to get the crude product. This crude product was purified by flash chromatography using Hexane: Ethyl acetate to get the desired N'-(2-chloro-4-(3-fluorobenzyl)-5-methylphenyl)-N-methylformimidamide (600 mg) as a gum. $^1$H-NMR (400 MHz, DMSO-d6) δ 7.60 (d, 1H), 7.31 (td, 1H), 7.22-7.12 (1H), 7.09 (s, 1H), 7.05-6.88 (m, 3H), 6.72 (s, 1H), 3.88 (s, 2H), 2.77 (d, 3H), 2.10 (s, 3H)

Example 14

4-(3-chloro-4-fluorobenzyl)-2,5-dimethyl-N—[(Z)-morpholin-4-ylmethylidene]aniline Step A and Step B were carried out as described in above examples.

Step C: Preparation of N-(4-(3-chloro-4-fluorobenzyl)-2,5-dimethylphenyl)-1-morpholinomethanimine To a solution of 4-(3-chloro-4-fluorobenzyl)-2,5-dimethylaniline (0.3 g, 1.137 mmol) in trimethyl orthoformate (10 ml) was added p-toluenesulfonic acid monohydrate (10.82 mg, 0.057 mmol) and stirred for 4 hours at 103° C. The reaction mixture was concentrated under reduced pressure to get the residue which was taken in 1,4-dioxane (10.00 ml). Morpholine (0.991 ml, 11.37 mmol) was added and reaction mixture was again heated to 103° C. for 2 hours. After completion of the reaction, the reaction mixture was concentrated under reduced pressure to get the residue. This was purified by column chromatography using Hexane: Ethyl acetate as eluent to get desired N-(4-(3-chloro-4-fluorobenzyl)-2,5-dimethylphenyl)-1-morpholinomethanimine (270 mg) as a gum. $^1$H-NMR (400 MHz, DMSO-d6) δ 7.61 (s, 1H), 7.37-7.26 (m, 1H), 7.24 (dd, 1H), 7.15-7.00 (m, 1H), 6.88 (s, 1H), 6.60 (s, 1H), 3.83 (s, 2H), 3.68-3.55 (m, 4H), 3.44 (br, 4H), 2.10 (s, 3H), 2.07 (s, 3H)

Example 15

4-(3-chloro-4-fluorobenzyl)-2,5-dimethyl-N—[(Z)-piperidin-1-ylmethylidene]aniline Step A and Step B were carried out as described in above examples.

Step C: Preparation of N-(4-(3-chloro-4-fluorobenzyl)-2,5-dimethylphenyl)-1-(piperidin-1-yl)methanimine To a solution of 4-(3-chloro-4-fluorobenzyl)-2,5-dimethylaniline (0.3 g, 1.137 mmol) in trimethyl orthoformate (10 ml) was added p-toluenesulfonic acid monohydrate (10.82 mg, 0.057 mmol) and stirred for 4 hours at 103° C. The reaction mixture was concentrated under reduced pressure to get a residue. To this residue was added 1,4-dioxane (10 ml) and piperidine (0.969 g, 11.37 mmol) and reaction mixture was heated to 103° C. for 2 hours. After completion of the reaction, the volatiles were evaporated under reduced pressure to get the crude compound. This crude product was purified by flash chromatography with Hexane: Ethyl acetate to get desired N-(4-(3-chloro-4-fluorobenzyl)-2,5-dimethylphenyl)-1-(piperidin-1-yl)methanimine (301 mg) as a gum. $^1$H-NMR (400 MHz, DMSO-d6) δ 7.53 (s, 1H), 7.29 (dd, 1H), 7.24 (dd, 1H), 7.15-7.00 (m, 1H), 6.86 (s, 1H), 6.56 (s, 1H), 3.82 (s, 2H), 3.59-3.32 (4H), 2.09 (s, 3H), 2.06 (s, 3H), 1.67-1.54 (m, 2H), 1.54-1.41 (m, 4H)

Example 16

4-(3-bromo-2-fluorobenzyl)-2,5-dimethyl-N—[(Z)-morpholin-4-ylmethylidene]aniline Step A and Step B were carried out as described in above examples.

Step C: Preparation of N-(4-(3-bromo-2-fluorobenzyl)-2,5-dimethylphenyl)-1-morpholinomethanimine To a solution of 4-(3-bromo-2-fluorobenzyl)-2,5-dimethylaniline (0.25 g, 0.811 mmol) in trimethyl orthoformate (10 ml) was added p-toluenesulfonic acid monohydrate (7.71 mg, 0.041 mmol) was stirred for 4 hours at 103° C. Then reaction mixture was concentrated under reduced pressure to get an intermediate. To this intermediate was added 1,4-dioxane (10 ml) and morpholine (0.71 ml, 8.11 mmol) and heated to 103° C. for 2 hours. After completion of the reaction, the volatiles were evaporated under reduced pressure to get crude product This crude product was purified by flash chromatography using Hexane: Ethyl acetate to get desired N-(4-(3-bromo-2-fluorobenzyl)-2,5-dimethylphenyl)-1-morpholino methanimine (250 mg) as a gum. $^1$H-NMR (400 MHz, DMSO-d6) δ 7.61 (s, 1H), 7.56-7.49 (m, 1H), 7.05 (t, 1H), 7.03-6.96 (m, 1H), 6.81 (s, 1H), 6.61 (s, 1H), 3.88 (s, 2H), 3.64-3.57 (m, 4H), 3.54-3.34 (4H), 2.11 (s, 3H), 2.07 (s, 3H)

Example 17

4-(3-bromo-2-fluorobenzyl)-2,5-dimethyl-N—[(Z)-piperidin-1-ylmethylidene]aniline Step A and Step B were carried out as described in above examples.

Step C: Preparation of N-(4-(3-bromo-2-fluorobenzyl)-2,5-dimethylphenyl)-1-(piperidin-1-yl)methanimine To a solution of 4-(3-bromo-2-fluorobenzyl)-2,5-dimethylaniline (0.25 g, 0.811 mmol) in trimethyl orthoformate (10 ml) was added p-toluenesulfonic acid monohydrate (7.71 mg, 0.041 mmol) and was stirred for 4 hours at 103° C. The reaction mixture was concentrated under reduced pressure to get an intermediate. To this intermediate was added 1,4-dioxane (10 ml) and piperidine (0.691 g, 8.11 mmol) and the reaction mixture was again heated to 103° C. for 2 hours. After completion of the reaction, reaction mixture was concentrated under reduced pressure to get crude product. This crude product was purified by flash chromatography using Hexane: Ethyl acetate to get desired N-(4-(3-bromo-2-fluorobenzyl)-2,5-dimethylphenyl)-1-(piperidin-1-yl) methanimine (280 mg) as a gum. $^1$H-NMR (400 MHz, DMSO-d6) δ 7.54 (s, 1H), 7.53-7.47 (m, 1H), 7.05 (t, 1H), 7.03-6.94 (m, 1H), 6.79 (s, 1H), 6.58 (s, 1H), 3.87 (s, 2H), 3.59-3.32 (4H), 2.10 (s, 3H), 2.07 (s, 3H), 1.66-1.55 (m, 2H), 1.55-1.41 (m, 4H)

Example 18

N-ethyl-N'-[4-(4-fluorobenzyl)-2,5-dimethylphenyl]-N-methylimidoformamide

Step A and Step B were carried out as described in above examples.

Step C: Preparation of N-ethyl-N-(4-(4-fluorobenzyl)-2,5-dimethylphenyl)-N-methylformimidamide To a solution of 4-(4-fluorobenzyl)-2,5-dimethylaniline (0.3 g, 1.308 mmol) in trimethyl orthoformate (10 ml) was added p-toluenesulfonic acid monohydrate (0.012 g, 0.065 mmol) and was stirred for 4 hours at 103° C. Then reaction mixture was concentrated under reduced pressure to get an intermediate. To this intermediate 1,4-dioxane (10 ml) and N-ethylmethylamine (1.137 ml, 13.08 mmol) and the reaction mixture was again heated to 103° C. for 2 hours. After completion of the reaction, the reaction mixture was concentrated under reduced pressure to get crude product. This crude product was purified by flash chromatography using Hexane: Ethyl acetate to get desired N-ethyl-N'-(4-(4-fluorobenzyl)-2,5-dimethylphenyl)-N-methylformimidamide (0.3 g) as a gum.

Example 19

N-ethyl-N'-[4-(3-methoxybenzyl)-2,5-dimethylphenyl]-N-methylimidoformamide

Step A: Preparation of N'-(2,5-dimethyl-4-(4,4,5,5-tetramethyl-1,3,2-dioxaborolan-2-yl)phenyl)-N-ethyl-N-methylformimidamide A solution of N'-(4-bromo-2,5-dimethylphenyl)-N-ethyl-N-methylimidoformamide (2.7 g, 10.03 mmol) in 1,4-dioxane (27 ml) was added DIBORANE PINACOLONE (5.09 g, 20.06 mmol) and potassium acetate (3.94 g, 40.1 mmol). Nitrogen gas was purged for 20 minutes and then the catalyst $PdCl_2(dppf)$-$CH_2Cl_2$ adduct (0.819 g, 1.003 mmol) was added under nitrogen environment and reaction mixture was heated to 110° C. for 2 hours. Then reaction mixture was concentrated under reduced pressure to get crude product. This crude product was purified by flash chromatography using Hexane: Ethyl acetate to get the desired N-(2,5-dimethyl-4-(4,4,5,5-tetramethyl-1,3,2-dioxaborolan-2-yl)phenyl)-N-ethyl-N-methylformimidamide (2.5 g) as a gum. LCMS (M+H) 317.25

Step B: Preparation of N-ethyl-N'-(4-(3-methoxybenzyl)-2,5-dimethylphenyl)-N-methylformimidamide The solution of N'-(2,5-dimethyl-4-(4,4,5,5-tetramethyl-1,3,2-dioxaborolan-2-yl)phenyl)-N-ethyl-N-methylformimidamide (0.45 g, 1.423 mmol), 1-(bromomethyl)-3-methoxybenzene (0.429 g, 2.134 mmol) and potassium carbonate (0.590 g, 4.27 mmol) in 1,4-dioxane (10 ml)-water (0.01 ml) was purged nitrogen for 20 minutes $Pd(Ph_3P)_4$ (0.164 g, 0.142 mmol) was added to the reaction mixture and heated to 110° C. for 2 hours. After the completion of the reaction, the reaction mixture was concentrated under reduced pressure and the crude product was purified with preparative HPLC to get desired N-ethyl-N-(4-(3-methoxybenzyl)-2,5-dimethylphenyl)-N-methyl-formimidamide (0.3 g) as a gum. $^1$H-NMR (400 MHz, DMSO-d6) δ 7.59-7.44 (bs, 1H), 7.12 (d, 2H), 7.01 (d, 2H), 6.83-6.78 (s, 1H), 6.51 (s, 1H), 3.75 (s, 2H), 3.42-3.30 (bs, 2H), 2.87 (s, 3H), 2.39 (s, 3H), 2.06 (s, 3H), 2.05 (s, 3H), 1.07 (t, 3H)

Example 20

N-ethyl-N'-(4-(methoxy(phenyl)methyl)-2,5-dimethylphenyl)-N-methyl formimidamide A solution (4-amino-2,5-dimethylphenyl)(phenyl)methanol (0.7 g, 3.08 mmol) in trimethyl orthoformate (20 ml) with p-toluenesulfonic acid monohydrate (0.029 g, 0.154 mmol) was stirred for 4 hours at 103° C. Then reaction mixture was concentrated under reduced pressure to get an intermediate. To this intermediate 1,4-dioxane (20 ml) and N-ethylmethylamine (2.68 ml, 30.8 mmol) was charged and reaction mixture again heated to 103° C. for 2 hours. After completion of the reaction, the reaction mixture was concentrated under reduced pressure to get the residue, which was then purified by column chromatography on silica gel using Hexane: Ethyl acetate as eluent to give the desired N-ethyl-N'-(4-(methoxy(phenyl)methyl)-2,5-dimethylphenyl)-N-methylformimidamide (0.4 g) as a gum. $^1$H-NMR (400 MHz, DMSO-d6) δ7.60 (bs, 1H), 7.36-7.18 (m, 5H), 7.03 (s, 1H), 6.52 (s, 1H), 5.35 (s, 1H), 3.48-3.34 (bs, 1H), 3.32-3.24 (bs, 1H), 3.20 (s, 3H), 2.91 (s, 3H), 2.14 (s, 3H), 2.11 (s, 3H), 1.11 (t, 3H)

Example 21

N'-(2,5-dimethyl-4-(2-phenyl-1,3-dithiolan-2-yl)phenyl)-N-ethyl-N-methyl Formimidamide

Step A: Preparation of N-(2,5-dimethyl-4-(2-phenyl-1,3-dithiolan-2-yl) phenyl)acetamide To a solution of N-(4-benzoyl-2,5-dimethylphenyl)acetamide (1.5 g, 5.61 mmol) in anhydrous $CH_2Cl_2$ (25 ml) was added ethane-1,2-dithiol (1.057 g, 11.22 mmol), and acetic acid (0.642 ml, 11.22 mmol) was cooled to 0° C. followed by addition of boron trifluoride etherate (0.782 ml, 6.17 mmol) and reaction mixture was allowed to stirred at room temperature overnight. Reaction mixture was diluted with dichloromethane followed by quenched with dropwise pouring of reaction mixture in to aqueous NaOH solution, mixture was separated, combined organic layer were dried over anhydrous $Na_2SO_4$ and concentrated. The crude product was purified by column chromatography to provide the desired N-(2,5-dimethyl-4-(2-phenyl-1,3-dithiolan-2-yl)phenyl)acetamide (1.8 g). LCMS (M+H) 344.50

Step B: Preparation of 2,5-dimethyl-4-(2-phenyl-1,3-dithiolan-2-yl)aniline

To a solution of N-(2,5-dimethyl-4-(2-phenyl-1,3-dithiolan-2-yl)phenyl)acetamide (2.75 g, 8.01 mmol) in ethanol (25 ml) and water (20.00 ml), a solution of potassium hydroxide (8.98 g, 160 mmol) was added and reaction mixture was allowed to heat at 90° C. for 15 hours. Reaction mixture was evaporated under reduced pressure; the residue was diluted with water (150 ml) and extracted with ethyl acetate (3×150 ml). The combined organic layers were dried over anhydrous sodium sulphate and concentrated. The crude compound was purified by column chromatography to provide the desired product 2,5-dimethyl-4-(2-phenyl-1,3-dithiolan-2-yl)aniline (1.2 g). LCMS (M+H) 302

Step C: Preparation of N'-(2,5-dimethyl-4-(2-phenyl-1,3-dithiolan-2-yl)phenyl)-N-ethyl-N-methyl-formimidamide To a solution of 2,5-dimethyl-4-(2-phenyl-1,3-dithiolan-2-yl)aniline (270 mg, 0.896 mmol) in trimethyl orthoformate (25 ml) was added PTSA (10 mg) and reaction mixture was allowed to heat at 103° C. for 4 hours. The solvent was evaporated under reduced pressure. The residue was charged with dioxane (25.00 ml) followed by addition of the N-ethylmethylamine (0.779 ml, 8.96 mmol) reaction mixture, reaction mixture was allowed to heat at 103° C. for 2 hours. after complete conversion of starting material, reaction mixture was concentrated under reduced pressure, the crude compound was purified by preparative HPLC to provide desired N'-(2,5-dimethyl-4-(2-phenyl-1,3-dithiolan-2-yl)phenyl)-N-ethyl-N-methylformimidamide (220 mg). $^1$H-NMR (400 MHz, DMSO-d6) δ 7.79 (s, 1H), 7.64 (s, 1H), 7.38 (d, 2H), 7.23-7.27 (m, 2H), 7.16-7.20 (m, 1H), 6.52 (s, 1H), 3.51-3.40 (3H), 3.40-3.32 (3H), 2.91 (s, 3H), 2.20 (s, 3H), 1.74 (s, 3H), 1.11 (t, 3H)

As described herein the compounds of general formula (I) shows an extremely high fungicidal activity which is exerted with respect to numerous phytopathogenic fungi which attacks on important agricultural crops. Compounds of present invention were assessed for activity against one or more of the following:

Biological Test Examples (In Vitro Test)

Example 1: *Pyricularia oryzae* (Rice Blast)

Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature and 60% relative humidity for seven days and radial growth was measured. Compounds 1, 2, 3, 4, 5, 6, 7, 8, 9, 10, 11, 12, 13, 14, 15, 16, 17, 18, 20, 21, 22, 23, 24, 25, 26, 27, 28, 29, 30, 31, 32, 33, 34, 35, 36, 37, 38, 39, 41, 42, 43, 44, 45, 46, 47, 48, 49, 50, 51, 52, 54, 55, 56, 57, 58, 59, 60, 61, 63, 64, 66, 67, 68, 69, 70, 71, 72, 73, 74, 75, 76, 77, 78, 79, 80, 81, 82, 83, 84, 85, 86, 87, 88, 89, 92, 93, 94, 95, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133. 134, 135, 136, 137, 138, 139, 140, 141, 142, 143, 144, 145, 146, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 188, 189, 190, 193, 194, 195, 196, 197, 198, 199, 200, 201, 202, 203, 204, 205, 206, 207, 208, 209, 210, 211, 212, 213, 214, 215, 216, 219, 220, 221, 222, 223, 224, 225, 226, 227, 228, 229, 230, 231, 232, 233, 234, 237, 238, 239, 242, 243, 244, 245, 246, 247, 248, 249, 250, 251, 252, 253, 254, 255, 256, 257, 258, 259, 260, 261, 262, 263, 264, 265, 266, 267, 269, 270, 271 & 273 at 300 ppm gave more than 75% control in these tests when compared to the untreated check which showed extensive disease development.

Example 2: *Rhizoctonia solani* (Rice Sheath Blight/Potato Black Scurf)

Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature and 60% relative humidity for seven days and radial growth was measured. Compounds 1, 2, 3, 4, 5, 6, 7, 8, 9, 10, 11, 13, 14, 15, 16, 17, 18, 20, 21, 22, 23, 24, 25, 26, 27, 28, 29, 30, 31, 32, 33, 34, 35, 36, 37, 39, 41, 42, 43, 44, 45, 46, 47, 48, 49, 50, 51, 52, 54, 55, 56, 57, 58, 59, 60, 61, 63, 66, 67, 68, 69, 70, 71, 72, 74, 75, 76, 77, 78, 79, 80, 81, 82, 83, 84, 85, 86, 87, 88, 89, 92, 93, 94, 95, 97, 98, 99, 100, 101, 102, 103, 104, 105, 106, 107, 108, 109, 110, 111, 112, 113, 114, 115, 116, 117, 118, 119, 120, 121, 122, 123, 124, 127, 128, 129, 130, 131, 132, 133. 134, 135, 136, 137, 138, 139, 140, 141, 142, 143, 144, 145, 146, 147, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 189, 191, 193, 196, 197, 198, 199, 200, 201, 204, 205, 206, 207, 208, 209, 210, 211, 212, 213, 214, 215, 216, 220, 221, 222, 223, 224, 225, 226, 227, 228, 229, 230, 231, 232, 239, 243, 244, 245, 246, 247, 248, 249, 250, 251, 252, 253, 254, 255, 256, 257, 258, 259, 261, 262, 263, 264, 265, 267, 269, 270, 271 & 273 and 33 at 300 ppm gave more than 80% control in these tests when compared to the untreated check which showed extensive disease development.

Example 3: *Botrytis cinerea* (Gray Mold)

Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 22° C. temperature and 90% relative humidity for seven days and radial growth was measured. Compounds 1, 3, 4, 5, 6, 7, 8, 9, 10, 11, 13, 14, 15, 16, 17, 18, 21, 22, 23, 26, 27, 28, 29, 30, 32, 35, 37, 40, 41, 42, 43, 44, 45, 46, 47, 48, 49, 50, 51, 52, 53, 54, 55, 56, 57, 58, 59, 60, 63, 65, 66, 67, 69, 70, 71, 74, 75, 76, 77, 78, 79, 80, 81, 82, 83, 84, 85, 86, 87, 88, 89, 92, 93, 94, 95, 97, 98, 99, 101, 102, 103, 104, 105, 106, 107, 108, 109, 110, 113, 114, 116, 117, 118, 119, 120, 121, 123, 124, 128, 129, 130, 131, 132, 133. 134, 135, 136, 137, 138, 139, 140, 141, 142, 143, 144, 145, 146, 149, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 193, 195, 196, 197, 198, 199, 200, 201, 204, 206, 207, 208, 209, 210, 211, 212, 213, 214, 217, 219, 220, 221, 222, 223, 224, 225, 230, 232, 233, 234, 235, 236, 238, 239, 242, 244, 245, 246, 247, 248, 249, 250, 251, 252, 253, 254, 255, 256, 257, 258, 259, 260, 261, 262, 263, 264, 265, 266, 267, 269, 270, 271, 272 & 273 at 300 ppm gave more than 80% in these tests when compared to the untreated check which showed extensive disease development.

Example 4: *Alternaria solani* (Early Blight of Tomato/Potato)

Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature and 60% relative humidity for seven days and radial growth was measured. Compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 37, 39, 41, 42, 43, 44, 45, 46, 47, 48, 49, 50, 51, 52, 53, 54, 55, 56, 57, 58, 59, 60, 61, 63, 66, 67, 68, 69, 70, 71, 72, 74, 75, 76, 77, 78, 79, 80, 81, 82, 83, 84, 85, 86, 87, 88, 89, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133. 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 184, 185, 186, 195, 196, 197, 198, 199, 200, 201, 202, 203, 204, 205, 206, 207, 208, 209, 210, 211, 212, 213, 214, 215, 216, 218, 219, 220, 221, 222, 223, 224, 225, 226, 227, 228, 229, 230, 231, 232, 233, 234, 237, 238, 239, 242, 243, 244, 245, 246, 247, 248, 249, 250, 251, 252, 253, 254, 255, 256, 257, 258, 259, 260, 261, 262, 263, 264, 265, 266, 267, 269, 270, 271, 272 & 273 at 300 ppm gave more than 75% control in these tests when compared to the untreated check which showed extensive disease development.

Example 5: *Colletotrichum capsici* (Anthracnose)

Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature and 60% relative humidity for seven days and radial growth was measured. Compounds 1, 3, 4, 5, 6, 7, 8, 9, 10, 11, 13, 14, 15, 16, 17, 18, 20, 21, 22, 23, 25, 26, 27, 28, 29, 30, 32, 34, 35, 37, 39, 41, 42, 43, 44, 45, 46, 47, 48, 49, 50, 51, 52, 53, 54, 57, 58, 59, 60, 63, 66, 67, 69, 70, 71, 72, 74, 75, 76, 78, 79, 80, 81, 82, 83, 84, 85, 86, 87, 92, 93, 94, 95, 99, 100, 102, 103, 104, 105, 106, 107, 108, 109, 110, 111, 112, 113, 114, 115, 116, 117, 118, 119, 120, 121, 122, 123, 124, 127, 128, 129, 130, 131, 132, 133. 134, 135, 136, 137, 138, 139, 140, 142, 143, 144, 145, 146, 153, 154, 155, 156, 157, 158, 159, 160, 161, 162, 163, 164, 165, 166, 167, 168, 169, 170, 171, 172, 173, 174, 175, 176, 177, 178, 179, 180, 184, 185, 186, 195, 196, 197, 198, 199, 200, 201, 203, 204, 205, 206, 207, 208, 209, 210, 211, 212, 213, 214, 215, 220, 221, 222, 223, 225, 239, 243, 245, 246, 249, 254, 255, 256, 257, 258, 259, 260, 261, 262, 263, 269, & 270 at 300 ppm gave more than 80% control in these tests when compared to the untreated check which showed extensive disease development.

Example 6: *Septoria lycopersici* (Leaf Spot of Tomato)

Compounds were dissolved in 0.3% DMSO & then added to Potato Dextrose Agar medium just prior to dispensing it into Petri dishes. 5 ml medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature and 70% relative humidity for seven days and radial growth was measured. Compounds 1, 3, 4, 5, 6, 7, 8, 9, 13, 14, 15, 16, 17, 18, 20, 22, 23, 24, 25, 26, 27, 28, 29, 30, 31, 32, 33, 34, 35, 37, 41, 42, 43, 44, 45, 46, 47, 48, 49, 50, 51, 52, 53, 54, 55, 56, 57, 58, 59, 60, 63, 64, 66, 67, 68, 69, 70, 71, 72, 74, 81, 82, 83, 84, 86, 92, 93, 94, 102, 104, 105, 106, 108, 109, 110, 111, 112, 113, 114, 116, 117, 118, 128, 129, 130, 131, 133. 134, 135, 138, 139, 142, 143, 144, 145, 146, 154, 157, 158, 159, 160, 161, 162, 163, 164, 165, 166, 167, 168, 169, 170, 171, 172, 173, 174, 175, 176, 177, 178, 185, 186, 195, 196, 197, 198, 199, 200, 201, 206, 207, 208, 209, 210, 211, 212, 213, 214, 215, 216, 220, 221, 222, 223, 224, 225, 228, 229, 243, 244, 245, 246, 248, 249, 250, 252, 254, 255, 256, 257, 258, 259, 260, 261, 262, 263, 270 & 271 at 300 ppm gave more than 70% control in these tests when compared to the untreated check which showed extensive disease development.

Example 7: *Fusarium culmorum* (Foot Rot of Cereals)

Compounds were dissolved in 0.3% DMSO & then added to Potato Dextrose Agar medium just prior to dispensing it into petri dishes. 5 ml medium with compound in the desired concentration was dispensed into 60 mm sterile petri-plates. After solidification each plate was seeded with 51 nm size mycelial disc taken form periphery of actively growing virulent culture plate. Plates were incubated in growth chambers at 25° C. temperature and 60% relative humidity for seven days and radial growth was measured. Compounds 1, 4, 5, 6, 7, 9, 11, 14, 15, 16, 17, 18, 22, 23, 26, 27, 28, 29, 30, 31, 32, 41, 42, 43, 44, 45, 46, 47, 48, 49, 50, 51, 52, 53, 54, 55, 56, 57, 58, 59, 60, 63, 66, 67, 68, 69, 70, 71, 72, 74, 75, 76, 77, 78, 79, 80, 81, 82, 83, 84, 87, 92, 93, 94, 99, 104, 105, 108, 109, 110, 111, 112, 113, 114, 117, 118, 119, 120, 121, 129, 132, 136, 137, 138, 139, 142, 143, 144, 145, 146, 153, 154, 155, 156, 157, 158, 159, 160, 161, 162, 165, 167, 169, 170, 171, 172, 173, 174, 175, 176, 178, 179, 180, 181, 185, 186, 189, 196, 197, 198, 199, 200, 201, 206, 207, 208, 209, 210, 211, 212, 213, 214, 215, 220, 221, 222, 223, 224, 225, 239, 249, 250, 252, 253, 256, 257, 258, 259, 260, 261, 262, 263, 269 & 271 at 300 ppm gave 75% control in these tests when compared to the untreated check which showed extensive disease development.

Biological Test Examples (Greenhouse)

Example A: *Pyricularia oryzae* Test in Rice

Compounds were dissolved in 2% DMSO/Acetone & then mixed with water to calibrated spray volume of 50 ml. This 50 ml spray solution was poured into the spray bottles for further applications.

To test the preventive activity of compounds, healthy young rice seedlings/plants raised in the greenhouse were sprayed with active compound preparation at the stated application rates inside the spray cabinets using hallowcone nozzles. One day after treatment, the plants were inoculated with spore suspension (sterile water) containing $1.4 \times 10^6$ *Pyricularia oryzae* inoculum. The inoculated plants were then kept in greenhouse chamber at 24° C. temperature and 95% Relative Humidity for disease expression.

A visual assessment of compound's performance was carried by rating the disease severity (0-100% scale) on treated plants on 3, 7, 10 and 15 days after application.

Efficacy (% control) of the compounds was calculated by comparing the disease rating in the treatment with untreated control. The sprayed plants were also assessed for compound's phytotoxic effects by recording symptoms like necrosis, chlorosis & stunting. Compounds 26, 44, 48, 51, 63, 87, 93, 94, 96, 103, 110, 112, 120, 133, 135, 148, 149 & 183 at 500 ppm gave 70-100% control in these tests when compared to untreated check which showed extensive disease development. None of these compounds showed any phytotoxicity to rice crop.

Example B: *Fusarium culmorum* Test in Wheat

Compounds were dissolved in 2% DMSO/Acetone & then mixed with water to calibrated spray volume of 50 ml. This 50 ml spray solution was poured into the spray bottles for further applications.

To test the preventive activity of compounds, healthy young wheat plants raised in the greenhouse were sprayed with active compound preparation at the stated application rates inside the spray cabinets using hallowcone nozzles. One day after treatment, the plants were inoculated with spore suspension (2% Malt) containing $2 \times 10^6$ *Fusarium culmorum* inoculum. The inoculated plants were then kept in greenhouse chamber at 24° C. temperature and 80-90% relative humidity for disease expression.

A visual assessment of compound's performance was carried by rating the disease severity (0-100% scale) on treated plants on 3, 7, 10 and 15 days after application. Efficacy (% control) of the compounds was calculated by comparing the disease rating in the treatment with untreated control. The sprayed plants were also assessed for compound's phytotoxic effects by recording symptoms like necrosis, chlorosis and stunting. Compounds 1, 7, 12, 13, 16, 17, 18, 19, 22, 23, 28, 30, 32, 33, 35, 41, 42, 57, 75, 76, 77, 81, 96, 101, 136, 149, 157, 160 172 & 183 at 500 ppm gave 70-100% control in these tests when compared to untreated check which showed extensive disease development. None of these compounds showed any phytotoxicity to wheat crop.

Example C: *Botrytis cinera* Test in Tomato

Compounds were dissolved in 2% DMSO/Acetone & then mixed with water to calibrated spray volume of 50 ml. This 50 ml spray solution was poured into the spray bottles for further applications.

To test the preventive activity of compounds, healthy young bean/chili plants raised in the greenhouse were sprayed with active compound preparation at the stated application rates inside the spray cabinets using hallowcone nozzles. One day after treatment, the plants were inoculated with spore suspension (2% Malt) containing $1.2 \times 10^6$ *Botrytis cinera* inoculum. The inoculated plants were then kept in greenhouse chamber at 18-20° C. temperature and 90-100% relative humidity for disease expression.

A visual assessment of compound's performance was carried by rating the disease severity (0-100% scale) on treated plants on 3, 7, 10 & 15 days after application. Efficacy (% control) of the compounds was calculated by comparing the disease rating in the treatment with untreated control. The sprayed plants were also assessed for compound's phytotoxic effects by recording symptoms like necrosis, chlorosis and stunting. Compounds 1, 2, 3, 4, 5, 6, 7, 9, 10, 11, 12, 13, 14, 15, 17, 18, 19, 22, 23, 24, 25, 27, 28, 29, 31, 32, 40, 43, 59, 90, 94, 101, 102, 103, 104, 105, 133, 166, 170, 179, 180 & 184 at 500 ppm gave 70-100% control in these tests when compared to untreated check which showed extensive disease development. None of these compounds showed any phytotoxicity to Tomato crop.

Example D: *Alternaria solani* Test in Tomato

Compounds were dissolved in 2% DMSO/Acetone & then mixed with water to calibrated spray volume of 50 ml. This 50 ml spray solution was poured into the spray bottles for further applications.

To test the preventive activity of compounds, healthy young Tomato plants raised in the greenhouse were sprayed with active compound preparation at the stated application rates inside the spray cabinets using hallowcone nozzles. One day after treatment, the plants were inoculated with spore suspension (2% Malt) containing $0.24 \times 10^6$ *Alternaria solani* inoculum. The inoculated plants were then kept in greenhouse chamber at 22-24° C. temperature and 90-95% relative humidity for disease expression.

A visual assessment of compound's performance was carried by rating the disease severity (0-100% scale) on treated plants on 3, 7, 10 and 15 days after application. Efficacy (% control) of the compounds was calculated by comparing the disease rating in the treatment with untreated control. The sprayed plants were also assessed for compound's phytotoxic effects by recording symptoms like necrosis, chlorosis and stunting. Compounds 2, 8, 9, 23, 25, 27, 29, 31, 32, 35, 36, 40, 41, 42, 48, 50, 68, 71, 97, 115, 128, 160, 161, 170, 174, 175, 176, 178, 179, 180 & 180 at 500 ppm gave 70-100% control in these tests when compared to untreated check which showed extensive disease development. None of these compounds showed any phytotoxicity to tomato crop.

The following table 3 shows the comparative analysis of the compound reported in the prior art (WO200046184) and that of the present invention.

TABLE 3

| Compound | Dose/ppm | PYRIOR | RHIZSO | BOTRCI | ALTESO | COLLCA | CORYCA | FUSACU |
|---|---|---|---|---|---|---|---|---|
| | | | | | % inhibition | | | |
| Comparative compound: N'-(4-(cyano(3-(trifluoromethyl)phenyl)methyl)-2,5-dimethylphenyl)-N,N-dimethylformimidamide | 300 | 100 | 80.9 | 77.3 | 79.8 | 41.3 | 58.7 | 0 |
| Compound of the present invention: N'-(4-benzyl-2-chloro-5-methylphenyl)-N-ethyl-N-methylformimidamide | 300 | 100 | 100 | 94.5 | 100 | 100 | 71.2 | 94.5 |

TABLE 3-continued

| Compound | Dose/ ppm | PYRIOR | RHIZSO | BOTRCI | ALTESO | COLLCA | CORYCA | FUSACU |
|---|---|---|---|---|---|---|---|---|
| | | | | | % inhibition | | | |
| Compound of the present invention: N'-(4-benzyl-2,5-dimethylphenyl)-N-ethyl-N-methylformimidamide | 300 | 100 | 100 | 100 | 100 | 100 | 100 | 100 |
| Compound of the present invention: N'-(2-chloro-4-(2-fluorobenzyl)-5-methylphenyl)-N-ethyl-N-methylformimidamide | 300 | 100 | 100 | 100 | 100 | 100 | 100 | 100 |
| Compound of the present invention: N-ethyl-N'-(4-(2-fluorobenzyl)-2,5-dimethylphenyl)-N-methylformimidamide | 300 | 100 | 100 | 100 | 100 | 100 | 100 | 100 |
| Compound of the present invention: N'-(4-(cyano(3-(trifluoromethyl)phenyl)methyl)-2,5-dimethylphenyl)-N-ethyl-N-methylformimidamide | 300 | 100 | 100 | 100 | 100 | 100 | 64.4 | 0 |

| Scientific Name of Pathogen | EPPO Code for Pathogen |
|---|---|
| *Alternaria solani* | ALTESO |
| *Botrytis cinerea* | BOTRCI |
| *Colletotrichum capsici* | COLLCA |
| *Pyricularia oryzae* | PYRIOR |
| *Rhizoctonia solano* | RHIZSO |
| *Fusariumculmorum* | FUSACU |
| *Corynespora cassicola* | CORYCA |

From the above comparison and analysis, it can be concluded that the compounds of the present invention show unexpectedly higher biological activity for the tested pathogens as compared to that of the comparative compound Having described the invention with reference to certain preferred aspects, other aspects will become apparent to one skilled in the art from consideration of the specification. It will be apparent to those skilled in the art that many modifications, both to materials and methods, may be practiced without departing from the scope of the invention.

We claim:

1. A compound of general formula (I)

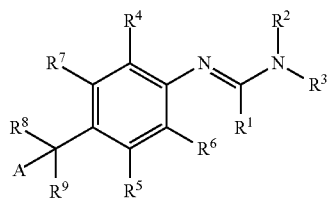

(I)

wherein,

R$^1$ is selected from the group consisting of hydrogen, CN, C$_{1-6}$-alkyl, C$_{1-6}$-alkoxy, C$_{1-6}$-alkylthio, C$_{2-6}$-alkenyl, C$_{2-6}$-alkynyl, C$_{1-6}$-haloalkyl and C$_{3-8}$ cycloalkyl, R$^2$ is selected from the group consisting of CN, OR', C$_{2-12}$-alkyl, C$_{2-12}$-alkenyl, C$_{2-12}$-alkynyl, C$_{1-12}$-haloalkyl, C$_{2-12}$-haloalkenyl, C$_{2-12}$-haloalkynyl and C$_{3-8}$-cycloalkyl: one or more carbon atoms of said cyclic ring system may be replaced by heteroatoms selected from the group consisting of N, O and S(O)$_n$;

R$^3$ is selected from the group consisting of hydrogen, CN, OR', C$_{1-12}$-alkyl, C$_{2-12}$-alkenyl, C$_{2-12}$-alkynyl, C$_{1-12}$-haloalkyl, C$_{2-12}$-haloalkenyl, C$_{2-12}$-haloalkynyl and C$_{3-8}$-cycloalkyl; wherein one or more carbon atoms of said cyclic ring system may be replaced by heteroatoms selected from the group consisting of N, O and S(O)$_n$; or R$^1$ and R$^2$, R$^2$ and R$^3$ or R$^1$ and R$^3$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a four to seven membered non-aromatic ring, which for its part may be substituted by one or more X, R', OR', SR', NR'$_2$, SiR'$_3$, CN and CONR'$_2$; or each group of R$^1$, R$^2$ and R$^3$ may optionally be substituted by one or more groups selected from the group consisting of X, R', OR', SR', NR'$_2$, SiR'$_3$, COOR', CN and CONR'$_2$;

R$^4$ and R$^5$, are independently selected from the group consisting of hydrogen, X, CN, SCN, SF$_5$, S(O)$_n$R", SiR'$_3$, OR", NR'R", (C=O)—R", CR'=NR", C$_{1-12}$-alkyl, C$_{2-12}$-alkenyl, C$_{2-12}$-alkynyl, C$_{1-12}$-haloalkyl, C$_{2-12}$-haloalkenyl, C$_{2-12}$-haloalkynyl, C$_{1-12}$-haloalkoxy, C$_{1-12}$-haloalkylthio, C$_{3-8}$-cycloalkyl, C$_{3-8}$-cycloalkyloxy, C$_{3-8}$-cycloalkylthio, C$_{5-18}$-aryl, C$_{7-19}$-aralkyl and C$_{7-19}$-alkaryl; wherein one or more carbon atoms of said cyclic ring system may be replaced by heteroatoms selected from the group consisting of N, O and S(O)$_n$;

R$^6$ and R$^7$ are independently selected from the group consisting of hydrogen, X, CN, S(O)$_n$R", OR", NR'R", C$_{1-6}$-alkyl, C$_{2-6}$-alkenyl, C$_{2-6}$-alkynyl, C$_{1-6}$-haloalkyl, C$_{2-6}$-haloalkenyl, C$_{1-6}$-haloalkoxy, C$_{1-6}$-haloalkylthio, C$_{3-8}$-cycloalkyl, C$_{3-8}$-cycloalkoxy, C$_{3-6}$-cycloalkylthio; or R$^4$ and R$^7$ or R$^5$ and R$^6$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a four to seven membered ring, which for its part may be substituted by one or more X, R', OR', SR', NR'$_2$, SiR'$_3$, COOR', CN and CONR'$_2$; or each group of R$^4$, R$^5$, R$^6$ and R$^7$ may optionally be substituted by one or more groups selected from the group consisting of X, R', OR', SR', NR'$_2$, SiR'$_3$, COOR', CN, and CONR'$_2$;

R$^8$ and R$^9$ are independently selected from the group consisting of hydrogen, X, CN, OS(O)$_n$R", SiR'$_3$, OSiR'$_3$, (C=O)—R", C$_{1-6}$-alkyl, C$_{2-6}$-alkenyl, C$_{2-6}$-alkynyl, C$_{1-6}$-alkoxy, C$_{2-6}$-alkenyloxy, C$_{2-6}$-alkynyloxy, C$_{1-6}$ haloalkyl, C$_{2-6}$-haloalkenyl, C$_{2-6}$-haloalkynyl, C$_{1-6}$-haloalkoxy, C$_{3-8}$-cycloalkyl, and C$_{3-8}$-cycloalkyloxy, wherein one or more carbon atoms of said cyclic ring system may be replaced by heteroatoms selected from the group consisting of N, O and S(O)$_n$; or R$^6$ and R$^9$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a three to seven membered ring, which for its part may be substituted by one or more X, R', OR', SR', NR'$_2$, SiR'$_3$, COOR', CN and CONR'$_2$; or R$^8$ and R$^9$ together with the atom to which they are attached may form a group of =C(R'R"), =S or =NR";

A is selected from the group consisting of fused or non-fused C$_{6-18}$-aryl and C$_{5-18}$-heteroaryl, wherein one or more carbon atoms are replaced by heteroatoms selected from N, O, S and optionally including 1 to 3 ring members selected from the group consisting of C(=O), C(=S), S(O)$_m$, SiR'$_2$ and further optionally substituted by one or more groups of R$^{10}$; with the proviso that heteroaryl does not represent thiazolyl or thiadiazolyl;

phenyl$^{10}$ is selected from the group consisting of hydrogen, X, CN, SCN, SF$_5$, R", OR", NO$_2$, NR"$_2$, SiR'$_3$, (C=O)—R", S(O)$_n$R", OS(O)$_n$R", NR'S(O)$_n$R", OSiR'$_3$, C$_{1-8}$-alkyl-S(O)$_n$R", C$_{1-8}$-alkyl-(C=O)—R", CR'=NR", S(O)$_n$C$_{5-18}$-aryl, S(O)$_n$C$_{7-19}$-aralkyl, S(O)$_n$C$_{7-19}$-alkaryl, C$_{1-12}$-alkyl, C$_{2-12}$-alkenyl, C$_{2-12}$-alkynyl, C$_{1-12}$-haloalkyl, C$_{2-12}$-haloalkenyl, C$_{2-12}$-haloalkynyl, C$_{1-12}$-alkoxy, C$_{1-12}$-alkylthio, C$_{1-12}$-holoalkoxy, C$_{1-12}$-haloalkylthio, C$_{3-12}$-cycloalkyl, C$_{4-8}$-cycloalkenyl, C$_{5-8}$-cycloalkynyl, C$_{3-8}$-cycloalkyloxy, C$_{3-8}$-cycloalkylthio, C$_{7-19}$-aralkyl, C$_{7-19}$-alkaryl, bicyclic C$_{5-12}$-alkyl and bicycle C$_{7-12}$-alkenyl; one or more carbon atoms of said cyclic ring system may be replaced by heteroatoms selected from the group consisting of N, O, and S(O)$_n$; or two R$^{10}$ together with the atom to which they are attached or together with further atoms selected from the group consisting of C, N, O, S and optionally including 1 to 3 ring members selected from the group consisting of C(=O), C(=S), S(O)$_m$ and SiR'$_3$ may form a four to ten membered ring, which for its part may be substituted by one or more X, R', OR', SR', NR'$_2$, SiR'$_3$, COOR', CN and CONR'$_2$;

each group of R$^8$ and R$^9$ may optionally be substituted by one or more groups selected from the group consisting of X, R', OR', SR', NR'$_2$, SiR'$_3$, COOR', CN, and CONR'$_2$;

R$^{10}$ may optionally be substituted by one or more groups selected from the group consisting of X, R', SR', NR'$_2$, SiR'$_3$, COOR', CN, and CONR'$_2$;

X represents halogen;

R' is selected from the groups consisting of hydrogen, straight chain or branched chain C$_{1-6}$-alkyl and cyclic C$_{3-8}$-alkyl; wherein each group of R' is optionally substituted by one or more X;

R" is selected from the groups consisting of hydrogen, NR'$_2$, OR', straight chain or branched chain C$_{1-6}$-alkyl, C$_{1-6}$-haloalkyl and cyclic C$_{3-8}$-alkyl; wherein each group of R" is optionally substituted by one or more groups selected from the group consisting of X, R', OR', SR', NR'$_2$, SiR'$_3$, COOR', CN, and CONR'$_2$, or R" is phenyl which is optionally substituted by one or more R';

m and n represent integers, n=0, 1 or 2; and m=1 or 2;

and agronomically acceptable salts, metallic complexes, stereo-isomers, diastereoisomers, enantiomers, tautomers, or N-oxides thereof.

2. The compound of general formula (I) according to claim 1, wherein

R$^1$ is selected from the group consisting of hydrogen, C$_{1-6}$-alkyl, C$_{1-6}$-alkoxy, C$_{1-6}$-alkylthio, C$_{1-6}$-haloalkyl and C$_{3-8}$cycloalkyl;

R$^2$ is selected from the group consisting of C$_{2-6}$-alkyl, C$_{2-6}$-alkenyl, C$_{2-12}$-alkynyl, C$_{1-6}$-alkoxy, C$_{1-6}$-haloalkyl and C$_{3-8}$-cycloalkyl;

R$^3$ is selected from the group consisting of C$_{1-6}$-alkyl, C$_{2-6}$-alkenyl, C$_{2-12}$-alkynyl, C$_{1-6}$-alkoxy, C$_{1-6}$-haloalkyl and C$_{3-8}$-cycloalkyl; or R$^1$ and R$^2$, R$^2$ and R$^3$ or R$^1$ and R$^3$ together with the atoms to which they are attached or together with further atoms selected from the group consisting of C, N, O, S and optionally including 1 to 3 ring members selected from the group consisting of C(=O), C(=S), S(O)$_m$ and SiR'$_2$ may form a four to seven membered non-aromatic ring, which for its part may be substituted by one or more X, R', OR', SR' and CN;

R$^4$ and R$^5$ are selected from the group consisting of X, CN, S(O)$_n$R", NR'R", (C=O)—R", CR'=NR", C$_{1-6}$-alkyl, C$_{2-6}$alkenyl, C$_{1-6}$-haloalkyl, C$_{1-6}$-haloalkylthio, C$_{3-8}$-cycloalkyl and C$_{3-8}$cycloalkylthio;

R$^6$ and R$^7$ are selected from the group consisting of hydrogen, X, CN, S(O)$_n$R", NR'R", C$_{1-6}$-alkyl, C$_{2-6}$-alkenyl, C$_{1-6}$-haloalkyl, C$_{1-6}$-haloalkylthio, C$_{3-8}$-cycloalkyl and C$_{3-8}$-cycloalkylthio; or R$^4$ and R$^7$ or R$^5$ and R$^6$ together with the atom to which they are attached or together with further atoms selected from the group consisting of C, N, O, S and optionally including 1 to 3 ring members selected from the group consisting of C(=O), C(=S), S(O)$_m$ and SiR'$_3$ may form a four to seven membered ring, which for its part may be substituted by one or more X, R', OR', SR', NR'$_2$, SiR'$_3$, COOR', CN, and CONR'$_2$;

each group of R$^4$, R$^5$, R$^6$ and R$^7$ may optionally be substituted by one or more groups selected from the group consisting of X, R', OR', SR', NR'$_2$, SiR'$_3$, COOR', CN and CONR'$_2$;

R$^8$ and R$^9$ are selected from the group consisting of hydrogen, X, CN, OS(O)$_n$R", OSiR'$_3$, (C=O)—R", C$_{1-6}$-alkyl, C$_{1-6}$-haloalkyl, C$_{2-6}$-alkenyl, C$_{1-4}$-alkoxy, C$_{2-6}$-alkenyloxy, C$_{2-6}$-alkynyloxy, C$_{1-4}$-haloalkoxy, C$_{3-8}$cycloalkyl, and C$_{3-8}$-cycloalkoxy; or R$^8$ and R$^9$ together with the atom to which they are attached or together with further atoms selected from the group consisting of C, N, O, S may form a three to six membered ring, which for its part may be substituted by one or more X, R', OR', SR', NR'$_2$, SiR'$_3$, COOR', CN and CONR'$_2$;

phenyl$^{10}$ is selected from the group consisting of X, CN, SCN, SF$_5$, R", OR", NO$_2$, NR"$_2$, SiR'$_3$, OS(O)$_n$R", OSiR'$_3$, NR'S(O)$_n$R", (C=O)—R", S(O)$_n$R", C$_{1-8}$-alkyl-S(O)$_n$R", C$_{1-6}$-alkyl-(C=O)—R", CR'=NR", C$_{2-6}$alkenyl, C$_{2-6}$-alkynyl, C$_{1-6}$-haloalkyl, C$_{2-6}$-haloalkenyl, C$_{1-12}$-alkoxy, C$_{1-12}$-alkylthio, C$_{1-12}$-holoalkoxy, C$_{1-12}$-haloalkylthio, C$_{3-8}$-cycloalkyl, C$_{4-8}$-cycloalkenyl, C$_{3-8}$-cycloalkyloxy and C$_{3-8}$-cycloalkylthio; or two R$^{10}$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a four to ten membered ring, which for its part may be substituted by one or more X, R', OR', SR', NR'$_2$, SIR'$_3$, COOR', CN and CONR'$_2$;

A is selected from the group consisting of phenyl, napthalenyl, furyl, thienyl, pyrrolyl, isoxazolyl, isothiazolyl, pyrazolyl, oxazolyl, imidazolyl, oxadiazolyl, triazolyl, pyridinyl, pyridazinyl, pyrimidinyl, pyrazinyl, triazinyl, indolyl, benzimidazolyl, indazolyl, benzofuranyl, benzothiophenyl, benzothiazolyl, benzoxazolyl, quinolinyl, isoquinolinyl, iquinazolinyl and cinnonyl; wherein each group of A is optionally substituted with one or more group of R$^{10}$;

R$^1$ to R$^9$ may further optionally be substituted by one or more groups selected from the group consisting of X, R", OR', SR', NR'2, SiR'$_3$, COOR', CN and CONR'$_2$;

R$^{10}$ may optionally be substituted by one or more groups selected from the group consisting of X, R', SR', NR'$_2$, SiR'$_3$, COOR', CN, and CONR'$_2$;

and agronomically acceptable salts, stereo-isomers, diastereoisomers, enantiomers, tautomers, or N-oxides thereof.

3. The compound of general formula (I) according to claim 1, wherein

R$^1$ is selected from the group consisting of hydrogen and C$_{1-6}$-alkyl;

R$^2$ is selected from the group consisting of C$_{1-6}$alkyl and C$_{1-6}$-haloalkyl;

R$^3$ is selected from the group consisting of C$_{1-6}$-alkyl and C$_{1-6}$-haloalkyl;

R$^4$ and R$^5$ are selected from the group consisting of X, CN, S(O)$_n$R", C$_{1-6}$-alkyl, C$_{1-6}$-haloalkyl and C$_{3-8}$-cycloalkyl;

R$^6$ and R$^7$ are selected from the group consisting of hydrogen, X, C$_{1-6}$-alkyl and C$_{1-6}$-haloalkyl;

R$^8$ and R$^9$ are selected from the group consisting of hydrogen, X, C$_{1-4}$-alkyl, C$_{1-4}$-haloalkyl, C$_{1-4}$-alkoxy, C$_{1-4}$-haloalkoxy, and C$_{3-8}$-cycloalkyl; or R$^8$ and R$^9$ together with the atom to which they are attached or together with further atoms selected from the group consisting of C, N, O, S may form a three to four membered ring, which for its part may be substituted by one or more X, R', OR', SR', NR'$_2$, SiR'$_3$, COOR', CN and CONR'$_2$;

phenyl$^{10}$ is selected from the group consisting of X, CN, SCN, SF$_5$, R", OR", NO$_2$, NR"$_2$, SiR'$_3$, (C=O)—R", S(O)$_n$R", OS(O)$_n$R", NR'S(O)$_n$R", OSiR'$_3$, C$_{1-8}$-alkyl-S(O)$_n$R", C$_{1-6}$-alkyl-(C=O)—R", CR'=NR", S C$_{1-6}$-alkyl, C$_{2-6}$-alkenyl, C$_{2-6}$-alkynyl, C$_{1-6}$-haloalkyl, C$_{2-6}$-haloalkenyl, C C$_{1-12}$-alkoxy, C$_{1-12}$-alkylthio, C$_{1-12}$-holoalkoxy, C$_{1-12}$-haloalkylthio, C$_{3-8}$-cycloalkyl, C$_{4-6}$-cycloalkenyl, C$_{3-8}$-cycloalkyloxy and C$_{3-6}$-cycloalkylthio; or two R$^{10}$ together with the atom to which they are attached or together with further atoms selected from the group consisting of C, N, O, S and optionally including 1 to 3 ring members selected from the group consisting of C(=O), C(=S), S(O)$_m$ and SiR'$_2$ may form a four to ten membered ring, which for its part may be substituted by one or more X, R', OR', SR', NR'$_2$, SiR'$_3$, COOR', CN and CONR'$_2$;

A is selected from the group consisting of phenyl, napthalenyl, thienyl, isothiazolyl, pyridinyl, pyridazinyl, pyrimidinyl, pyrazinyl and quinolinyl; wherein each group of A is optionally substituted with one or more group of R$^{10}$;

R$^1$ to R$^9$ may further optionally be substituted by one or more groups selected from the group consisting of X, R", OR', SR', NR'$_2$, SIR'$_3$, COOR', CN and CONR'$_2$;

R$^{10}$ may optionally be substituted by one or more groups selected from the group consisting of X, R', SR', NR'$_2$, SiR'$_3$, COOR', CN, and CONR'$_2$;

and agronomically acceptable salts, stereo-isomers, diastereoisomers, enantiomers, tautomers, or N-oxides thereof.

4. The compound according to claim 1, wherein said compound of general formula (I) is selected from the group consisting of:

N'-(4-benzyl-2,5-dimethylphenyl)-N-ethyl-N-methylformimidamide;

N-ethyl-N'-(4-(methoxy(phenyl)methyl)-2,5-dimethylphenyl)-N-methylformimidamide;

N'-(4-(3,5-dichlorobenzyl)-2,5-dimethylphenyl)-N-ethyl-N-methylformimidamide;

N'-(4-(4-bromobenzyl)-2,5-dimethylphenyl)-N-ethyl-N-methylformimidamide;

N'-(4-(3,4-dichlorobenzyl)-2,5-dimethylphenyl)-N-ethyl-N-methylformimidamide;

N'-(2,5-dimethyl-4-(3-methylbenzyl)phenyl)-N-ethyl-N-methylformimidamide;

N'-(4-(4-chlorobenzyl)-2,5-dimethylphenyl)-N-ethyl-N-methylformimidamide;

N'-(2,5-dimethyl-4-(4-(methylthio)benzyl)phenyl)-N-ethyl-N-methylformimidamide;

N'-(2,5-dimethyl-4-(4-methylbenzyl)phenyl)-N-ethyl-N-methylformimidamide;

N'-(2-bromo-4-(4-bromobenzyl)-3,6-dimethylphenyl)-N-ethyl-N-methylformimidamide;

N'-(4-(3-chlorobenzyl)-2,5-dimethylphenyl)-N-ethyl-N-methylformimidamide;

N'-(2,5-dimethyl-4-(4-(methylsulfonyl)benzyl)phenyl)-N-ethyl-N-methylformimidamide;

N'-(4-(3-bromobenzyl)-2-chloro-5-methylphenyl)-N-ethyl-N-methylformimidamide;

N'-(4-(3-bromobenzyl)-2,5-dimethylphenyl)-N-ethyl-N-methylformimidamide;

N-ethyl-N'-(4-(2-fluorobenzyl)-2,5-dimethylphenyl)-N-methylformimidamide;

N'-(2-chloro-4-(2-fluorobenzyl)-5-methylphenyl)-N-ethyl-N-methylformimidamide;

N'-(2-chloro-4-(2-chlorobenzyl)-5-methylphenyl)-N-ethyl-N-methylformimidamide;

N'-(4-(2-chlorobenzyl)-2,5-dimethylphenyl)-N-ethyl-N-methylformimidamide;

N-(2,5-dimethyl-4-(4-(methylsulfinyl)benzyl)phenyl)-N-ethyl-N-methylformimidamide;

N'-(2-chloro-4-(3,4-dichlorobenzyl)-5-methylphenyl)-N-ethyl-N-methylformimidamide;
N'-(2-chloro-4-(3,5-dichlorobenzyl)-5-methylphenyl)-N-ethyl-N-methylformimidamide;
N'-(4-(4-bromobenzyl)-2-chloro-5-methylphenyl)-N-ethyl-N-methylformimidamide;
N'-(2,5-dimethyl-4-(2-(methylthio)benzyl)phenyl)-N-ethyl-N-methylformimidamide;
N'-(2,5-dimethyl-4-(2-(methylsulfinyl)benzyl)phenyl)-N-ethyl-N-methylformimidamide;
N'-(2,5-dimethyl-4-(2-(methylsulfonyl)benzyl)phenyl)-N-ethyl-N-methylformimidamide;
N'-(4-(2,5-dimethylbenzyl)-2,5-dimethylphenyl)-N-ethyl-N-methylformimidamide;
N'-(4-(3-bromo-2-fluorobenzyl)-2,5-dimethylphenyl)-N-ethyl-N-methylformimidamide;
N'-(4-(3-chloro-4-fluorobenzyl)-2,5-dimethylphenyl)-N-ethyl-N-methylformimidamide;
N-ethyl-N'-(4-(3-fluorobenzyl)-2,5-dimethylphenyl)-N-methylformimidamide;
N'-(2-chloro-4-(3-fluorobenzyl)-5-methylphenyl)-N-ethyl-N-methylformimidamide;
N'-(2,5-dimethyl-4-((Z)-(methylimino)(phenyl)methyl)phenyl)-N-ethyl-N-methylformimidamide;
N'-(2,5-dimethyl-4-(2-methylbenzyl)phenyl)-N-ethyl-N-methylformimidamide;
N'-(2,5-dimethyl-4-(2-phenyl-1,3-dithiolan-2-yl)phenyl)-N-ethyl-N-methylformimidamide;
N-(4-(3-chloro-4-fluorobenzyl)-2,5-dimethylphenyl)-1-morpholinomethanimine;
N-(4-(3-chloro-4-fluorobenzyl)-2,5-dimethylphenyl)-1-(piperidin-1-yl)methanimine;
N-(4-(3-bromo-2-fluorobenzyl)-2,5-dimethylphenyl)-1-morpholinomethanimine;
N-(4-(3-bromo-2-fluorobenzyl)-2,5-dimethylphenyl)-1-(piperidin-1-yl)methanimine;
N-(2-chloro-4-(3-fluorobenzyl)-5-methylphenyl)-1-morpholinomethanimine;
N-(2-chloro-4-(3-fluorobenzyl)-5-methylphenyl)-1-(piperidin-1-yl)methanimine;
N-(2-chloro-4-(2-chlorobenzyl)-5-methylphenyl)-1-morpholinomethanimine;
N'-(4-(3-bromo-2-fluorobenzyl)-2,5-dimethylphenyl)-N-methylformimidamide;
N'-(2-chloro-4-(3-fluorobenzyl)-5-methylphenyl)-N-methylformimidamide;
N'-(2-chloro-5-methyl-4-(3-methylbenzyl)phenyl)-N-ethyl-N-methylformimidamide;
N'-(2-chloro-5-methyl-4-(4-methylbenzyl)phenyl)-N-ethyl-N-methylformimidamide;
N-ethyl-N'-(4-(3-methoxybenzyl)-2,5-dimethylphenyl)-N-methylformimidamide;
N'-(2,5-dimethyl-4-(3-(trifluoromethyl)benzyl)phenyl)-N-ethyl-N-methylformimidamide;
N'-(4-(3-cyanobenzyl)-2,5-dimethylphenyl)-N-ethyl-N-methylformimidamide;
N'-(4-(4-cyanobenzyl)-2,5-dimethylphenyl)-N-ethyl-N-methylformimidamide;
N'-(2,5-dimethyl-4-(3-nitrobenzyl)phenyl)-N-ethyl-N-methylformimidamide;
N'-(2,5-dimethyl-4-(2-nitrobenzyl)phenyl)-N-ethyl-N-methylformimidamide;
N'-(2,5-dimethyl-4-(3-(trifluoromethoxy)benzyl)phenyl)-N-ethyl-N-methylformimidamide;
N-ethyl-N'-(4-(3-fluoro-5-(trifluoromethyl)benzyl)-2,5-dimethylphenyl)-N-methylformimidamide;
N'-(2,5-dimethyl-4-(2-methyl-5-(trifluoromethyl)benzyl)phenyl)-N-ethyl-N-methylformimidamide;
N-ethyl-N'-(4-(4-methoxybenzyl)-2,5-dimethylphenyl)-N-methylformimidamide;
N-(4-(2-fluorobenzyl)-2,5-dimethylphenyl)-1-morpholinomethanimine;
N-(4-(4-fluorobenzyl)-2,5-dimethylphenyl)-1-morpholinomethanimine;
N-ethyl-N'-(4-(4-fluorobenzyl)-2,5-dimethylphenyl)-N-methylformimidamide;
N-(4-(2-fluorobenzyl)-2,5-dimethylphenyl)-1-(piperidin-1-yl)methanimine;
N-(4-(2-chlorobenzyl)-2,5-dimethylphenyl)-1-(piperidin-1-yl)methanimine;
N-(4-(4-fluorobenzyl)-2,5-dimethylphenyl)-1-(piperidin-1-yl)methanimine;
N'-(4-(2-fluorobenzyl)-2,5-dimethylphenyl)-N-methoxy-N-methylformimidamide;
N'-(4-(2-chlorobenzyl)-2,5-dimethylphenyl)-N-methoxy-N-methylformimidamide;
N-(4-(2-chlorobenzyl)-2,5-dimethylphenyl)-1-morpholinomethanimine;
N-cyano-N-(4-(2-fluorobenzyl)-2,5-dimethylphenyl)formimidamide;
N'-(4-(2-chlorobenzyl)-2,5-dimethylphenyl)-N-cyanoformimidamide;
N'-(4-(2-fluorobenzyl)-2,5-dimethylphenyl)-N-isopropylformimidamide;
N'-(4-(2-chlorobenzyl)-2,5-dimethylphenyl)-N-isopropylformimidamide;
N'-(2-chloro-4-(4-cyanobenzyl)-5-methylphenyl)-N-ethyl-N-methylformimidamide;
N'-(2-chloro-4-(4-methoxybenzyl)-5-methylphenyl)-N-ethyl-N-methylformimidamide;
N'-(2-chloro-4-(3-methoxybenzyl)-5-methylphenyl)-N-ethyl-N-methylformimidamide;
N'-(2-chloro-5-methyl-4-(3-nitrobenzyl)phenyl)-N-ethyl-N-methylformimidamide;
N'-(2-chloro-4-(3-cyanobenzyl)-5-methylphenyl)-N-ethyl-N-methylformimidamide;
N'-(4-(difluoro(phenyl)methyl)-2-iodo-3,6-dimethylphenyl)-N-ethyl-N-methylformimidamide;
N'-(4-benzyl-2-chloro-5-methylphenyl)-N-ethyl-N-methylformimidamide;
N'-(2-chloro-5-methyl-4-(2-nitrobenzyl)phenyl)-N-ethyl-N-methylformimidamide;
N'-(2-chloro-4-(4-fluorobenzyl)-5-methylphenyl)-N-ethyl-N-methylformimidamide;
N'-(2-chloro-5-methyl-4-(4-((trifluoromethyl)thio)benzyl)phenyl)-N-ethyl-N-methylformimidamide;
N'-(2-chloro-4-(3-chlorobenzyl)-5-methylphenyl)-N-ethyl-N-methylformimidamide;
N'-(2-chloro-4-(4-chlorobenzyl)-5-methylphenyl)-N-ethyl-N-methylformimidamide;
N'-(2-chloro-5-methyl-4-(3-(trifluoromethyl)benzyl)phenyl)-N-ethyl-N-methylformimidamide;
N'-(4-(2-fluorobenzyl)-2,5-dimethylphenyl)-N-isopropyl-N-methylformimidamide;
N'-(4-(2-chlorobenzyl)-2,5-dimethylphenyl)-N-isopropyl-N-methylformimidamide;
N-allyl-N'-(4-(2-fluorobenzyl)-2,5-dimethylphenyl)-N-methylformimidamide;
N-allyl-N'-(4-(2-chlorobenzyl)-2,5-dimethylphenyl)-N-methylformimidamide;
N-(4-(2-fluorobenzyl)-2,5-dimethylphenyl)-1-thiomorpholinomethanimine;

N-(4-(2-chlorobenzyl)-2,5-dimethylphenyl)-1-thiomorpholinomethanimine;
N-(cyclopropylmethyl)-N-(4-(2-fluorobenzyl)-2,5-dimethylphenyl)-N-methylformimidamide;
N-(cyclopropylmethyl)-N'-(4-(2-fluorobenzyl)-2,5-dimethylphenyl)-N-isopropylformimidamide;
N'-(4-(2-chlorobenzyl)-2,5-dimethylphenyl)-N-(cyclopropylmethyl)-N-isopropylformimidamide;
N'-(4-(2-chlorobenzyl)-2,5-dimethylphenyl)-N-cyano-N-(cyanomethyl)formimidamide;
N-cyano-N-(cyanomethyl)-N'-(4-(2-fluorobenzyl)-2,5-dimethylphenyl)formimidamide;
N'-(2,5-dimethyl-4-(4-(((trifluoromethyl)thio)benzyl)phenyl)-N-ethyl-N-methylformimidamide;
N'-(2,5-dimethyl-4-(2-(trifluoromethyl)benzyl)phenyl)-N-ethyl-N-methylformimidamide;
N'-(2,5-dimethyl-4-(4-(trifluoromethyl)benzyl)phenyl)-N-ethyl-N-methylformimidamide;
N'-(2-chloro-4-(4-chloro-3-fluorobenzyl)-5-methylphenyl)-N-ethyl-N-methylformimidamide;
N'-(4-(3,5-bis(trifluoromethyl)benzyl)-2-chloro-5-methylphenyl)-N-ethyl-N-methylformimidamide;
N'-(2,5-dimethyl-4-(4-(trifluoromethyl)benzyl)phenyl)-N-ethyl-N-methylformimidamide;
N'-(2,5-dimethyl-4-(4-(trifluoromethyl)benzyl)phenyl)-N-ethyl-N-methylformimidamide;
N'-(2-chloro-4-(2-chloro-4-fluorobenzyl)-5-methylphenyl)-N-ethyl-N-methylformimidamide;
N'-(2-chloro-4-(2-cyanobenzyl)-5-methylphenyl)-N-ethyl-N-methylformimidamide;
N'-(2-chloro-5-methyl-4-(4-(trifluoromethyl)benzyl)phenyl)-N-ethyl-N-methylformimidamide;
N'-(2-chloro-5-methyl-4-(2-(trifluoromethoxy)benzyl)phenyl)-N-ethyl-N-methylformimidamide;
N'-(2-chloro-5-methyl-4-(2-(trifluoromethyl)benzyl)phenyl)-N-ethyl-N-methylformimidamide;
N'-(2,5-dimethyl-4-(4-methyl-3-(trifluoromethyl)benzyl)phenyl)-N-ethyl-N-methylformimidamide;
N'-(4-(4-chloro-3-fluorobenzyl)-2,5-dimethylphenyl)-N-ethyl-N-methylformimidamide;
N'-(4-(3,5-bis(trifluoromethyl)benzyl)-2,5-dimethylphenyl)-N-ethyl-N-methylformimidamide;
N'-(4-(3-(1-cyanoethyl)benzyl)-2,5-dimethylphenyl)-N-ethyl-N-methylformimidamide;
N'-(4-(4-chloro-3-methylbenzyl)-2,5-dimethylphenyl)-N-ethyl-N-methylformimidamide;
N-ethyl-N'-(4-(4-fluoro-3-methylbenzyl)-2,5-dimethylphenyl)-N-methylformimidamide;
N'-(4-(2-chloro-4-fluorobenzyl)-2,5-dimethylphenyl)-N-ethyl-N-methylformimidamide;
N'-(4-(3-(dimethylamino)benzyl)-2,5-dimethylphenyl)-N-ethyl-N-methylformimidamide;
N'-(4-(2,3-dimethylbenzyl)-2,5-dimethylphenyl)-N-ethyl-N-methylformimidamide;
N'-(4-(3,4-dimethylbenzyl)-2,5-dimethylphenyl)-N-ethyl-N-methylformimidamide;
N'-(4-(3,5-dimethylbenzyl)-2,5-dimethylphenyl)-N-ethyl-N-methylformimidamide;
N'-(4-(2-cyanobenzyl)-2,5-dimethylphenyl)-N-ethyl-N-methylformimidamide;
N'-(2,5-dimethyl-4-(2-(trifluoromethoxy)benzyl)phenyl)-N-ethyl-N-methylformimidamide;
N'-(2,5-dimethyl-4-(4-(trifluoromethoxy)benzyl)phenyl)-N-ethyl-N-methylformimidamide;
N'-(4-(3-chloro-2-fluorobenzyl)-2,5-dimethylphenyl)-N-ethyl-N-methylformimidamide;
N'-(2-chloro-4-(4-fluoro-3-methylbenzyl)-5-methylphenyl)-N-ethyl-N-methylformimidamide;
N'-(2-chloro-4-(4-chloro-3-methylbenzyl)-5-methylphenyl)-N-ethyl-N-methylformimidamide;
N'-(2-chloro-5-methyl-4-(4-(trifluoromethoxy)benzyl)phenyl)-N-ethyl-N-methylformimidamide;
N'-(2-chloro-5-methyl-4-(2-methylbenzyl)phenyl)-N-ethyl-N-methylformimidamide;
N'-(2-chloro-4-(3-chloro-2-fluorobenzyl)-5-methylphenyl)-N-ethyl-N-methylformimidamide;
N'-(2-chloro-5-methyl-4-(3-(trifluoromethoxy)benzyl)phenyl)-N-ethyl-N-methylformimidamide;
N'-(2-chloro-4-(2-chloro-3-fluorobenzyl)-5-methylphenyl)-N-ethyl-N-methylformimidamide;
N'-(2-chloro-4-(3-chloro-2-fluoro-5-(trifluoromethyl)benzyl)-5-methylphenyl)-N-ethyl-N-methylformimidamide;
N'-(4-(cyano(phenyl)methyl)-2,5-dimethylphenyl)-N-ethyl-N-methylformimidamide;
N'-(2-chloro-4-(2,3-dichlorobenzyl)-5-methylphenyl)-N-ethyl-N-methylformimidamide;
N'-(2-chloro-4-(3,5-difluorobenzyl)-5-methylphenyl)-N-ethyl-N-methylformimidamide;
N'-(2-chloro-4-(3,5-dimethylbenzyl)-5-methylphenyl)-N-ethyl-N-methylformimidamide;
N'-(4-(2-chloro-3-fluorobenzyl)-2,5-dimethylphenyl)-N-ethyl-N-methylformimidamide;
N'-(4-(3,5-difluorobenzyl)-2,5-dimethylphenyl)-N-ethyl-N-methylformimidamide;
N'-(4-(2,3-dichlorobenzyl)-2,5-dimethylphenyl)-N-ethyl-N-methylformimidamide;
N'-(4-(3-chloro-2-fluoro-5-(trifluoromethyl)benzyl)-2,5-dimethylphenyl)-N-ethyl-N-methylformimidamide;
N'-(4-(3-chloro-5-fluorobenzyl)-2,5-dimethylphenyl)-N-ethyl-N-methylformimidamide;
N'-(2-chloro-4-(4-chloro-3-(trifluoromethyl)benzyl)-5-methylphenyl)-N-ethyl-N-methylformimidamide;
N'-(2-chloro-4-(3-fluoro-4-(trifluoromethyl)benzyl)-5-methylphenyl)-N-ethyl-N-methylformimidamide;
N'-(2-chloro-4-(3,4-difluorobenzyl)-5-methylphenyl)-N-ethyl-N-methylformimidamide;
N'-(2-chloro-4-(3-fluoro-4-methylbenzyl)-5-methylphenyl)-N-ethyl-N-methylformimidamide;
N'-(2-chloro-4-(3-fluoro-5-methylbenzyl)-5-methylphenyl)-N-ethyl-N-methylformimidamide;
N'-(2,5-dichloro-4-(3-methylbenzyl)phenyl)-N-ethyl-N-methylformimidamide;
N'-(4-(4-chloro-3-(trifluoromethyl)benzyl)-2,5-dimethylphenyl)-N-ethyl-N-methylformimidamide;
N'-(4-(2-chloro-5-fluorobenzyl)-2,5-dimethylphenyl)-N-ethyl-N-methylformimidamide;
N-ethyl-N'-(4-(3-fluoro-4-methylbenzyl)-2,5-dimethylphenyl)-N-methylformimidamide;
N'-(4-(4-chloro-3-(trifluoromethoxy)benzyl)-2,5-dimethylphenyl)-N-ethyl-N-methylformimidamide;
N'-(4-(3,4-difluorobenzyl)-2,5-dimethylphenyl)-N-ethyl-N-methylformimidamide;
N'-(2,5-dichloro-4-(4-methylbenzyl)phenyl)-N-ethyl-N-methylformimidamide;
N'-(2,5-dichloro-4-(3-fluorobenzyl)phenyl)-N-ethyl-N-methylformimidamide;
N'-(2,5-dichloro-4-(2-fluorobenzyl)phenyl)-N-ethyl-N-methylformimidamide;
N'-(2,5-dichloro-4-(2-chlorobenzyl)phenyl)-N-ethyl-N-methylformimidamide;
N'-(2,5-dichloro-4-(2-methylbenzyl)phenyl)-N-ethyl-N-methylformimidamide;

N'-(2,5-dichloro-4-(3-chlorobenzyl)phenyl)-N-ethyl-N-methylformimidamide;
N'-(4-(2,6-dichlorobenzyl)-2,5-dimethylphenyl)-N-ethyl-N-methylformimidamide;
N'-(4-(2-bromobenzyl)-2,5-dimethylphenyl)-N-ethyl-N-methylformimidamide;
N'-(4-(2-chloro-6-fluorobenzyl)-2,5-dimethylphenyl)-N-ethyl-N-methylformimidamide;
N-ethyl-N'-(4-(3-fluoro-5-methoxybenzyl)-2,5-dimethylphenyl)-N-methylformimidamide;
N-ethyl-N'-(4-(5-fluoro-2-methylbenzyl)-2,5-dimethylphenyl)-N-methylformimidamide;
N-ethyl-N'-(4-(3-fluoro-4-(trifluoromethyl)benzyl)-2,5-dimethylphenyl)-N-methylformimidamide;
N'-(4-(2-chloro-5-(trifluoromethyl)benzyl)-2,5-dimethylphenyl)-N-ethyl-N-methylformimidamide;
N'-(4-(2,5-dichlorobenzyl)-2,5-dimethylphenyl)-N-ethyl-N-methylformimidamide;
N'-(4-(2,4-difluorobenzyl)-2,5-dimethylphenyl)-N-ethyl-N-methylformimidamide;
N'-(4-(2,4-dichlorobenzyl)-2,5-dimethylphenyl)-N-ethyl-N-methylformimidamide;
N-ethyl-N'(4-(2-fluorobenzyl)phenyl)-N-methylformimidamide;
N'-(4-(2-chlorobenzyl)phenyl)-N-ethyl-N-methylformimidamide;
N'-(2-chloro-4-(5-fluoro-2-methylbenzyl)-5-methylphenyl)-N-ethyl-N-methylformimidamide;
N'-(2-chloro-4-(2,5-dichlorobenzyl)-5-methylphenyl)-N-ethyl-N-methylformimidamide;
N'-(2-chloro-4-(4-fluoro-2-methylbenzyl)-5-methylphenyl)-N-ethyl-N-methylformimidamide;
N'-(2-chloro-4-(2-chloro-5-(trifluoromethyl)benzyl)-5-methylphenyl)-N-ethyl-N-methylformimidamide;
N'-(2-chloro-4-(3-fluoro-5-methoxybenzyl)-5-methylphenyl)-N-ethyl-N-methylformimidamide;
N-(2-chloro-4-(2,3-dimethylbenzyl)-5-methylphenyl)-N-ethyl-N-methylformimidamide;
N-ethyl-N'-(5-fluoro-2-methyl-4-(3-methylbenzyl)phenyl)-N-methylformimidamide;
N-ethyl-N'-(5-fluoro-4-(3-fluorobenzyl)-2-methylphenyl)-N-methylformimidamide;
N'-(4-(3-chlorobenzyl)-5-fluoro-2-methylphenyl)-N-ethyl-N-methylformimidamide;
N'-(4-(2-chlorobenzyl)-5-fluoro-2-methylphenyl)-N-ethyl-N-methylformimidamide;
N-ethyl-N'-(5-fluoro-2-methyl-4-(4-methylbenzyl)phenyl)-N-methylformimidamide;
N'-(2-chloro-4-(3-chloro-5-fluorobenzyl)-5-methylphenyl)-N-ethyl-N-methylformimidamide;
N'-(2-chloro-4-(4-chloro-3-(trifluoromethoxy)benzyl)-5-methylphenyl)-N-ethyl-N-methylformimidamide;
N'-(2-chloro-4-(2-chloro-5-fluorobenzyl)-5-methylphenyl)-N-ethyl-N-methylformimidamide;
N'-(2-chloro-4-(2,4-dichlorobenzyl)-5-methylphenyl)-N-ethyl-N-methylformimidamide;
N'-(2-chloro-4-(2,4-difluorobenzyl)-5-methylphenyl)-N-ethyl-N-methylformimidamide;
N'-(2-chloro-4-(4-fluoro-3-(trifluoromethyl)benzyl)-5-methylphenyl)-N-ethyl-N-methylformimidamide;
N'-(2,5-dichloro-4-(3-(trifluoromethoxy)benzyl)phenyl)-N-ethyl-N-methylformimidamide;
N'-(2,5-dichloro-4-(3-(trifluoromethyl)benzyl)phenyl)-N-ethyl-N-methylformimidamide;
N'-(2-chloro-4-(2-chloro-6-fluorobenzyl)-5-methylphenyl)-N-ethyl-N-methylformimidamide;
N-ethyl-N'-(5-fluoro-4-(2-fluorobenzyl)-2-methylphenyl)-N-methylformimidamide;
N-ethyl-N'-(5-fluoro-2-methyl-4-(2-methylbenzyl)phenyl)-N-methylformimidamide;
N'-(2-chloro-4-(cyano(4-(trifluoromethyl)phenyl)methyl)-5-methylphenyl)-N-ethyl-N-methylformimidamide;
N'-(2-chloro-4-(cyano(3-(trifluoromethyl)phenyl)methyl)-5-methylphenyl)-N-ethyl-N-methylformimidamide;
N'-(2-chloro-4-(cyano(4-fluorophenyl)methyl)-5-methylphenyl)-N-ethyl-N-methylformimidamide;
N'-(2-chloro-4-((3-chloro-4-fluorophenyl)(cyano)methyl)-5-methylphenyl)-N-ethyl-N-methylformimidamide;
N'-(2-chloro-4-(cyano(p-tolyl)methyl)-5-methylphenyl)-N-ethyl-N-methylformimidamide;
N'-(2-chloro-4-((2-chlorophenyl)(cyano)methyl)-5-methylphenyl)-N-ethyl-N-methylformimidamide;
N'-(2-chloro-4-((4-chlorophenyl)(cyano)methyl)-5-methylphenyl)-N-ethyl-N-methylformimidamide;
N'-(2-chloro-4-(cyano(3-fluorophenyl)methyl)-5-methylphenyl)-N-ethyl-N-methylformimidamide;
N'-(2-chloro-4-(2,6-dichlorobenzyl)-5-methylphenyl)-N-ethyl-N-methylformimidamide;
N-ethyl-N'-(5-fluoro-2-methyl-4-(3-(trifluoromethyl)benzyl)phenyl)-N-methylformimidamide;
N'-(2-cyclopropyl-4-(3-fluorobenzyl)-5-methylphenyl)-N-ethyl-N-methylformimidamide;
N'-(2-cyclopropyl-5-methyl-4-(3-methylbenzyl)phenyl)-N-ethyl-N-methylformimidamide;
N'-(4-(3-chlorobenzyl)-2-cyclopropyl-5-methylphenyl)-N-ethyl-N-methylformimidamide;
N-ethyl-N'-(4-(3-fluoro-5-methylbenzyl)-2,5-dimethylphenyl)-N-methylformimidamide;
N-ethyl-N'-(4-(2-fluoro-4-(trifluoromethyl)benzyl)-2,5-dimethylphenyl)-N-methylformimidamide;
N'-(2,5-dimethyl-4-(pyridin-2-ylmethyl)phenyl)-N-ethyl-N-methylformimidamide;
N'-(2-chloro-4-(2,6-difluorobenzyl)-5-methylphenyl)-N-ethyl-N-methylformimidamide;
N'-(2-chloro-5-methyl-4-(pyridin-3-ylmethyl)phenyl)-N-ethyl-N-methylformimidamide;
N-ethyl-N'-(2-fluoro-5-methyl-4-(3-(trifluoromethyl)benzyl)phenyl)-N-methylformimidamide;
N-ethyl-N'-(2-fluoro-5-methyl-4-(3-(trifluoromethoxy)benzyl)phenyl)-N-methylformimidamide;
N-ethyl-N'-(2-fluoro-5-methyl-4-(2-(trifluoromethoxy)benzyl)phenyl)-N-methylformimidamide;
N'-(4-(3-chlorobenzyl)-2-fluoro-5-methylphenyl)-N-ethyl-N-methylformimidamide;
N-ethyl-N'-(2-fluoro-4-(3-fluorobenzyl)-5-methylphenyl)-N-methylformimidamide;
N-ethyl-N'-(2-fluoro-5-methyl-4-(3-methylbenzyl)phenyl)-N-methylformimidamide;
N-ethyl-N'-(2-fluoro-5-methyl-4-(4-methylbenzyl)phenyl)-N-methylformimidamide;
N-ethyl-N'-(2-fluoro-5-methyl-4-(2-methylbenzyl)phenyl)-N-methylformimidamide;
N'-(4-(2-chlorobenzyl)-2-fluoro-5-methylphenyl)-N-ethyl-N-methylformimidamide;
N-ethyl-N'-(2-fluoro-4-(2-fluorobenzyl)-5-methylphenyl)-N-methylformimidamide;
N'-(2,5-dimethyl-4-((Z)-(methylimino)(o-tolyl)methyl)phenyl)-N-ethyl-N-methylformimidamide;
N-ethyl-N'-(4-(3-fluorobenzyl)-5-methyl-2-(methylsulfonyl)phenyl)-N-methylformimidamide;

N'-(4-(3-chlorobenzyl)-5-methyl-2-(methylsulfonyl)phenyl)-N-ethyl-N-methylformimidamide;
N'-(2-bromo-3,6-dimethyl-4-(2-methylbenzyl)phenyl)-N-ethyl-N-methylformimidamide;
N'-(2-chloro-4-(2-fluoro-6-(trifluoromethyl)benzyl)-5-methylphenyl)-N-ethyl-N-methylformimidamide;
N'-(2-cyclopropyl-4-(2-fluorobenzyl)-5-methylphenyl)-N-ethyl-N-methylformimidamide;
N'-(2-cyclopropyl-5-methyl-4-(4-methylbenzyl)phenyl)-N-ethyl-N-methylformimidamide;
N'-(4-(2-chlorobenzyl)-2-cyclopropyl-5-methylphenyl)-N-ethyl-N-methylformimidamide;
N'-(2-cyclopropyl-5-methyl-4-(3-(trifluoromethoxy)benzyl)phenyl)-N-ethyl-N-methylformimidamide;
N-ethyl-N'-(2-fluoro-4-(4-methylbenzyl)-5-(trifluoromethyl)phenyl)-N-methylformimidamide;
N'-(4-(2-chlorobenzyl)-2-fluoro-5-(trifluoromethyl)phenyl)-N-ethyl-N-methylformimidamide;
N-ethyl-N'-(2-fluoro-4-(2-fluorobenzyl)-5-(trifluoromethyl)phenyl)-N-methylformimidamide;
N-ethyl-N'-(2-fluoro-4-(2-methylbenzyl)-5-(trifluoromethyl)phenyl)-N-methylformimidamide;
N'-(4-(3-chlorobenzyl)-2-fluoro-5-(trifluoromethyl)phenyl)-N-ethyl-N-methylformimidamide;
N-ethyl-N'-(2-fluoro-4-(3-fluorobenzyl)-5-(trifluoromethyl)phenyl)-N-methylformimidamide;
N-ethyl-N'-(2-fluoro-4-(3-methylbenzyl)-5-(trifluoromethyl)phenyl)-N-methylformimidamide;
N-ethyl-N'-(2-fluoro-5-(trifluoromethyl)-4-(3-(trifluoromethyl)benzyl)phenyl)-N-methylformimidamide;
N-ethyl-N'-(2-fluoro-4-(3-(trifluoromethoxy)benzyl)-5-(trifluoromethyl)phenyl)-N-methylformimidamide;
N-ethyl-N-methyl-N'-(5-methyl-4-(2-methylbenzyl)-2-(methylsulfonyl)phenyl)formimidamide;
N-ethyl-N-methyl-N'-(5-methyl-4-(4-methylbenzyl)-2-(methylsulfonyl)phenyl)formimidamide;
N'-(5-chloro-4-(cyano(5-fluoro-2-methylphenyl)methyl)-2-methylphenyl)-N-ethyl-N-methylformimidamide;
methyl 2-(2-chloro-4-(((ethyl(methyl)amino)methylene)amino)-5-methylphenyl)-2-(3-chlorophenyl)acetate;
N'-(4-(1-(4-bromophenyl)vinyl)-5-chloro-2-methylphenyl)-N-ethyl-N-methylformimidamide;
2-(2-chloro-4-(((ethyl(methyl)amino)methylene)amino)-5-methylphenyl)-2-(3-fluorophenyl)-N,N-dimethylpropanamide;
2-(2-chloro-4-(((ethyl(methyl)amino)methylene)amino)-5-methylphenyl)-2-(5-fluoro-2-methylphenyl)-N,N-dimethylacetamide;
N'-(5-chloro-4-((4-chloro-3-fluorophenyl)(cyano)methyl)-2-methylphenyl)-N-ethyl-N-methylformimidamide;
N'-(2,5-difluoro-4-(2-fluorobenzyl)phenyl)-N-ethyl-N-methylformimidamide;
N'-(4-(3-chlorobenzyl)-2,5-difluorophenyl)-N-ethyl-N-methylformimidamide;
N'-(2,5-difluoro-4-(3-methylbenzyl)phenyl)-N-ethyl-N-methylformimidamide;
N'-(2,5-difluoro-4-(4-methylbenzyl)phenyl)-N-ethyl-N-methylformimidamide;
N'-(4-(2-chlorobenzyl)-5-cyano-2-methylphenyl)-N-ethyl-N-methylformimidamide;
N'-(5-cyano-4-(2-fluorobenzyl)-2-methylphenyl)-N-ethyl-N-methylformimidamide;
N'-(5-cyano-2-methyl-4-(2-methylbenzyl)phenyl)-N-ethyl-N-methylformimidamide;
N'-(4-(3-chlorobenzyl)-5-cyano-2-methylphenyl)-N-ethyl-N-methylformimidamide;
N'-(5-cyano-4-(3-fluorobenzyl)-2-methylphenyl)-N-ethyl-N-methylformimidamide;
N'-(5-cyano-2-methyl-4-(3-methylbenzyl)phenyl)-N-ethyl-N-methylformimidamide;
N'-(5-cyano-2-methyl-4-(4-methylbenzyl)phenyl)-N-ethyl-N-methylformimidamide;
N'-(4-(2-chlorobenzyl)-2,5-difluorophenyl)-N-ethyl-N-methylformimidamide;
N'-(2,5-difluoro-4-(2-methylbenzyl)phenyl)-N-ethyl-N-methylformimidamide;
N'-(5-chloro-4-(2-chlorobenzyl)-2-methylphenyl)-N-ethyl-N-methylformimidamide;
N'-(5-chloro-4-(2-fluorobenzyl)-2-methylphenyl)-N-ethyl-N-methylformimidamide;
N'-(5-chloro-2-methyl-4-(2-methylbenzyl)phenyl)-N-ethyl-N-methylformimidamide;
N'-(5-chloro-4-(3-chlorobenzyl)-2-methylphenyl)-N-ethyl-N-methylformimidamide;
N'-(5-chloro-4-(3-fluorobenzyl)-2-methylphenyl)-N-ethyl-N-methylformimidamide;
N'-(5-chloro-2-methyl-4-(3-methylbenzyl)phenyl)-N-ethyl-N-methylformimidamide;
N'-(5-chloro-2-methyl-4-(4-methylbenzyl)phenyl)-N-ethyl-N-methylformimidamide;
N'-(4-(2-chlorobenzyl)-2-cyclopropyl-5-(trifluoromethyl)phenyl)-N-ethyl-N-methylformimidamide;
N'-(2-cyclopropyl-4-(3-methylbenzyl)-5-(trifluoromethyl)phenyl)-N-ethyl-N-methylformimidamide;
N-(2-cyclopropyl-4-(4-methylbenzyl)-5-(trifluoromethyl)phenyl)-N-ethyl-N-methylformimidamide;
N'-(4-(3-chlorobenzyl)-2-cyclopropyl-5-(trifluoromethyl)phenyl)-N-ethyl-N-methylformimidamide;
N'-(2-cyclopropyl-4-(3-fluorobenzyl)-5-(trifluoromethyl)phenyl)-N-ethyl-N-methylformimidamide;
N'-(2-cyclopropyl-4-(4-cyclopropylbenzyl)-3,6-dimethylphenyl)-N-ethyl-N-methylformimidamide;
N'-(2-cyclopropyl-4-(2-methylbenzyl)-5-(trifluoromethyl)phenyl)-N-ethyl-N-methylformimidamide;
N'-(2,5-difluoro-4-(3-fluorobenzyl)phenyl)-N-ethyl-N-methylformimidamide;
N'-(4-(2-chlorobenzyl)naphthalen-1-yl)-N-ethyl-N-methylformimidamide;
N-ethyl-N-methyl-N'-(4-(2-methylbenzyl)naphthalen-1-yl)formimidamide;
N'-(2-chloro-4-(cyano(3-(trifluoromethyl)phenyl)methyl)-5-methylphenyl)-N-ethyl-N-methylformimidamide hydrochloride;
N-ethyl-N-methyl-N'-(5-methyl-4-(3-methylbenzyl)-2-(methylsulfonyl)phenyl)formimidamide;
N-ethyl-N'-(4-(2-fluorobenzyl)-5-methyl-2-(methylsulfonyl)phenyl)-N-methylformimidamide;
N'-(4-(2-chlorobenzyl)-5-methyl-2-(methylsulfonyl)phenyl)-N-ethyl-N-methylformimidamide;
N-ethyl-N-methyl-N'-(5-methyl-2-(methylsulfonyl)-4-(3-(trifluoromethyl)benzyl)phenyl)formimidamide;
N-ethyl-N-methyl-N'-(5-methyl-2-(methylsulfonyl)-4-(3-(trifluoromethoxy)benzyl)phenyl)formimidamide;
N-ethyl-N'-(5-fluoro-2-methyl-4-(3-(trifluoromethoxy)benzyl)phenyl)-N-methylformimidamide;
N-ethyl-N-methyl-N-(5-methyl-4-(2-methylbenzyl)-2-(methylsulfonyl)phenyl)formimidamide;
N-ethyl-N-methyl-N'-(5-methyl-4-(4-methylbenzyl)-2-(methylsulfonyl)phenyl)formimidamide;
N'-(4-(3-chlorobenzyl)-5-methyl-2-(methylsulfonyl)phenyl)-N-ethyl-N-methylformimidamide;
N-ethyl-N'-(4-(3-fluorobenzyl)-5-methyl-2-(methylsulfonyl)phenyl)-N-methylformimidamide;

N-ethyl-N-methyl-N'-(5-methyl-4-(3-methylbenzyl)-2-(methylsulfonyl)phenyl)formimidamide;
N-ethyl-N'-(4-(2-fluorobenzyl)-5-methyl-2-(methylsulfonyl)phenyl)-N-methylformimidamide;
N'-(4-(2-chlorobenzyl)-5-methyl-2-(methylsulfonyl)phenyl)-N-ethyl-N-methylformimidamide;
N-ethyl-N-methyl-N-(5-methyl-2-(methylsulfonyl)-4-(3-(trifluoromethyl)benzyl)phenyl)formimidamide;
N-ethyl-N-methyl-N-(5-methyl-2-(methylsulfonyl)-4-(3-(trifluoromethoxy)benzyl)phenyl)formimidamide; and
N-ethyl-N'-(5-fluoro-2-methyl-4-(3-(trifluoromethoxy)benzyl)phenyl)-N-methylformimidamide; and
N'-(4-(cyano(3-(trifluromethyl)phenyl)methyl)-2,5-dimethylphenyl)-N-ethyl-N-methylformimidamide;
and agronomically acceptable salts, stereo-isomers, diastereoisomers, enantiomers, tautomers, or N-oxides thereof.

5. A composition for controlling or preventing against phytopathogenic microorganisms, comprising a compound of general formula (I) according to claim 1 and one or more inert carriers.

6. The composition according to claim 5, wherein said composition further comprises one or more active compounds selected from fungicides, insecticides, nematicides, acaricides, biopesticides, herbicides, plant growth regulators, antibiotics, fertilizers and/or mixtures thereof.

7. The composition according to claim 5, wherein the concentration of compound of general formula (I) is ranging from 1 to 90% by weight with respect to the total weight of the composition.

8. The composition according to claim 5, wherein the concentration of compound of general formula (I) is ranging from 5 to 50% by weight with respect to the total weight of the composition.

9. A method for controlling phytopathogenic fungi, bacteria, insects, nematodes, and mites, the process comprising:
applying the compound of claim 1 to agricultural crops and/or horticultural crops.

10. A method for control or prevention of phytopathogenic fungi, the process comprising:
applying the compound of claim 1 to agricultural crops and/or horticultural crops.

11. A method for control or prevention of phytopathogenic fungi, bacteria, insects, nematodes, and mites, the process comprising:
applying the compound of claim 1 to agricultural crops and/or horticultural crops.

12. The method of claim 9, wherein said agricultural crops are selected from the group consisting of cereals, corn, rice, leguminous plants, fruits and fruit trees, nuts and nut trees, citrus and citrus trees, horticultural plants, cucurbitaceae, oleaginous plants, tobacco, coffee, tea, cacao, sugar beet, sugar cane, cotton, potato, tomato, onions, peppers and other vegetables, and ornamentals.

13. A method of controlling or preventing infestation of useful plants by phytopathogenic microorganisms in agricultural crops and/or horticultural crops wherein the compound of general formula (I) according to claim 1, is applied to the plants, to parts thereof or the locus thereof.

14. A method of controlling or preventing infestation of useful plants by phytopathogenic microorganisms in agricultural crops and/or horticultural crops wherein the compound of general formula (I) according to claim 1, is applied to the seeds of plants.

15. A method of controlling or preventing phytopathogenic microorganisms in agricultural crops and/or horticultural crops using the compound of general formula (I) according to claim 1, which consists in applying effective dosages of the compound or compositions comprising the compound in amounts ranging from 1 g to 5 kg per hectare of the agricultural and/or horticultural crops.

16. The method of claim 11, wherein said agricultural crops are selected from the group consisting of cereals, corn, rice, leguminous plants, fruits and fruit trees, nuts and nut trees, citrus and citrus trees, horticultural plants, cucurbitaceae, oleaginous plants, tobacco, coffee, tea, cacao, sugar beet, sugar cane, cotton, potato, tomato, onions, vegetables, and ornamentals.

17. A compound of general formula (I) is selected from the group consisting of:
N'-(4-benzyl-2,5-dimethylphenyl)-N-ethyl-N-methylformimidamide;
N-ethyl-N'-(4-(methoxy(phenyl)methyl)-2,5-dimethylphenyl)-N-methylformimidamide;
N'-(4-(3,5-dichlorobenzyl)-2,5-dimethylphenyl)-N-ethyl-N-methylformimidamide;
N'-(4-(4-bromobenzyl)-2,5-dimethylphenyl)-N-ethyl-N-methylformimidamide;
N'-(4-(3,4-dichlorobenzyl)-2,5-dimethylphenyl)-N-ethyl-N-methylformimidamide;
N'-(2,5-dimethyl-4-(3-methylbenzyl)phenyl)-N-ethyl-N-methylformimidamide;
N'-(4-(4-chlorobenzyl)-2,5-dimethylphenyl)-N-ethyl-N-methylformimidamide;
N'-(2,5-dimethyl-4-(4-(methylthio)benzyl)phenyl)-N-ethyl-N-methylformimidamide;
N'-(2,5-dimethyl-4-(4-methylbenzyl)phenyl)-N-ethyl-N-methylformimidamide;
N'-(2-bromo-4-(4-bromobenzyl)-3,6-dimethylphenyl)-N-ethyl-N-methylformimidamide;
N'-(4-(3-chlorobenzyl)-2,5-dimethylphenyl)-N-ethyl-N-methylformimidamide;
N'-(2,5-dimethyl-4-(4-(methylsulfonyl)benzyl)phenyl)-N-ethyl-N-methylformimidamide;
N'-(4-(3-bromobenzyl)-2-chloro-5-methylphenyl)-N-ethyl-N-methylformimidamide;
N'-(4-(3-bromobenzyl)-2,5-dimethylphenyl)-N-ethyl-N-methylformimidamide;
N-ethyl-N'-(4-(2-fluorobenzyl)-2,5-dimethylphenyl)-N-methylformimidamide;
N'-(2-chloro-4-(2-fluorobenzyl)-5-methylphenyl)-N-ethyl-N-methylformimidamide;
N'-(2-chloro-4-(2-chlorobenzyl)-5-methylphenyl)-N-ethyl-N-methylformimidamide;
N'-(4-(2-chlorobenzyl)-2,5-dimethylphenyl)-N-ethyl-N-methylformimidamide;
N'-(2,5-dimethyl-4-(4-(methylsulfinyl)benzyl)phenyl)-N-ethyl-N-methylformimidamide;
N'-(2-chloro-4-(3,4-dichlorobenzyl)-5-methylphenyl)-N-ethyl-N-methylformimidamide;
N'-(2-chloro-4-(3,5-dichlorobenzyl)-5-methylphenyl)-N-ethyl-N-methylformimidamide;
N'-(4-(4-bromobenzyl)-2-chloro-5-methylphenyl)-N-ethyl-N-methylformimidamide;
N'-(2,5-dimethyl-4-(2-(methylthio)benzyl)phenyl)-N-ethyl-N-methylformimidamide;
N'-(2,5-dimethyl-4-(2-(methylsulfinyl)benzyl)phenyl)-N-ethyl-N-methylformimidamide;
N'-(2,5-dimethyl-4-(2-(methylsulfonyl)benzyl)phenyl)-N-ethyl-N-methylformimidamide;
N'-(4-(2,5-dimethylbenzyl)-2,5-dimethylphenyl)-N-ethyl-N-methylformimidamide;
N'-(4-(3-bromo-2-fluorobenzyl)-2,5-dimethylphenyl)-N-ethyl-N-methylformimidamide;

N'-(4-(3-chloro-4-fluorobenzyl)-2,5-dimethylphenyl)-N-ethyl-N-methylformimidamide;
N-ethyl-N'-(4-(3-fluorobenzyl)-2,5-dimethylphenyl)-N-methylformimidamide;
N'-(2-chloro-4-(3-fluorobenzyl)-5-methylphenyl)-N-ethyl-N-methylformimidamide;
N'-(2,5-dimethyl-4-((Z)-(methylimino)(phenyl)methyl)phenyl)-N-ethyl-N-methylformimidamide;
N'-(2,5-dimethyl-4-(2-methylbenzyl)phenyl)-N-ethyl-N-methylformimidamide;
N'-(2,5-dimethyl-4-(2-phenyl-1,3-dithiolan-2-yl)phenyl)-N-ethyl-N-methylformimidamide;
N-(4-(3-chloro-4-fluorobenzyl)-2,5-dimethylphenyl)-1-morpholinomethanimine;
N-(4-(3-chloro-4-fluorobenzyl)-2,5-dimethylphenyl)-1-(piperidin-1-yl)methanimine;
N-(4-(3-bromo-2-fluorobenzyl)-2,5-dimethylphenyl)-1-morpholinomethanimine;
N-(4-(3-bromo-2-fluorobenzyl)-2,5-dimethylphenyl)-1-(piperidin-1-yl)methanimine;
N-(2-chloro-4-(3-fluorobenzyl)-5-methylphenyl)-1-morpholinomethanimine;
N-(2-chloro-4-(3-fluorobenzyl)-5-methylphenyl)-1-(piperidin-1-yl)methanimine;
N-(2-chloro-4-(2-chlorobenzyl)-5-methylphenyl)-1-morpholinomethanimine;
N'-(4-(3-bromo-2-fluorobenzyl)-2,5-dimethylphenyl)-N-methylformimidamide;
N'-(2-chloro-4-(3-fluorobenzyl)-5-methylphenyl)-N-methylformimidamide;
N'-(2-chloro-5-methyl-4-(3-methylbenzyl)phenyl)-N-ethyl-N-methylformimidamide;
N'-(2-chloro-5-methyl-4-(4-methylbenzyl)phenyl)-N-ethyl-N-methylformimidamide;
N-ethyl-N'-(4-(3-methoxybenzyl)-2,5-dimethylphenyl)-N-methylformimidamide;
N'-(2,5-dimethyl-4-(3-(trifluoromethyl)benzyl)phenyl)-N-ethyl-N-methylformimidamide;
N'-(4-(3-cyanobenzyl)-2,5-dimethylphenyl)-N-ethyl-N-methylformimidamide;
N'-(4-(4-cyanobenzyl)-2,5-dimethylphenyl)-N-ethyl-N-methylformimidamide;
N'-(2,5-dimethyl-4-(3-nitrobenzyl)phenyl)-N-ethyl-N-methylformimidamide;
N'-(2,5-dimethyl-4-(2-nitrobenzyl)phenyl)-N-ethyl-N-methylformimidamide;
N'-(2,5-dimethyl-4-(3-(trifluoromethoxy)benzyl)phenyl)-N-ethyl-N-methylformimidamide;
N-ethyl-N'-(4-(3-fluoro-5-(trifluoromethyl)benzyl)-2,5-dimethylphenyl)-N-methylformimidamide;
N'-(2,5-dimethyl-4-(2-methyl-5-(trifluoromethyl)benzyl)phenyl)-N-ethyl-N-methylformimidamide;
N-ethyl-N'-(4-(4-methoxybenzyl)-2,5-dimethylphenyl)-N-methylformimidamide;
N-(4-(2-fluorobenzyl)-2,5-dimethylphenyl)-1-morpholinomethanimine;
N-(4-(4-fluorobenzyl)-2,5-dimethylphenyl)-1-morpholinomethanimine;
N-ethyl-N'-(4-(4-fluorobenzyl)-2,5-dimethylphenyl)-N-methylformimidamide;
N-(4-(2-fluorobenzyl)-2,5-dimethylphenyl)-1-(piperidin-1-yl)methanimine;
N-(4-(2-chlorobenzyl)-2,5-dimethylphenyl)-1-(piperidin-1-yl)methanimine;
N-(4-(4-fluorobenzyl)-2,5-dimethylphenyl)-1-(piperidin-1-yl)methanimine;
N'-(4-(2-fluorobenzyl)-2,5-dimethylphenyl)-N-methoxy-N-methylformimidamide;
N'-(4-(2-chlorobenzyl)-2,5-dimethylphenyl)-N-methoxy-N-methylformimidamide;
N-(4-(2-chlorobenzyl)-2,5-dimethylphenyl)-1-morpholinomethanimine;
N-cyano-N-(4-(2-fluorobenzyl)-2,5-dimethylphenyl)formimidamide;
N'-(4-(2-chlorobenzyl)-2,5-dimethylphenyl)-N-cyanoformimidamide;
N'-(4-(2-fluorobenzyl)-2,5-dimethylphenyl)-N-isopropylformimidamide;
N'-(4-(2-chlorobenzyl)-2,5-dimethylphenyl)-N-isopropylformimidamide;
N'-(2-chloro-4-(4-cyanobenzyl)-5-methylphenyl)-N-ethyl-N-methylformimidamide;
N'-(2-chloro-4-(4-methoxybenzyl)-5-methylphenyl)-N-ethyl-N-methylformimidamide;
N'-(2-chloro-4-(3-methoxybenzyl)-5-methylphenyl)-N-ethyl-N-methylformimidamide;
N'-(2-chloro-5-methyl-4-(3-nitrobenzyl)phenyl)-N-ethyl-N-methylformimidamide;
N'-(2-chloro-4-(3-cyanobenzyl)-5-methylphenyl)-N-ethyl-N-methylformimidamide;
N'-(4-(difluoro(phenyl)methyl)-2-iodo-3,6-dimethylphenyl)-N-ethyl-N-methylformimidamide;
N'-(4-benzyl-2-chloro-5-methylphenyl)-N-ethyl-N-methylformimidamide;
N'-(2-chloro-5-methyl-4-(2-nitrobenzyl)phenyl)-N-ethyl-N-methylformimidamide;
N'-(2-chloro-4-(4-fluorobenzyl)-5-methylphenyl)-N-ethyl-N-methylformimidamide;
N'-(2-chloro-5-methyl-4-(4-((trifluoromethyl)thio)benzyl)phenyl)-N-ethyl-N-methylformimidamide;
N'-(2-chloro-4-(3-chlorobenzyl)-5-methylphenyl)-N-ethyl-N-methylformimidamide;
N'-(2-chloro-4-(4-chlorobenzyl)-5-methylphenyl)-N-ethyl-N-methylformimidamide;
N'-(2-chloro-5-methyl-4-(3-(trifluoromethyl)benzyl)phenyl)-N-ethyl-N-methylformimidamide;
N'-(4-(2-fluorobenzyl)-2,5-dimethylphenyl)-N-isopropyl-N-methylformimidamide;
N'-(4-(2-chlorobenzyl)-2,5-dimethylphenyl)-N-isopropyl-N-methylformimidamide;
N-allyl-N'-(4-(2-fluorobenzyl)-2,5-dimethylphenyl)-N-methylformimidamide;
N-allyl-N'-(4-(2-chlorobenzyl)-2,5-dimethylphenyl)-N-methylformimidamide;
N-(4-(2-fluorobenzyl)-2,5-dimethylphenyl)-1-thiomorpholinomethanimine;
N-(4-(2-chlorobenzyl)-2,5-dimethylphenyl)-1-thiomorpholinomethanimine;
N-(cyclopropylmethyl)-N-(4-(2-fluorobenzyl)-2,5-dimethylphenyl)-N-methylformimidamide;
N-(cyclopropylmethyl)-N'-(4-(2-fluorobenzyl)-2,5-dimethylphenyl)-N-isopropylformimidamide;
N'-(4-(2-chlorobenzyl)-2,5-dimethylphenyl)-N-(cyclopropylmethyl)-N-isopropylformimidamide;
N'-(4-(2-chlorobenzyl)-2,5-dimethylphenyl)-N-cyano-N-(cyanomethyl)formimidamide;
N-cyano-N-(cyanomethyl)-N'-(4-(2-fluorobenzyl)-2,5-dimethylphenyl)formimidamide;
N'-(2,5-dimethyl-4-(4-((trifluoromethyl)thio)benzyl)phenyl)-N-ethyl-N-methylformimidamide;
N'-(2,5-dimethyl-4-(2-(trifluoromethyl)benzyl)phenyl)-N-ethyl-N-methylformimidamide;

N'-(2,5-dimethyl-4-(4-(trifluoromethyl)benzyl)phenyl)-N-ethyl-N-methylformimidamide;
N'-(2-chloro-4-(4-chloro-3-fluorobenzyl)-5-methylphenyl)-N-ethyl-N-methylformimidamide;
N'-(4-(3,5-bis(trifluoromethyl)benzyl)-2-chloro-5-methylphenyl)-N-ethyl-N-methylformimidamide;
N'-(2,5-dimethyl-4-(4-(trifluoromethyl)benzyl)phenyl)-N-ethyl-N-methylformimidamide;
N'-(2,5-dimethyl-4-(4-(trifluoromethyl)benzyl)phenyl)-N-ethyl-N-methylformimidamide;
N'-(2-chloro-4-(2-chloro-4-fluorobenzyl)-5-methylphenyl)-N-ethyl-N-methylformimidamide;
N'-(2-chloro-4-(2-cyanobenzyl)-5-methylphenyl)-N-ethyl-N-methylformimidamide;
N'-(2-chloro-5-methyl-4-(4-(trifluoromethyl)benzyl)phenyl)-N-ethyl-N-methylformimidamide;
N'-(2-chloro-5-methyl-4-(2-(trifluoromethoxy)benzyl)phenyl)-N-ethyl-N-methylformimidamide;
N'-(2-chloro-5-methyl-4-(2-(trifluoromethyl)benzyl)phenyl)-N-ethyl-N-methylformimidamide;
N'-(2,5-dimethyl-4-(4-methyl-3-(trifluoromethyl)benzyl)phenyl)-N-ethyl-N-methylformimidamide;
N'-(4-(4-chloro-3-fluorobenzyl)-2,5-dimethylphenyl)-N-ethyl-N-methylformimidamide;
N'-(4-(3,5-bis(trifluoromethyl)benzyl)-2,5-dimethylphenyl)-N-ethyl-N-methylformimidamide;
N'-(4-(3-(1-cyanoethyl)benzyl)-2,5-dimethylphenyl)-N-ethyl-N-methylformimidamide;
N'-(4-(4-chloro-3-methylbenzyl)-2,5-dimethylphenyl)-N-ethyl-N-methylformimidamide;
N-ethyl-N'-(4-(4-fluoro-3-methylbenzyl)-2,5-dimethylphenyl)-N-methylformimidamide;
N'-(4-(2-chloro-4-fluorobenzyl)-2,5-dimethylphenyl)-N-ethyl-N-methylformimidamide;
N'-(4-(3-(dimethylamino)benzyl)-2,5-dimethylphenyl)-N-ethyl-N-methylformimidamide;
N'-(4-(2,3-dimethylbenzyl)-2,5-dimethylphenyl)-N-ethyl-N-methylformimidamide;
N'-(4-(3,4-dimethylbenzyl)-2,5-dimethylphenyl)-N-ethyl-N-methylformimidamide;
N'-(4-(3,5-dimethylbenzyl)-2,5-dimethylphenyl)-N-ethyl-N-methylformimidamide;
N'-(4-(2-cyanobenzyl)-2,5-dimethylphenyl)-N-ethyl-N-methylformimidamide;
N'-(2,5-dimethyl-4-(2-(trifluoromethoxy)benzyl)phenyl)-N-ethyl-N-methylformimidamide;
N'-(2,5-dimethyl-4-(4-(trifluoromethoxy)benzyl)phenyl)-N-ethyl-N-methylformimidamide;
N'-(4-(3-chloro-2-fluorobenzyl)-2,5-dimethylphenyl)-N-ethyl-N-methylformimidamide;
N'-(2-chloro-4-(4-fluoro-3-methylbenzyl)-5-methylphenyl)-N-ethyl-N-methylformimidamide;
N'-(2-chloro-4-(4-chloro-3-methylbenzyl)-5-methylphenyl)-N-ethyl-N-methylformimidamide;
N'-(2-chloro-5-methyl-4-(4-(trifluoromethoxy)benzyl)phenyl)-N-ethyl-N-methylformimidamide;
N'-(2-chloro-5-methyl-4-(2-methylbenzyl)phenyl)-N-ethyl-N-methylformimidamide;
N'-(2-chloro-4-(3-chloro-2-fluorobenzyl)-5-methylphenyl)-N-ethyl-N-methylformimidamide;
N'-(2-chloro-5-methyl-4-(3-(trifluoromethoxy)benzyl)phenyl)-N-ethyl-N-methylformimidamide;
N'-(2-chloro-4-(2-chloro-3-fluorobenzyl)-5-methylphenyl)-N-ethyl-N-methylformimidamide;
N'-(2-chloro-4-(3-chloro-2-fluoro-5-(trifluoromethyl)benzyl)-5-methylphenyl)-N-ethyl-N-methylformimidamide;
N'-(4-(cyano(phenyl)methyl)-2,5-dimethylphenyl)-N-ethyl-N-methylformimidamide;
N'-(2-chloro-4-(2,3-dichlorobenzyl)-5-methylphenyl)-N-ethyl-N-methylformimidamide;
N'-(2-chloro-4-(3,5-difluorobenzyl)-5-methylphenyl)-N-ethyl-N-methylformimidamide;
N'-(2-chloro-4-(3,5-dimethylbenzyl)-5-methylphenyl)-N-ethyl-N-methylformimidamide;
N'-(4-(2-chloro-3-fluorobenzyl)-2,5-dimethylphenyl)-N-ethyl-N-methylformimidamide;
N'-(4-(3,5-difluorobenzyl)-2,5-dimethylphenyl)-N-ethyl-N-methylformimidamide;
N'-(4-(2,3-dichlorobenzyl)-2,5-dimethylphenyl)-N-ethyl-N-methylformimidamide;
N'-(4-(3-chloro-2-fluoro-5-(trifluoromethyl)benzyl)-2,5-dimethylphenyl)-N-ethyl-N-methylformimidamide;
N'-(4-(3-chloro-5-fluorobenzyl)-2,5-dimethylphenyl)-N-ethyl-N-methylformimidamide;
N'-(2-chloro-4-(4-chloro-3-(trifluoromethyl)benzyl)-5-methylphenyl)-N-ethyl-N-methylformimidamide;
N'-(2-chloro-4-(3-fluoro-4-(trifluoromethyl)benzyl)-5-methylphenyl)-N-ethyl-N-methylformimidamide;
N'-(2-chloro-4-(3,4-difluorobenzyl)-5-methylphenyl)-N-ethyl-N-methylformimidamide;
N'-(2-chloro-4-(3-fluoro-4-methylbenzyl)-5-methylphenyl)-N-ethyl-N-methylformimidamide;
N'-(2-chloro-4-(3-fluoro-5-methylbenzyl)-5-methylphenyl)-N-ethyl-N-methylformimidamide;
N'-(2,5-dichloro-4-(3-methylbenzyl)phenyl)-N-ethyl-N-methylformimidamide;
N'-(4-(4-chloro-3-(trifluoromethyl)benzyl)-2,5-dimethylphenyl)-N-ethyl-N-methylformimidamide;
N'-(4-(2-chloro-5-fluorobenzyl)-2,5-dimethylphenyl)-N-ethyl-N-methylformimidamide;
N-ethyl-N'-(4-(3-fluoro-4-methylbenzyl)-2,5-dimethylphenyl)-N-methylformimidamide;
N'-(4-(4-chloro-3-(trifluoromethoxy)benzyl)-2,5-dimethylphenyl)-N-ethyl-N-methylformimidamide;
N'-(4-(3,4-difluorobenzyl)-2,5-dimethylphenyl)-N-ethyl-N-methylformimidamide;
N'-(2,5-dichloro-4-(4-methylbenzyl)phenyl)-N-ethyl-N-methylformimidamide;
N'-(2,5-dichloro-4-(3-fluorobenzyl)phenyl)-N-ethyl-N-methylformimidamide;
N'-(2,5-dichloro-4-(2-fluorobenzyl)phenyl)-N-ethyl-N-methylformimidamide;
N'-(2,5-dichloro-4-(2-chlorobenzyl)phenyl)-N-ethyl-N-methylformimidamide;
N'-(2,5-dichloro-4-(2-methylbenzyl)phenyl)-N-ethyl-N-methylformimidamide;
N'-(2,5-dichloro-4-(3-chlorobenzyl)phenyl)-N-ethyl-N-methylformimidamide;
N'-(4-(2,6-dichlorobenzyl)-2,5-dimethylphenyl)-N-ethyl-N-methylformimidamide;
N'-(4-(2-bromobenzyl)-2,5-dimethylphenyl)-N-ethyl-N-methylformimidamide;
N'-(4-(2-chloro-6-fluorobenzyl)-2,5-dimethylphenyl)-N-ethyl-N-methylformimidamide;
N-ethyl-N'-(4-(3-fluoro-5-methoxybenzyl)-2,5-dimethylphenyl)-N-methylformimidamide;
N-ethyl-N'-(4-(5-fluoro-2-methylbenzyl)-2,5-dimethylphenyl)-N-methylformimidamide;
N-ethyl-N'-(4-(3-fluoro-4-(trifluoromethyl)benzyl)-2,5-dimethylphenyl)-N-methylformimidamide;
N'-(4-(2-chloro-5-(trifluoromethyl)benzyl)-2,5-dimethylphenyl)-N-ethyl-N-methylformimidamide;

N'-(4-(2,5-dichlorobenzyl)-2,5-dimethylphenyl)-N-ethyl-N-methylformimidamide;
N'-(4-(2,4-difluorobenzyl)-2,5-dimethylphenyl)-N-ethyl-N-methylformimidamide;
N'-(4-(2,4-dichlorobenzyl)-2,5-dimethylphenyl)-N-ethyl-N-methylformimidamide;
N-ethyl-N'(4-(2-fluorobenzyl)phenyl)-N-methylformimidamide;
N'-(4-(2-chlorobenzyl)phenyl)-N-ethyl-N-methylformimidamide;
N'-(2-chloro-4-(5-fluoro-2-methylbenzyl)-5-methylphenyl)-N-ethyl-N-methylformimidamide;
N'-(2-chloro-4-(2,5-dichlorobenzyl)-5-methylphenyl)-N-ethyl-N-methylformimidamide;
N'-(2-chloro-4-(4-fluoro-2-methylbenzyl)-5-methylphenyl)-N-ethyl-N-methylformimidamide;
N'-(2-chloro-4-(2-chloro-5-(trifluoromethyl)benzyl)-5-methylphenyl)-N-ethyl-N-methylformimidamide;
N'-(2-chloro-4-(3-fluoro-5-methoxybenzyl)-5-methylphenyl)-N-ethyl-N-methylformimidamide;
N-(2-chloro-4-(2,3-dimethylbenzyl)-5-methylphenyl)-N-ethyl-N-methylformimidamide;
N-ethyl-N'-(5-fluoro-2-methyl-4-(3-methylbenzyl)phenyl)-N-methylformimidamide;
N-ethyl-N'-(5-fluoro-4-(3-fluorobenzyl)-2-methylphenyl)-N-methylformimidamide;
N'-(4-(3-chlorobenzyl)-5-fluoro-2-methylphenyl)-N-ethyl-N-methylformimidamide;
N'-(4-(2-chlorobenzyl)-5-fluoro-2-methylphenyl)-N-ethyl-N-methylformimidamide;
N-ethyl-N'-(5-fluoro-2-methyl-4-(4-methylbenzyl)phenyl)-N-methylformimidamide;
N'-(2-chloro-4-(3-chloro-5-fluorobenzyl)-5-methylphenyl)-N-ethyl-N-methylformimidamide;
N'-(2-chloro-4-(4-chloro-3-(trifluoromethoxy)benzyl)-5-methylphenyl)-N-ethyl-N-methylformimidamide;
N'-(2-chloro-4-(2-chloro-5-fluorobenzyl)-5-methylphenyl)-N-ethyl-N-methylformimidamide;
N'-(2-chloro-4-(2,4-dichlorobenzyl)-5-methylphenyl)-N-ethyl-N-methylformimidamide;
N'-(2-chloro-4-(2,4-difluorobenzyl)-5-methylphenyl)-N-ethyl-N-methylformimidamide;
N'-(2-chloro-4-(4-fluoro-3-(trifluoromethyl)benzyl)-5-methylphenyl)-N-ethyl-N-methylformimidamide;
N'-(2,5-dichloro-4-(3-(trifluoromethoxy)benzyl)phenyl)-N-ethyl-N-methylformimidamide;
N'-(2,5-dichloro-4-(3-(trifluoromethyl)benzyl)phenyl)-N-ethyl-N-methylformimidamide;
N'-(2-chloro-4-(2-chloro-6-fluorobenzyl)-5-methylphenyl)-N-ethyl-N-methylformimidamide;
N-ethyl-N'-(5-fluoro-4-(2-fluorobenzyl)-2-methylphenyl)-N-methylformimidamide;
N-ethyl-N'-(5-fluoro-2-methyl-4-(2-methylbenzyl)phenyl)-N-methylformimidamide;
N'-(2-chloro-4-(cyano(4-(trifluoromethyl)phenyl)methyl)-5-methylphenyl)-N-ethyl-N-methylformimidamide;
N'-(2-chloro-4-(cyano(3-(trifluoromethyl)phenyl)methyl)-5-methylphenyl)-N-ethyl-N-methylformimidamide;
N'-(2-chloro-4-(cyano(4-fluorophenyl)methyl)-5-methylphenyl)-N-ethyl-N-methylformimidamide;
N'-(2-chloro-4-((3-chloro-4-fluorophenyl)(cyano)methyl)-5-methylphenyl)-N-ethyl-N-methylformimidamide;
N'-(2-chloro-4-(cyano(p-tolyl)methyl)-5-methylphenyl)-N-ethyl-N-methylformimidamide;
N'-(2-chloro-4-((2-chlorophenyl)(cyano)methyl)-5-methylphenyl)-N-ethyl-N-methylformimidamide;
N'-(2-chloro-4-((4-chlorophenyl)(cyano)methyl)-5-methylphenyl)-N-ethyl-N-methylformimidamide;
N'-(2-chloro-4-(cyano(3-fluorophenyl)methyl)-5-methylphenyl)-N-ethyl-N-methylformimidamide;
N'-(2-chloro-4-(2,6-dichlorobenzyl)-5-methylphenyl)-N-ethyl-N-methylformimidamide;
N-ethyl-N'-(5-fluoro-2-methyl-4-(3-(trifluoromethyl)benzyl)phenyl)-N-methylformimidamide;
N'-(2-cyclopropyl-4-(3-fluorobenzyl)-5-methylphenyl)-N-ethyl-N-methylformimidamide;
N'-(2-cyclopropyl-5-methyl-4-(3-methylbenzyl)phenyl)-N-ethyl-N-methylformimidamide;
N'-(4-(3-chlorobenzyl)-2-cyclopropyl-5-methylphenyl)-N-ethyl-N-methylformimidamide;
N-ethyl-N'-(4-(3-fluoro-5-methylbenzyl)-2,5-dimethylphenyl)-N-methylformimidamide;
N-ethyl-N'-(4-(2-fluoro-4-(trifluoromethyl)benzyl)-2,5-dimethylphenyl)-N-methylformimidamide;
N'-(2,5-dimethyl-4-(pyridin-2-ylmethyl)phenyl)-N-ethyl-N-methylformimidamide;
N'-(2-chloro-4-(2,6-difluorobenzyl)-5-methylphenyl)-N-ethyl-N-methylformimidamide;
N'-(2-chloro-5-methyl-4-(pyridin-3-ylmethyl)phenyl)-N-ethyl-N-methylformimidamide;
N-ethyl-N'-(2-fluoro-5-methyl-4-(3-(trifluoromethyl)benzyl)phenyl)-N-methylformimidamide;
N-ethyl-N'-(2-fluoro-5-methyl-4-(3-(trifluoromethoxy)benzyl)phenyl)-N-methylformimidamide;
N-ethyl-N'-(2-fluoro-5-methyl-4-(2-(trifluoromethoxy)benzyl)phenyl)-N-methylformimidamide;
N'-(4-(3-chlorobenzyl)-2-fluoro-5-methylphenyl)-N-ethyl-N-methylformimidamide;
N-ethyl-N'-(2-fluoro-4-(3-fluorobenzyl)-5-methylphenyl)-N-methylformimidamide;
N-ethyl-N'-(2-fluoro-5-methyl-4-(3-methylbenzyl)phenyl)-N-methylformimidamide;
N-ethyl-N-(2-fluoro-5-methyl-4-(4-methylbenzyl)phenyl)-N-methylformimidamide;
N-ethyl-N'-(2-fluoro-5-methyl-4-(2-methylbenzyl)phenyl)-N-methylformimidamide;
N'-(4-(2-chlorobenzyl)-2-fluoro-5-methylphenyl)-N-ethyl-N-methylformimidamide;
N-ethyl-N'-(2-fluoro-4-(2-fluorobenzyl)-5-methylphenyl)-N-methylformimidamide;
N'-(2,5-dimethyl-4-((Z)-(methylimino)(o-tolyl)methyl)phenyl)-N-ethyl-N-methylformimidamide;
N-ethyl-N'-(4-(3-fluorobenzyl)-5-methyl-2-(methylsulfonyl)phenyl)-N-methylformimidamide;
N'-(4-(3-chlorobenzyl)-5-methyl-2-(methylsulfonyl)phenyl)-N-ethyl-N-methylformimidamide;
N'-(2-bromo-3,6-dimethyl-4-(2-methylbenzyl)phenyl)-N-ethyl-N-methylformimidamide;
N'-(2-chloro-4-(2-fluoro-6-(trifluoromethyl)benzyl)-5-methylphenyl)-N-ethyl-N-methylformimidamide;
N'-(2-cyclopropyl-4-(2-fluorobenzyl)-5-methylphenyl)-N-ethyl-N-methylformimidamide;
N'-(2-cyclopropyl-5-methyl-4-(4-methylbenzyl)phenyl)-N-ethyl-N-methylformimidamide;
N'-(4-(2-chlorobenzyl)-2-cyclopropyl-5-methylphenyl)-N-ethyl-N-methylformimidamide;
N'-(2-cyclopropyl-5-methyl-4-(3-(trifluoromethoxy)benzyl)phenyl)-N-ethyl-N-methylformimidamide;
N-ethyl-N'-(2-fluoro-4-(4-methylbenzyl)-5-(trifluoromethyl)phenyl)-N-methylformimidamide;

N'-(4-(2-chlorobenzyl)-2-fluoro-5-(trifluoromethyl)phenyl)-N-ethyl-N-methylformimidamide;
N-ethyl-N'-(2-fluoro-4-(2-fluorobenzyl)-5-(trifluoromethyl)phenyl)-N-methylformimidamide;
N-ethyl-N'-(2-fluoro-4-(2-methylbenzyl)-5-(trifluoromethyl)phenyl)-N-methylformimidamide;
N'-(4-(3-chlorobenzyl)-2-fluoro-5-(trifluoromethyl)phenyl)-N-ethyl-N-methylformimidamide;
N-ethyl-N'-(2-fluoro-4-(3-fluorobenzyl)-5-(trifluoromethyl)phenyl)-N-methylformimidamide;
N-ethyl-N'-(2-fluoro-4-(3-methylbenzyl)-5-(trifluoromethyl)phenyl)-N-methylformimidamide;
N-ethyl-N'-(2-fluoro-5-(trifluoromethyl)-4-(3-(trifluoromethyl)benzyl)phenyl)-N-methylformimidamide;
N-ethyl-N'-(2-fluoro-4-(3-(trifluoromethoxy)benzyl)-5-(trifluoromethyl)phenyl)-N-methylformimidamide;
N-ethyl-N-methyl-N'-(5-methyl-4-(2-methylbenzyl)-2-(methylsulfonyl)phenyl)formimidamide;
N-ethyl-N-methyl-N'-(5-methyl-4-(4-methylbenzyl)-2-(methylsulfonyl)phenyl)formimidamide;
N'-(5-chloro-4-(cyano(5-fluoro-2-methylphenyl)methyl)-2-methylphenyl)-N-ethyl-N-methyl;
methyl 2-(2-chloro-4-(((ethyl(methyl)amino)methylene)amino)-5-methylphenyl)-2-(3-chlorophenyl)acetate;
N'-(4-(1-(4-bromophenyl)vinyl)-5-chloro-2-methylphenyl)-N-ethyl-N-methylformimidamide;
2-(2-chloro-4-(((ethyl(methyl)amino)methylene)amino)-5-methylphenyl)-2-(3-fluorophenyl)-N,N-dimethylpropanamide;
2-(2-chloro-4-(((ethyl(methyl)amino)methylene)amino)-5-methylphenyl)-2-(5-fluoro-2-methylphenyl)-N,N-dimethylacetamide;
N'-(5-chloro-4-((4-chloro-3-fluorophenyl)(cyano)methyl)-2-methylphenyl)-N-ethyl-N-methylformimidamide;
N'-(2,5-difluoro-4-(2-fluorobenzyl)phenyl)-N-ethyl-N-methylformimidamide;
N'-(4-(3-chlorobenzyl)-2,5-difluorophenyl)-N-ethyl-N-methylformimidamide;
N'-(2,5-difluoro-4-(3-methylbenzyl)phenyl)-N-ethyl-N-methylformimidamide;
N'-(2,5-difluoro-4-(4-methylbenzyl)phenyl)-N-ethyl-N-methylformimidamide;
N'-(4-(2-chlorobenzyl)-5-cyano-2-methylphenyl)-N-ethyl-N-methylformimidamide;
N'-(5-cyano-4-(2-fluorobenzyl)-2-methylphenyl)-N-ethyl-N-methylformimidamide;
N'-(5-cyano-2-methyl-4-(2-methylbenzyl)phenyl)-N-ethyl-N-methylformimidamide;
N'-(4-(3-chlorobenzyl)-5-cyano-2-methylphenyl)-N-ethyl-N-methylformimidamide;
N'-(5-cyano-4-(3-fluorobenzyl)-2-methylphenyl)-N-ethyl-N-methylformimidamide;
N'-(5-cyano-2-methyl-4-(3-methylbenzyl)phenyl)-N-ethyl-N-methylformimidamide;
N'-(5-cyano-2-methyl-4-(4-methylbenzyl)phenyl)-N-ethyl-N-methylformimidamide;
N'-(4-(2-chlorobenzyl)-2,5-difluorophenyl)-N-ethyl-N-methylformimidamide;
N'-(2,5-difluoro-4-(2-methylbenzyl)phenyl)-N-ethyl-N-methylformimidamide;
N'-(5-chloro-4-(2-chlorobenzyl)-2-methylphenyl)-N-ethyl-N-methylformimidamide;
N'-(5-chloro-4-(2-fluorobenzyl)-2-methylphenyl)-N-ethyl-N-methylformimidamide;
N'-(5-chloro-2-methyl-4-(2-methylbenzyl)phenyl)-N-ethyl-N-methylformimidamide;
N'-(5-chloro-4-(3-chlorobenzyl)-2-methylphenyl)-N-ethyl-N-methylformimidamide;
N'-(5-chloro-4-(3-fluorobenzyl)-2-methylphenyl)-N-ethyl-N-methylformimidamide;
N'-(5-chloro-2-methyl-4-(3-methylbenzyl)phenyl)-N-ethyl-N-methylformimidamide;
N'-(5-chloro-2-methyl-4-(4-methylbenzyl)phenyl)-N-ethyl-N-methylformimidamide;
N'-(4-(2-chlorobenzyl)-2-cyclopropyl-5-(trifluoromethyl)phenyl)-N-ethyl-N-methylformimidamide;
N'-(2-cyclopropyl-4-(3-methylbenzyl)-5-(trifluoromethyl)phenyl)-N-ethyl-N-methylformimidamide;
N'-(2-cyclopropyl-4-(4-methylbenzyl)-5-(trifluoromethyl)phenyl)-N-ethyl-N-methylformimidamide;
N'-(4-(3-chlorobenzyl)-2-cyclopropyl-5-(trifluoromethyl)phenyl)-N-ethyl-N-methylformimidamide;
N'-(2-cyclopropyl-4-(3-fluorobenzyl)-5-(trifluoromethyl)phenyl)-N-ethyl-N-methylformimidamide;
N'-(2-cyclopropyl-4-(4-cyclopropylbenzyl)-3,6-dimethylphenyl)-N-ethyl-N-methylformimidamide;
N'-(2-cyclopropyl-4-(2-methylbenzyl)-5-(trifluoromethyl)phenyl)-N-ethyl-N-methylformimidamide;
N'-(2,5-difluoro-4-(3-fluorobenzyl)phenyl)-N-ethyl-N-methylformimidamide;
N'-(4-(2-chlorobenzyl)naphthalen-1-yl)-N-ethyl-N-methylformimidamide;
N-ethyl-N-methyl-N'-(4-(2-methylbenzyl)naphthalen-1-yl)formimidamide;
N'-(2-chloro-4-(cyano(3-(trifluoromethyl)phenyl)methyl)-5-methylphenyl)-N-ethyl-N-methylformimidamide hydrochloride;
N-ethyl-N-methyl-N'-(5-methyl-4-(3-methylbenzyl)-2-(methylsulfonyl)phenyl)formimidamide;
N-ethyl-N'-(4-(2-fluorobenzyl)-5-methyl-2-(methylsulfonyl)phenyl)-N-methylformimidamide;
N'-(4-(2-chlorobenzyl)-5-methyl-2-(methylsulfonyl)phenyl)-N-ethyl-N-methylformimidamide;
N-ethyl-N-methyl-N'-(5-methyl-2-(methylsulfonyl)-4-(3-(trifluoromethyl)benzyl)phenyl)formimidamide;
N-ethyl-N-methyl-N'-(5-methyl-2-(methylsulfonyl)-4-(3-(trifluoromethoxy)benzyl)phenyl)formimidamide;
N-ethyl-N'-(5-fluoro-2-methyl-4-(3-(trifluoromethoxy)benzyl)phenyl)-N-methylformimidamide;
N-ethyl-N-methyl-N-(5-methyl-4-(2-methylbenzyl)-2-(methylsulfonyl)phenyl)formimidamide;
N-ethyl-N-methyl-N'-(5-methyl-4-(4-methylbenzyl)-2-(methylsulfonyl)phenyl)formimidamide;
N'-(4-(3-chlorobenzyl)-5-methyl-2-(methylsulfonyl)phenyl)-N-ethyl-N-methylformimidamide;
N-ethyl-N'-(4-(3-fluorobenzyl)-5-methyl-2-(methylsulfonyl)phenyl)-N-methylformimidamide;
N-ethyl-N-methyl-N'-(5-methyl-4-(3-methylbenzyl)-2-(methylsulfonyl)phenyl)formimidamide;
N-ethyl-N'-(4-(2-fluorobenzyl)-5-methyl-2-(methylsulfonyl)phenyl)-N-methylformimidamide;
N'-(4-(2-chlorobenzyl)-5-methyl-2-(methylsulfonyl)phenyl)-N-ethyl-N-methylformimidamide;
N-ethyl-N-methyl-N-(5-methyl-2-(methylsulfonyl)-4-(3-(trifluoromethyl)benzyl)phenyl)formimidamide;
N-ethyl-N-methyl-N-(5-methyl-2-(methylsulfonyl)-4-(3-(trifluoromethoxy)benzyl)phenyl)formimidamide; and
N-ethyl-N'-(5-fluoro-2-methyl-4-(3-(trifluoromethoxy)benzyl)phenyl)-N-methylformimidamide;

and agronomically acceptable salts, stereo-isomers, diastereoisomers, enantiomers, tautomers, or N-oxides thereof.

18. A Compound of formula (I),

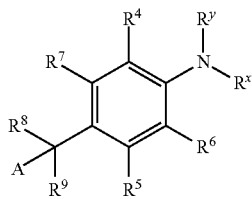

wherein,
R¹ is selected from the group consisting of hydrogen, $C_{1-6}$-alkyl, $C_{1-6}$-haloalkyl and $C_{3-8}$-cycloalkyl;
R² is selected from the group consisting of $C_{2-6}$-alkyl, $C_{2-6}$-alkenyl, $C_{2-12}$-alkynyl, $C_{1-6}$-alkoxy, $C_{1-6}$-haloalkyl and $C_{3-8}$-cycloalkyl;
R³ is selected from the group consisting of $C_{1-6}$-alkyl, $C_{2-6}$-alkenyl, $C_{2-12}$-alkynyl, $C_{1-6}$-alkoxy, $C_{1-6}$-haloalkyl and $C_{3-8}$-cycloalkyl; or
R⁴ is selected from the group consisting of X, CN, $S(O)_nR''$, $C_{1-6}$-alkyl, $C_{2-6}$-alkenyl, $C_{1-6}$-haloalkyl, $C_{1-6}$-haloalkylthio and $C_{3-8}$-cycloalkyl;
R⁵ is selected from the group consisting of X, CN, $S(O)_nR'$, NR'R', OR', $C_{1-6}$-alkyl, $C_{2-6}$-alkenyl, $C_{1-6}$-alkoxy, and $C_{3-8}$-cycloalkyl;
R⁶ and R⁷ are selected from the group consisting of hydrogen, X, CN, $C_{1-6}$-alkyl, $C_{1-6}$-haloalkyl, and $C_{3-8}$-cycloalkyl;
R⁸ and R⁹ are selected from the group consisting of hydrogen, X, CN, (C=O)—R'', $C_{1-6}$-alkyl, $C_{1-6}$-haloalkyl, $C_{2-6}$-alkenyl, $C_{1-4}$-alkoxy, $C_{3-8}$-cycloalkyl, and $C_{3-8}$-cycloalkoxy; or
R⁸ and R⁹ together with the atom to which they are attached or together with further atoms selected from the group consisting of C, N, O, S may form a three to six membered ring, which for its part may be substituted by one or more X, R', OR', SR', NR'₂, SiR'₃, COOR', CN and CONR'₂;

A is selected from the group consisting of phenyl, napthalenyl, pyridinyl, pyridazinyl, pyrimidinyl and pyrazinyl: wherein each group of A is optionally substituted with one or more group of $R^{10}$;
phenyl¹⁰ is selected from the group consisting of X, CN, SCN, SF₅, R'', OR'', NO₂, NR''₂, SiR'₃, $OS(O)_nR''$, OSiR'₃, $NR'S(O)_nR''$, (O=O)—R'', $S(O)_nR''$, $C_{1-8}$-alkyl-$S(O)_nR''$, $C_{1-6}$-alkyl-(C=O)—R'', CR'=NR'', $C_{1-12}$-alkyl, $C_{2-6}$-alkenyl, $C_{2-6}$-alkynyl, $C_{1-6}$-haloalkyl, $C_{2-6}$-haloalkenyl, $C_{1-12}$-alkoxy, $C_{1-12}$-alkylthio, $C_{1-12}$-holoalkoxy, $C_{1-12}$-haloalkylthio, $C_{3-8}$-cycloalkyl, $C_{4-8}$-cycloalkenyl, $C_{3-8}$-cycloalkyloxy and $C_{3-8}$-cycloalkylthio; or
two $R^{10}$ together with the atom to which they are attached or together with further atoms selected from the group consisting of C, N, O, S and optionally including 1 to 3 ring members selected from the group consisting of C(=O), C(=S), $S(O)_m$ and SiR'₂ may form a four to ten membered ring, which for its part may be substituted by one or more X, R', OR', SR', NR'₂, SiR'₃, COOR', CN and CONR'₂,
X represents halogen;
R' is selected from the groups consisting of hydrogen, straight chain or branched chain $C_{1-6}$-alkyl and cyclic $C_{3-8}$-alkyl; wherein each group of R'' is optionally substituted by one or more X;
R'' is selected from the groups consisting of hydrogen, NR'₂, OR', straight chain or branched chain $C_{1-6}$-alkyl, $C_{1-6}$-haloalkyl and cyclic $C_{3-8}$-alkyl; wherein each group of R'' is optionally substituted by one or more groups selected from the group consisting of X, R', OR', SR', NR'₂, SiR'₃, COOR', CN, and CONR'₂, or
R'' is phenyl which is optionally substituted by one or more R';
and agronomically acceptable salts, stereo-isomers, diastereoisomers, enantiomers, tautomers, or N-oxides thereof.

* * * * *